(12) United States Patent
Joseph et al.

(10) Patent No.: US 6,645,983 B1
(45) Date of Patent: Nov. 11, 2003

(54) PHARMACEUTICAL COMPOSITIONS COMPRISING 4-QUINOLONES FOR TREATING CANCERS

(75) Inventors: Benoît Joseph, Saint Jean le Blanc (FR); Francis Darro, Bruxelles (BE); Gérald Guillaumet, Saint Jean le Blanc (FR); Robert Kiss, Wauthier-Braine (BE); Armand Frydman, Verrieres le Buisson (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 10/049,512

(22) PCT Filed: Aug. 11, 2000

(86) PCT No.: PCT/FR00/02310

§ 371 (c)(1),
(2), (4) Date: Feb. 13, 2002

(87) PCT Pub. No.: WO01/12607

PCT Pub. Date: Feb. 22, 2002

(30) Foreign Application Priority Data

Aug. 13, 1999 (FR) .............................. 99 10492

(51) Int. Cl.[7] ........................ A61K 31/44; A61K 31/47; C07D 215/16; C07D 491/08
(52) U.S. Cl. ........................ 514/312; 514/291; 546/90; 546/153
(58) Field of Search .................................. 514/312, 291; 546/153, 90

(56) References Cited

U.S. PATENT DOCUMENTS 5,726,184 A    3/1998    Zelle

FOREIGN PATENT DOCUMENTS

| WO | WO 94/02145 | 2/1994 |
| WO | WO 98/17662 | 4/1998 |
| WO | WO 9817662 | * 4/1998 |

OTHER PUBLICATIONS

CA 130:332267, abstract, Traxler, 1999.*
CA 128:308401, Traxler, abstract, 1998.*
CA 106:4833, Meth–Cohn, 1986.*
Mingxia Xu et al., "1H NMR of 3–Phenyl–4(1h)–Quinolone Derivatives", Chemical Abstracts, vol. 131, No. 4, Jul. 26, 1999 XP–002136387.
M. Xu et al., "BI–H NMR of 3–Phenyl–4(1H)–Quinolone Derivatives", Chemical Abstracts, vol. 16, No. 2, 1999, p. 169–172, XP–002136390.

* cited by examiner

Primary Examiner—D. Margaret Seaman
(74) Attorney, Agent, or Firm—Young & Thompson

(57) ABSTRACT

A non-cytotoxic pharmaceutical composition acting on the proliferation of clonogenic cells in malignant tumors and including an efficient amount of a compound selected among the compounds of formula (I) and (Ia).

17 Claims, No Drawings

PHARMACEUTICAL COMPOSITIONS COMPRISING 4-QUINOLONES FOR TREATING CANCERS

The present invention relates to pharmaceutical compositions comprising 4-quinolones or compounds derived therefrom.

A cancer is a somatic gene disorder in which genetic dysfunctions are amplified as the tumor process progresses from the state of a precancerous lesion to that of a malignant transformation, the cancer tumor becoming metastatic and often resistant to cytotoxic drugs.

Despite considerable efforts conducted in all developed countries, in particular through experimental and clinical research programs, the death rate due to the various cancers (solid tumors and hematological neoplasias) remains unacceptably high. In many countries, the cancer death rate is the second largest, just after cardiovascular diseases.

In terms of newly diagnosed cancers, the distribution between solid tumors and hematological neoplasias (bone marrow, blood, lymphatic system) shows that 9 out of 10 cancers are solid tumors. Contrary to what is observed in hematological oncology (therapeutic success in 40 to 90% of blood cell cancers), only a small number of advanced or disseminated solid tumors respond to chemotherapy treatments alone. It is partly for this reason that the overall death rate by cancer increased in the USA between 1973 and 1992.

Unfortunately, it is not sure that this tendency might be reversed solely by the appearance, alongside the established chemotherapeutic arsenal, of new antitumor drugs such as taxanes (paclitaxel and docetaxel) which interfere with the formation of microtubules (W. P. Mc Guire et al., Am. Intern. Med., 1989), topoisomerase I inhibitors derived from camptothecin (topotecan and irinotecan), vinorelbin (new alkaloid derived from periwinkle), gemcitabine (new cytotoxic antimetabolic agent), raltitrexed (thymidylate synthetase inhibitor) and miltefosine (first representative of the alkyl-lysophospholipid family) These treatments are added, either as a first line treatment or as a second line treatment, to drugs whose specific activity is now well established, for instance doxorubicin, cisplatin, vincristine, methotrexate and 5-fluorouracil.

The vast majority of the conventional chemotherapy treatments or of the treatments based on these new compounds consists in administering highly cytotoxic compounds either in monodrug therapy or in multidrug therapy. The therapeutic efficacy of these treatments is often limited by the intensity of the side effects, which makes it necessary to reduce the number of administrations and the duration of the treatments, whereas for certain solid tumors, therapeutic protocols by intensifying the dose improve the efficacy.

Another of the current difficulties in anticancer chemotherapy is due to the fact that many populations of malignant cells show considerable resistance to the established cytotoxic substances. Usually, this situation results from the existence of multidrug resistance genes or from the frequency of genetic mutations in certain types of tumor. Thus, cancer treatment requires new approaches, complementary to those currently used, and intended to combat more effectively the extension and heterogeneity of the tumor charge and the acquisition of "cytotoxic multidrug" resistance.

A first approach is that of preventing or treating "multidrug-resistant" (MDR) cancers by using substances that inhibit or bring about the reversibility of the MDR resistance possibly associated with the expression of the glycoprotein-P membrane transporter. Such an approach is described in U.S. Pat. No. 5,726,184. Other new approaches are already showing promise. This is the case for the induction of apoptosis, the inhibition of tumor angiogenesis and metastatic processes, not to mention gene therapy or immunotherapy.

The inventors have become interested in a different approach. The desired objective was to render the tumor cell population more sensitive to the reference anticancer treatments in order to achieve a twofold benefit:

1) to increase the cytotoxic activity and thus the efficacy of cytotoxic anticancer drugs, and
2) to reduce the frequency and severity of certain side effects by means of reducing the dosage which might follow the induction of the increase in antitumor efficacy.

It is this strategy that is at the origin of the discovery of compositions capable of inducing a highly significant increase in the cytotoxic activity of tested anticancer drugs. The inventors have become interested in a particular group of novel derivatives of the 3-aryl-4-quinolone family. These compositions have the capacity either of stimulating the recruitment of clonogenic cells in the tumor, making it more sensitive to the conventional treatment with cytotoxic agents, or of inhibiting the proliferation of clonogenic cells, thus contributing toward the regression of the tumor. They have the advantage of having no intrinsic cytotoxicity, unlike, on the one hand, tyrosine kinase inhibitors of the essentially 7-chloro 3-aryl-4-quinolone family, described in WO 98/17662 and claimed in the treatment of benign or malignant tumors, and more specifically for treating psoriasis, neoplasias, in particular epithelial neoplasias, and also for treating leukemias and attacks of the immune system, and, on the other hand, 2-aryl-4-quinolone derivatives described in WO 94/02145 for their intrinsic antitumor properties.

X. Mingxia et al. (Bopuxue 1993; 927–929) have described the synthesis of 4-quinolone derivatives with estrogenic and antiosteoporotic properties. Y. L. Kanghou et al. (Zhogguo Haiyang Yaowu, 1989; 8: 2–9) have synthesized novel 4-quinolone derivatives described as antispasmodic and antiarrhythmic agents. M. Croissey et al. have proposed a synthetic process by thermal cyclization for the preparation of 2- and 4-quinolones (Heterocycle 1997, 45, 683–690), whereas Price et al. compare the infrared spectra of a series of 2- and 4-quinolone derivatives (Aust. J. Chem. 1959; 12: 589–600).

One subject of the present invention is thus the use, in the treatment of cancers with at least one antitumor agent chosen from cytotoxic agents, of a compound with activity on the proliferation of clonogenic cells in tumors, but that has no intrinsic antitumor activity (allowing a therapeutic use), which is chosen from the compounds of formulae:

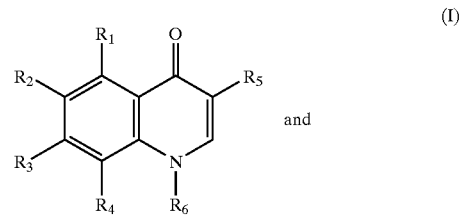

and

-continued

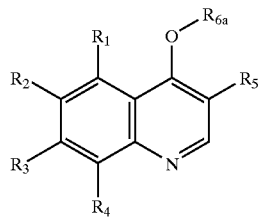

(Ia)

in which:
- $R_1$ is chosen from H, OH, $C_1$–$C_4$ alkyl groups, $C_2$–$C_4$ alkenyl groups, $C_1$–$C_4$ alkoxy groups, phenyl groups or a phenyl group substituted 1 to 3 times with groups chosen from H, OH, a group —$OCOR_7$, $R_7$ being a $C_1$–$C_4$ alkyl group, a group —O—$SO_2$—$R'_7$, $R'_7$ being a $C_1$–$C_4$ alkyl group or a $CF_3$ group, and a group —$NR_{16}R_{17}$, $R_{16}$ and $R_{17}$ being chosen, independently of each other, from hydrogen, $C_1$–$C_4$ alkyl groups, $C_2$–$C_4$ alkenyl groups, phenyl($C_1$–$C_4$)alkyl groups, a phenyl($C_1$–$C_4$)alkyl group substituted 1 to 3 times on the alkyl group with groups chosen from H, OH and $C_1$–$C_4$ alkoxy, or a dimethylamino ($C_1$–$C_4$)alkyl group, or together forming, with the nitrogen atom, a 5- or 6-membered heterocycle optionally comprising one or more hetero atoms chosen from oxygen, nitrogen and sulfur, or a methylpiperazinyl group,
- $R_2$, $R_3$ and $R_4$ are chosen, independently of each other, from H, OH, a $C_1$–$C_4$ alkyl group, a $C_1$–$C_4$ alkoxy group, a group —$OCOR_7$, and a group derived from a saccharide, at least one of the substituents $R_2$, $R_3$ or $R_4$ being other than H, and $R_2$ and $R_3$ together possibly forming a methylenedioxy group,
- $R_5$ is a phenyl group or a phenyl group substituted 1 to 3 times with groups chosen from H, OH, a $C_1$–$C_4$ alkoxy group, a group —OCO—$R_7$, a phenyl($C_1$–$C_4$)alkoxy group, a group —O—$SO_2$—$R'_7$, $R'_7$ being a $C_1$–$C_4$ alkyl group or a $CF_3$ group, a benzylamino group and a group derived from a saccharide,
- $R_6$ is chosen from H, a $C_1$–$C_4$ alkyl group, a $C_2$–$C_4$ alkenyl group, a group —CO—$R_8$ and a group —A—$R_9$,
- $R_{6a}$ is chosen from a $C_1$–$C_4$ alkyl group, a $C_2$–$C_4$ alkenyl group, a group —CO—$R_8$ and a group —A—$R_9$,
- $R_8$ being a $C_1$–$C_4$ alkyl group,
- A being a $C_1$–$C_4$ alkylene group,
- $R_9$ being chosen from 5- or 6-membered heterocyclic groups containing 1 to 4 hetero atoms chosen from oxygen, sulfur and nitrogen, CN, hydroxyl, —$COOR_{10}$ and —$CONR_{11}R_{12}$ groups, a group —$NR_{13}R_{14}$, a group —$COR_{15}$ and a group $OSO_2R_{16}$,
- $R_{10}$, $R_{11}$, $R_{12}$, $R_{13}$, $R_{14}$ and $R_{15}$ being independently chosen from a hydrogen atom, a $C_1$–$C_4$ alkyl group and a phenyl ($C_1$–$C_4$) alkyl group,
- $R_{16}$ being chosen from a phenyl group and a ($C_1$–$C_4$) alkylphenyl group,
- $R_4$ and $R_6$ also possibly forming together a —CO—$CH_2$—$CH_2$— group.

The cytotoxic agents may be used at their usual dose and, in this case, their efficacy is improved, or at lower doses given the increase in their antitumor efficacy, to reduce the severity of the side effects (e.g.: leukopenia, nausea, vomiting, etc.) that are almost always encountered.

The subject of the present invention is also a composition with activity on the proliferation of clonogenic cells in tumors by interfering with the generation of clonogenic cells, either by stimulating the proliferation and recruitment, or by inhibiting the proliferation, and which comprises an effective amount of a compound of formulae:

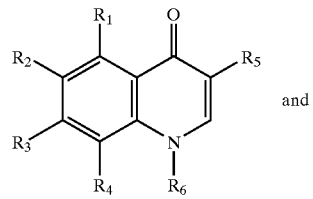

(I)

and

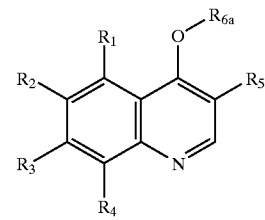

(Ia)

in which:
- $R_1$ is chosen from H, OH, $C_1$–$C_4$ alkyl groups, $C_2$–$C_4$ alkenyl groups, $C_1$–$C_4$ alkoxy groups, phenyl groups or a phenyl group substituted 1 to 3 times with groups chosen from H, OH, a group —$OCOR_7$, $R_7$ being a $C_1$–$C_4$ alkyl group, a group —O—$SO_2$—$R'_7$, $R'_7$ being a $C_1$–$C_4$ alkyl group or a $CF_3$ group, and a group —$NR_{16}R_{17}$, $R_{16}$ and $R_{17}$ being chosen, independently of each other, from hydrogen, $C_1$–$C_4$ alkyl groups, $C_2$–$C_4$ alkenyl groups, phenyl($C_1$–$C_4$)alkyl groups, a phenyl($C_1$–$C_4$)alkyl group substituted 1 to 3 times on the alkyl group with groups chosen from H, OH and $C_1$–$C_4$ alkoxy, or a dimethylamino ($C_1$–$C_4$)alkyl group, or together forming, with the nitrogen atom, a 5- or 6-membered heterocycle optionally comprising one or more hetero atoms chosen from oxygen, nitrogen and sulfur, or a methylpiperazinyl group,
- $R_2$, $R_3$ and $R_4$ are chosen, independently of each other, from H, OH, a $C_1$–$C_4$ alkyl group, a $C_1$–$C_4$ alkoxy group, a group —$OCO$—$R_7$, and a group derived from a saccharide, $R_2$ and $R_3$ together possibly forming a methylenedioxy group,
- $R_5$ is a phenyl group or a phenyl group substituted 1 to 3 times with groups chosen from H, OH, a $C_1$–$C_4$ alkoxy group, a group —$OCOR_7$, a phenyl($C_1$–$C_4$)alkoxy group, a group —O—$SO_2$—$R'_7$, $R'_7$ being a $C_1$–$C_4$ alkyl group or a $CF_3$ group, a benzylamino group and a group derived from a saccharide,
- $R_6$ is chosen from H, a $C_1$–$C_4$ alkyl group, a $C_2$–$C_4$ alkenyl group, a group —CO—$R_8$ and a group —A—$R_9$,
- $R_{6a}$ is chosen from a $C_1$–$C_4$ alkyl group, a $C_2$–$C_4$ alkenyl group, a group —CO—$R_8$ and a group —A—$R_9$,
- $R_8$ being a $C_1$–$C_4$ alkyl group,
- A being a $C_1$–$C_4$ alkylene group,
- $R_9$ being chosen from 5- or 6-membered heterocyclic groups containing 1 to 4 hetero atoms chosen from oxygen, sulfur and nitrogen, CN, hydroxyl, —$COOR_{10}$ and —$CONR_{11}R_{12}$ groups, a group —$NR_{13}R_{14}$, a group —$COR_{15}$ and a group $OSO_2R_{16}$,
- $R_{10}$, $R_{11}$, $R_{12}$, $R_{13}$, $R_{14}$ and $R_{15}$ being independently chosen from a hydrogen atom, a $C_1$–$C_4$ alkyl group and a phenyl ($C_1$–$C_4$) alkyl group, $R_{16}$ being chosen from a phenyl group and a ($C_1$–$C_4$) alkylphenyl group, $R_4$ and $R_6$ also possibly forming together a —CO—$CH_2$—$CH_2$— group.

The subject of the present invention is also novel compounds, namely compounds of formulae:

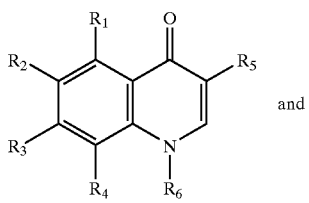

(I)

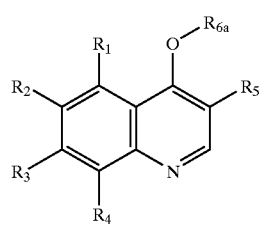

(Ia)

in which:

$R_1$ is chosen from H, OH, $C_1$–$C_4$ alkyl groups, $C_2$–$C_4$ alkenyl groups, $C_1$–$C_4$ alkoxy groups, phenyl groups or a phenyl group substituted 1 to 3 times with groups chosen from H, OH, a group —$OCOR_7$, $R_7$ being a $C_1$–$C_4$ alkyl group, a group —O—$SO_2$—$R'_7$, $R'_7$ being a $C_1$–$C_4$ alkyl group or a $CF_3$ group, and a group —$NR_{16}R_{17}$, $R_{16}$ and $R_{17}$ being chosen, independently of each other, from hydrogen, $C_1$–$C_4$ alkyl groups, $C_2$–$C_4$ alkenyl groups, phenyl($C_1$–$C_4$)alkyl groups, a phenyl($C_1$–$C_4$)alkyl group substituted 1 to 3 times on the alkyl group with groups chosen from H, OH and $C_1$–$C_4$ alkoxy, or a dimethylamino ($C_1$–$C_4$)alkyl group, or together forming, with the nitrogen atom, a 5- or 6-membered heterocycle optionally comprising one or more hetero atoms chosen from oxygen, nitrogen and sulfur, or a methylpiperazinyl group, $R_2$, $R_3$ and $R_4$ are chosen, independently of each other, from H, OH, a $C_1$–$C_4$ alkyl group, a $C_1$–$C_4$ alkoxy group, a group —OCO—$R_7$, and a group derived from a saccharide, $R_2$ and $R_3$ together possibly forming a methylenedioxy group, $R_5$ is a phenyl group or a phenyl group substituted 1 to 3 times with groups chosen from H, OH, a $C_1$–$C_4$ alkoxy group, a group —$OCOR_7$, a phenyl($C_1$–$C_4$)alkoxy group, a group —O—$SO_2$—$R'_7$, $R'_7$ being a $C_1$–$C_4$ alkyl group or a $CF_3$ group, a benzylamino group and a group derived from a saccharide, $R_6$ is chosen from H, a $C_1$–$C_4$ alkyl group, a $C_2$–$C_4$ alkenyl group, a group —CO—$R_8$ and a group —A—$R_9$, $R_{6a}$ is chosen from a $C_1$–$C_4$ alkyl group, a $C_2$–$C_4$ alkenyl group, a group —CO—$R_8$ and a group —A—$R_9$, $R_8$ being a $C_1$–$C_4$ alkyl group, A being a $C_1$–$C_4$ alkylene group, $R_9$ being chosen from 5- or 6-membered heterocyclic groups containing 1 to 4 hetero atoms chosen from oxygen, sulfur and nitrogen, CN, hydroxyl, —$COOR_{10}$ and —$CONR_{11}R_{12}$ groups, a group —$NR_{13}R_{14}$, a group —$COR_{15}$ and a group $OSO_2R_{16}$, $R_{10}$, $R_{11}$, $R_{12}$, $R_{13}$, $R_{14}$ and $R_{15}$ being independently chosen from a hydrogen atom, a $C_1$–$C_4$ alkyl group and a phenyl ($C_1$–$C_4$) alkyl group, $R_{16}$ being chosen from a phenyl group and a ($C_1$–$C_4$) alkylphenyl group, $R_4$ and $R_6$ also possibly forming together a —CO—$CH_2$—$CH_2$— group, with the exclusion of the compounds in which:

$R_1$, $R_2$, $R_4$, $R_6$=H, $R_3$=OH and $R_5$ is a phenyl, 4-methoxyphenyl, 2,4-dimethoxyphenyl or 2,5-dimethoxyphenyl group, $R_1$=OH or $OCH_3$, $R_2$=H, $R_3$=$OCH_3$, $R_4$=H, $R_5$=4-methoxyphenyl and $R_6$=H, $R_1$=$OCH_3$, $R_2$=H, $R_3$=$OCH_3$, $R_4$=H, $R_5$=4-methoxyphenyl and $R_6$=$CH_3$, $R_1$=OH, $R_2$=H, $R_3$=OH, $R_4$=H, $R_5$=4-hydroxyphenyl and $R_6$=$CH_3$, $R_1$=H, $R_2$=H, $R_3$=$OCH_3$, $R_4$=H, $R_5$=phenyl and $R_6$=H, $R_1$=H, $R_2$=H, $R_3$=$OCH_3$, $R_4$=H, $R_5$=phenyl and $R_6$=$CH_3$, $R_1$=H, $R_2$=H, $R_3$=OH, $R_4$=$OCH_3$, $R_5$=phenyl and $R_6$=H, $R_1$, $R_2$, $R_3$, $R_4$, $R_6$=H and $R_5$=phenyl or 4-methoxyphenyl, $R_1$, $R_2$, $R_3$, $R_4$, =H, $R_5$=phenyl or 4-methoxyphenyl and $R_6$=$COCH_3$, $R_1$, $R_2$, $R_3$, $R_4$, =H, $R_5$=phenyl and $R_6$=$CH_3$, $R_1$, $R_2$, $R_3$, $R_4$, $R_6$=H and $R_5$=4-methoxyphenyl, 2-methoxyphenyl or 4-methylphenyl.

One particular group of compounds is that consisting of the compounds of formula I or Ia in which:

$R_1$ is chosen from H, OH, $C_1$–$C_4$ alkyl groups, $C_2$–$C_4$ alkenyl groups, $C_1$–$C_4$ alkoxy groups, phenyl groups or a phenyl group substituted 1 to 3 times with groups chosen from H, OH, a group —$OCOR_7$, $R_7$ being a $C_1$–$C_4$ alkyl group, a group —O—$SO_2$—$R'_7$, $R'_7$ being a $C_1$–$C_4$ alkyl group or a $CF_3$ group, and a benzylamino group, $R_2$, $R_3$ and $R_4$ are chosen, independently of each other, from H, OH, a $C_1$–$C_4$ alkyl group, a $C_1$–$C_4$ alkoxy group, a group —OCO—$R_7$, and a group derived from a saccharide, $R_2$ and $R_3$ together possibly forming a methylenedioxy group, $R_5$ is a phenyl group or a phenyl group substituted 1 to 3 times with groups chosen from H, OH, a $C_1$–$C_4$ alkoxy group, a group —$OCOR_7$, a phenyl($C_1$–$C_4$)alkoxy group, a group —O—$SO_2$-$R'_7$, $R'_7$ being a $C_1$–$C_4$ alkyl group or a $CF_3$ group, a benzylamino group and a group derived from a saccharide, $R_6$ is chosen from H, a $C_1$–$C_4$ alkyl group, a group —CO—$R_8$ and a group —A—$R_9$, $R_{6a}$ is chosen from a $C_1$–$C_4$ alkyl group, a group —CO—$R_8$ and a group —A—$R_9$, $R_8$ being a $C_1$–$C_4$ alkyl group, A being a $C_1$–$C_4$ alkylene group, $R_9$ being chosen from 5- or 6-membered heterocyclic groups containing 1 to 4 hetero atoms chosen from oxygen, sulfur and nitrogen, a CN group, —$COOR_{10}$ and —$CONR_{11}R_{12}$ groups, a group —$NR_{13}R_{14}$ and a group —$COR_{15}$, $R_{10}$, $R_{11}$, $R_{12}$, $R_{13}$, $R_{14}$ and $R_{15}$ being independently chosen from a hydrogen atom, a $C_1$–$C_4$ alkyl group and a phenyl($C_1$–$C_4$) alkyl group, $R_4$ and $R_6$ also possibly forming together a —CO—$CH_2$—$CH_2$— group.

Another particular group of compounds is that consisting of the compounds of formula I or Ia in which:

$R_5$ is a phenyl, 4-methoxyphenyl, 2,4-dimethoxyphenyl or 2,5-dimethoxyphenyl group.

Another particular group of compounds is that consisting of the compounds of formula I or Ia in which:

$R_1$ is chosen from $C_1$–$C_4$ alkyl groups, $C_2$–$C_4$ alkenyl groups, phenyl groups or a phenyl group substituted 1 to 3 times with groups chosen from H, OH, a group —$OCOR_7$, $R_7$ being a $C_1$–$C_4$ alkyl group, a group —O—$SO_2$—$R'_7$, $R'_7$ being a $C_1$–$C_4$ alkyl group or a $CF_3$ group, and a group —$NR_{16}R_{17}$, $R_{16}$ and $R_{17}$ being chosen, independently of each other, from hydrogen, $C_1$–$C_4$ alkyl groups, $C_2$–$C_4$ alkenyl groups, phenyl ($C_1$–$C_4$)alkyl groups, a phenyl($C_1$–$C_4$)alkyl group substituted 1 to 3 times on the alkyl group with groups chosen from H, OH and $C_1$–$C_4$ alkoxy, or a dimethylamino ($C_1$–$C_4$)alkyl group, or together forming, with the nitrogen atom, a 5- or 6-membered heterocycle optionally comprising one or more hetero atoms chosen from oxygen, nitrogen and sulfur, or a methylpiperazinyl group, and $R_2$, $R_3$ and $R_4$ are chosen from a hydrogen atom and a $C_1$–$C_4$ alkoxy group.

Another particular group of compounds is that consisting of the compounds of formula I or Ia in which:

$R_1$, $R_2$, $R_3$ and $R_4$ are chosen from a hydrogen atom and a $C_1$–$C_4$ alkoxy group.

In the preceding definitions, the expression "group derived from a saccharide" denotes a group which forms a heteroside with the rest of the molecule. On hydrolysis, these heterosides are capable of giving a compound of formula I or Ia with a hydroxyl group and a saccharide. The saccharides may especially be monosaccharides (glucose or rhamnose) or disaccharides (for example rutinose).

In the chemotherapeutic treatment of cancers with cytotoxic agents, the compounds of formulae (I) and (Ia) may be administered at the start of the chemotherapeutic treatments either once or over several days at the start of these treatments (for example from 5 to 7 days) and, depending on the chemotherapy protocol, at the start of each treatment cycle (for example for 2 to 5 days) during each cure.

The compounds of formulae (I) and (Ia) are advantageously administered by perfusion (generally for 1 to 3 hours) at doses of from 1 to 50 mg/kg/day or 40 to 2000 mg/m²/day.

In order to obtain a maximum effect on the production (inhibition or stimulation) of clonogenic cells, the compounds of formulae (I) and (Ia) must be administered such that the tissue concentrations obtained are as high as can possibly be envisaged.

For the treatment protocols in the acute phases of cures, the intravenous route is preferred, using:

ready-to-use perfusion solutions (bags, bottles, etc.) intended to be administered without modification by intravenous perfusion using a perfusion line and at the recommended flow rate;

lyophilizates to be dissolved for intravenous perfusion using pharmaceutical solutions known to those skilled in the art;

for maintenance treatments, it is also possible to envisage the oral route when the chemotherapy treatment favors the oral administration of cytostatic agents. To this end, lyophilized tablets (for oral or perlingual absorption), immediate-release or delayed-release tablets, oral solutions, suspensions, granules, gel capsules, etc. may be used.

The cytotoxic agents may be chosen from:
i) intercalating agents, in particular doxorubicin (Adriamycin), daunorubicin, epirubicin, idarubicin, zorubicin, aclarubicin, pirarubicin, acridine, mitoxanthrone, actinomycin D, eptilinium acetate;
ii) alkylating agents chosen from platinum derivatives (cisplatin, carboplatin, oxaliplatin);
iii) a compound chosen from the other groups of alkylating agents:
  cyclophosphamide, ifosfamide, chlormetrine, melphalan, chlorambucil, estramustine,
  busulfan, mitomycin C,
  nitrosoureas: BCNU (carmustine), CCNU (lomustine), fotemustine, streptozotocin,
  triazines or derivatives: procarbazine, dacarbazine, pipobroman,
  ethyleneimines: altretamine, triethylene-thio-phosphoramide,
iv) a compound chosen from the other groups of anti-metabolic agents:
  antifolic agents: methotrexate, raltitrexed,
  antipyrimidine agents: 5-fluorouracil (5-FU), cytarabine (Ara-C),
  hydroxyurea
  antipurine agents: purinethol, thioguanine, pentostatin, cladribine,
  cytotoxic nucleoside synthesis inducers: gemcitabine,
v) a compound chosen from the other groups of tubulin-affinity agents,
  vinca alkaloids which disrupt the mitotic spindle: vincristine, vinblastine, vindesine, navelbine,
  agents which block the depolymerization of the mitotic spindle: paclitaxel, docetaxel,
  agents which induce DNA cleavage by inhibition of topoisomerase II: etoposide, teniposide,
  topoisomerase I inhibitors which induce DNA cleavage: topotecan, irinotecan,
vi) a DNA splitting or fragmenting agent, such as bleomycin,
vii) one of the following compounds: plicamycin, L-asparaginase, mitoguazone, dacarbazine,
viii) an anticancer progestative steroid; medroxyprogesterone, megestrol,
ix) an anticancer estrogen steroid: diethylstilbestrol; tetrasodium fosfestrol,
x) an antiestrogen agent: tamoxifen, droloxifen, raloxifen, aminoglutethimide,
xi) a steroidal antiandrogenic agent (eg cyproterone) or a non-steroidal antiandrogenic agent (flutamide, nilutamide).

In particular, the compounds of formulae (I) and (Ia) may be combined with all the major treatments with cytotoxic agents used in solid tumor polychemo-therapies, such as:
doxorubicin
alkylating agents: oxazophorines (cyclophosphamide, ifosfamide, chlorambucil, melphalan)
nitrosoureas
mitomycin C
antimetabolites such as methotrexate, 5-FU, Ara-C, capecitabine
agents which interfere with tubulin: vinca alkaloids (vincristine, vinblastine, vindesine, navelbine), taxoids (paclitaxel, docetaxel), epipo-dophyllotoxin derivatives (etoposide, teniposide)
bleomycin
topoisomerase I inhibitors: topotecan, irinotecan.

Similarly, the compounds of formulae (I) and (Ia) may be combined with the treatments with the major cytotoxic agents used in oncohematology for the treatment of blood cancers:

Hodgkin's disease: cyclophosphamide, mechlorethamine, chlorambucil, melphalan, ifosfamide, etoposide, doxorubicin, daunorubicin;

acute leukemias: methotrexate, 6-mercaptopurine, cytarabine, vinblastine, vincristine, doxorubicin, daunorubicin, L-asparaginase;

non-Hodgkin's malignant lymphomas: mechlorethamine, chlorambucil, cyclophosphamide, melphalan, ifosfamide, methotrexate, cytarabine, vinblastine, vincristine, etoposide, doxorubicin, daunorubicin, carmustine, lomustine, cisplatin;

chronic lymphoid leukemias: mechlorethamine, chlorambucil, cyclophosphamide, melphalan, ifosfamide.

In general, the compounds of formulae (I) and (Ia) may be prepared according to the following reaction schemes:

SCHEME I

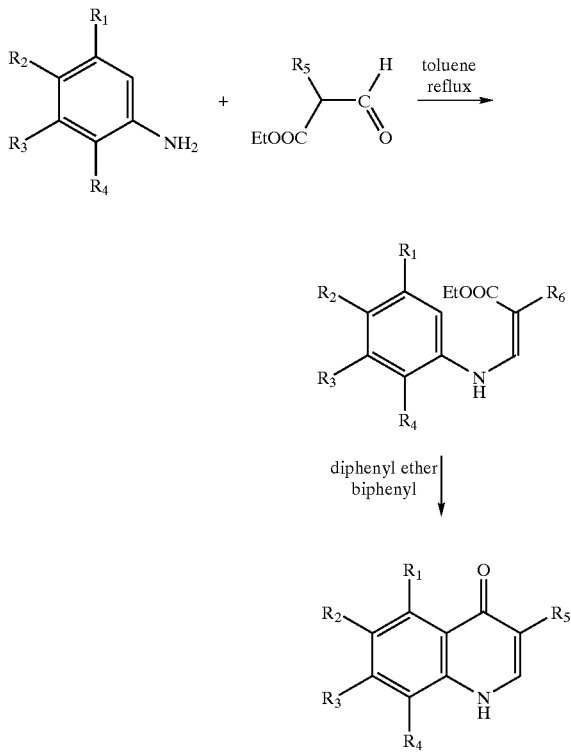

SCHEME II

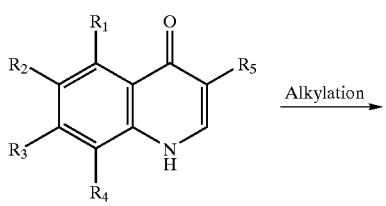

-continued

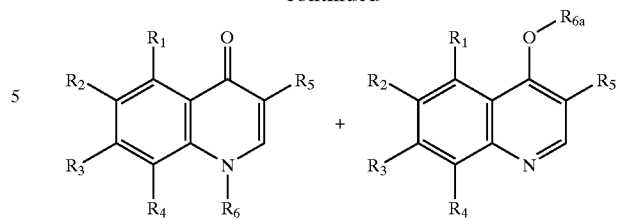

A reagent of the type $XR_6$ in which X=I, Br or Cl may be used as alkylating reagent.

In addition, it is possible to convert some or all of the alkoxy groups into hydroxyl groups according to known methods. Similarly, the hydroxyl groups may be converted into ester or sulfonate according to the known methods, the sulfonates in turn possibly being converted into alkenyl, phenyl or substituted phenyl groups and groups —$NR_{16}R_{17}$ according to the known methods.

Similarly, it is possible to convert, by known methods, a group —A—$COOR_{10}$, in which $R_{10}$ is an alkyl or phenylalkyl group, into a group —A—COOH and to convert a group —A—COOH into a group —A—$CONR_{11}R_{12}$.

The compounds in which $R_4$ and $R_6$ form a —CO—$CH_2$—$CH_2$— group may be obtained by cyclization of a compound in which $R_4$=H and $R_6$=—$CH_2$—$CH_2$—COOH.

EXAMPLE 1

3-Phenyl-1,4-dihydro-4-quinolinone (compound 2)
CRL 8326 a) Ethyl α-formylphenylacetate

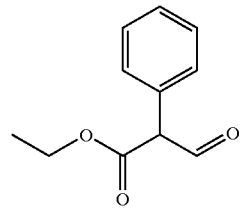

4.50 g (0.11 mol) of 60% sodium hydride, washed beforehand with petroleum ether, are suspended in 35 ml of ether under a nitrogen atmosphere. The flask is placed in an ice bath. In a first stage, 7.60 ml (0.09 mol) of ethyl formate are added to the initial mixture, then 10 ml of ethyl phenylacetate (0.06 mol) are added very slowly (monitor the evolution of hydrogen to avoid a runaway reaction). Once the addition is complete, the solution is stirred at 35° C. for 3–4 hours. The mixture becomes white and pasty. During the stirring, it is essential to ensure that a runaway reaction does not occur (if necessary, add ether). The reaction mixture is filtered and the white solid obtained is washed with ether. This solid is dissolved in water and the resulting solution is then acidified with 10% HCl. The final compound is extracted with ethyl acetate (twice). The organic phase is dried over $MgSO_4$ and then evaporated under reduced pressure to give 10.00 g (71%) of ethyl ∀-formylphenylacetate in the form of a colorless oil.

b) Ethyl (Z)-3-anilino-2-phenyl-2-propenoate (Compound 1)

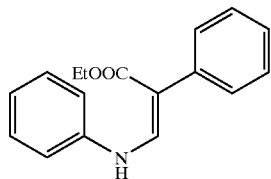

A solution of aniline (1.40 ml, 15.36 mmol) and ethyl ∀-formylphenylacetate (3.25 g, 1.1 eq) in toluene (20 ml) is refluxed for 18 hours. After cooling, the mixture is diluted with toluene (10 ml) and then acidified with 10% HCl. After extraction, the organic phase obtained is dried over $MgSO_4$ and then evaporated under reduced pressure. The residue is purified by chromatography on a column of silica (eluent: 7/3 PE/EtOAc) to give 2.46 g (60%) of compound 1 (Z isomer) in the form of a yellow oil.

IR (film): <3296, 1664, 1622, 1599, 1584 $cm^{-1}$ $^1$H NMR (250 MHz, $CDCl_3$): δ1.34 (t, 3H, J=7.2 Hz, $CH_3$), 4.29 (q, 2H, J=7.2 Hz, $CH_2$), 7.01–7.07 (m, 3H, $H_{Ar}$), 7.26–7.40 (m, 7H, $H_{Ar}$), 7.44 (d, 1H, J=12.8 Hz, =CH), 10.37 (broad d, 1H, J=12.8 Hz, NH).

$^{13}$C NMR (62.90 MHz, $CDCl_3$): δ14.4, 59.8, 102.9, 115.5 (2), 122.6, 126.0, 127.9 (2), 129.4 (2), 129.6 (2), 137.9, 140.7, 143.6, 169.2.

MS (ion spray): m/z 268 $(M+H)^+$

Anal. calculated for $C_{17}H_{17}NO_2$: C, 76.38; H, 6.41; N, 5.24. Found: C, 76.15; H, 6.30; N, 5.29 c) 3-Phenyl-1,4-dihydro-4-quinolinone (Compound 2)-CRL 8326

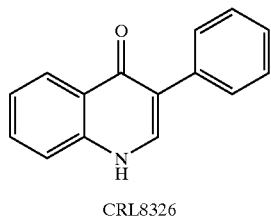

CRL8326

Compound 1 (1.10 g, 4.11 mmol) is added portionwise and rapidly with stirring, to a solution of biphenyl (1.70 g) and diphenyl ether (13.10 g) heated to 250° C. After 10 minutes, the heating is stopped. During the cooling, the quinolone 2 precipitates out in the reaction medium. This product is collected by filtration and then rinsed with petroleum ether. After drying, 859 mg (94%) of compound 2 are obtained in the form of white crystals.

m.p. 253–254° C. (EtOH)

IR (KBr): <1628, 1615, 1583, 1562, 1515 $cm^{-1}$ $^1$H NMR (250 MHz, DMSO-$d_6$): δ7.25–7.42 (m, 4H, $H_{Ar}$), 7.57–7.74 (m, 4H, $H_{Ar}$), 8.15 (s, 1H, =CH), 8.20 (d, 1H, J=7.5 Hz, $H_{Ar}$), 12.00 (broad s, 1H, NH)

$^{13}$C NMR (62.90 MHz, DMSO-$d_6$): δ118.2, 119.7, 123.3, 125.4, 125.6, 125.8, 127.8 (2), 128.4 (2), 131.5, 136.2, 138.1, 139.3, 174.7.

MS (ion spray): m/z 222 $(M+H)^+$

Anal. calculated for $C_{15}H_{11}NO$: C, 81.43; H, 5.01; N, 6.33. Found: C, 81.65; H, 4.80; N, 6.10.

EXAMPLE 2

8-Methoxy-3-phenyl-1,4-dihydro-4-quinolinone (compound 4)-CRL 8328 a) Ethyl (Z)-3-(2-methoxyanilino)-2-phenyl-2-propenoate (compound 3)

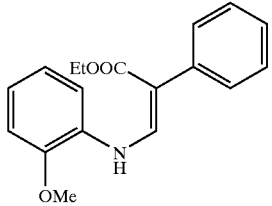

A solution of 2-methoxyaniline (1.20 ml, 10.64 mmol) and ethyl ∀-formylphenylacetate (2.25 g, 1.1 eq) in toluene (20 ml) is refluxed for 18 hours. After cooling, the reaction mixture is diluted with toluene (10 ml) and then acidified with 10% HCl. After extraction, the organic phase obtained is dried over $MgSO_4$ and then evaporated under reduced pressure. The residue is purified by chromatography on a column of silica (eluent: $CH_2Cl_2$) to give 2.15 g (68%) of compound 3 (Z isomer) in the form of a yellow oil.

IR (KBr): <3295, 1667, 1617, 1589, 1509 $cm^{-1}$ $^1$H NMR (250 MHz, $CDCl_3$): δ1.28 (t, 3H, J=7.2 Hz, $CH_3$), 3.87 (s, 3H, $OCH_3$), 4.26 (q, 2H, J=7.2 Hz, $CH_2$), 6.81–7.00 (m, 3H, $H_{Ar}$), 7.16–7.44 (m, 6H, $H_{Ar}$), 7.42 (d, 1H, J=12.5 Hz, =CH); 10.49 (broad d, 1H, J=12.5 Hz, NH).

$^{13}$C NMR (62.90 MHz, $CDCl_3$): δ14.2, 55.6, 59.6, 103.1, 110.6, 112.1, 121.0, 122.0, 125.7, 127.7 (2), 129.3 (2), 130.1, 138.1, 142.2, 147.8, 168.7.

MD (ion spray): m/z 298 $(M+H)^+$

Anal. calculated for $C_{18}H_{19}NO_3$: C, 72.71; H, 6.44; N, 4.71. Found: C, 72.60; H, 6.65; N, 4.70 b) 8-Methoxy-3-phenyl-1,4-dihydro-4-quinolinone (compound 4)-CRL 8328

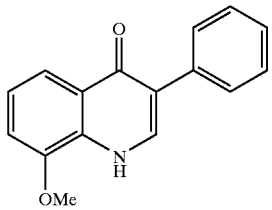

CRL8328

Compound 3 (1.10 g, 3.70 mmol) is added portionwise and rapidly, with stirring, to a solution of biphenyl (1.52 g) and diphenyl ether (11.60 g) at 250° C. After 10 minutes, the heating is stopped. During the cooling, the final product 4 precipitates out in the reaction medium. This product is collected by filtration and then rinsed with petroleum ether. After drying, 762 mg (82%) of compound 4 are obtained in the form of white crystals.

m.p.: 148–149° C. (EtOH)

IR (KBr): <1624, 1618, 1577, 1553, 1527 $cm^{-1}$ $^1$H NMR (250 MHz, DMSO-$d_6$): δ4.00 (s, 3H, $OCH_3$), 7.25–7.41 (m, 5H, $H_{Ar}$), 7.67 (broad d, 2H, J=7.8 Hz, $H_{Ar}$), 7.75 (dd, 1H, J=3.0, 7.5 Hz, $H_{Ar}$), 7.90 (s, 1H, =CH), 11.64 (broad s, 1H, NH).

$^{13}$C NMR (62.90 MHz, DMSO-$d_6$): δ56.7, 111.2, 117.3, 120.5, 123.3, 126.8, 127.3, 128.4 (2), 128.8 (2), 131.1, 136.8, 138.4, 149.3, 174.8.

MS (ion spray): m/z 252 (M+H)$^+$

Anal. calculated for $C_{16}H_{13}NO_2$: C, 76.48; H, 5.21; N, 5.57. Found: C, 76.18; H, 5.00; N, 5.60.

EXAMPLE 3

6-Methoxy-3-phenyl-1,4-dihydro-4-quinolinone (compound 6)-CRL 8488 a) Ethyl (Z)-3-(4-methoxyanilino)-2-phenyl-2-propenoate

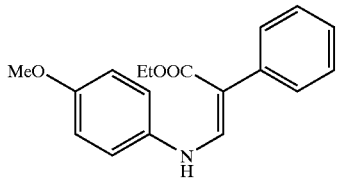

A solution of 4-methoxyaniline (1.76 g, 14.29 mol) and ethyl ∀-formylphenylacetate (3.02 g, 1.1 eq) in toluene (20 ml) is refluxed for 18 hours. After cooling, the reaction mixture is diluted with toluene (15 ml) and then acidified with 10% HCl. After extraction, the organic phase obtained is dried over MgSO$_4$ and then evaporated under reduced pressure. The residue is taken up in methanol, from which compound 5 (Z isomer) crystallizes (2.68 g, 63%).

m.p.: 64–65° C. (MeOH)

IR (KBr): <3290, 1661, 1584, 1517 cm$^{-1}$ $^1$H NMR (250 MHz, CDCl$_3$): δ1.29 (t, 3H, J=7.2 Hz, CH$_3$), 3.78 (s, 3H, OCH$_3$), 4.26 (q; 2H, J=7.2 Hz, CH$_2$), 6.85 (d, 2H, J=9.0 Hz, H$_{Ar}$), 6.96 (d, 2H, J=9.0 Hz, H$_{Ar}$), 7.24–7.41 (m, 6H, H$_{Ar}$+=CH), 10.27 (broad d, 1H, J=12.5 Hz, NH).

$^{13}$C NMR (62.90 MHz, CDCl$_3$): δ14.4, 55.6, 59.7, 101.7, 114.9 (2), 117.2 (2), 125.8, 127.9 (2), 129.4 (2), 134.4, 138.1, 144.8, 155.6, 169.4.

MS (ion spray): m/z 298 (M+H)$^+$

Anal. calculated for $C_{18}H_{19}NO_3$: C, 72.71; H, 6.44; N, 4.71. Found: C, 73.00; H, 6.42; N, 4.87.

b) 6-Methoxy-3-phenyl-1,4-dihydro-4-quinolinone (compound 6)-CRL 8488

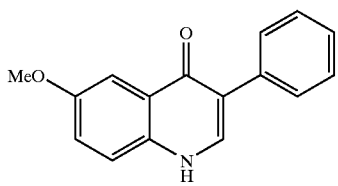

Compound 5 (600 mg, 2.02 mmol) is added portionwise and rapidly, with stirring, to a solution of biphenyl (885 mg) and diphenyl ether (6.5 g) heated to 250° C. After 10 minutes, the heating is stopped. During the cooling, the quinolone 6 precipitates out in the reaction medium. This product is collected by filtration and then rinsed with petroleum ether. After drying, 411 mg (81%) of compound 6 are obtained in the form of white crystals.

m.p.: 355–356° C. (washing with EtOH)

IR (KBr): <3214, 1624, 1600, 1591, 1549, 1512 cm$^{-1}$ $^1$H NMR (250 MHz, DMSO-d$_6$): δ4.00 (s, 3H, OCH$_3$), 7.26–7.41 (m, 4H, H$_{Ar}$), 7.54–7.61 (m, 2H, H$_{Ar}$), 7.73 (d, 2H, J=8.0 Hz, H$_{Ar}$), 8.11 (s, 1H, =CH), 12.00 (broad s, 1H, NH).

MS (ion spray): m/z 252 (M+H)$^+$

Anal. calculated for $C_{16}H_{13}NO_2$: C, 76.48; H, 5.21; N, 5.57. Found: C, 76.29; H, 5.37; N, 5.67.

EXAMPLE 4

6-Methoxy-1-methyl-3-phenyl-1,4-dihydro-4-quinolinone (compound 7)-CRL 8379

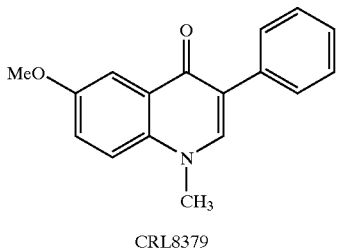

CRL8379

200 mg (0.79 mmol) of compound 6 are dissolved in 10 ml of anhydrous N,N-dimethylformamide (DMF) under a nitrogen atmosphere. 823 mg of potassium carbonate (7.5 eq) and then 0.15 ml of methyl iodide (3 eq) are successively added to this suspension. The reaction is stirred at room temperature for 18 hours. The solvents are evaporated off. The residue obtained is taken up in CH$_2$Cl$_2$ and washed twice with water. The organic phase obtained is dried over MgSO$_4$ and then evaporated under reduced pressure. The crude solid is recrystallized from ethanol to give 200 mg (95%) of derivative 7.

m.p.: 156–157° C. (washing with EtOH)

IR (KBr); <1627, 1616, 1576, 1560, 1507 cm$^{-1}$ $^1$H NMR (250 MHz, DMSO-d$_6$): δ3.87 (s, 3H, NCH$_3$), 3.91 (s, 3H, OCH$_3$), 7.27–7.42 (m, 4H, H$_{Ar}$), 7.68 (d, 1H, J=9.0 Hz, H$_{Ar}$), 7.73–7.77 (m, 3H, H$_{Ar}$), 8.25 (s, 1H, =CH)

$^{13}$C NMR (62.90 MHz, DMSO-d$_6$): δ40.2, 55.4, 105.9, 118.5, 121.7, 125.4, 126.3, 127.8 (2), 128.3 (2), 134.5, 136.1, 143.0, 155.8, 173.4.

MS (ion spray): m/z 266 (M+H)$^+$

Anal. calculated for $C_{17}H_{15}NO_2$: C, 76.96; H, 5.70; N, 5.28. Found: C, 77.33; H, 5.79; N, 5.09.

EXAMPLE 5

7-Methoxy-3-phenyl-1,4-dihydro-4-quinolinone (compound 9)-CRL 8359 a) Ethyl (Z)-3-(3-methoxyanilino)-2-phenyl-2-propenoate (compound 8)

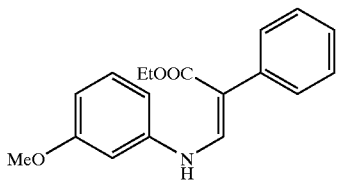

A solution of 3-methoxyaniline (1.55 ml, 13.79 mol) and ethyl ∀-formylphenylacetate (2.92 g, 1.1 eq) in toluene (20 ml) is refluxed for 18 hours. After cooling, the reaction mixture is diluted with toluene (15 ml) and then acidified with 10% HCl. After extraction, the organic phase obtained is dried over MgSO$_4$ and then evaporated under reduced pressure. The residue is purified by chromatography on a column of silica (eluent: CH$_2$Cl$_2$) to give 2.30 g (56%) of compound 8 (Z isomer) in the form of a yellow solid which crystallizes from methanol.

m.p.: 49–50° C. (MeOH)

IR (KBr): <3305, 1665, 1588 cm$^{-1}$

¹H NMR (250 MHz, CDCl₃): δ1.29 (t, 3H, J=7.2 Hz, CH₃), 3.79 (s, 3H, OCH₃), 4.25 (q, 2H, J=7.2 Hz, CH₂) 6.53–6.61 (m, 3H, H$_{Ar}$), 6.16–7.35 (m, 6H, H$_{Ar}$), 7.39 (d, 1H, J=12.5 Hz, =CH), 10.32 (broad d, 1H, J=12.5 Hz, NH).

¹³C NMR (62.90 MHz, CDCl₃): δ14.4, 55.2, 59.9, 101.6, 103.0, 108.0 (2), 126.0, 127.9 (2), 129.5 (2), 130.5, 137.9, 142.0, 143.5, 160.8, 169.2.

MS (ion spray): m/z 298 (M+H)⁺

Anal. calculated for C₁₈H₁₉NO₃: C, 72.71; H, 6.44; N, 4.71. Found: C, 72.56; H, 6.61; N, 4.54.

b) 7-Methoxy-3-phenyl-1,4-dihydro-4-quinolinone (compound 9)-CRL 8359

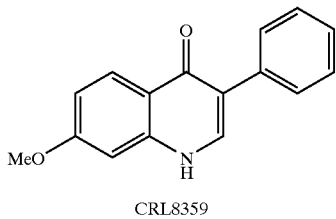

CRL8359

Compound 8 (600 mg, 2.02 mmol) is added portionwise and rapidly, with stirring, to a solution of biphenyl (885 mg) and diphenyl ether (6.50 g) heated to 250° C. After 10 minutes, the heating is stopped. During the cooling, the crude quinolone precipitates out in the reaction medium. This product is collected by filtration and then rinsed with petroleum ether. The product is then taken up in hot ethanol. After cooling, the insoluble solid is filtered off to give 477 mg (94%) of compound 9 in the form of white crystals.

m.p.: 297–298° C. (washing with EtOH)

IR (KBr): <3225, 1634, 1616, 1591, 1560, 1519 cm⁻¹

¹H NMR (250 MHz, DMSO-d₆): δ3.86 (s, 3H, OCH₃), 6.95 (dd, 1H, J=2.5, 8.8 Hz, H$_{Ar}$), 6.97 (d, 1H, J=2.5 Hz, H$_{Ar}$), 7.23–7.40 (m, 3H, H$_{Ar}$), 7.70 (d, 2H, J=9.0 Hz, H$_{Ar}$), 8.07 (s, 1H, =CH), 8.10 (d, 1H, J=8.8 Hz, H$_{Ar}$), 11.81 (broad s, 1H, NH).

¹³C NMR (62.90 MHz, DMSO-d₆): δ55.9, 99.4, 113.9, 120.1, 120.7, 126.8, 128.0, 128.3 (2), 128.9 (2), 136.7, 138.3, 141.5, 162.3, 174.8.

MS (ion spray): m/z 252 (M+H)⁺

Anal. calculated for C₁₆H₁₃NO₂: C, 76.48; H, 5.21; N, 5.57. Found: C, 76.80; H, 5.39; N, 5.66.

EXAMPLE 6

5,8-Dimethoxy-1-methyl-3-phenyl-1,4-dihydro-4-quinolinone (compound 11)-CRL8353 a) Ethyl (Z)-3-(2,5-dimethoxyanilino)-2-phenyl-2-propenoate (compound 10)

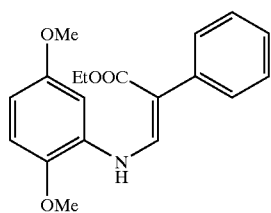

A solution of 2,5-dimethoxyaniline (1.76 g, 11.49 mmol) and ethyl ∀-formylphenylacetate (2.43 g, 1.1 eq) in toluene (20 ml) is refluxed for 18 hours. After cooling, the reaction mixture is diluted with toluene (10 ml) and then acidified with 10% HCl. After extraction, the organic phase obtained is dried over MgSO₄ and then evaporated under reduced pressure. The isolated residue is crystallized from methanol and then filtered through a sinter funnel to give 2.71 g (72%) of compound 10.

m.p.: 93–94° C. (MeOH)

IR (KBr): <3262, 1672, 1605, 1590, 1514 cm⁻¹

¹H NMR (250 MHz, CDCl₃): δ1.32 (t, 3H, J=7.2 Hz, CH₃), 3.76 (s, 3H, OCH₃), 3.91 (s, 3H, OCH₃), 4.30 (q, 2H, J=7.2 Hz, CH₂), 6.47 (dd, 1H, J=2.8, 8.9 Hz, H$_{Ar}$) 6.65 (d, 1H, J=2.8 Hz, H$_{Ar}$), 6.81 (d, 1H, J=8.9 Hz, H$_{Ar}$), 7.20–7.45 (m, 6H, H$_{Ar}$+=CH), 10.45 (broad d, 1H, J=12.5 Hz, NH).

¹³C NMR (62.90 MHz, CDCl₃): δ14.4, 55.7, 56.3, 59.9, 99.8, 103.7, 105.4, 111.6, 126.0, 127.9 (2), 129.5 (2), 131.1, 138.1, 142.0, 142.5, 154.3, 168.8.

MS (ion spray): m/z 328 (M+H)⁺

Anal. calculated for C₁₉H₂₁NO₄: C, 69.71; H, 6.47; N, 4.28. Found: C, 70.02; H, 6.52; N, 4.18.

b) 5,8-Dimethoxy-3-phenyl-1,4-dihydro-4-quinolinone (compound 11) CRL 8353

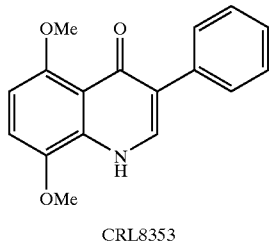

CRL8353

Compound 10 (1.20 g, 3.66 mmol) is added rapidly, with stirring, to a solution of biphenyl (1.52 g) and diphenyl ether (11.60 g) heated to 250° C. After 10 minutes, the heating is stopped. During the cooling, the final product 11 precipitates out in the reaction medium. The crude product is collected by filtration and then rinsed with petroleum ether. This product is taken up in ethanol. The suspension is refluxed with stirring. After cooling and filtration, 753 mg (73%) of compound 11 are obtained in the form of white crystals.

m.p.: 231–232° C. (washing with EtOH)

IR (KBr): <1617, 1576, 1558, 1524 cm⁻¹

¹H NMR (250 MHz, DMSO-d₆): δ3.75 (s, 3H, OCH₃), 3.93 (s, 3H, OCH₃), 6.67 (d, 1H, J=8.8 Hz, H$_{Ar}$), 7.14 (d, 1H, J=8.8 Hz, H$_{Ar}$), 7.23–7.39 (m, 3H, H$_{Ar}$), 7.58–7.61 (m, 2H, H$_{Ar}$), 7.74 (s, 1H, =CH), 11.20 (broad s, 1H, NH).

¹³C NMR (62.90 MHz, DMSO-d₆): δ56.3, 56.4, 104.0, 111.4, 117.1, 122.3, 126.4, 127.8 (2), 128.6 (2), 132.2, 135.7, 136.3, 141.8, 153.2, 174.6.

MS (ion spray): m/z 282 (M+H)⁺

Anal. calculated for C₁₇H₁₅NO₃: C, 72.58; H, 5.37; N, 4.98. Found: C, 72.83; H, 5.26; N, 5.09.

EXAMPLE 7

5,8-Dimethoxy-1-methyl-3-phenyl-1,4-dihydro-4-quinolinone (compound 12)-CRL 8383

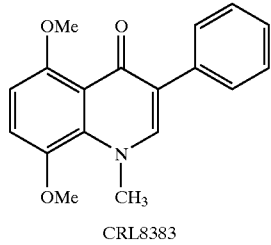

CRL8383

400 mg (1.42 mmol) of compound 11 are dissolved in 15 ml of anhydrous N,N-dimethylformamide (DMF) under a nitrogen atmosphere. 1.47 g of potassium carbonate (7.5 eq) and then 0.26 ml of methyl iodide (3 eq) are successively added to this suspension. The reaction is stirred at room temperature for 6 hours. The solvents are evaporated off. The residue obtained is taken up in $CH_2Cl_2$ and washed twice with water. The organic phase obtained is dried over $MgSO_4$ and then evaporated under reduced pressure. The residue is purified on a column of silica gel (eluent: 7/3 $CH_2Cl_2$/EtOAc) to give 293 mg (70%) of derivative 12.

m.p.: 125–126° C. (washing with EtOAc)

IR (KBr): <1631, 1592, 1569 cm$^{-1}$ $^1$H NMR (250 MHz, CDCl$_3$): δ3.86 (s, 3H, NCH$_3$), 3.90 (s, 3H, OCH$_3$), 4.03 (s, 3H, OCH$_3$), 6.71 (d, 1H, J=9.0 Hz, H$_{Ar}$), 7.05 (d, 1H, J=9.0 Hz, H$_{Ar}$), 7.26–7.36 (m, 3H, H$_{Ar}$) 7.42 (s, 1H, =CH), 7.66 (d, 2H, J=7.8 Hz, H$_{Ar}$).

$^{13}$C NMR (62.90 MHz, CDC$_3$): δ46.7, 56.9, 57.1, 105.6, 115.0, 120.2, 123.4, 126.8, 127.9 (2), 128.9 (2), 134.5, 135.5, 143.8, 155.2, 175.8.

MS (ion spray): m/z 296 (M+H)$^+$

Anal. calculated for $C_{18}H_{17}NO_3$: C, 73.20; H, 5.80; N, 4.74. Found: C, 72.88; H, 5.96; N, 4.94.

EXAMPLE 8

6,7-Dimethoxy-3-phenyl-1,4-dihydro-4-quinolinone (compound 14)-CRL 8355 a) Ethyl (Z)-3-(3,4-dimethoxyanilino)-2-phenyl-2-propenoate (compound 13)

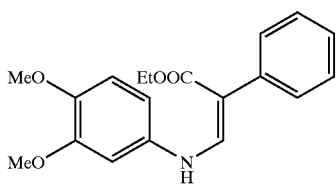

A solution of 3,4-dimethoxyaniline (1.50 g, 9.79 mmol) and ethyl ∀-formylphenylacetate (2.07 g, 1.1 eq) in toluene (20 ml) is refluxed for 18 hours. After cooling, the reaction mixture is diluted with toluene (10 ml) and then acidified with 10% HCl. After extraction, the organic phase obtained is dried over $MgSO_4$ and then evaporated under reduced pressure. The residue is purified by chromatography on a column of silica (eluent: $CH_2Cl_2$) to give 1.92 g (60%) of compound 13 in the form of an oil which crystallizes from methanol.

m.p. : 107–108° C. (MeOH)

IR (KBr): <3270, 1658, 1615, 1587, 1519 cm$^-$ $^1$H NMR (250 MHz, CDCl$_3$): δ1.29 (t, 3H, J=7.2 Hz, CH$_3$), 3.84 (s, 3H, OCH$_3$), 3.86 (s, 3H, OCH$_3$), 4.25 (q, 2H, J=7.2 Hz, CH$_2$), 6.54–6.58 (m, 2H, H$_{Ar}$), 6.80 (d, 1H, J=9.2 Hz, H$_{Ar}$), 7.21–7.48 (m, 6H, H$_{Ar}$+=CH), 10.30 (broad d, 1H, J=12.5 Hz, NH).

$^{13}$C NMR (62.90 MHz, CDCl$_3$): δ14.3, 55.9, 56.2, 59.7, 101.0, 101.9, 106.9, 112.3, 125.8, 127.9 (2), 129.5 (2), 134.5, 138.0, 144.5, 145.0, 149.9, 169.3.

MS (ion spray): m/z 328 (M+H)$^+$

Anal. calculated for $C_{19}H_{21}NO_4$: C, 69.71; H, 6.47; N, 4.28. Found: C, 69.83; H, 6.63; N, 4.26.

b) 6,7-Dimethoxy-3-phenyl-1,4-dihydro-4-quinolinone (compound 14)-CRL 8355

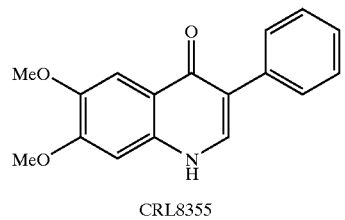

CRL8355

Compound 13 (500 mg, 1.53 mmol) is added portionwise and rapidly, with stirring, to a solution of biphenyl (675 mg) and diphenyl ether (4.90 g) heated to 250° C. After 10 minutes, the heating is stopped. During the cooling, the final product 14 precipitates out in the reaction medium. This product is collected by filtration and then rinsed with petroleum ether. After drying, 391 mg (91%) of compound 14 are obtained in the form of gray crystals.

m.p.: 331–332° C. (washing with EtOH)

IR (KBr): <3228, 1620, 1590, 1545, 1508 cm$^{-1}$ $^1$H NMR (250 MHz, DMSO-d$_6$): δ3.85 (s, 3H, OCH$_3$), 3.88 (s, 3H, OCH$_3$), 7.02 (s, 1H, H$_{Ar}$), 7.23–7.40 (m, 3H, H$_{Ar}$), 7.57 (s, 1H, H$_{Ar}$), 7.73 (d, 2H, J=8.2 Hz, H$_{Ar}$), 8.04 (s, 1H, =CH), 11.82 (broad s, 1H, NH).

$^{13}$C NMR (62.90 MHz, DMSO-d$_6$): δ55.5, 55.7, 99.0, 104.8, 118.8, 119.8, 126.1, 127.8 (2), 128.4 (2), 134.9, 136.6 (2), 146.7, 152.8, 173.5.

MS (ion spray): m/z 282 (M+H)$^+$

Anal. calculated for $C_{17}H_{15}NO_3$: C, 72.58; H, 5.37; N, 4.98. Found: C, 72.85; H, 5.54; N, 5.17.

EXAMPLE 9

5,7-Dimethoxy-3-phenyl-1,4-dihydro-4-quinolinone (compound 16) CRL 8352 a) Ethyl (Z)-3-(3,5-dimethoxyanilino)-2-phenyl-2-propenoate (compound 15)

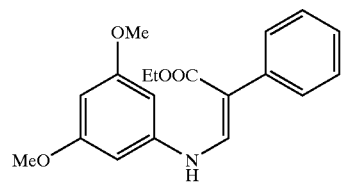

1.54 g (10.05 mmol) of 3,5-dimethoxyaniline and 2.12 g (1.1 eq) of ethyl ∀-formylphenylacetate in 20 ml of toluene are stirred at reflux for 18 hours under a nitrogen atmosphere. After cooling, the reaction mixture is diluted with toluene (20 ml), acidified with 10% HCl and then extracted. The organic phase is dried over $MgSO_4$, filtered and then evaporated under reduced pressure. The residue obtained is taken up in methanol, from which compound 15 crystallizes. The product is collected by filtration. The filtrate itself is stored in a freezer at −78° C., where derivative 15 crystallizes again. The two combined portions give 2.47 g (75%) of compound 15 (Z isomer).

m.p.: 75–76° C. (MeOH)

IR (KBr): <3274, 1664, 1618, 1593 cm$^{-1}$ $^1$H NMR (250 MHz, CDCl$_3$): δ1.27 (t, 3H, J=7.2 Hz, CH$_3$), 3.71 (s, 6H, OCH$_3$), 4.23 (q, 2H, J=7.2 Hz, CH$_2$), 6.10–6.14 (m, 3H, H$_{Ar}$), 7.18–7.37 (m, 6H, H$_{Ar}$+=CH), 10.27 (broad d, 1H, J=12.5 Hz, NH).

$^{13}$C NMR (62.90 MHz, CDCl$_3$): δ14.4, 55.4 (2), 59.9, 94.2 (2), 94.7, 103.1, 126.1, 127.9 (2), 129.5 (2), 137.8, 142.5, 143.4, 161.8 (2), 169.3.

MS (ion spray): m/z 328 (M+H)$^+$

Anal. calculated for C$_{19}$H$_{21}$NO$_4$: C, 69.71; H, 6.47; N, 4.28. Found: C, 69.42; H, 6.29; N, 4.30.

b) 5,7-Dimethoxy-3-phenyl-1,4-dihydro-4-quinolinone (compound 16)-CRL 8352

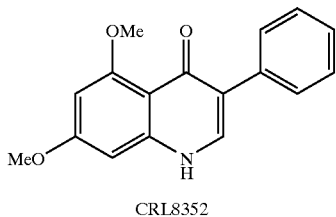

CRL8352

Compound 15 (1.20 g, 3.67 mmol) is added portionwise and rapidly, with stirring, to a solution of biphenyl (1.52 g) and diphenyl ether (11.60 g) heated to 250° C. After 10 minutes, the heating is stopped. During the cooling, the quinoline 16 precipitates out in the reaction medium. This product is collected by filtration and then rinsed with petroleum ether. After drying, 650 mg (63%) of compound 16 are obtained in the form of white crystals.

m.p.: 254–255° C. (washing with EtOH)

IR (KBr): <3268, 1631, 1598, 1567, 1522 cm$^{-1}$ $^1$H NMR (250 MHz, DMSO-d$_6$): δ3.81 (s, 3H, OCH$_3$), 3.90 (s, 3H, OCH$_3$), 6.36 (d, 1H, J=2.0 Hz, H$_{Ar}$), 6.45 (d, 1H, J=2.0 Hz, H$_{Ar}$), 7.32–7.42 (m, 3H, H$_{Ar}$), 7.69 (d, 2H, J=7.0 Hz, H$_{Ar}$), 8.01 (s, 1H, =CH), 11.81 (s, 1H, NH).

$^{13}$C NMR (62.90 MHz, DMSO-d$_6$): δ55.5, 55.7, 91.2, 94.5, 111.4, 121.6, 126.1, 127.9 (2), 128.6 (2), 135.7, 136.5, 143.5, 161.4, 161.8, 174.3.

MS (ion spray): m/z 282 (M+H)$^+$

Anal. calculated for C$_{17}$H$_{15}$NO$_3$: C, 72.58; H, 5.37; N, 4.98. Found: C, 72.31; H, 5.40; N, 5.23.

EXAMPLE 10

5,7-Dimethoxy-3-phenyl-1-methyl-1,4-dihydro-4-quinolinone (compound 17)-CRL 8489

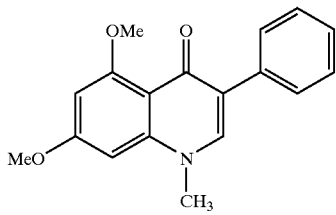

200 mg (0.71 mmol) of compound 16 are added to 10 ml of anhydrous N,N-dimethylformamide (DMF) under a nitrogen atmosphere. 734 mg of anhydrous K$_2$CO$_3$ (7.5 eq) and then 0.13 ml of methyl iodide (3 eq) are successively added to this suspension. The reaction is stirred at room temperature for 18 hours. The solvents are evaporated off. The residue is taken up in CH$_2$Cl$_2$ and washed twice with water. The organic phase obtained is dried over MgSO$_4$ and then evaporated under reduced pressure. The crude residue is purified on a column of silica (eluent: 9/1 CH$_2$Cl$_2$/EtOAc) to give 162 mg (77%) of derivative 17.

m.p.: 179–180° C. (washing with ethanol)

IR (KBr): <1634, 1611, 1588, 1506 cm$^{-1}$ $^1$H NMR (250 MHz, CDCl$_3$): δ3.68 (s, 3H, NCH$_3$), 3.90 (s, 3H, OCH$_3$), 3.94 (s, 3H, OCH$_3$), 6.24 (d, 1H, J=2.2 Hz, H$_{Ar}$), 6.37 (d, 1H, J=2.2 Hz, H$_{Ar}$), 7.20–7.38 (m, 3H, H$_{Ar}$), 7.44 (s, 1H, =CH), 7.60–7.64 (m, 2H, H$_{Ar}$).

$^{13}$C NMR (62.90 MHz, CDCl$_3$): δ41.7, 55.5, 56.3, 89.9, 94.6, 112.8, 123.9, 126.9, 128.0 (2), 129.1 (2), 135.8, 140.8, 144.3, 162.8, 163.1, 175.8.

MS (ion spray): m/z 296 (M+H)$^+$

Anal. calculated for C$_{18}$H$_{17}$NO$_3$: C, 73.20; H, 5.80; N, 4.74. Found: C, 73.37; H, 5.67; N, 4.95.

EXAMPLE 11

3-(4-Methoxyphenyl)-1,4-dihydro-4-quinolinone (compound 19)-CRL8327 a) Ethyl α-formyl-4-methoxyphenylacetate

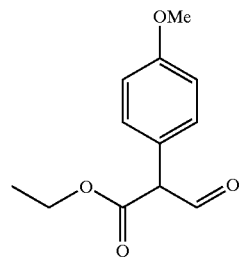

4.08 g (0.10 mol) of 60% sodium hydride in oil are suspended in 35 ml of ether under a nitrogen atmosphere. The flask is placed in an ice bath. In a first stage, 6.86 ml (0.08 mol) of ethyl formate are added to the initial mixture, then 10 ml of ethyl p-methoxyphenylacetate (0.06 mol) are added very slowly (monitor the evolution of hydrogen to avoid runaway reaction). Once the addition is complete, the solution is stirred at 35° C. for 3–4 hours. The mixture becomes white and pasty. During the stirring, it is essential to ensure that a runaway reaction does not occur (if necessary, add ether). The reaction mixture is filtered and the white solid obtained is washed with ether. This solid is dissolved in water and the resulting solution is then acidified with 10% HCl. The final compound is extracted with ethyl acetate (twice). The organic phase is dried over MgSO$_4$ and then evaporated under reduced pressure to give 9.60 g (77%) of ethyl ∀-formyl-4-methoxyphenylacetate in the form of a brown oil.

b) Ethyl (Z)-3-anilino-2-(4-methoxyphenyl)-2-propenoate (compound 18)

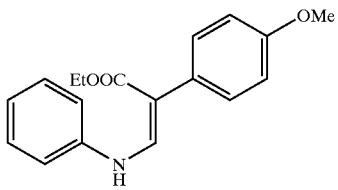

A solution of aniline (1.85 ml, 20.30 mmol) and ethyl ∀-formyl-4-methoxyphenylacetate (4.96 g, 1.1 eq) in toluene (15 ml) is refluxed for 18 hours. After cooling, the reaction mixture is diluted with toluene (10 ml) and then acidified with 10% HCl. After extraction, the organic phase obtained is dried over $MgSO_4$ and then evaporated under reduced pressure. The residue is purified by chromatography on a column of silica (eluent: 4/6 $PE/CH_2Cl_2$) to give 4.29 g (71%) of compound 18 (Z isomer) in the form of a yellow oil.

IR (film): <3302, 1665, 1621, 1584 $cm^{-1}$ $^1$H NMR (250 MHz, $CDCl_3$): δ1.30 (t, 3H, J=7.2 Hz, $CH_3$), 3.83 (s, 3H, $OCH_3$), 4.24 (q, 2H, J=7.2 Hz, $CH_2$), 6.87–7.00 (m, 5H, $H_{Ar}$), 7.24–7.33 (m, 4H, $H_{Ar}$), 7.36 (d, 1H, J=12.5 Hz, =CH), 10.26 (broad d, 1H, J=12.5 Hz, NH).

$^{13}$C NMR (62.90 MHz, $CDCl_3$): δ14.3, 55.1, 59.8, 102.4, 113.3 (2), 115.4 (2), 122.3, 129.6 (2), 130.2, 130.5 (2), 140.7, 143.0, 158.0, 169.4.

MS (ion spray): m/z 298 $(M+H)^+$

Anal. calculated for $C_{18}H_{19}NO_3$: C, 72.71; H, 6.44; N, 4.71. Found: C, 72.47; H, 6.63; N, 4.50.

c) 3-(4-Methoxyphenyl)-1,4-dihydro-4-quinolinone (compound 19)-CRL 8327

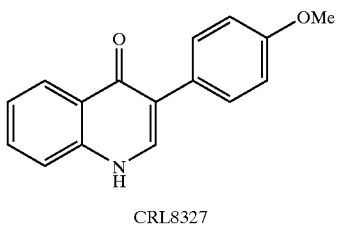

CRL8327

Compound 18 (1.81 g, 6.09 mmol) is added portionwise and rapidly, with stirring, to a solution of biphenyl (2.30 g) and diphenyl ether (17.58 g) heated to 250° C. After 10 minutes, the heating is stopped. During the cooling, the quinolone 19 precipitates out in the reaction medium. This product is collected by filtration and then rinsed with petroleum ether. After drying, 1.40 g (91%) of compound 19 are obtained in the form of white crystals.

m.p.: 292–293° C. (EtOH)

IR (KBr): <1629, 1607, 1562, 1561, 1516 $cm^{-1}$ $^1$H NMR (250 MHz, DMSO-$d_6$): δ3.77 (s, 3H, $OCH_3$), 6.94 (d, 2H, J=8.8 Hz, $H_{Ar}$), 7.31 (t, 1H, J=7.8 Hz, $H_{Ar}$), 7.54–7.67 (m, 4H, $H_{Ar}$), 8.09 (s, 1H, =CH), 8.19 (d, 1H, J=7.8 Hz, $H_{Ar}$), 11.96 (s, 1H, NH)

$^{13}$C NMR (62.90 MHz, DMSO-$d_6$): δ55.5, 113.7 (2), 119.6, 119.8, 123.4, 126.0, 126.3, 129.2, 129.9 (2), 131.6, 138.5, 140.2, 158.3, 175.1.

MS (ion spray): m/z 252 $(M+H)^+$

Anal. calculated for $C_{16}H_{13}NO_2$: C, 76.48; H, 5.21; N, 5.57. Found: C, 76.08; H, 5.03; N, 5.60.

EXAMPLE 12

8-Methoxy-3-(4-methoxyphenyl)-1,4-dihydro-4-quinolinone (compound 21)-CRL 8329 a) Ethyl (Z)-3-(2-methoxyanilino)-2-(4-methoxyphenyl)-2-propenoate (compound 20)

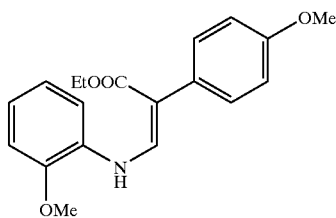

A solution of 2-methoxyaniline (1.25 ml, 11.08 mmol) and ethyl ∀-formyl-4-methoxyphenylacetate (2.70 g, 1.1 eq) in toluene (20 ml) is refluxed for 18 hours. After cooling, the reaction mixture is diluted with toluene (10 ml) and then acidified with 10% HCl. After extraction, the organic phase obtained is dried over $MgSO_4$ and then evaporated under reduced pressure. The residue is purified by chromatography on a column of silica (eluent: $CH_2Cl_2$) to give 1.96 g (54%) of compound 20 (Z isomer) in the form of a yellow oil which crystallizes from methanol.

m.p.: 58–59° C. (MeOH)

IR (KBr): <3316, 1665, 1640, 1614, 1596 $cm^{-1}$ $^1$H NMR (250 MHz, $CDCl_3$): δ1.31 (t, 3H, J=7.2 Hz, $CH_3$), 3.83 (s, 3H, $OCH_3$), 3.87 (s, 3H, $OCH_3$), 4.28 (q, 2H, J=7.2 Hz, =$CH_2$), 6.87–7.07 (m, 6H, $H_{Ar}$), 7.28 (d, 2H, J=8.8 Hz, $H_{Ar}$), 7.39 (d, 1H, J=13.0 Hz, =CH), 10.39 (broad d, 1H, J=13.0 Hz, NH).

$^{13}$C NMR (62.90 MHz, $CDCl_3$): δ14.5, 55.3, 55.8, 59.8, 102.9, 110.8, 112.2, 113.4 (2), 121.1, 122.0, 130.5, 130.7 (3), 141.8, 148.0, 158.0, 169.1.

MS (ion spray): m/z 328 $(M+H)^+$

Anal. calculated for $C_{19}H_{21}NO_4$: C, 69.71; H, 6.47; N, 4.28. Found: C, 69.39; H, 6.40; N, 4.52.

b) 8-Methoxy-3-(4-methoxyphenyl)-1,4-dihydro-4-quinolinone (compound 21) CRL 8329

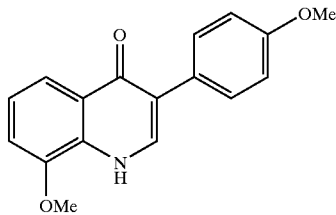

CRL8329

Compound 20 (1.30 g, 3.97 mmol) is added portionwise and rapidly, with stirring, to a solution of biphenyl (1.36 g) and diphenyl ether (10.40 g) heated to 250° C. After 10 minutes, the heating is stopped. During the cooling of the reaction medium, the product precipitates out. 972 mg (87%) of compound 21 are thus collected by filtration in the form of white crystals.

m.p.: 192–193° C. (EtOH)

IR (KBr): <3250, 1611, 1545 $cm^{-1}$ $^1$H NMR (250 MHz, DMSO-$d_6$): δ3.79 (s, 3H, $OCH_3$), 4.05 (s, 3H, $OCH_3$), 6.96 (d, 2H, J=8.8 Hz, $H_{Ar}$), 7.21–7.29 (m, 2H, $H_{Ar}$), 7.62 (d, 2H, J=8.8 Hz, $H_{Ar}$), 7.75 (dd, 1H, J=2.8, 7.0 Hz, $H_{Ar}$), 7.86 (s, 1H, =CH), 11.57 (broad s, 1H, NH).

EXAMPLE 13

6-Methoxy-3-(4-methoxyphenyl)-1,4-dihydro-4-quinolinone (compound 23)-CRL 8490 a) Ethyl (Z)-3-(4-methoxyanilino)-2-(4-methoxyphenyl)-2-propenoate (compound 22)

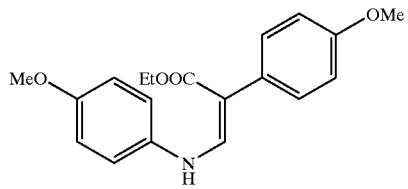

A solution of 4-methoxyaniline (1.47 g, 11.94 mmol) and ethyl ∀-formyl-4-methoxyphenylacetate (2.92 g, 1.1 eq) in toluene (25 ml) is refluxed for 18 hours. After cooling, the reaction mixture is diluted with toluene (15 ml) and then acidified with 10% HCl. After extraction, the organic phase obtained is dried over MgSO₄ and then evaporated under reduced pressure. The residue is purified by chromatography on a column of silica (eluent: $CH_2Cl_2$) to give 2.89 g (74%) of compound 22 (Z isomer) in the form of a yellow solid which crystallizes from methanol.

m.p.: 90–91° C. (MeOH)

IR (KBr): <3283, 1660, 1613, 1586, 1518 cm⁻¹

¹H NMR (250 MHz, CDCl₃): δ1.32 (t, 3H, J=7.2 Hz, CH₃), 3.79 (s, 3H, OCH₃), 3.84 (s, 3H, OCH₃) 4.27 (q, 2H, J=7.2 Hz, CH₂), 6.87–7.02 (m, 6H, $H_{Ar}$), 7.27–7.33 (m, 3H, $H_{Ar}$+=CH), 10.24 (broad d, 1H, J=13.0 Hz, NH).

¹³C NMR (62.90 MHz, CDCl₃): δ14.4, 55.2, 55.5, 59.6, 101.2, 113.3 (2), 114.9 (2), 116.8 (2), 130.5 (2), 134.4, 141.2, 155.4, 157.9, 169.5.

MS (ion spray): m/z 328 (M+H)⁺

Anal. calculated for $C_{19}H_{21}NO_4$: C, 69.71; H, 6.47; N, 4.28. Found: C, 69.99; H, 6.62; N, 4.10.

b) 6-Methoxy-3-(4-methoxyphenyl)-1,4-dihydro-4-quinolinone (compound 23)-CRL 8490

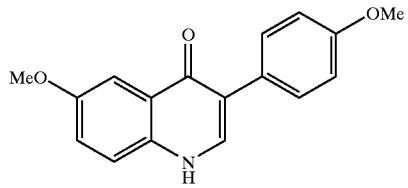

Compound 22 (1.00 g, 3.05 mmol) is added portionwise and rapidly, with stirring, to a solution of biphenyl (1.35 g) and diphenyl ether (9.80 g) heated to 250° C. After 10 minutes, the heating is stopped. During the cooling, the quinolone 23 precipitates out in the reaction medium. This product is collected by filtration and then rinsed with petroleum ether. After drying, 790 mg (92%) of compound 23 are obtained in the form of white crystals.

m.p.: 335–336° C. (washing with EtOH)

IR (KBr): <3212, 1621, 1607, 1588, 1557, 1515 cm⁻¹

¹H NMR (250 MHz, DMSO-d₆): δ3.78 (s, 3H, OCH₃), 3.85 (s, 3H, OCH₃), 6.95 (d, 2H, J=8.8 Hz, $H_{Ar}$), 7.29 (dd, 1H, J=3.0, 9.0 Hz, $H_{Ar}$), 7.54 (d, 1H, J=9.0 Hz, $H_{Ar}$), 7.60 (d, 1H, J=3.0 Hz, $H_{Ar}$), 7.68 (d, 2H, J=8.8 Hz, $H_{Ar}$), 8.06 (s, 1H, =CH), 12.0 (broad s, 1H, NH).

¹³C NMR (62.90 MHz, DMSO-d₆): δ55.1, 55.3, 104.7, 113.3 (2), 118.4, 119.9, 122.0, 125.3, 126.7, 128.7, 129.4 (2), 133.9, 155.6, 157.9, 173.9.

MS (ion spray): m/z 282 (M+H)⁺

Anal. calculated for $C_{17}H_{15}NO_3$: C, 72.58; H, 5.37; N, 4.98. Found: C, 72.77; H, 5.40; N, 4.80.

EXAMPLE 14

6-Methoxy-3-(4-methoxyphenyl)-1-methyl-1,4-dihydro-4-quinolinone (compound 24)-CRL 8378

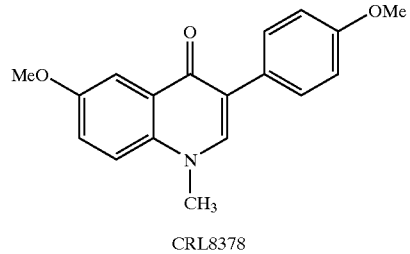

CRL8378

200 mg (0.71 mmol) of compound 23 are dissolved in 10 ml of anhydrous N,N-dimethylformamide (DMF) under a nitrogen atmosphere. 736 mg of potassium carbonate (7.5 eq) and then 0.13 ml of methyl iodide (3 eq) are successively added to this suspension. The reaction is stirred at room temperature for 18 hours. The solvents are evaporated off. The residue obtained is taken up in ethyl acetate and washed twice with water. The organic phase obtained is dried over MgSO₄ and then evaporated under reduced pressure. The residue is purified on a column of silica (eluent: 9/1 $CH_2Cl_2$/EtOAc) to give 188 mg (90%) of compound 24 in the form of white crystals.

m.p.: 139–140° C. (EtOH)

IR (KBr): <1608, 1559, 1512 cm⁻¹

¹H NMR (250 MHz, DMSO-d₆): δ3.78 (s, 3H, NCH₃), 3.87 (s, 3H, OCH₃), 3.90 (s, 3H, OCH₃), 6.96 (d, 2H, J=8.8 Hz, $H_{Ar}$), 7.38 (dd, 1H, J=3.0, 9.3 Hz, $H_{Ar}$), 7.65–7.72 (m, 4H, $H_{Ar}$), 8.20 (s, 1H, =CH).

¹³C NMR (62.90 MHz, DMSO-d₆): δ40.3, 55.1, 55.4, 105.8, 113.3 (2), 118.3, 118.4, 121.6, 127.7, 128.4 129.4 (2), 134.5, 142.5, 155.7, 157.9, 173.5.

MS (ion spray): m/z 296 (M+H)⁺

Anal. calculated for $C_{18}H_{17}NO_3$: C, 72.95; H, 6.12; N, 4.73. Found: C, 73.06; H, 6.01; N, 4.60.

EXAMPLE 15

7-Methoxy-3-(4-methoxyphenyl)-1,4-dihydro-4-quinolinone (compound 26)-CRL8358 and 5-methoxy-3-(4-methoxyphenyl)-1,4-dihydro-4-quinolinone (compound 27)-CRL8491 a) Ethyl (Z)-3-(3-methoxyanilino)-2-(4-methoxyphenyl)-2-propenate (25)

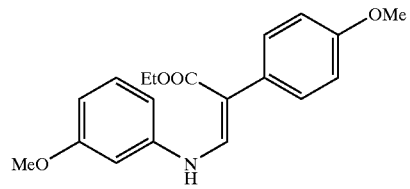

A solution of 3-methoxyaniline (1.75 ml, 15.57 mmol) and ethyl ∀-formyl-4-methoxyphenylacetate (3.81 g), 1.1 eq) in toluene (25 ml) is refluxed for 18 hours. After cooling, the reaction mixture is diluted with toluene (15 ml) and then acidified with 10% HCl. After extraction, the organic phase obtained is dried over $MgSO_4$ and then evaporated under reduced pressure. The residue is purified by chromatography on a column of silica (eluent: $CH_2Cl_2$) to give 3.57 g (70%) of compound 25 (Z isomer) in the form of a white solid which crystallizes from methanol.

m.p.: 60–61° C. (MeOH)

IR (KBr): <3306, 1668, 1626, 1600, 1586 cm$^{-1}$ $^1$H NMR (250 MHz, CDCl$_3$): δ1.29 (t, 3H, J=7.2 Hz, CH$_3$), 3.79 (s, 3H, OCH$_3$), 3.82 (s, 3H, OCH$_3$), 4.25 (q, 2H, J=7.2 Hz, CH$_2$), 6.53–6.61 (m, 3H, H$_{Ar}$), 6.88 (d, 2H, J=8.8 Hz, H$_{Ar}$), 7.19 (t, 1H, J=8.0 Hz, H$_{Ar}$), 7.25 (d, 2H, J=8.8 Hz, H$_{Ar}$), 7.34 (d, 1H, J=12.5 Hz, =CH), 10.25 (broad d, 1H, J=12.5 Hz, NH).

$^{13}$C NMR (62.90 MHz, CDCl$_3$): δ14.4, 55.3 (2), 59.9, 101.5, 102.6, 107.9, 108.0, 113.4 (2), 130.3, 130.5, 130.7 (2), 142.1, 143.0, 158.1, 160.9, 169.5.

MS (ion spray): m/z 328 (M+H)$^+$

Anal. calculated for C$_{19}$H$_{21}$NO$_4$: C, 69.71; H, 6.47; N, 4.28. Found: C, 69.47; H, 6.63; N, 4.41.

b) 7-Methoxy-3-(4-methoxyphenyl)-1,4-dihydro-4-quinolinone (compound 26)-CRL8358

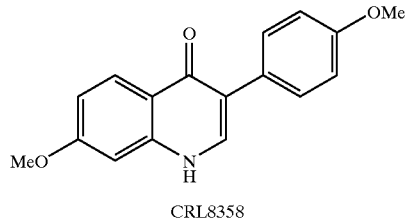

CRL8358

Compound 25 (1.00 g, 3.05 mmol) is added portionwise and rapidly, with stirring, to a solution of biphenyl (1.35 g) and diphenyl ether (9.80 g) heated to 250° C. After 10 minutes, the heating is stopped. During the cooling, the quinolone 25 precipitates out in the reaction medium. This product is collected by filtration and then rinsed with petroleum ether. The white solid is washed again with ethanol. After drying, 440 mg (51%) of compound 26 are obtained.

m.p.: 306–307° C (washing with EtOH)

IR (KBr): <3225, 1636, 1590, 1560, 1517 cm$^{-1}$ $^1$H NMR (250 MHz, DMSO-d$_6$): δ3.78 (s, 3H, OCH$_3$), 3.86 (s, 3H, OCH$_3$), 6.91–6.97 (m, 4H, H$_{Ar}$), 7.65 (d, 2H, J=8.8 Hz, H$_{Ar}$), 8.01 (s, 1H, =CH), 8.09 (d, 1H, J=8.8 Hz, H$_{Ar}$), 11.74 (broad s, 1H, NH).

$^{13}$C NMR (62.90 MHz, DMSO-d$_6$): δ55.1, 55.4, 98.8, 113.3 (2), 119.4, 120.1, 125.4, 127.4, 128.5, 129.4 (2), 137.0, 141.0, 157.9, 161.7, 174.4.

MS (ion spray): m/z 282 (M+H)$^+$

Anal. calculated for C$_{17}$H$_{15}$NO$_3$: C, 72.58; H, 5.37; N, 4.98. Found: C, 72.80; H, 5.51; N, 4.78.

c) 5-Methoxy-3-(4-methoxyphenyl)-1,4-dihydro-4-quinolinone (compound 27)-CRL8491

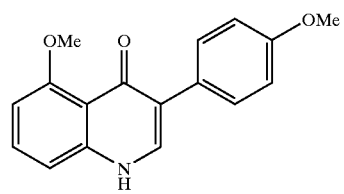

The filtrate obtained above (which contained compound 26) is evaporated to give 43 mg (5%) of compound 27.

m.p.: 215–216° C. (EtOH)

IR (KBr): <1664, 1628, 1573, 1518 cm$^{-1}$ $^1$H NMR (250 MHz, DMSO-d$_6$): δ3.77 (s, 3H, OCH$_3$), 3.80 (s, 3H, OCH$_3$), 6.73 (d, 1H, J=7.8 Hz, H$_{Ar}$), 6.92 (d, 2H, J=8.8 Hz, H$_{Ar}$), 7.05 (d, 1H, J=7.8 Hz, H$_{Ar}$), 7.47 (t, 1H, J=7.8 Hz, H$_{Ar}$), 7.53 (d, 2H, J=8.8 Hz, H$_{Ar}$) 7.85 (s, 1H, =CH), 11.74 (broad s, 1H, NH).

$^{13}$C NMR (62.90 MHz, DMSO-d$_6$): δ55.5, 56.2, 104.6, 110.6, 113.7 (2), 116.7, 122.0, 129.1, 130.2 (2), 132.3, 136.1, 142.6, 158.4, 160.4, 175.1.

MS (ion spray): m/z 312 (M+H)$^+$

Anal. calculated for C$_{17}$H$_{15}$NO$_3$: C, 72.58; H, 5.37; N, 4.98. Found: C, 72.36; H, 5.19; N, 5.13.

EXAMPLE 16

5,8-Dimethoxy-3-(4-methoxyphenyl)-1,4-dihydro-4-quinolinone (compound 29)-CRL 8351 a) Ethyl (Z)-3-(2,5-dimethoxyanilino)-2-(4-methoxyphenyl)-2-propenoate (compound 28)

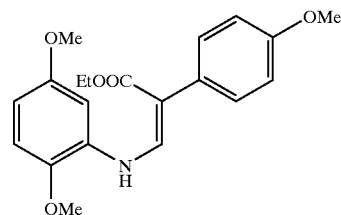

A solution of 2,5-dimethoxyaniline (1.07 g, 7.00 mmol) and ethyl ∀-formyl-4-methoxyphenylacetate (1.71 g, 1.1 eq) in toluene (15 ml) is refluxed for 18 hours. After cooling, the reaction mixture is diluted with toluene (15 ml) and then acidified with 10% HCl. After extraction, the organic phase obtained is dried over $MgSO_4$ and then evaporated under reduced pressure. The isolated residue is crystallized from methanol and then filtered on a sinter funnel to give 1.30 g (52%) of compound 28.

m.p.: 65–66° C. (EtOH)

IR (KBr): <3288, 1667, 1593, 1514 cm$^{-1}$ $^1$H NMR (250 MHz, CDCl$_3$): δ1.30 (t, 3H, J=7.2 Hz, CH$_3$), 3.75 (s, 3H, OCH$_3$), 3.82 (s, 3H, OCH$_3$), 3.90 (s, 3H, OCH$_3$), 4.28 (q, 2H, J=7.2 Hz, CH$_2$), 6.44 (dd, 1H, J=2.8, 8.9 Hz, H$_{Ar}$), 6.63 (d, 1H, J=2.8 Hz, H$_{Ar}$), 6.80 (d, 1H, J=9.0 Hz, H$_{Ar}$), 6.88 (d, 2H, J=8.8 Hz, H$_{Ar}$), 7.26 (d, 2H, J=8.8 Hz, H$_{Ar}$), 7.31 (d, 1H, J=12.5 Hz, =CH), 10.37 (broad d, 1H, J=12.5 Hz, NH).

$^{13}$C NMR (62.90 MHz, DMSO-d$_6$): δ14.4, 55.3, 55.7, 56.4, 59.9, 100.0, 103.3, 105.2, 111.6, 113.4 (2), 130.5, 130.6 (2), 131.3, 141.4, 142.4, 158.1, 154.4, 169.0

MS (ion spray): m/z 358 (M+H)$^+$

Anal. calculated for C$_{20}$H$_{23}$NO$_5$: C, 67.21; H, 6.49; N, 3.92. Found: C, 66.97; H, 6.56; N, 4.08.

b) 5,8-Dimethoxy-3-(4-methoxyphenyl)-1,4-dihydro-4-quinolinone (compound 29) CRL 8351

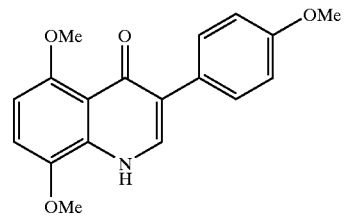

CRL8351

Compound 28 (1.10 g, 3.08 mmol) is added portionwise and rapidly, with stirring, to a solution of biphenyl (3.00 g)

and diphenyl ether (7.51 g) heated to 250° C. After 10 minutes, the heating is stopped. During the cooling, the quinolone 29 precipitates out in the reaction medium. This product is collected by filtration and then rinsed with petroleum ether. After drying, 680 mg (71%) of compound 29 are obtained in the form of white crystals.

m.p.: 124–125° C. (EtOH)

IR (KBr): <3282, 1618, 1580, 1560, 1532 cm$^{-1}$ $^1$H NMR (250 MHz, DMSO-d$_6$): δ3.74 (s, 3H, OCH$_3$), 3.77 (s, 3H, OCH$_3$), 3.93 (s, 3H, OCH$_3$), 6.66 (d, 1H, J=8.8 Hz, H$_{Ar}$), 6.92 (d, 2H, J=9.0 Hz, H$_{Ar}$), 7.13 (d, 1H, J=8.8 Hz, H$_{Ar}$), 7.52 (d, 2H, J=9.0 Hz, H$_{Ar}$), 7.68 (s, 1H, =CH), 11.12 (broad s, 1H, NH).

$^{13}$C NMR (62.90 MHz, DMSO-d$_6$): δ55.0, 56.2, 56.3, 103.8, 111.2, 113.2 (2), 117.0, 122.0, 128.5, 129.6 (2), 132.1, 135.0, 141.8, 153.2, 157.9, 174.7.

MS (ion spray): m/z 312 (M+H)$^+$

Anal. calculated for C$_{18}$H$_{17}$NO$_4$: C, 69.44; H, 5.50; N, 4.50. Found: C, 69.29; H, 5.40; N, 4.55.

EXAMPLE 17

6,7-Dimethoxy-3-(4-methoxyphenyl)-1,4-dihydro-4-quinolinone (compound 31)-CRL 8354 a) Ethyl (Z)-3-(3,4-dimethoxyanilino)-2-(4-methoxyphenyl)-2-propenoate (compound 30)

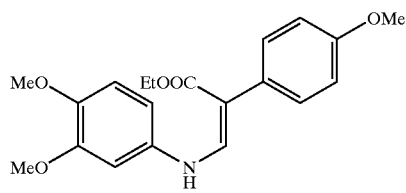

A solution of 3,4-dimethoxyaniline (1.76 g, 11.49 mmol) and ethyl ∀-formyl-4-methoxyphenylacetate (2.81 g, 1.1 eq) in toluene (20 ml) is refluxed for 18 hours. After cooling, the reaction mixture is diluted with toluene (10 ml) and then acidified with 10% HCl. After extraction, the organic phase obtained is dried over MgSO$_4$ and then evaporated under reduced pressure. The residue is purified by chromatography on silica gel (eluent: 7/3 PE/EtOAc) to give 2.67 g (65%) of compound 30 in the form of a pale yellow solid.

m.p.: 88–89° C. (EtOH)

IR (KBr): <1663, 1620, 1586, 1522, 1513 cm$^{-1}$ $^1$H NMR (250 MHz, CDCl$_3$): δ1.30 (t, 3H, J=7.2 Hz, CH$_3$), 3.82 (s, 3H, OCH$_3$), 3.85 (s, 3H, OCH$_3$), 3.87 (s, 3H, OCH$_3$), 4.28 (q, 2H, J=7.2 Hz, CH$_2$), 6.44 (dd, 1H, J=2.8, 9.0 Hz, H$_{Ar}$), 6.63 (d, 1H, J=2.8 Hz, H$_{Ar}$), 6.80 (d, 1H, J=9.0 Hz, H$_{Ar}$), 6.88 (d, 2H, J=8.8 Hz, H$_{Ar}$), 7.26 (d, 2H, J=8.8 Hz, H$_{Ar}$), 7.31 (d, 1H, J=12.5 Hz, =CH), 10.37 (broad d, 1H, J=12.5 Hz, NH).

$^{13}$C NMR (62.90 MHz, CDCl$_3$): δ14.5, 55.3, 56.0, 56.3, 59.8, 101.0, 101.5, 106.9, 112.3, 113.4 (2), 130.4 (2), 130.7, 134.9, 144.0, 145.0, 150.0, 158.0, 169.6.

MS (ion spray): m/z 358 (M+H)$^+$

Anal. calculated for C$_{20}$H$_{23}$NO$_5$: C, 67.21; H, 6.49; N, 3.92. Found: C, 67.49; H, 6.63; N, 3.82.

b) 6,7-Dimethoxy-3-(4-methoxyphenyl)-1,4-dihydro-4-quinolinone (compound 31) CRL 8354

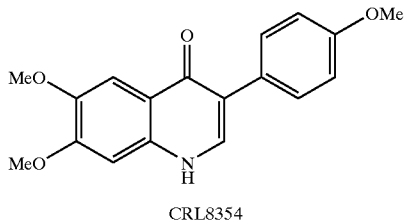

CRL8354

Compound 30 (900 mg, 2.52 mmol) is added portionwise and rapidly, with stirring, to a solution of biphenyl (1.18 g) and diphenyl ether (8.05 g) heated to 250° C. After 10 minutes, the heating is stopped. During the cooling, the final product precipitates out in the reaction medium. This product is collected by filtration and then rinsed thoroughly with petroleum ether. After drying, 667 mg (85%) of compound 31 are obtained in the form of white crystals.

m.p.: 310–311° C. (washing with EtOH)

IR (KBr): <3218, 1618, 1606, 1589, 1547, 1515 cm$^{-1}$ $^1$H NMR (250 MHz, DMSO-d$_6$): δ3.76 (s, 3H, OCH$_3$), 3.83 (s, 3H, OCH$_3$), 3.86 (s, 3H, OCH$_3$), 6.92 (d, 2H, J=8.8 Hz, H$_{Ar}$), 6.99 (s, 1H, H$_{Ar}$), 7.54 (s, 1H, H$_{Ar}$), 7.65 (d, 2H, J=8.8 Hz, H$_{Ar}$), 7.97 (s, 1H, =CH), 11.74 (broad s, 1H, NH).

$^{13}$C NMR (62.90 MHz, DMSO-d$_6$): δ55.0, 55.4, 55.6, 98.9, 104.7, 113.2 (2), 118.5, 119.7, 128.8, 129.4 (2), 134.8, 135.9, 146.6, 152.7, 157.8, 173.6.

MS (ion spray): m/z 312 (M+H)$^+$

Anal. calculated for C$_{18}$H$_{17}$NO$_4$: C, 69.44; H, 5.50; N, 4.50. Found: C, 69.19; H, 5.33; N, 4.65.

EXAMPLE 18

5,7-Dimethoxy-3-(4-methoxyphenyl)-1,4-dihydro-4-quinolinone (compound 33)-CRL 8337 a) Ethyl (Z)-3-(3,5-dimethylanilino)-2-(4-methoxyphenyl)-2-propenoate (compound 32)

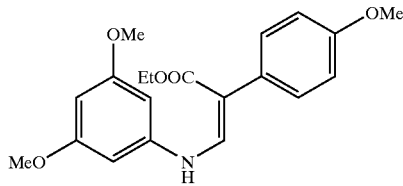

4.59 g (29.96 mmol) of 3,5-dimethoxyaniline and 7.32 g (1.1 eq) of ethyl ∀-formyl-4-methoxyphenylacetate in 20 mol of toluene are refluxed for 18 hours under a nitrogen atmosphere. After cooling, the reaction mixture is diluted with toluene (20 ml), acidified with 10% HCl and extracted. The organic phase is dried over MgSO$_4$, filtered and then evaporated under reduced pressure. The residue obtained is taken up in methanol, from which compound 32 crystallizes. The product is collected by filtration. The filtrate itself is stored in a freezer at −78° C., where compound 32 crystallizes again. The two combined portions give 6.10 g (57%) of compound 32 (Z isomer).

m.p.: 93–94° C. (EtOH)

IR (KBr): <1666, 1608, 1588, 1513 cm$^{-1}$ $^1$H NMR (250 MHz, CDCl$_3$): δ1.30 (t, 3H, J=7.2 Hz, CH$_3$), 3.78 (s, 6H, OCH$_3$), 3.84 (s, 3H, OCH$_3$), 4.26 (q, 2H, J=7.2 Hz, CH$_2$), 6.13–6.16 (m, 3H, H$_{Ar}$), 6.89 (d, 2H, J=7.5 Hz, H$_{Ar}$), 7.25–7.34 (m, 3H, H$_{Ar}$+=CH), 10.27 (broad d, 1H, J=12.5 Hz, NH).

$^{13}$C NMR (62.90 MHz, CDCl$_3$): δ14.4, 55.2, 55.3, 55.4, 59.9, 94.0 (2), 94.5, 102.6, 113.3 (2), 130.1, 130.6 (2), 142.5, 142.8, 158.1, 161.8 (2), 169.4.

MS (ion spray): m/z 358 (M+H)$^+$ b) 5,7-Dimethoxy-3-(4-methoxyphenyl)-1,4-dihydro-4-quinolinone (compound 33)-CRL 8337

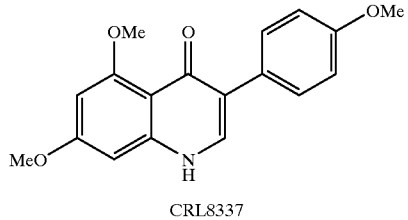

CRL8337

Compound 32 (3.1 g, 8.67 mmol) is added portionwise and rapidly to a solution of biphenyl (8.45 g) and diphenyl ether (21.13 g) heated to 250° C. After 10 minutes, the heating is stopped. During the cooling, the final product precipitates out in the reaction medium. The product is collected by filtration and then rinsed with petroleum ether. After drying, 900 mg of the final compound 33 are obtained in the form of white crystals. The filtrate itself is evaporated and then taken up in petroleum ether to give a viscous paste. The supernatant is removed and the residue is dissolved in ethyl acetate, from which the final product precipitates out again. After filtration through a sinter funnel and drying, 750 mg of compound 33 are collected. The overall reaction yield is 62%.

m.p.: 262–263° C. (washing with EtOH)

IR (KBr): <3261, 1625, 1606, 1557, 1519, 1511 cm$^{-1}$ $^1$H NMR (250 MHz, DMSO-d$_6$): δ3.76 (s, 6H, OCH$_3$), 3.82 (s, 3H, OCH$_3$), 6.30 (d, 1H, J=2.0 Hz, H$_{Ar}$), 6.49 (d, 1H, J=2.0 Hz, H$_{Ar}$), 6.90 (d, 2H, J=7.5 Hz, H$_{Ar}$), 7.52 (d, 2H, J=7.5 Hz, H$_{Ar}$), 7.75 (s, 1H, =CH), 11.45 (broad s, 1H, NH).

$^{13}$C NMR (62.90 MHz, DMSO-d$_6$): δ55.5, 55.7, 56.1, 91.6, 94.9, 111.8, 113.6 (2), 121.8, 129.2, 130.1 (2), 135.4, 144.0, 158.3, 161.9, 162.2, 174.8.

MS (ion spray): m/z 312 (M+H)$^+$

EXAMPLE 19

5-Hydroxy-7-methoxy-3-(4-methoxyphenyl)-1,4-dihydro-4-quinolinone (compound 34)-CRL 8492

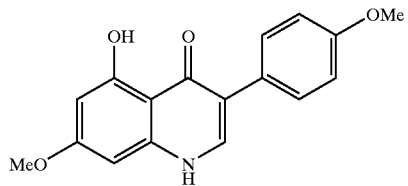

Compound 33 (1.00 g, 3.21 mmol) is dissolved in 30 ml of anhydrous N,N-dimethylformamide (DMF). Fifteen drops of 48% HBr in H$_2$O are added to the solution. The reaction is stirred at 90° C. for 5 hours. The DMF is evaporated off and the residue is taken up in 15 ml of CH$_2$Cl$_2$ and 15 ml of H$_2$O. After extraction, the organic phase is dried over MgSO$_4$ and then evaporated. The product obtained is recrystallized from ethanol to give 762 mg (80%) of compound 34.

m.p.: 236–237° C. (EtOH)

IR (KBr): ν 3206, 1667, 1610, 1557, 1515, 1448 cm$^{-1}$ $^1$H NMR (250 MHz, DMSO-d$_6$): δ3.77 (s, 3H, OCH$_3$), 3.81 (s, 3H, OCH$_3$), 6.19 (d, 1H, J=2.5 Hz, H$_{Ar}$), 6.43 (d, 1H, J=2.5 Hz, H$_{Ar}$), 6.96 (d, 2H, J=8.8 Hz, H$_{Ar}$), 7.60 (d, 2H, J=8.8 Hz, H$_{Ar}$), 8.07 (s, 1H, =CH), 12.23 (broad s, 1H, NH), 14.99 (s, 1H, OH)

$^{13}$C NMR (62.90 MHz, DMSO-d$_6$): δ55.1, 55.4, 89.5, 96.4, 108.3, 113.4 (2), 118.0, 126.9, 129.6 (2), 138.5, 141.4, 158.2, 163.0, 163.4, 179.1

MS (ion spray): m/z 298 (M+H)$^+$

EXAMPLE 20

5-Hydroxy-7-methoxy-3-(4-methoxyphenyl)-1-methyl-1,4-dihydro-4-quinolinone (compound 35)-CRL 8377

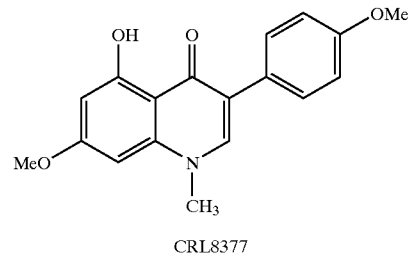

CRL8377

760 mg (2.56 mmol) of compound 34 are dissolved in 15 ml of anhydrous N,N-dimethylformamide (DMF) under a nitrogen atmosphere. 706 mg of potassium carbonate (2 eq) and then 0.16 ml of methyl iodide (1 eq) are successively added to this suspension. The reaction is stirred at room temperature for 2 hours. The solvents are evaporated off. The residue obtained is taken up in ethyl acetate and washed twice with water. The organic phase obtained is dried over MgSO$_4$ and then evaporated under reduced pressure. The crude solid is washed with hot ethyl acetate to give 710 mg (89%) of derivative 35.

m.p.: 166–167° C. (washing with EtAOc)

IR (KBr): ν 1648, 1615, 1561, 1516 cm$^{-1}$ $^1$H NMR (250 MHz, CDCl$_3$): δ3.74 (s, 3H, OCH$_3$), 3.83 (s, 3H, OCH$_3$), 3.88 (s, 3H, NCH$_3$), 6.17 (d, 1H, J=2.5 Hz, H$_{Ar}$), 6.38 (d, 1H, J=2.5 Hz, H$_{Ar}$), 6.95 (d, 2H, J=7.5 Hz, H$_{Ar}$), 7.50 (s, 1H, =CH), 7.54 (d, 2H, J=7.5 Hz, H$_{Ar}$), 15.22 (s, 1H, OH)

$^{13}$C NMR (62.90 MHz, DMSO-d$_6$): δ41.4, 55.3, 55.5, 89.1, 96.4, 109.0, 113.8 (2), 120.0, 126.4, 129.7 (2), 142.0, 142.2, 159.0, 164.3, 165.1, 179.6

MS (ion spray): m/z 312 (M+H)$^+$

Anal. calculated for C$_{18}$H$_{17}$NO$_4$: C, 69.44; H, 5.50; N, 4.50 Found: C, 69.27; H, 5.67, N, 4.47

EXAMPLE 21

7-Methoxy-3-(4-methoxyphenyl)-1-methyl-5-trifluoromethanesulfonate-1,4-dihydro-4-quinolinone (compound 36)-CRL 8493

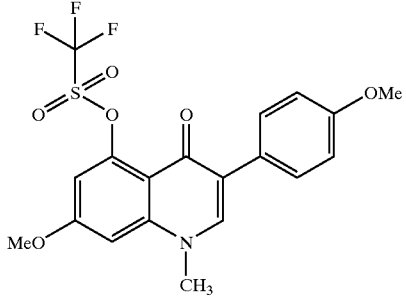

200 mg (0.64 mmol) of compound 35 are dissolved in 15 ml of anhydrous $CH_2Cl_2$ and 0.16 ml of pyridine (3 eq) at 0° C., under a nitrogen atmosphere. 0.32 ml of triflic anhydride (3 eq) is added to this solution at 0° C. The reaction is stirred at room temperature for 1.5 hours. The solvents are evaporated off. The residue obtained is taken up in $CH_2Cl_2$ and washed twice with saturated sodium hydrogen carbonate solution. The organic phase obtained is dried over $MgSO_4$ and then evaporated under reduced pressure. The residue is purified by chromatography on a column of silica (eluent: 4/6 EtOAc/PE) to give 201 mg (71%) of derivative 36.

m.p.: 184–185° C.

IR (KBr): v 1628, 1593, 1513 $cm^{-1}$ $^1$H NMR (250 MHz, $CDCl_3$): δ3.76 (s, 3H, $NCH_3$), 3.81 (s, 3H, $OCH_3$), 3.94 (s, 3H, $OCH_3$), 6.71 (s, 1H, $H_{Ar}$), 6.74 (s, 1H, $H_{Ar}$), 6.89 (d, 2H, J=8.5 Hz, $H_{Ar}$), 7.51 (d, 2H, J=8.5 Hz, $H_{Ar}$), 7.52 (s, 1H, =CH)

$^{13}$C NMR (62.90 MHz, DMSO-$d_6$): δ41.2, 55.1, 56.4, 99.5, 106.7, 113.2, 113.4 (2), 121.1, 127.2, 129.8 (2), 143.0, 143.1, 149.0, 158.3, 160.9, 172.9

MS (ion spray): m/z 444 $(M+H)^+$

EXAMPLE 22

7-Methoxy-3-(4-methoxyphenyl)-1-methyl-5-vinyl-1,4-dihydro-4-quinolinone (compound 37)-CRL 8494

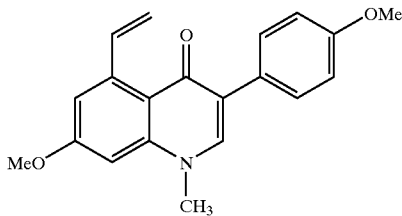

62 mg of tetrakis(triphenylphosphine)palladium (0) and 54 mg of lithium chloride are suspended in 4 ml of anhydrous of N,N-dimethylformamide (DMF) under a nitrogen atmosphere. In parallel, 400 mg (0.90 mmol) of compound 36 and 0.4 ml (1.5 eq) of vinyltributyltin are dissolved in 10 ml of anhydrous N,N-dimethylformamide (DMF). The solution containing the triflate is transferred into the first solution via a transfer needle. The final reaction mixture is stirred at 90° C. for 1.5 hours. After cooling, the solvent is evaporated off. The residue is taken up in ethyl acetate and then washed with 10% potassium fluoride solution. The organic phase obtained is dried over $MgSO_4$ and then evaporated under reduced pressure. The residue is purified by chromatography on a column of silica (eluent: 7/3 $CH_2Cl_2$/EtOAc) to give 200 mg (69%) of compound 37.

m.p.: 130–131° C. (EtAOc/PE)

IR (KBr): v 1624, 1603, 1582, 1506 $cm^{-1}$ $^1$H NMR (250 MHz, $CDCl_3$): δ3.68 (s, 3H, $NCH_3$), 3.80 (s, 3H, $OCH_3$), 3.90 (s, 3H, $OCH_3$), 5.29 (dd, 1H, J=1.8, 11.00 Hz, =$CH_2$), 5.45 (dd, 1H, J=1.8, 17.3 Hz, =$CH_2$), 6.59 (s, 1H, $H_{Ar}$), 6.89 (d, 2H, J=8.8 Hz, $H_{Ar}$), 6.91 (s, 1H, $H_{Ar}$), 7.45 (s, 1H, =CH), 7.52 (d, 2H, J=8.8 Hz, $H_{Ar}$), 8.10 (dd, 1H, J=11.0, 17.3 Hz, $CH_{vinyl}$)

$^{13}$C NMR (62.90 MHz, $CDCl_3$): δ41.3, 55.2, 55.4, 97.4, 111.7, 113.5 (2), 114.4, 118.8, 122.5, 127.8, 129.9 (2), 139.8, 140.8, 142.8, 144.2, 158.6, 161.3, 177.2

MS (ion spray): m/z 322 $(M+H)^+$

Anal. calculated for $C_{20}H_{19}NO_3$: C, 74.75; H, 5.96; N, 4.36; Found: C, 74.97; H, 6.16; N, 4.44

EXAMPLE 23

5-Ethyl-7-methoxy-3-(4-methoxyphenyl)-1-methyl-1,4-dihydro-4-quinolinone (compound 38)-CRL 8393

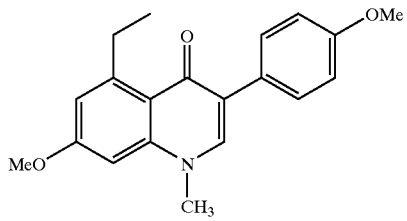

200 mg (0.62 mmol) of compound 37 are dissolved in 15 ml of ethyl acetate under a nitrogen atmosphere. 20 mg of palladium-on-charcoal (10%) are added to this solution. The hydrogenation is carried out using a Parr apparatus under 50 psi of hydrogen at room temperature for 7 hours. The catalyst is removed by filtration through celite. The filtrate is evaporated under reduced pressure. The residue is purified by chromatography on a column of silica (eluent: 9/1 $CH_2Cl_2$/EtOAc) to give 160 mg (79%) of compound 38.

m.p.: 124–125° C. (EtAOc)

(KBr): v 1634, 1610, 1586, 1557, 1508 $cm^{-1}$ $^1$H NMR (250 MHz, $CDCl_3$): δ1.29 (t, 3H, J=7.2 Hz, $CH_3$), 3.44 (q, 2H, J=7.2 Hz, $CH_2$), 3.67 (s, 3H, $NCH_3$), 3.80 (s, 3H, $OCH_3$), 3.89 (s, 3H, $OCH_3$), 6.51 (d, 1H, J=2.5 Hz, $H_{Ar}$), 6.74 (d, 1H, J=2.5 Hz, $H_{Ar}$), 6.91 (d, 2H, J=8.8 Hz, $H_{Ar}$), 7.44 (s, 1H, =CH), 7.52 (d, 2H, J=8.8 Hz, $H_{Ar}$)

$^{13}$C NMR (62.90 MHz, $CDCl_3$): δ15.4, 28.8, 40.5, 54.4 (2), 94.9, 112.5, 112.6 (2), 118.4, 121.8, 127.4, 129.1 (2), 139.6, 142.7, 149.8, 157.5, 160.3, 176.3

MS (ion spray): m/z 324 $(M+H)^+$

Anal. calculated for $C_{20}H_{21}NO_3$: C, 74.28; H, 6.55; N, 4.33 Found: C, 74.50; H, 6.31; N, 4.50

EXAMPLE 24

7-Methoxy-3-(4-methoxyphenyl)-1-methyl-5-phenyl-1,4-dihydro-4-quinolinone (compound 39)-CRL 8394

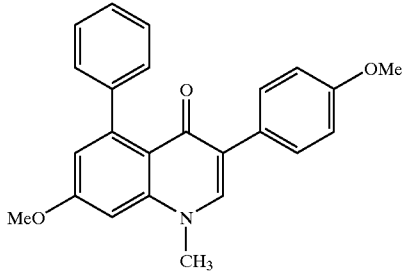

100 mg (0.22 mmol) of compound 35 and 17 mg of tetrakis(triphenylphosphine)palladium (0) are dissolved in 4 ml of dioxane, under a nitrogen atmosphere. The solution is stirred at room temperature for 30 minutes. 42 mg (1.5 eq) of phenylboronic acid dissolved in 2 ml of ethanol are added to the reaction solution, followed by addition of 2 ml of saturated sodium hydrogen carbonate solution. The two-phase mixture is stirred at reflux for 3 hours. After cooling, the dioxane is evaporated off and the aqueous phase obtained is extracted with ethyl acetate (2×5 ml). The organic phase is washed with saturated sodium chloride solution. The organic phase is dried over $MgSO_4$ and then evaporated under reduced pressure. The residue is purified by chromatography on a column of silica (eluent: 9/1 $CH_2Cl_2$/EtOAc) to give 60 mg (71%) of compound 39.

m.p.: 204–205° C.

IR (KBr): v 1635, 1612, 1579, 1558, 1510 cm$^{-1}$ $^1$H NMR (250 MHz, CDCl$_3$): δ3.78 (s, 3H, NCH$_3$), 3.80 (s, 3H, OCH$_3$), 3.93 (s, 3H, OCH$_3$), 6.75 (d, 1H, J=2.2 Hz, H$_{Ar}$), 6.77 (d, 1H, J=2.2 Hz, H$_{Ar}$), 6.85 (d, 2H, J=8.8 Hz, H$_{Ar}$), 7.26–7.34 (m, 5H, H$_{Ar}$), 7.48 (d, 2H, J=8.8 Hz, H$_{Ar}$), 7.53 (s, 1H, =CH)

$^{13}$C NMR (62.90 MHz, CDCl$_3$): δ41.4, 55.4, 55.7, 97.9, 113.6 (2), 115.5, 115.6, 118.8, 122.8, 126.4, 127.5 (2), 128.1 (2), 130.1 (2), 141.2, 143.2, 143.8, 146.8, 158.6, 160.8, 175.7

MS (ion spray): m/z 372 (M+H)$^+$

Anal. calculated for $C_{24}H_{21}NO_3$: C, 77.61; H, 5.70; N, 3.77. Found: C, 77.27; H, 5.81; N, 3.59

EXAMPLE 25

5,7-Dimethoxy-3-(4-methoxyphenyl)-1-methyl-1,4-dihydro-4-quinolinone (compound 40)-CRL 8340

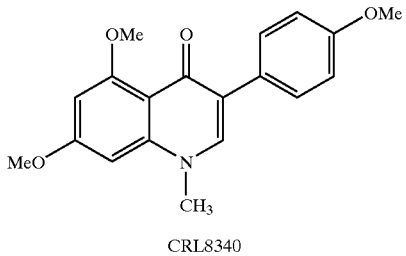

CRL8340

500 mg (1.61 mmol) of compound 33 are added to 20 ml of anhydrous N,N-dimethylformamide (DMF) under a nitrogen atmosphere. 1.66 g of anhydrous $K_2CO_3$ (7.5 eq) and then 0.30 ml of methyl iodide (3 eq) are successively added to this suspension. The reaction is stirred at room temperature for 18 hours. The solvents are evaporated off. The residue is taken up in $CH_2Cl_2$ and washed twice with water. The organic phase obtained is dried over $MgSO_4$ and then evaporated under reduced pressure. The crude residue is purified on a column of silica (eluent: 9/1 $CH_2Cl_2$/EtOAc) to give 418 mg (80%) of derivative 40.

m.p.: 172–173° C. (washing with EtOH)

IR (KBr): v 1636, 1610, 1587, 1505 cm$^{-1}$ $^1$H NMR (250 MHz, DMSO-d$_6$): δ3.76 (s, 3H, NCH$_3$), 3.77 (s, 3H, OCH$_3$), 3.79 (s, 3H, OCH$_3$), 3.86 (s, 3H, OCH$_3$), 6.43 (s, 1H, H$_{Ar}$), 6.49 (s, 1H, H$_{Ar}$), 6.91 (d, 2H, J=8.5 Hz, H$_{Ar}$), 7.54 (d, 2H, J=8.5 Hz, H$_{Ar}$), 7.92 (s, 1H, =CH)

$^{13}$C NMR (62.90 MHz, DMSO-d$_6$): δ40.9, 55.0, 55.5, 55.8, 90.5, 94.5, 111.8, 113.1 (2), 121.2, 128.4, 129.7 (2), 141.0, 143.9, 157.8, 161.9, 162.2, 173.9

MS (ion spray): m/z 326 (M+H)$^+$

EXAMPLE 26

1-Allyl-5,7-dimethoxy-3-(4-methoxyphenyl)-1,4-dihydro-4-quinolinone (compound 41)-CRL 8495 and 4-(allyloxy)-5,7-dimethoxy-3-(4-methoxyphenyl)quinoline (compound 42)-CRL 8496 a) 1-Allyl-5,7-dimethoxy-3-(4-methoxyphenyl)-1,4-dihydro-4-quinolinone (compound 41)-CRL 8495

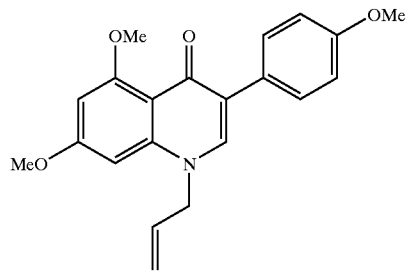

200 mg (0.64 mmol) of compound 33 are added to 10 ml of anhydrous N,N-dimethylformamide (DMF) under a nitrogen atmosphere. 666 mg of anhydrous potassium carbonate (7.5 eq) and then 0.17 ml of allyl bromide (3 eq) are successively added to this suspension. After stirring for 5 hours, a further 3 eq of allyl bromide are added to the reaction mixture. The reaction is stirred at room temperature for 18 hours. The solvents are evaporated off. The residue obtained is taken up in ethyl acetate and washed twice with water. The organic phase obtained is dried over $MgSO_4$ and then evaporated under reduced pressure. The residue obtained is purified by chromatography on a column of silica (eluent: 7/3 $CH_2Cl_2$/EtOAc) to give 25 mg (11%) of compound 42 and 160 mg (71%) of derivative 41.

m.p.: 169–170° C.

IR (KBr): v 1629, 1610, 1581, 1511 cm$^{-1}$ $^1$H NMR (250 MHz, CDCl$_3$): δ3.82 (s, 3H, OCH$_3$), 3.88 (s, 3H, OCH$_3$), 3.95 (s, 3H, OCH$_3$), 4.63–4.65 (m, 2H, CH$_2$), 5.20 (d, 1H, J=17.0 Hz, =CH$_2$), 5.32 (d, 1H, J=11.3 Hz, =CH$_2$), 5.92–6.07 (m, 1H, CH=), 6.27 (d, 1H, J=2.0 Hz, H$_{Ar}$), 6.35 (d, 1H, J=2.0 Hz, H$_{Ar}$), 6.91 (d, 2H, J=8.8 Hz, H$_{Ar}$), 7.45 (s, 1H, =CH), 7.60 (d, 2H, J=8.8 Hz, H$_{Ar}$)

$^{13}$C NMR (62.90 MHz, CDCl$_3$): δ55.1, 55.2, 55.6, 56.0, 90.2, 94.2, 112.6, 113.2 (2), 118.1, 123.3, 127.9, 129.9 (2), 131.2, 139.3, 143.3, 158.4, 162.3, 162.8, 175.6

MS (ion spray): m/z 352 (M+H)+
Anal. calculated for $C_{21}H_{21}NO_4$: C, 71.78; H, 6.02; N, 3.99. Found: C, 72.03; H, 5.88; N, 3.80 b) 4-(Allyloxy)-5,7-dimethoxy-3-(4-methoxyphenyl)-quinoline (compound 42)-CRL 8496

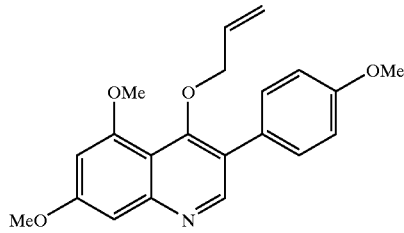

oil

IR (KBr): v 1617, 1567, 1512 cm$^{-1}$
$^1$H NMR (250 MHz, CDCl$_3$): δ3.87 (s, 3H, OCH$_3$), 3.94 (s, 3H, OCH$_3$), 3.96 (s, 3H, OCH$_3$), 4.16 (d, 2H, J=6.0 Hz, CH$_2$), 5.01 (d, 1H, J=8.5 Hz, =CH$_2$), 5.15 (d, 1H, J=17.0 Hz, =CH$_2$), 5.78–5.89 (m, 1H, =CH), 6.56 (d, 1H, J=2.0 Hz, H$_{Ar}$), 6.99 (d, 2H, J=8.8 Hz, H$_{Ar}$), 7.06 (d, 1H, J=2.0 Hz, H$_{Ar}$), 7.58 (d, 2H, J=8.8 Hz, H$_{Ar}$), 8.74 (s, 1H, H$_{Ar}$)
$^{13}$C NMR (62.90 MHz, CDCl$_3$): δ55.3, 55.5, 56.0, 75.0, 99.3, 100.5, 111.9, 113.8 (2), 117.8, 125.4, 127.8, 130.8 (2), 133.6, 152.7, 153.2, 157.0, 159.0, 159.8, 160.7
MS (ion spray): m/z 352 (M+H)+
Anal. calculated for $C_{21}H_{21}NO_4$: C, 71.78; H, 6.02; N, 3.99. Found: C, 71.67; H, 5.93; N, 4.21

EXAMPLE 27

1-(3-Butenyl)-5,7-dimethoxy-3-(4-methoxyphenyl)-1,4-dihydro-4-quinolinone (compound 43)-CRL 8497 and 4-(3-butenyloxy)-5,7-dimethoxy-3-(4-methoxyphenyl)quinoline (compound 44)-CRL 8498 a) 1-(3-Butenyl)-5,7-dimethoxy-3-(4-methoxyphenyl)-1,4-dihydro-4-quinolinone (compound 43)-CRL 8497

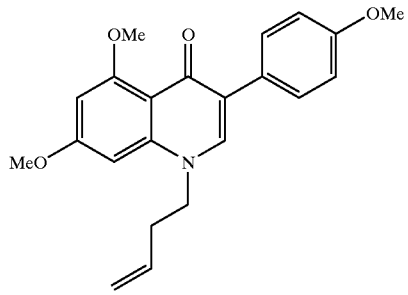

500 mg (1.61 mmol) of compound 33 are added to 10 ml of anhydrous N,N-dimethylformamide (DMF) under a nitrogen atmosphere. 1.67 g of anhydrous potassium carbonate (7.5 eq) and then 0.82 ml of 4-bromobut-1-ene (5 eq) are successively added to this suspension. The rection is stirred at room temperature for 18 hours. The solvents are evaported off. The residue is taken up in ethyl acetate and washed twice with water. The organic phase obtained is dried over MgSO$_4$ and then evaporated under reduced pressure. The crude product is purified by chromatography on a column of silica (eluent: 7/3 CH$_2$Cl$_2$/EtOAc) to give 47 mg (8%) of compound 44 and 335 mg (57%) of derivative 43.

oil

IR (KBr): v 1633, 1612, 1592, 1579 cm$^{-1}$
$^1$H NMR (250 MHz, CDCl$_3$): δ2.52 (q, 2H, J=7.0 Hz, CH$_2$), 3.75 (s, 3H, OCH$_3$), 3.84 (s, 3H, OCH$_3$), 3.88 (s, 3H, OCH$_3$), 3.99 (t, 2H, J=7.0 Hz, CH$_2$), 5.03 (dd, 1H, J=1.5, 17.2 Hz, =CH$_2$), 5.09 (d, 1H, J=9.8 Hz, =CH$_2$), 5.67–5.81 (m, 1H, =CH), 6.23 (d, 1H, J=2.5 Hz, H$_{Ar}$), 6.30 (d, 1H, J=2.5 Hz, H$_{Ar}$), 6.84 (d, 2H, J=8.8 Hz, H$_{Ar}$), 7.34 (s, 1H, =CH), 7.51 (d, 2H, J=8.8 Hz, H$_{Ar}$)
$^{13}$C NMR (62.90 MHz, CDCl$_3$): δ32.3, 53.0, 55.1, 55.2, 56.0, 89.7, 93.9, 112.7, 113.1 (2), 118.4, 122.8, 128.0, 129.8 (2), 133.1, 139.6, 142.8, 158.3, 162.3, 162.9, 175.5
MS (ion spray): m/z 352 (M+H)+
Anal. calculated for $C_{22}H_{23}NO_4$: C, 72.31; H, 6.34; N, 3.83. Found: C, 72.63; H, 6.14; N, 3.72 b) 4-(3-Butenyloxy)-5,7-dimethoxy-3-(4-methoxyphenyl)quinoline (compound 44)-CRL 8498

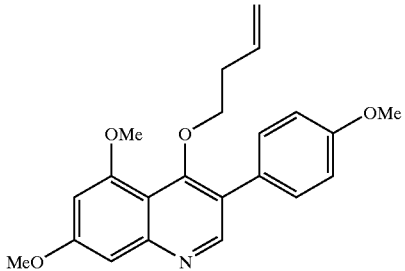

oil

IR (KBr): v 1616, 1568, 1514 cm$^{-1}$
$^1$H NMR (250 MHz, CDCl$_3$): δ2.31 (q, 2H, J=7.0 Hz, CH$_2$), 3.68 (t, 2H, J=7.0 Hz, CH$_2$), 3.86 (s, 3H, OCH$_3$) 3.93 (s, 3H, OCH$_3$), 3.96 (s, 3H, OCH$_3$), 4.96–5.03 (m, 2H, =CH$_2$), 5.60–5.77 (m, 1H, =CH), 6.54 (d, 1H, J=2.5 Hz, H$_{Ar}$), 6.99 (d, 2H, J=8.8 Hz, H$_{Ar}$), 7.04 (d, 1H, J=2.5 Hz, H$_{Ar}$), 7.56 (d, 2H, J=8.8 Hz, H$_{Ar}$), 8.72 (s, 1H, H$_{Ar}$)
$^{13}$C NMR (62.90 MHz, CDCl$_3$): δ34.4, 55.2, 55.3, 56.0, 73.6, 99.6, 100.4, 111.8, 113.8 (2), 116.5, 125.3, 127.8, 130.8 (2), 134.7, 152.7, 153.2, 156.9, 159.0, 160.2, 160.6
MS (ion spray): m/z 352 (M+H)+
Anal. calculated for $C_{22}H_{23}NO_4$: C, 72.31; H, 6.34; N, 3.83. Found: C, 72.56; H, 6.44; N, 4.02

EXAMPLE 28

1-[2-(1,3-Dioxolan-2-yl)ethyl]-5,7-dimethoxy-3-(4-methoxyphenyl)-1,4-dihydro-4-quinolinone (compound 45)-CRL 8499 and 4-[2-(1,3-dioxolan-2-yl)ethoxy]-5,7-dimethoxy-3-(4-methoxyphenyl) quinoline (compound 46)-CRL 8500 a) 1-[2-(1,3-Dioxolan-2-yl)ethyl]-5,7-dimethoxy-3-(4-methoxyphenyl)-1,4-dihydro-4-quinolinone (compound 45)-CRL 8499

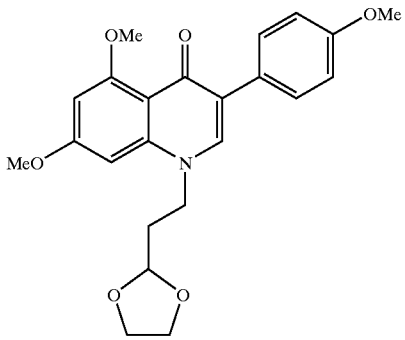

500 mg (1.61 mmol) of compound 33 are added to 10 ml of anhydrous N,N-dimethylformamide (DMF) under a nitrogen atmosphere. 1.67 g of anhydrous potassium carbonate (7.5 eq) and then 0.94 ml of 2-(2-bromoethyl)-1,3-dioxolane (5 eq) are successively added to this suspension. The reaction medium is stirred at room temperature for 18 hours. The solvents are evaporated off. The residue is taken up in ethyl acetate and washed twice with water. The organic phase obtained is dried over $MgSO_4$ and then evaporated under reduced pressure. The crude product is purified by chromatography on a column of silica (7/3 $CH_2Cl_2$/EtOAc) to give 139 mg (21%) of compound 46 and 450 mg (68%) of derivative 45.

m.p.: 141–142° C.

IR (KBr): ν cm$^{-1}$ $^1$H NMR (250 MHz, CDCl$_3$): δ2.20–2.28 (m, 2H, CH$_2$), 3.81 (s, 3H, OCH$_3$), 3.90 (s, 3H, OCH$_3$), 3.93 (s, 3H, OCH$_3$), 3.85–4.05 (m, 4H, CH$_2$), 4.18 (t, 2H, J=7.5 Hz, CH$_2$), 4.97 (t, 1H, J=3.8 Hz, CH), 6.34 (d, 1H, J=2.2 Hz, H$_{Ar}$), 6.42 (d, 1H, J=2.2 Hz, H$_{Ar}$), 6.90 (d, 2H, J=8.8 Hz, H$_{Ar}$), 7.48 (s, 1H, =CH), 7.58 (d, 2H, J=8.8 Hz, H$_{Ar}$)

$^{13}$C NMR (62.90 MHz, CDCl$_3$): δ31.7, 48.4, 55.2, 55.3, 56.1, 65.1 (2), 89.6, 94.3, 101.6, 112.8, 113.3 (2), 123.4, 128.1, 129.9 (2), 139.5, 142.9, 158.5, 162.6, 163.0, 175.6

MS (ion spray): m/z 412 (M+H)$^+$

Anal. calculated for C$_{23}$H$_{25}$NO$_6$: C, 67.14; H, 6.12; N, 3.40. Found: C, 67.41; H, 5.95; N, 3.17 b) 4-[2-(1,3-Dioxolan-2-yl)ethoxy]-5,7-dimethoxy-3-(4-methoxyphenyl)quinoline (compound 46)-CRL 8500

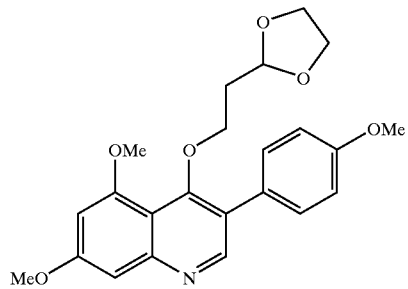

oil

IR (KBr): ν 1616, 1568, 1514 cm$^{-1}$ $^1$H NMR (250 MHz, CDCl$_3$): δ1.91 (q, 2H, J=7.0 Hz, CH$_2$), 3.73–3.88 (m, 6H, CH$_2$), 3.85 (s, 3H, OCH$_3$), 3.93 (s, 3H, OCH$_3$), 3.96 (s, 3H, OCH$_3$), 4.84 (t, 1H, J=4.7 Hz, CH), 6.54 (d, 1H, J=2.5 Hz, H$_{Ar}$), 6.98 (d, 2H, J=8.8 Hz, H$_{Ar}$), 7.05 (d, 1H, J=2.5 Hz, H$_{Ar}$), 7.54 (d, 2H, J=8.8 Hz, H$_{Ar}$), 8.71 (s, 1H, H$_{Ar}$)

$^{13}$C NMR (62.90 MHz, CDCl$_3$): δ34.5, 55.2, 55.5, 56.0, 64.7 (2), 70.3, 99.2, 100.3, 102.0, 111.8, 113.8 (2), 125.4, 127.7, 130.8 (2), 152.6, 153.1, 156.9, 159.0, 160.2, 160.7

MS (ion spray): m/z 412 (M+H)$^+$

Anal. calculated for C$_{23}$H$_{25}$NO$_6$: C, 67.14; H, 6.12; N, 3.40. Found: C, 66.81; H, 6.30; N, 3.62

EXAMPLE 29
N,N-Diethyl-2-[5,7-dimethoxy-3-(4-methoxyphenyl)-4-oxo-1,4-dihydro-1-quinolinyl]acetamide (compound 47)-CRL 8349

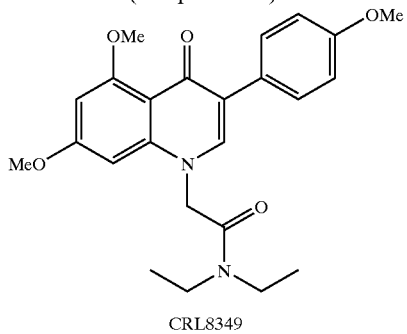

CRL8349

1.0 g (3.21 mmol) of compound 33 is dissolved in 30 ml of anhydrous N,N-dimethylformamide (DMF) under a nitrogen atmosphere. 115 mg (1.5 eq) of sodium hydride, washed beforehand in petroleum ether, are added portionwise to the reaction medium (exothermic reaction). 2-Chloro-N,N-diethylacetamide (0.88 ml, 2 eq) diluted in 5 ml of anhydrous N,N-dimethylformamide (DMF) is added to the medium. The reaction is heated for 3 hours at 90° C. After cooling, water is poured into the reaction mixture, which is then extracted with ethyl acetate (twice). The organic phase is dried over $MgSO_4$ and then evaporated under reduced pressure. The residue obtained is purified by chromatography on a column of silica (7/3 $CH_2Cl_2$/EtOAc) to give 1.17 g (86%) of compound 47.

m.p.: 245–246° C. (washing with EtOH)

IR (KBr): ν 1655, 1630, 1613, 1581 cm$^{-1}$ $^1$H NMR (250 MHz, CDCl$_3$): δ1.15 (t, 3H, J=7.2 Hz, CH$_3$), 1.27 (t, 3H, J=7.2 Hz, CH$_3$), 3.40–3.45 (m, 4H, CH$_2$), 3.81 (s, 3H, OCH$_3$), 3.83 (s, 3H, OCH$_3$), 3.92 (s, 3H, OCH$_3$), 4.70 (s, 2H, NCH$_2$CO), 5.98 (d, 1H, J=2.0 Hz, H$_{Ar}$), 6.32 (d, 1H, J=2.0 Hz, H$_{Ar}$), 6.88 (d, 2H, J=8.5 Hz, H$_{Ar}$), 7.34 (s, 1H, =CH), 7.56 (d, 2H, J=8.5 Hz, H$_{Ar}$)

$^{13}$C NMR (62.90 MHz, CDCl$_3$): δ13.0, 14.4, 40.9, 41.5, 54.8, 55.1, 55.2, 56.1, 89.8, 94.3, 112.5, 113.2 (2), 123.2, 128.0, 130.0 (2), 140.3, 143.8, 158.4, 162.3, 162.8, 164.8, 175.8

MS (ion spray): m/z 425 (M+H)$^+$

Anal. calculated for C$_{24}$H$_{28}$N$_2$O$_5$: C, 67.91; H, 6.65; N, 6.60. Found: C, 68.14; H, 6.80; N, 6.45

EXAMPLE 30
Ethyl 2-[5,7-dimethoxy-3-(4-methoxyphenyl)-4-oxo-1,4-dihydro-1-quinolinyl]acetate (compound 48)-CRL 8360 and ethyl 2-{[5,7-dimethoxy-3-(4-methoxyphenyl)-4-quinolinyl]oxy}acetate (compound 49)-CRL 8502 a) Ethyl 2-[5,7-dimethoxy-3-(4-methoxyphenyl)-4-oxo-1,4-dihydro-1-quinolinyl]acetate (compound 48)-CRL 8360

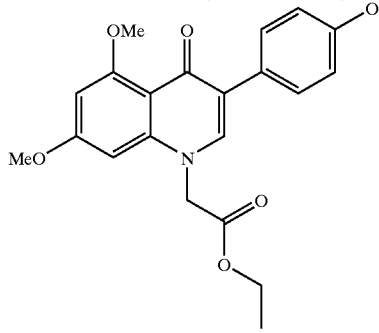

CRL8360

150 mg (0.48 mmol) of compound 33 are dissolved in 10 ml of anhydrous N,N-dimethylformamide (DMF) under a nitrogen atmosphere. 173 mg (1.5 eq) of sodium hydride, washed beforehand in petroleum ether, are added portionwise to the reaction medium (exothermic reaction). A solution of ethyl bromoacetate (0.11 ml, 2 eq) is added to the medium. The reaction is heated for 2.5 hours at 90° C. After cooling, water is poured into the reaction mixture, which is then stirred for 15 minutes. The solution is extracted with ethyl acetate (twice). The organic phase is dried over $MgSO_4$ and then evaporated under reduced pressure. The residue obtained is purified by chromatography on a column of silica (7/3 $CH_2Cl_2$/EtOAc) to give both 19 mg (10%) of compound 49 and 120 mg (63%) of derivative 48.

m.p.: 238–239° C. (EtAOc/PE)

IR (KBr): v 1747, 1635, 1614, 1582 $cm^{-1}$ $^1$H NMR (250 MHz, $CDCl_3$): δ1.25 (t, 3H, J=7.2 Hz, $CH_2CH_3$), 3.81 (s, 3H, $OCH_3$), 3.87 (s, 3H, $OCH_3$), 3.94 (s, 3H, $OCH_3$), 4.26 (q, 2H, J=7.2 Hz, $CH_2CH_3$), 4.66 (s, 2H, $CH_2CO$), 6.07 (d, 1H, J=2.0 Hz, $H_{Ar}$), 6.36 (d, 1H, J=2.0 Hz, $H_{Ar}$), 6.89 (d, 2H, J=8.5 Hz, $H_{Ar}$), 7.38 (s, 1H, =CH), 7.56 (d, 2H, J=8.5 Hz, $H_{Ar}$)

$^{13}$C NMR (62.90 MHz, $CDCl_3$): δ14.1, 55.0, 55.2, 55.3, 56.2, 62.2, 89.4, 94.4, 112.5, 113.4 (2), 124.0, 127.7, 130.1 (2), 139.8, 143.6, 158.7, 162.8, 163.2, 167.4, 175.9

MS (ion spray): m/z 398 $(M+H)^+$

Anal. calculated for $C_{22}H_{23}NO_6$: C, 66.49; H, 5.83; N, 3.52. Found: C, 66.23; H, 6.96; N, 3.75 b) Ethyl 2-{[5,7-dimethoxy-3-(4-methoxyphenyl)-4-quinolinyl]oxy}acetate (compound 49)-CRL 8502

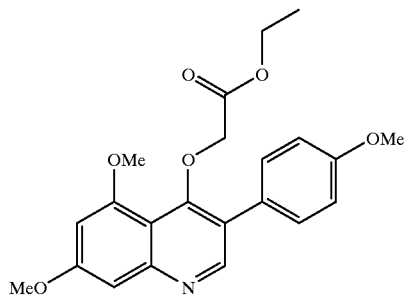

oil

IR (KBr): v 1739, 1617, 1569, 1514 $cm^{-1}$ $^1$H NMR (250 MHz, $CDCl_3$): δ1.26 (t, 3H, J=7.2 Hz, $CH_2CH_3$), 3.86 (s, 3H, $OCH_3$), 3.92 (s, 3H, $OCH_3$), 3.94 (s, 3H, $OCH_3$), 4.20 (q, 2H, J=7.2 Hz, $CH_2CH_3$), 4.21 (s, 2H, $CH_2CO$), 6.56 (d, 1H, J=2.2 Hz, $H_{Ar}$), 6.99 (d, 1H, J=8.8 Hz, $H_{Ar}$), 7.06 (d, 2H, J=2.2 Hz, $H_{Ar}$), 7.61 (d, 2H, J=8.8 Hz, $H_{Ar}$), 8.74 (s, 1H, =CH)

$^{13}$C NMR (62.90 MHz, $CDCl_3$): δ14.3, 55.4, 55.7, 56.2, 61.1, 68.3, 99.6, 100.6, 111.3, 114.2 (2), 125.1, 126.9, 130.9 (2), 152.8, 153.4, 156.8, 158.9, 159.4, 161.0, 168.5

MS (ion spray): m/z 398 $(M+H)^+$

Anal. calculated for $C_{22}H_{23}NO_6$: C, 66.49; H, 5.83; N, 3.52. Found: C, 66.55; H, 5.72; N, 3.46

EXAMPLE 31

[5,7-Dimethoxy-3-(4-methoxyphenyl)-4-oxo-1,4-dihydro-1-quinolinyl]acetonitrile (compound 50)-CRL 8372 and {[5,7-dimethoxy-3-(4-methoxyphenyl)-2-quinolinyl]-oxy}acetonitrile (compound 51)-CRL 8503 a) (5,7-Dimethoxy-3-(4-methoxyphenyl)-4-oxo-1,4-dihydro-1-quinolinyl]acetonitrile (compound 50)-CRL 8372

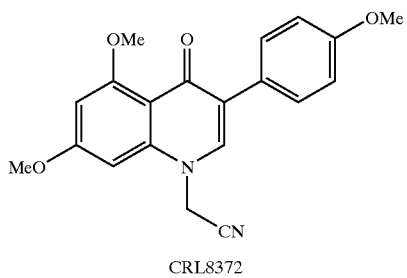

CRL8372

200 mg (0.64 mmol) of compound 33 are dissolved in 15 ml of anhydrous N,N-dimethylformamide (DMF) under a nitrogen atmosphere. 665 mg of anhydrous potassium carbonate (7.5 eq) and then 0.13 ml of bromoacetonitrile (3 eq) are successively added to this solution. The reaction is stirred at room temperature for 18 hours. The potassium carbonate is removed by filtration and the solvents are evaporated off. The residue is taken up in ethyl acetate and washed twice with water. The organic phase obtained is dried over $MgSO_4$ and then evaporated under reduced pressure. The crude solid is recrystallized from methanol to give 27 mg (12%) of compound 51 and 140 mg (62%) of derivative 50.

m.p.: 256–257° C. (EtOH)

IR (KBr): v 2216, 1660, 1607 $cm^{-1}$ $^1$H NMR (250 MHz, $CDCl_3$): δ3.82 (s, 3H, $OCH_3$), 3.96 (s, 6H, $OCH_3$), 4.83 (s, 2H, $CH_2$), 6.24 (d, 1H, J=2.0 Hz, $H_{Ar}$), 6.43 (d, 1H, J=2.0 Hz, $H_{Ar}$), 6.91 (d, 2H, J=8.8 Hz, $H_{Ar}$), 7.34 (s, 1H, =CH), 7.51 (d, 2H, J=8.8 Hz, $H_{Ar}$)

$^{13}$C NMR (62.90 MHz, DMSO-$d_6$): δ39.4, 55.1, 55.8, 56.0, 90.7, 94.8, 111.5, 113.1 (2), 115.9, 122.5, 127.6, 129.7 (2), 139.8, 142.5, 158.2, 162.3, 162.5, 174.2

MS (ion spray): m/z 351 $(M+H)^+$

Anal. calculated for $C_{20}H_{18}N_2O_4$: C, 68.56; H, 5.18; N, 8.00. Found: C, 68.67; H, 5.03; N, 7.78 b) {[5,7-Dimethoxy-3-(4-methoxyphenyl)-2-quinolinyl]oxy}acetonitrile (compound 51)-CRL 8503

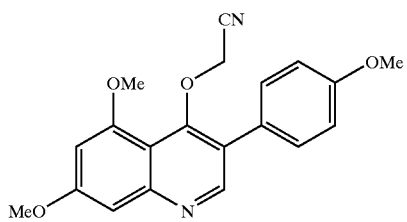

oil

IR (KBr): v 1616, 1572, 1516 $cm^{-1}$ $^1$H NMR (250 MHz, $CDCl_3$): δ3.88 (s, 3H, $OCH_3$), 3.96 (s, 3H, $OCH_3$), 4.03 (s, 3H, $OCH_3$), 4.39 (s, 2H, $OCH_2$), 6.63 (d, 1H, J=2.0 Hz, $H_{Ar}$), 7.04 (d, 2H, J=8.8 Hz, $H_{Ar}$), 7.09 (d, 1H, J=2.0 Hz, $H_{Ar}$), 7.55 (d, 2H, J=8.8 Hz, $H_{Ar}$), 8.77 (s, 1H, $H_{Ar}$)

$^{13}C$ NMR (62.90 MHz, $CDCl_3$): δ

MS (ion spray): m/z 351 (M+H)$^+$

Anal. calculated for $C_2C_{20}H_{18}N_2O_4$: C, 68.56; H, 5.18; N, 8.00. Found: C, 68.79; H, 4.95; N, 7.78

EXAMPLE 32

N-[3-(Dimethylamino)propyl]-5,7-dimethoxy-3-(4-methoxyphenyl)-1,4-dihydro-4-quinolinone (compound 52)-CRL 8357 and N-{2-[5,7-dimethoxy-3-(4-methoxyphenyl)-4-quinolyl]oxy}propyl-N,N-dimethylamine (compound 53)-CRL 8504 a) N-[3-(Dimethylamino)propyl]-5,7-dimethoxy-3-(4-methoxyphenyl)-1,4-dihydro-4-quinolinone (compound 52)-CRL 8357

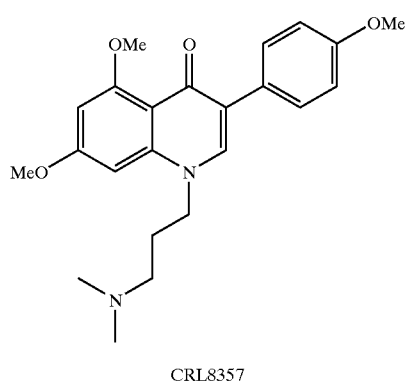

CRL8357

300 mg (0.96 mmol) of compound 33 are dissolved in 20 ml of anhydrous N,N-dimethylformamide (DMF) under a nitrogen atmosphere. 35 mg of sodium hydride (1.5 eq), washed beforehand in petroleum ether, are added portionwise to the reaction medium (exothermic reaction). 3-Dimethylaminopropyl chloride (234 mg, 2 eq) dissolved in 5 ml of anhydrous N,N-dimethylformamide (DMF) is added to the reaction medium. The reaction is heated at 90° C. for 2 hours. After cooling, the solvent is evaporated off. The residue is taken up in $CH_2Cl_2$ and water. After extraction, the organic phase is dried over $MgSO_4$ and then evaporated under reduced pressure. The residue obtained is purified by chromatography on a column of silica (8/2 $Et_2O$/MeOH and then 9/1 $CH_2Cl_2$/MeOH) to give 50 mg (13%) of compound 53 and 191 mg (50%) of derivative 52.

oil

IR (KBr): v 1636, 1609, 1594, 1514 cm$^{-1}$ $^1H$ NMR (250 MHz, $CDCl_3$): δ1.91–1.97 (m, 2H, $CH_2$), 2.18 (s, 6H, $CH_3$), 2.25 (t, 2H, J=7.2 Hz, $CH_2$), 3.78 (s, 3H, $OCH_3$), 3.86 (s, 3H, $OCH_3$), 3.90 (s, 3H, $OCH_3$), 4.07 (t, 2H, J=7.2 Hz, $CH_2$), 6.31 (d, 1H, J=2.0 Hz, $H_{Ar}$), 6.34 (d, 1H, J=2.0 Hz, $H_{Ar}$), 6.87 (d, 2H, J=8.5 Hz, $H_{Ar}$), 7.52 (s, 1H, =CH), 7.55 (d, 2H, J=8.5 Hz, $H_{Ar}$)

$^{13}C$ NMR (62.90 MHz, $CDCl_3$): δ25.7, 45.0 (2), 51.0, 55.0, 55.2, 55.4, 55.9, 89.7, 94.0, 112.7, 113.4 (2), 122.8, 128.0, 129.8 (2), 139.9, 142.9, 158.2, 162.3, 162.7, 175.5

MS: m/z 397 (M+H)$^+$

Anal. calculated for $C_{23}H_{28}N_2O_4$: C, 69.68; H, 7.12; N, 7.07. Found: C, 70.14; H, 6.90; N, 7.21 b) N-{2-[5,7-Dimethoxy-3-(4-methoxyphenyl)-4-quinolyl]oxy}propyl-N,N-dimethylamine (compound 53)-CRL 8504

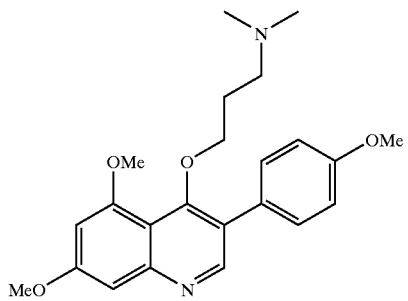

oil

IR (KBr): v 1617, 1568, 1514, 1246 cm$^{-1}$ $^1H$ NMR (250 MHz, $CDCl_3$): δ1.85–1.91 (m, 2H, $CH_2$), 2.36 (s, 6H, $CH_3$), 2.45 (t, 2H, J=7.0 Hz, $CH_2$), 3.71 (t, 2H, J=7.0 Hz, $CH_2$), 3.86 (s, 3H, $OCH_3$), 3.93 (s, 3H, $OCH_3$), 3.97 (s, 3H, $OCH_3$), 6.56 (d, 1H, J=2.2 Hz, $H_{Ar}$), 6.99 (d, 2H, J=8.8 Hz, $H_{Ar}$), 7.05 (d, 1H, J=2.2 Hz, $H_{Ar}$), 7.50 (d, 2H, J=8.8 Hz, $H_{Ar}$), 8.70 (s, 1H, $H_{Ar}$)

$^{13}C$ NMR (62.90 MHz, $CDCl_3$): δ26.6, 44.1 (2), 55.5, 55.7, 56.3, 56.4, 72.4, 99.6, 100.7, 111.6, 114.0 (2), 125.6, 127.9, 131.2 (2), 153.0, 153.2, 156.7, 158.9, 159.9, 160.9

MS (ion spray): m/z 397 (M+H)$^+$

Anal. calculated for $C_{23}H_{28}N_2O_4$: C, 69.68; H, 7.12; N, 7.07. Found: C, 69.53; H, 6.92; N, 7.16

EXAMPLE 33

N-[3-(Dimethylamino)ethyl]-5,7-dimethoxy-3-(4-methoxyphenyl)-1,4-dihydro-4-quinolinone (compound 54)-CRL 8350 and N-{2-[5,7-dimethoxy-3-(4-methoxyphenyl)-4-quinolyl]oxy}ethyl-N,N-dimethylamine (55)-CRL 8505 a) N-[3-(Dimethylamino)ethyl]-5,7-dimethoxy-3-(4-methoxyphenyl)-1,4-dihydro-4-quinolinone (compound 54)-CRL 8350

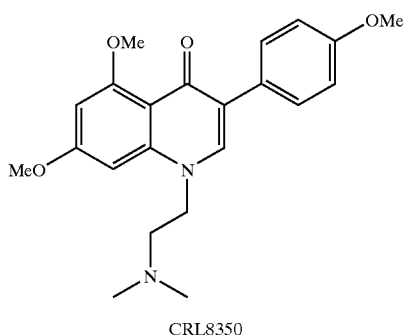

CRL8350

300 mg (0.96 mmol) of compound 33 are dissolved in 10 ml of anhydrous N,N-dimethylformamide (DMF) under a nitrogen atmosphere. 35 mg of sodium hydride (1.5 eq), washed beforehand in petroleum ether, are added portionwise to the reaction medium (exothermic reaction). 3-Dimethylaminoethyl chloride (206 mg, 2 eq) dissolved in 5 ml of anhydrous DMF is added to the reaction medium. The reaction is heated at 90° C. for 2–3 hours. After cooling, the solvent is evaporated off. The residue is taken up in $CH_2Cl_2$ and water. After extraction, the organic phase is dried over $MgSO_4$ and then evaporated under reduced pressure. The residue obtained is purified by chromatography on a column of silica gel treated with triethylamine (eluent: 99.5/0.5 $CH_2Cl_2$/MeOH) to give 55 mg (15%) of compound 55 and 221 mg (60%) of derivative 54.

m.p.: 172–173° C. (EtOH)

IR (KBr): v 1637, 1609, 1594, 1514 cm$^{-1}$ $^1$H NMR (250 MHz, CDCl$_3$): δ2.26 (s, 6H, CH$_3$), 2.64 (t, 2H, J=7.2 Hz, CH$_2$), 3.76 (s, 3H, OCH$_3$), 3.84 (s, 3H, OCH$_3$), 3.89 (s, 3H, OCH$_3$), 4.03 (t, 2H, J=7.2 Hz, CH$_2$), 6.29 (d, 2H, J=2.0 Hz, H$_{Ar}$), 6.84 (d, 2H, J=8.8 Hz, H$_{Ar}$), 7.40 (s, 1H, =CH), 7.52 (d, 2H, J=8.8 Hz, H$_{Ar}$)

$^{13}$C NMR (62.90 MHz, CDCl$_3$): δ45.6 (2), 51.9, 55.1, 55.2, 56.0, 56.8, 89.5, 94.0, 112.7, 113.2 (2), 123.0, 128.0, 129.9 (2), 139.7, 143.0, 158.3, 162.4, 162.9, 175.5

MS: m/z 383 (M+H)$^+$

Anal. calculated for C$_{22}$H$_{26}$N$_2$O$_4$: C, 69.09; H, 6.85; N, 7.32. Found: C, 68.87; H, 7.01; N, 7.49 b) N-{2-[5,7-Dimethoxy-3-(4-methoxyphenyl)-4-quinolyl]oxy}ethyl-N,N-dimethylamine (55)-CRL 8505

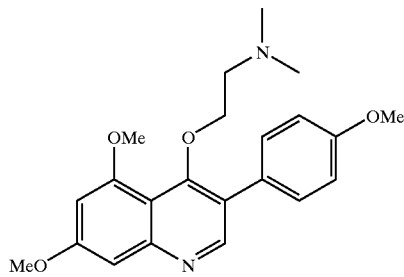

m.p.: 100–101° C. (EtOH)

IR (KBr): v 1616, 1577, 1566, 1512, 1243 cm$^{-1}$ $^1$H NMR (250 MHz, CDCl$_3$): δ2.16 (s, 6H, NCH$_3$), 2.46 (t, 2H, J=6.5 Hz, NCH$_2$), 3.73 (t, 2H, J=6.5 Hz, OCH$_2$), 3.77 (s, 3H, OCH$_3$), 3.94 (s, 3H, OCH$_3$), 3.97 (s, 3H, OCH$_3$), 6.55 (d, 1H, J=2.2 Hz, H$_{Ar}$), 6.99 (d, 2H, J=8.8 Hz, H$_{Ar}$), 7.05 (d, 1H, J=2.2 Hz, H$_{Ar}$), 7.56 (d, 2H, J=8.8 Hz, H$_{Ar}$), 8.71 (s, 1H, H$_{Ar}$)

$^{13}$C NMR (62.90 MHz, CDCl$_3$): δ45.6 (2), 55.3, 55.5, 56.0, 58.8, 71.7, 99.2, 100.4, 111.8, 113.8 (2), 125.4, 127.7, 130.9 (2), 152.8, 153.3, 157.0, 159.1, 160.5, 160.7

MS (ion spray): m/z 383 (M+H)$^+$

Anal. calculated for C$_{22}$H$_{26}$N$_2$O$_4$: C, 69.09; H, 6.85; N, 7.32. Found: C, 68.87; H, 6.69; N, 7.47

EXAMPLE 34

5,8-Dimethoxy-3-(4-methoxyphenyl)-1,4-dihydro-4-quinolinone (compound 56)-CRL 8371

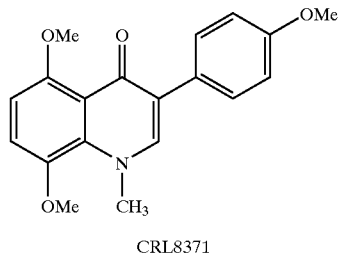

CRL8371

400 mg (1.28 mmol) of compound 29 are added to 20 ml of anhydrous N,N-dimethylformamide (DMF) under a nitrogen atmosphere. 1.33 g of anhydrous K$_2$CO$_3$ (7.5 eq) and then 0.24 ml of methyl iodide (3 eq) are successively added to this suspension. The reaction is stirred at room temperature for 18 hours. The solvents are evaporated off. The residue is taken up in CH$_2$Cl$_2$ and washed twice with water. The organic phase obtained is dried over MgSO$_4$ and then evaporated under reduced pressure. The crude residue is purified on a column of silica (eluent: CH$_2$Cl$_2$ and then EtOAc) to give 313 mg (75%) of derivative 56.

m.p.: 78–79° C. (EtOAc/PE)

IR (KBr): v 1630, 1589, 1568, 1511 cm$^{-1}$ $^1$H NMR (250 MHz, CDCl$_3$): δ3.82 (s, 3H, NCH$_3$), 3.87 (s, 3H, OCH$_3$), 3.90 (s, 3H, OCH$_3$), 4.04 (s, 3H, OCH$_3$), 6.70 (d, 1H, J=8.8 Hz, H$_{Ar}$), 6.92 (d, 2H, J=8.8 Hz, H$_{Ar}$), 7.05 (d, 1H, J=8.8 Hz, H$_{Ar}$), 7.40 (s, 1H, =CH), 7.60 (d, 2H, J=8.8 Hz, H$_{Ar}$)

$^{13}$C NMR (62.90 MHz, CDCl$_3$): δ46.8, 55.3, 56.9, 57.1, 105.4, 113.5 (2), 114.9, 120.0, 123.1, 127.8, 130.0 (2), 134.5, 143.4, 143.8, 155.1, 158.6, 176.0

MS (ion spray): m/z 326 (M+H)$^+$

Anal. calculated for C$_{19}$H$_{19}$NO$_4$: C, 70.14; H, 5.89; N, 4.30. Found: C, 69.85; H, 5.75; N, 4.13

EXAMPLE 35

N,N-Diethyl-2-[5,8-dimethoxy-3-(4-methoxyphenyl)-4-oxo-1,4-dihydro-1-quinolinyl]acetamide (compound 57)-CRL 8380

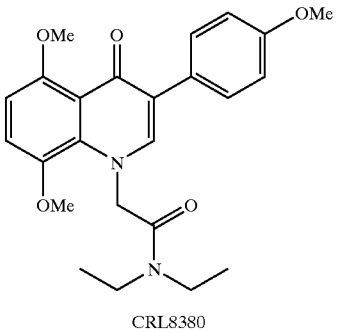

CRL8380

300 mg (0.96 mmol) of compound 29 are dissolved in 15 ml of anhydrous N,N-dimethylformamide (DMF) under a nitrogen atmosphere. 35 mg (1.44 mmol, 1.5 eq) of NaH, washed beforehand in petroleum ether, are added portion-wise to the reaction medium (exothermic reaction). 2-Chloro-N,N-diethylacetamide (2 eq) is added. The reaction is heated at 90° C. for 3 hours. After cooling, the solvent is evaporated. The residue is taken up in ethyl acetate. The organic phase is washed with water, dried over MgSO$_4$ and then evaporated under reduced pressure. The residue obtained is purified by chromatography on a column of silica (7/3 CH$_2$Cl$_2$/EtOAc) to give 258 mg (63%) of compound 57.

m.p.: 162–163° C. (EtOAc)

IR (KBr): v 1653, 1627, 1604, 1570, 1513 cm$^{-1}$ $^1$H NMR (250 MHz, CDCl$_3$): δ1.17 (t, 3H, J=7.0 Hz, CH$_3$), 1.28 (t, 3H, J=7.0 Hz, CH$_3$), 3.36 (q, 2H, J=7.0 Hz, CH$_2$), 3.45 (q, 2H, J=7.0 Hz, CH$_2$), 3.73 (s, 3H, OCH$_3$), 3.80 (s, 3H, OCH$_3$), 3.88 (s, 3H, OCH$_3$), 5.02 (s, 2H, CH$_2$CO), 6.65 (d, 1H, J=9.0 Hz, H$_{Ar}$), 6.87 (d, 2H, J=8.8 Hz, H$_{Ar}$), 6.98 (d, 1H, J=9.0 Hz, H$_{Ar}$), 7.29 (s, 1H, =CH), 7.61 (d, 2H, J=8.8 Hz, H$_{Ar}$)

$^{13}$C NMR (62.90 MHz, CDCl$_3$): δ13.1, 14.1, 40.6, 41.1, 55.2, 57.2, 57.5, 58.5, 105.5, 113.3 (2), 114.9, 119.9, 123.3, 127.7, 130.1 (2), 134.2, 143.2, 143.6, 155.3, 158.6, 166.4, 176.1

MS (ion spray): m/z 425 (M+H)$^+$

Anal. calculated for C$_{24}$H$_{28}$N$_2$O$_5$: C, 67.91; H, 6.65; N, 6.60. Found: C, 68.29; H, 6.78; N, 6.43

EXAMPLE 36

Ethyl 2-[5,8-dimethoxy-3-(4-methoxyphenyl)-4-oxo-1,4-dihydro-1-quinolinyl]acetate (compound 58)-CRL 8381 and ethyl 2-{[5,8-dimethoxy-3-(4-methoxyphenyl)-4-quinolinyl]oxy}acetate (compound 59)-CRL 8506 a) Ethyl 2-[5,8-dimethoxy-3-(4-methoxyphenyl)-4-oxo-1,4-dihydro-1-quinolinyl]acetate (compound 58)-CRL 8381

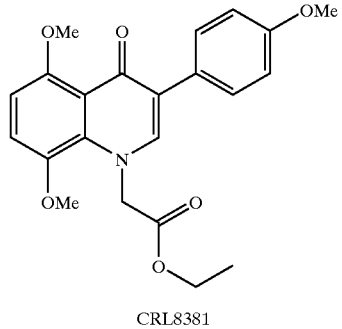

CRL8381

300 mg (0.96 mmol) of compound 29 are dissolved in 15 ml of anhydrous N,N-dimethylformamide (DMF) under a nitrogen atmosphere. 35 mg (1.5 eq) of NaH, washed beforehand in petroleum ether, are added portionwise to the reaction solution (exothermic reaction), at 0° C. A solution of ethyl bromoacetate (0.22 ml, 2 eq) diluted in 5 ml of DMF is added to the medium. The reaction is heated at 90° C. for 3 hours. After cooling, the water is poured into the reaction mixture. The reaction solution is extracted with ethyl acetate (twice). The organic phase obtained is dried over $MgSO_4$ and then evaporated under reduced pressure. The residue obtained is purified by chromatography on a column of silica (7/3 $CH_2Cl_2$/EtOAc) to give 47 mg (12%) of compound 59 and 212 mg (55%) of derivative 58.

m.p.: 116–117° C. (washing with $Et_2O$)

IR (KBr): v 1752, 1634, 1592, 1572, 1514 $cm^{-1}$ $^1$H NMR (250 MHz, $CDCl_3$): δ1.28 (t, 3H, J=7.0 Hz, $CH_3$), 3.77 (s, 3H, $OCH_3$), 3.81 (s, 3H, $OCH_3$), 3.85 (s, 3H, $OCH_3$), 4.25 (q, 2H, J=7.0 Hz, $CH_2$), 4.90 (s, 2H, $CH_2$), 6.69 (d, 1H, J=8.8 Hz, $H_{Ar}$), 6.89 (d, 2H, J=8.8 Hz, $H_{Ar}$), 6.99 (d, 1H, J=8.8 Hz, $H_{Ar}$), 7.30 (s, 1H, =CH), 7.60 (d, 2H, J=8.8 Hz, $H_{Ar}$)

$^{13}$C NMR (62.90 MHz, $CDCl_3$): δ14.2, 55.2, 56.5, 56.9, 59.1, 61.4, 105.6, 113.4 (2), 114.1, 119.7, 123.6, 127.5, 130.0 (2), 133.5, 142.9, 142.9, 155.1, 158.7, 168.3, 176.1

MS (ion spray): m/z 398 $(M+H)^+$

Anal. calculated for $C_{22}H_{23}NO_6$: C, 66.49; H, 5.83; N, 3.52. Found: C, 66.19; H, 5.96; N, 3.72 b) Ethyl 2-{[5,8-dimethoxy-3-(4-methoxyphenyl)-4-quinolinyl]oxy}acetate (compound 59)-CRL 8506

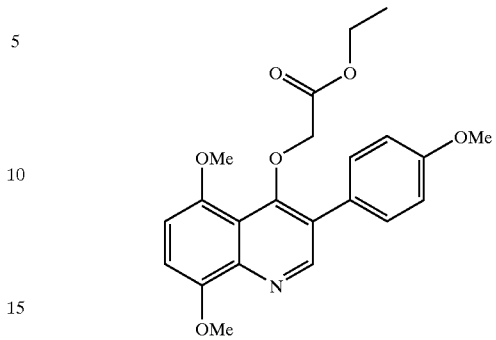

m.p.: 90–91° C. (washing with $Et_2O$)

IR (KBr): v 1763, 1611, 1590, 1517 $cm^{-1}$ $^1$H NMR (250 MHz, $CDCl_3$): δ1.24 (t, 3H, J=7.0 Hz, $CH_3$), 3.86 (s, 3H, $OCH_3$), 3.90 (s, 3H, $OCH_3$), 4.05 (s, 3H, $OCH_3$), 4.20 (q, 2H, J=7.0 Hz, $CH_2$), 4.23 (s, 2H, $CH_2$), 6.83 (d, 1H, J=8.8 Hz, $H_{Ar}$), 6.96 (d, 2H, J=8.8 Hz, $H_{Ar}$), 7.00 (d, 1H, J=8.8 Hz, $H_{Ar}$), 7.63 (d, 2H, J=8.8 Hz, $H_{Ar}$), 8.88 (s, 1H, =CH)

$^{13}$C NMR (62.90 MHz, $CDCl_3$): δ14.3, 55.4, 56.2, 56.5, 61.1, 70.1, 106.3, 107.3, 114.2 (2), 116.8, 126.7, 127.6, 131.1 (2), 142.5, 149.2, 149.9, 152.1, 158.4, 159.6, 168.5

MS (ion spray): m/z 398 $(M+H)^+$

Anal. calculated for $C_{22}H_{23}NO_6$: C, 66.49; H, 5.83; N, 3.52. Found: C, 66.17; H, 6.01; N, 3.67

EXAMPLE 37

1-[3-(Dimethylamino)propyl]-5,8-dimethoxy-3-(4-methoxyphenyl)-1,4-dihydro-4-quinolinone (compound 60)-CRL 8507 and N-{2-[5,8-dimethoxy-3-(4-methoxyphenyl)-4-quinolyl]oxy}propyl-N,N-dimethylamine (compound 61)-CRL 8508 a) 1-[3-(Dimethylamino)propyl]-5,8-dimethoxy-3-(4-methoxyphenyl)-1,4-dihydro-4-quinolinone (compound 60)-CRL 8507

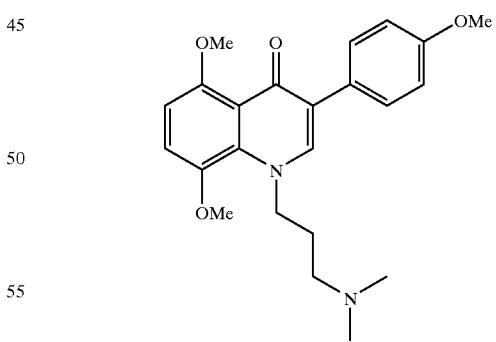

300 mg (0.96 mmol) of compound 29 are dissolved in 10 ml of anhydrous N,N-dimethylformamide (DMF) under a nitrogen atmosphere. 35 mg (1.5 eq) of NaH, washed beforehand in petroleum ether, are added portionwise to the reaction solution (exothermic reaction), at 0° C. 3-Dimethylaminopropyl chloride (305 mg, 2 eq) dissolved in 5 ml of anhydrous N,N-dimethylformamide (DMF) is added to the reaction medium. The reaction is heated at 90° C. for 3 hours. After cooling, water is poured into the reaction mixture. The reaction solution is extracted with ethyl acetate (twice). The organic phase obtained is dried over $MgSO_4$ and then evaporated under reduced pressure. The residue obtained is purified by chromatography on a column of silica (95/5 EtOAc/$NH_3$ and then 1% MeOH) to give 46 mg (12%) of compound 61 and 283 mg (74%) of derivative 60.

oil

IR (film): v 1629, 1598, 1569, 1512 $cm^{-1}$ $^1$H NMR (250 MHz, $CDCl_3$): δ1.84 (t, 2H, J=7.0 Hz, $CH_2$), 2.11 (s, 6H, $CH_3$), 2.11–2.16 (m, 2H, $CH_2$), 3.77 (s, 3H, $OCH_3$), 3.84 (s, 3H, $OCH_3$), 3.86 (s, 3H, $OCH_3$), 4.42 (t, 2H, J=7.0 Hz, $CH_2$), 6.67 (d, 1H, J=8.8 Hz, $H_{Ar}$), 6.87 (d, 2H, J=8.8 Hz, $H_{Ar}$), 6.99 (d, 1H, J=8.8 Hz, $H_{Ar}$), 7.52 (s, 1H, =CH), 7.59 (d, 2H, J=8.8 Hz, $H_{Ar}$)

$^{13}$C NMR (62.90 MHz, $CDCl_3$): δ28.5, 45.0 (2), 55.2, 56.0, 56.1, 56.7, 56.9, 105.5, 113.4 (2), 114.2, 120.5, 122.8, 128.0, 129.9 (2), 133.1, 143.3, 143.5, 155.1, 158.6, 176.2

MS (ion spray): m/z 397 (M+H)$^+$

Anal. calculated for $C_{23}H_{28}N_2O_4$: C, 69.68; H, 7.12; N, 7.07. Found: C, 69.77; H, 6.80; N, 7.03 b) N-{2-[5,8-Dimethoxy-3-(4-methoxyphenyl)-4-quinolyl]oxy}propyl-N,N-dimethylamine (compound 61)-CRL 8508

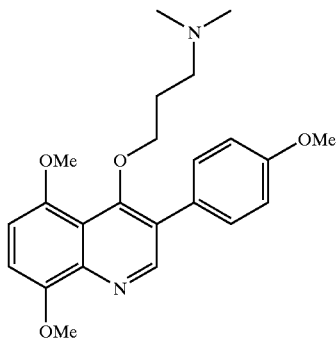

oil

IR (film): v 1611, 1588, 1515 $cm^{-1}$ $^1$H NMR (250 MHz, $CDCl_3$): δ1.69–1.75 (m, 2H, $CH_2$), 2.11 (s, 6H, $CH_3$), 2.19 (t, 2H, J=7.0 Hz, $CH_2$), 3.68 (t, 2H, J=7.0 Hz, $CH_2$), 3.84 (s, 3H, $OCH_3$), 3.93 (s, 3H, $OCH_3$), 4.02 (s, 3H, $OCH_3$), 6.80 (d, 1H, J=8.8 Hz, $H_{Ar}$), 6.92 (d, 2H, J=8.8 Hz, $H_{Ar}$), 7.48 (d, 1H, J=8.8 Hz, $H_{Ar}$), 7.56 (d, 2H, J=8.8 Hz, $H_{Ar}$), 8.84 (s, 1H, =CH)

$^{13}$C NMR (62.90 MHz, $CDCl_3$): δ28.3, 45.4 (2), 55.4, 56.2, 56.5, 56.7, 73.4, 105.9, 107.0, 114.0 (2), 117.4, 127.7, 128.0, 131.1 (2), 142.6, 149.5, 149.9, 152.1, 159.4, 160.1

MS (ion spray): m/z 397 (M+H)$^+$

Anal. calculated for $C_{23}H_{28}N_2O_4$: C, 69.68; H, 7.12; N, 7.07. Found: C, 69.43; H, 6.99; N, 6.88

EXAMPLE 38

N-[3-(Dimethylamino)ethyl]-5,8-dimethoxy-3-(4-methoxyphenyl)-1,4-dihydro-4-quinolinone (compound 62)-CRL 8382 and N-{2-[5,8-dimethoxy-3-(4-methoxyphenyl)-4-quinolyl]oxy}ethyl-N,N-dimethylamine (compound 63)-CRL 8370 a) N-[3-(Dimethylamino)ethyl]-5,8-dimethoxy-3-(4-methoxyphenyl)-1,4-dihydro-4-quinolinone (compound 62)-CRL 8382

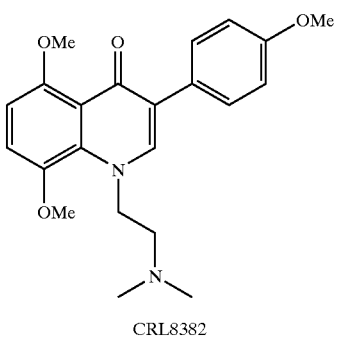

CRL8382

300 mg (0.96 mmol) of compound 29 are dissolved in 10 ml of anhydrous N,N-dimethylformamide (DMF) under a nitrogen atmosphere. 35 mg (1.5 eq) of NaH, washed beforehand in petroleum ether, are added portionwise to the reaction solution (exothermic reaction), at 0° C. 3-Dimethylaminoethyl chloride (280 mg, 2 eq) dissolved in 5 ml of anhydrous N,N-dimethylformamide (DMF) is added to the reaction medium. The reaction is heated at 90° C. for 3 hours. After cooling, water is poured into the reaction mixture. The reaction solution is extracted with ethyl acetate (twice). The organic phase obtained is dried over $MgSO_4$ and then evaporated under reduced pressure. The residue obtained is purified by chromatography on a column of silica (7/3 $CH_2Cl_2$/EtOAc) to give 40 mg (11%) of compound 63 and 236 mg (64%) of derivative 62.

m.p.: 69–70° C. (washing with $Et_2O$)

IR (KBr): v 1627, 1590, 1570, 1514 $cm^{-1}$ $^1$H NMR (250 MHz, $CDCl_3$): δ2.23 (s, 6H, $CH_3$), 2.61 (t, 2H, J=7.0 Hz, $CH_2$), 3.78 (s, 3H, $OCH_3$), 3.85 (s, 3H, $OCH_3$), 3.87 (s, 3H, $OCH_3$), 4.44 (t, 2H, J=7.0 Hz, $CH_2$), 6.66 (d, 1H, J=9.0 Hz, $H_{Ar}$), 6.88 (d, 2H, J=8.8 Hz, $H_{Ar}$), 6.99 (d, 1H, J=9.0 Hz, $H_{Ar}$), 7.44 (s, 1H, =CH), 7.60 (d, 2H, J=8.8 Hz, $H_{Ar}$)

$^{13}$C NMR (62.90 MHz, $CDCl_3$): δ45.8 (2), 55.3, 55.8, 56.5, 56.9, 59.6, 105.4, 113.4 (2), 114.0, 120.3, 123.1, 128.0, 130.0 (2), 133.3, 143.1, 143.3, 155.1, 158.6, 176.1

MS (ion spray): m/z 383 (M+H)$^+$

Anal. calculated for $C_{22}H_{26}N_2O_4$: C, 69.09; H, 6.85; N, 7.32. Found: C, 68.78; H, 6.67; N, 7.16 b) N-{2-[5,8-Dimethoxy-3-(4-methoxyphenyl)-4-quinolyl]oxy}ethyl-N,N-dimethylamine (compound 63)-CRL 8370

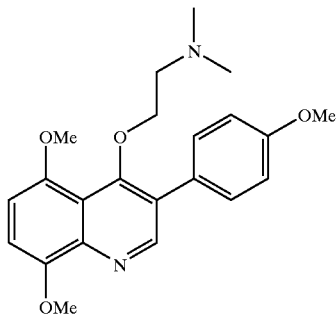

oil

IR (film): v 1611, 1582, 1514 cm$^{-1}$ $^1$H NMR (250 MHz, CDCl$_3$): δ2.16 (s, 6H, NCH$_3$), 2.48 (t, 2H, J=6.5 Hz, CH$_2$), 3.75 (t, 2H, J=6.5 Hz, CH$_2$), 3.87 (s, 3H, OCH$_3$), 3.96 (s, 3H, OCH$_3$), 4.05 (s, 3H, OCH$_3$), 6.82 (d, 1H, J=8.8 Hz, H$_{Ar}$), 6.94 (d, 2H, J=8.8 Hz, H$_{Ar}$), 7.00 (d, 1H, J=9.0 Hz, H$_{Ar}$), 7.59 (d, 2H, J=9.0 Hz, H$_{Ar}$), 8.85 (s, 1H, =CH)

$^{13}$C NMR (62.90 MHz, CDCl$_3$): δ45.7 (2), 55.5, 56.2, 56.5, 58.9, 71.9, 105.8, 107.1, 114.0 (2), 117.4, 127.7, 128.0, 131.1 (2), 142.6, 149.6, 149.9, 152.1, 159.4, 160.3

MS (ion spray): m/z 383 (M+H)$^+$

Anal. calculated for C$_{22}$H$_{26}$N$_2$O$_4$: C, 69.09; H, 6.85; N, 7.32. Found: C, 68.77; H, 6.80; N, 7.22

EXAMPLE 39

1-[2-(1,3-Dioxolan-2-yl)ethyl]-5,8-dimethoxy-3-(4-methoxyphenyl)-1,4-dihydro-4-quinolinone (compound 64)-CRL 8509 and 4-[2-(1,3-dioxolan-2-yl)ethoxy]-5,8-dimethoxy-3-(4-methoxyphenyl)quinoline (example 65)-CRL 8510 a) 1-[2-(1,3-Dioxolan-2-yl)ethyl]-5,8-dimethoxy-3-(4-methoxyphenyl)-1,4-dihydro-4-quinolinone (compound 64)-CRL 8509

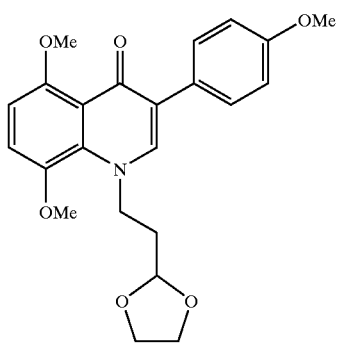

300 mg (0.96 mmol) of compound 29 are added to 10 ml of anhydrous N,N-dimethylformamide (DMF) under a nitrogen atmosphere. 1.00 g of anhydrous K$_2$CO$_3$ (7.5 eq) and then 0.34 ml of 2-(2-bromoethyl)-1,3-dioxolane (3 eq) are successively added to this suspension. The reaction medium is stirred at room temperature for 18 hours. The solvents are evaporated off. The residue is taken up in ethyl acetate and washed twice with water. The organic phase obtained is dried over MgSO$_4$ and then evaporated under reduced pressure. The crude product is purified by chromatography on a column of silica (EtOAc and then 95/5 EtOAc/MeOH) to give 105 mg (26%) of compound 65 and 240 mg (61%) of derivative 64.

oil

IR (film): v 1631, 1596, 1568, 1512 cm$^{-1}$ $^1$H NMR (250 MHz, CDCl$_3$): δ2.12–2.19 (m, 2H, CH$_2$), 3.81 (s, 3H, OCH$_3$), 3.89 (s, 3H, OCH$_3$), 3.90 (s, 3H, OCH$_3$), 3.80–3.97 (m, 4H, CH$_2$), 4.53 (t, 2H, J=7.2 Hz, CH$_2$), 4.83 (t, 1H, J=4.4 Hz, CH), 6.70 (d, 1H, J=9.0 Hz, H$_{Ar}$), 6.91 (d, 1H, J=8.8 Hz, H$_{Ar}$), 7.03 (d, 2H, J=9.0 Hz, H$_{Ar}$), 7.49 (s, 1H, =CH), 7.62 (d, 2H, J=8.8 Hz, H$_{Ar}$)

$^{13}$C NMR (62.90 MHz, CDCl$_3$): δ34.7, 53.5, 55.4, 56.7, 57.1, 65.1 (2), 102.0, 105.7, 113.6 (2), 114.2, 120.6, 123.3, 128.1, 130.1, 133.3 (2), 143.0, 143.4, 155.3, 158.7, 176.3

MS (ion spray): m/z 412 (M+H)$^+$

Anal. calculated for C$_{23}$H$_{25}$NO$_4$: C, 67.14; H, 6.12; N, 3.40. Found: C, 66.82; H, 6.28; N, 3.31 b) 4-[2-(1,3-Dioxolan-2-yl)ethoxy]-5,8-dimethoxy-3-(4-methoxyphenyl)quinoline (compound 65)-CRL 8510

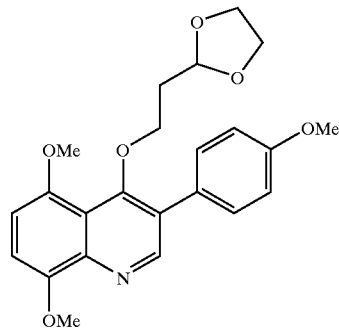

oil

IR (film): v 1611, 1584, 1572, 1517 cm$^{-1}$ $^1$H NMR (250 MHz, CDCl$_3$): δ1.86–1.93 (m, 2H, CH$_2$), 3.70–3.84 (m, 6H, CH$_2$), 3.81 (s, 3H, OCH$_3$), 3.91 (s, 3H, OCH$_3$), 4.00 (s, 3H, OCH$_3$), 4.80 (t, 2H, J=5.0 Hz, CH), 6.77 (d, 1H, J=8.5 Hz, H$_{Ar}$), 6.90 (d, 1H, J=8.5 Hz, H$_{Ar}$), 6.96 (d, 2H, J=8.5 Hz, H$_{Ar}$), 7.55 (d, 2H, J=8.5 Hz, H$_{Ar}$), 8.81 (s, 1H, =CH)

$^{13}$C NMR (62.90 MHz, CDCl$_3$): δ34.5, 53.5, 56.1, 56.3, 64.7 (2), 70.5, 102.0, 105.7, 107.0, 113.9 (2), 117.2, 127.5, 127.9, 131.0 (2), 142.4, 149.4, 149.7, 152.0, 159.3, 159.9

MS (ion spray): m/z 412 (M+H)$^+$

Anal. calculated for C$_{23}$H$_{25}$NO$_4$: C, 67.14; H, 6.12; N, 3.40. Found: C, 67.31; H, 6.36; N, 3.56

EXAMPLE 40

5-Hydroxy-8-methoxy-3-(4-methoxyphenyl)-1,4-dihydro-4-quinolinone (compound 66)-CRL 8391

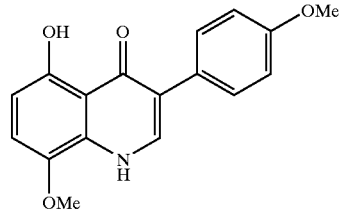

1.00 g (3.22 mmol) of compound 29 is dissolved in 15 ml of anhydrous N,N-dimethylformamide (DMF) under a nitrogen atmosphere, followed by addition of 10 drops of a solution of 48% HBr in H$_2$O. The reaction is stirred at reflux for 2 hours. The solvents are evaporated off. The residue is taken up in CH$_2$Cl$_2$ and washed twice with water. The organic phase obtained is dried over MgSO$_4$ and then evaporated under reduced pressure. The crude residue is purified on a column of silica (eluent: 9/1 CH$_2$Cl$_2$/EtOAc) to give 850 mg (89%) of derivative 66.

m.p.: 169–170° C. (EtOH)

IR (KBr): v 3254, 3222, 1651, 1612, 1589, 1567, 1515 cm$^{-1}$ $^1$H NMR (250 MHz, CDCl$_3$): δ3.71 (s, 3H, OCH$_3$), 3.84 (s, 3H, OCH$_3$), 6.55 (d, 1H, J=8.8 Hz, H$_{Ar}$), 6.86 (d, 2H, J=8.8 Hz, H$_{Ar}$), 6.92 (d, 1H, J=8.8 Hz, H$_{Ar}$), 7.43 (d, 2H, J=8.8 Hz, H$_{Ar}$), 7.56 (s, 1H, =CH), 10.21 (broad s, 1H, NH), 13.56 (s, 1H, OH)

$^{13}$C NMR (62.90 MHz, CDCl$_3$): δ55.3, 56.4, 106.5, 113.1, 113.9 (2), 114.0, 120.9, 126.7, 129.9 (2), 130.3, 137.3, 139.4, 154.3, 158.9, 180.6

MS (ion spray): m/z 298 (M+H)$^+$

Anal. calculated for C$_{17}$H$_{15}$NO$_4$: C, 68.68; H, 5.09; N, 4.71. Found: C, 69.03; H, 5.32; N, 4.66

EXAMPLE 41

5-Hydroxy-8-methoxy-3-(4-methoxyphenyl)-1-methyl-1,4-dihydro-4-quinolinone (compound 67)-CRL 8392

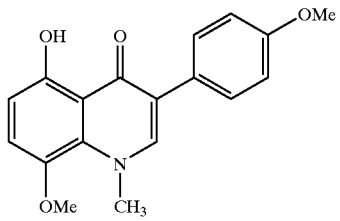

850 mg (2.86 mmol) of compound 66 are dissolved in 15 ml of anhydrous N,N-dimethylformamide (DMF) under a nitrogen atmosphere. 790 mg of anhydrous K$_2$CO$_3$ (2 eq) and then 0.18 ml of methyl iodide (1 eq) are successively added to this solution. The reaction is stirred at room temperature for 18 hours. The solvents are evaporated off. The residue is taken up in CH$_2$Cl$_2$ and washed twice with water. The organic phase obtained is dried over MgSO$_4$ and then-evaporated under reduced pressure. The crude residue is purified on a column of silica (eluent: 9/1 CH$_2$Cl$_2$/EtOAc) to give 863 mg (97%) of derivative 67.

m.p.: 140–141° C. (EtOAc/EP)

IR (KBr): v 1636, 1621, 1571, 1563, 1517 cm$^{-1}$ $^1$H NMR (250 MHz, CDCl$_3$): δ3.84 (s, 3H, NCH$_3$), 3.85 (s, 3H, OCH$_3$), 4.15 (s, 3H, OCH$_3$), 6.68 (d, 1H, J=8.8 Hz, H$_{Ar}$), 6.96 (d, 2H, J=8.8 Hz, H$_{Ar}$), 7.11 (d, 1H, J=8.8 Hz, H$_{Ar}$), 7.53 (s, 1H, =CH), 7.54 (d, 2H, J=8.8 Hz, H$_{Ar}$), 14.80 (s, 1H, OH)

$^{13}$C NMR (62.90 MHz, CDCl$_3$): δ47.3, 55.4, 57.8, 108.8, 113.8 (2), 115.4, 118.2, 120.0, 126.5. 129.8 (2), 131.9, 141.0, 145.5, 156.6, 158.9, 179.9

MS (ion spray): m/z 312 (M+H)$^+$

Anal. calculated for C$_{18}$H$_{17}$NO$_4$: C, 69.44; H, 5.50; N, 4.50. Found: C, 69.76; H, 5.32; N, 4.69

EXAMPLE 42

8-Methoxy-3-(4-methoxyphenyl)-1-methyl-5-trifluoro-methanesulfonate-1,4-dihydro-4-quinolinone (compound 68)-CRL 8511

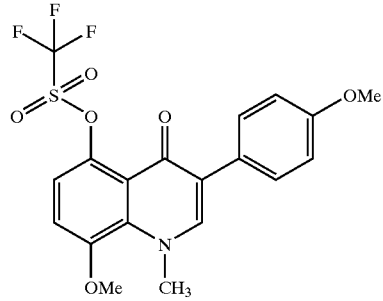

400 mg (1.28 mmol) of compound 67 are dissolved in 15 ml of anhydrous CH$_2$Cl$_2$ and 0.32 ml of pyridine (3 eq) at 0° C., under a nitrogen atmosphere. 0.65 ml of triflic anhydride (3 eq) diluted in 5 ml of anhydrous CH$_2$Cl$_2$ at 0° C. is added to this solution. The reaction is stirred at room temperature for 1.5 hours. The solvents are evaporated off. The residue obtained is taken up in CH$_2$Cl$_2$ and washed twice with saturated sodium hydrogen carbonate solution. The organic phase obtained is dried over MgSO$_4$ and then evaporated under reduced pressure. The crude product is recrystallized from ethyl acetate to give 397 mg (70%) of derivative 68.

m.p.: 179–180° C. (EtOAc)

IR (KBr): v 1630, 1610, 1592, 1560, 1515 cm$^{-1}$ $^1$H NMR (250 MHz, CDCl$_3$): δ3.78 (s, 3H, NCH$_3$), 3.93 (s, 3H, OCH$_3$), 4.05 (s, 3H, OCH$_3$), 6.85 (d, 2H, J=8.8 Hz, H$_{Ar}$), 6.98 (d, 1H, J=8.8 Hz, H$_{Ar}$), 7.03 (d, 1H, J=8.8 Hz, H$_{Ar}$), 7.46 (s, 1H, =CH), 7.53 (d, 2H, J=8.8 Hz, H$_{Ar}$)

$^{13}$C NMR (62.90 MHz, CDCl$_3$): δ46.3, 54.4, 55.6, 110.8, 112.8 (2), 116.1, 121.1, 122.4, 125.9, 128.9 (2), 132.7, 141.2, 143.6, 149.2, 158.0, 173.0

MS (ion spray): m/z 444 (M+H)$^+$

EXAMPLE 43

8-Methoxy-3-(4-methoxyphenyl)-1-methyl-5-vinyl-1,4-dihydro-4-quinolinone (compound 69)-CRL 8512

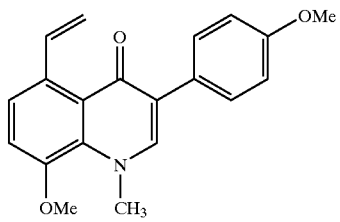

31 mg (6 mol%) of tetrakis(triphenylphosphine)palladium (0) and 54 mg of lithium chloride are suspended in 2 ml of anhydrous N,N-dimethylformamide under a nitrogen atmosphere. In parallel, 200 mg (0.45 mmol) of compound 68 and 0.2 ml (1.5 eq) of vinyltributyltin are dissolved in 5 ml of anhydrous N,N-dimethylformamide. The solution containing the triflate is poured into the first solution via a transfer needle. The final reaction mixture is stirred at reflux for 1 hour 30 minutes. After cooling, the solvent is evaporated off. The residue is taken up in ethyl acetate and then washed with 10% potassium fluoride solution. The organic phase obtained is dried over MgSO$_4$ and then evaporated off under reduced pressure. The residue is purified by chromatography on a column of silica (eluent: 6/4 PE/EtOAc) to give 123 mg (85%) of compound 69.

m.p.: 104–105° C. (washing with Et$_2$O)

IR (KBr): ν 1623, 1591, 1560, 1514 cm$^{-1}$ $^1$H NMR (250 MHz, CDCl$_3$): δ3.80 (s, 3H, OCH$_3$), 3.88 (s, 3H, OCH$_3$), 4.02 (s, 3H, NCH$_3$), 5.17 (dd, 1H, J=1.9, 10.7 Hz, =CH$_2$), 5.30 (dd, 1H, J=1.9, 17.5 Hz, =CH$_2$), 6.90 (d, 2H, J=8.8 Hz, H$_{Ar}$), 7.00 (d, 1H, J=8.3 Hz, H$_{Ar}$), 7.21 (d, 1H, J=8.3 Hz, H$_{Ar}$), 7.42 (s, 1H, =CH), 7.58 (d, 2H, J=8.8 Hz, H$_{Ar}$), 7.97 (dd, 1H, J=10.7, 17.5 Hz, CH$_{vinyl}$)

$^{13}$C NMR (62.90 MHz, CDCl$_3$): δ47.1, 55.3, 56.2, 112.0, 112.9, 113.5 (2), 122.1, 124.0, 126.7, 127.8, 129.8 (2), 132.8, 134.1, 140.3, 144.0, 149.7, 158.6, 177.0

MS (ion spray): m/z 322 (M+H)$^+$

Anal. calculated for C$_{20}$H$_{19}$NO$_3$: C, 74.75; H, 5.96; N, 4.36. Found: C, 74.53; H, 5.78; N, 4.10

EXAMPLE 44

5-Ethyl-8-methoxy-3-(4-methoxyphenyl)-1-methyl-1,4-dihydro-4-quinolinone (compound 70)-CRL 8414

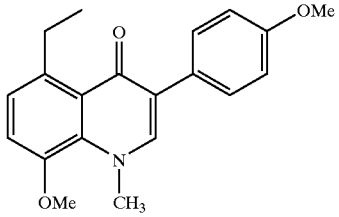

190 mg (0.60 mmol) of compound 69 are dissolved in 15 ml of ethyl acetate under a nitrogen atmosphere. 19 mg of palladium-on-charcoal (10%) are added to this solution. The hydrogenation is carried out using Parr apparatus under 50 psi of hydrogen at room temperature for 7 hours. The catalyst is removed by filtration through Celite. The filtrate is evaporated under reduced pressure. The residue is purified by chromatography on a column of silica (eluent: 9/1 CH$_2$Cl$_2$/EtOAc) to give 155 mg (81%) of compound 70.

m.p.: 94–95° C. (EtOAc)

IR (KBr): ν 1624, 1588, 1567, 1511 cm$^{-1}$ $^1$H NMR (250 MHz, CDCl$_3$): δ1.27 (t, 3H, J=7.2 Hz, CH$_3$), 3.37 (q, 2H, J=7.2 Hz, CH$_2$), 3.82 (s, 3H, OCH$_3$), 3.89 (s, 3H, OCH$_3$), 4.03 (s, 3H, NCH$_3$), 6.94 (d, 2H, J=8.8 Hz, H$_{Ar}$), 7.00 (d, 1H, J=8.3 Hz, H$_{Ar}$), 7.04 (d, 1H, J=8.3 Hz, H$_{Ar}$), 7.43 (s, 1H, =CH), 7.56 (d, 2H, J=8.8 Hz, H$_{Ar}$)

$^{13}$C NMR (62.90 MHz, CDCl$_3$): δ17.0, 29.4, 47.1, 55.5, 56.5, 113.6, 113.9 (2), 122.8, 125.3, 127.5, 128.4, 130.1 (2), 134.1, 139.9, 143.8, 148.5, 158.8, 177.6

MS (ion spray): m/z 324 (M+H)$^+$

Anal. calculated for C$_{20}$H$_{21}$NO$_3$: C, 74.28; H, 6.55; N, 4.33. Found: C, 74.50; H, 6.41; N, 4.23

EXAMPLE 45

8-Methoxy-3-(4-methoxyphenyl)-1-methyl-5-phenyl-1,4-dihydro-4-quinolinone (compound 71)-CRL 8405

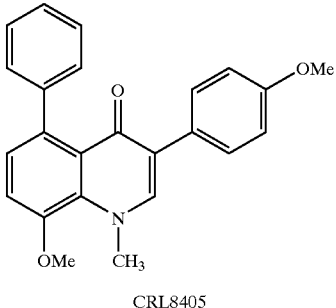

CRL8405

200 mg (0.45 mmol) of compound 68 and 32 mg of tetrakis(triphenylphosphine)palladium (0) are dissolved in 8 ml of dioxane under a nitrogen atmosphere. The solution is stirred at room temperature for 30 minutes. Phenylboronic acid (84 mg, 1.5 eq) dissolved in 5 ml of ethanol is added to the reaction solution, followed by addition of 5 ml of saturated sodium hydrogen carbonate solution. The two-phase mixture is stirred at reflux for 3 hours. After cooling, the dioxane is evaporated off and the aqueous phase obtained is extracted with ethyl acetate (2×5 ml). The organic phase is washed with saturated sodium chloride solution. The organic phase is dried over MgSO$_4$ and then evaporated under reduced pressure. The residue is purified by chromatography on a column of silica (eluent: 6/4 EtOAc/PE) to give 105 mg (60%) of compound 71.

m.p.: 180–181° C. (EtOAc)

IR (KBr): ν 1629, 1588, 1565, 1511 cm$^{-1}$ $^1$H NMR (250 MHz, CDCl$_3$): δ3.78 (s, 3H, OCH$_3$), 4.00 (s, 3H, OCH$_3$), 4.12 (s, 3H, NCH$_3$), 6.86 (d, 2H, J=8.8 Hz, H$_{Ar}$), 7.03 (d, 1H, J=8.3 Hz, H$_{Ar}$), 7.09 (d, 1H, J=8.3 Hz, H$_{Ar}$), 7.23–7.32 (m, 5H, H$_{Ar}$), 7.48 (s, 1H, =CH), 7.52 (d, 2H, J=8.8 Hz, H$_{Ar}$)

$^{13}$C NMR (62.90 MHz, CDCl$_3$): δ47.2, 55.4, 56.5, 112.3, 113.7 (2), 122.5, 125.8, 126.9, 127.4 (2), 127.5, 128.1, 128.3 (2), 130.1 (2), 133.3, 136.4, 144.2, 144.4, 149.7, 158.7, 175.6

MS (ion spray): m/z 372 (M+H)$^+$

Anal. calculated for C$_{24}$H$_{21}$NO$_3$: C, 77.61; H, 5.70; N, 3.77. Found: C, 77.87; H, 5.89; N, 3.69

EXAMPLE 46

5-Benzylamino-7-methoxy-3-(4-methoxyphenyl)-1-methyl-1,4-dihydro-4-quinolinone (compound 72)-CRL 8424

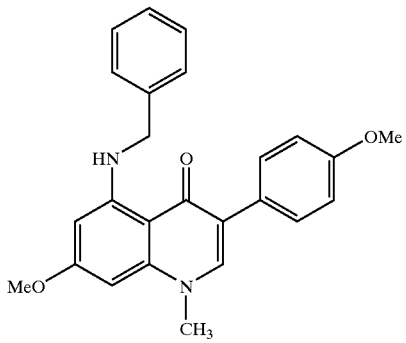

CRL8424

Compound 36 (200 mg, 0.45 mmol) and benzylamine (0.24 ml, 2.2 mmol) are dissolved in dioxane (2 ml) in a sealed tube. The final solution is heated at 100° C. for 16 hours. After cooling and evaporation of the solvent, the residue is purified by chromatography on a column of silica treated with triethylamine (eluent: 4/6 PE/EtOAc) to give 150 mg (83%) of derivative 72.

m.p.: 176–177° C. (EtOAc)

IR (KBr): ν 3174, 1632, 1607, 1570, 1557, 1508, 1471 cm$^{-1}$ $^1$H NMR (250 MHz, CDCl$_3$): δ3.62 (s, 3H, NCH$_3$), 3.77 (s, 3H, OCH$_3$), 3.82 (s, 3H, CH$_3$), 4.44 (d, 2H, J=5.6 Hz, CH$_2$), 5.85 (s, 1H, H$_{Ar}$), 5.87 (s, 1H, H$_{Ar}$), 6.94 (d, 2H, J=8.8 Hz, H$_{Ar}$), 7.22–7.33 (m, 3H, H$_{Ar}$), 7.38–7.41 (m, 3H, =CH +H$_{Ar}$), 7.48 (d, 2H, J=8.8 Hz, H$_{Ar}$), 11.02 (t, 1H, J=5.6 Hz, NH)

$^{13}$C NMR (62.90 MHz, CDCl$_3$): δ41.6, 47.3, 55.2, 55.5, 85.2, 89.7, 108.1, 113.8 (2), 122.0, 127.1, 127.4 (2), 128.1, 128.7 (2), 130.2 (2), 138.8, 140.5, 144.4, 153.8, 158.8, 163.6, 178.9

MS (ion spray): m/z 401 (M+1)$^+$

Anal. calculated for C$_{25}$H$_{24}$N$_2$O$_3$: C, 74.98; H, 6.04; N, 6.99. Found: C, 75.25; H, 5.89; N, 7.13

EXAMPLE 47

Methyl 3-[5,7-dimethoxy-3-(4-methoxyphenyl)-4-oxo-1,4-dihydro-1-quinolinyl]propanoate (compound 73)-CRL 8404

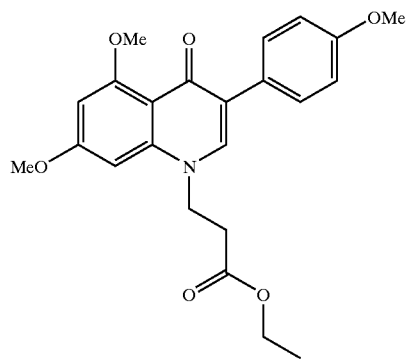

CRL8404

400 mg (1.30 mmol) of compound 33 are added to 15 ml of anhydrous N,N-dimethylformamide under a nitrogen atmosphere. 1.33 g of anhydrous K$_2$CO$_3$ (7.5 eq) and then 0.5 ml of ethyl 3-bromopropionate (3 eq) are successively added to this suspension. The reaction medium is stirred at room temperature for 18 hours. The solvents are evaporated off. The residue is taken up in ethyl acetate and then washed twice with water. The organic phase obtained is dried over MgSO$_4$ and then evaporated under reduced pressure. The crude product is purified by chromatography on a column of silica (98/2 CH$_2$Cl$_2$/MeOH) to give 170 mg (32%) of derivative 73.

m.p.: 128–129° C. (EtOAc)

IR (KBr): ν 1720, 1634, 1609, 1590, 1513 cm$^{-1}$ $^1$H NMR (250 MHz, CDCl$_3$): δ1.22 (t, 3H, J=7.2 Hz, CH$_3$), 2.86 (t, 2H, J=6.8 Hz, CH$_2$), 3.81 (s, 3H, OCH$_3$), 3.91 (s, 3H, OCH$_3$), 3.94 (s, 3H, OCH$_3$), 4.15 (q, 2H, J=6.8 Hz, CH$_2$), 4.37 (t, 2H, J=6.5 Hz, CH$_2$), 6.30 (d, 1H, J=2.0 Hz, H$_{Ar}$), 6.36 (d, 1H, J=2.0 Hz, H$_{Ar}$), 6.90 (d, 2H, J=8.8 Hz, H$_{Ar}$), 7.57 (d, 2H, J=8.8 Hz, H$_{Ar}$), 7.59 (s, 1H, =CH)

$^{13}$C NMR (62.90 MHz, CDCl$_3$): δ14.2, 33.2, 49.2, 55.4, 55.6, 56.4, 61.5, 89.8, 94.4, 112.9, 113.6 (2), 123.6, 128.0, 130.3 (2), 140.1, 142.8, 158.8, 162.9, 163.4, 170.8, 175.8

MS (ion spray): m/z 412 (M+H)$^+$

Anal. calculated for C$_{23}$H$_{25}$NO$_6$: C, 67.14; H, 6.12; N, 3.40. Found: C, 67.37; H, 5.89; N, 3.47

EXAMPLE 48

3-[5,7-Dimethoxy-3-(4-methoxyphenyl)-4-oxo-1,4-dihydro-1-quinolinyl]propanenitrile (compound 74)-CRL 8412

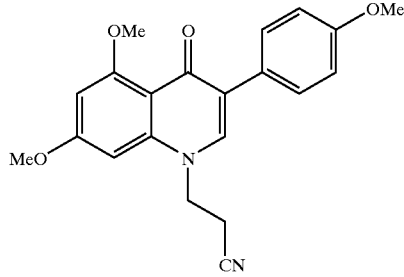

300 mg (1.00 mmol) of compound 33 are added to 15 ml of anhydrous N,N-dimethylformamide under a nitrogen atmosphere. 1.00 g of anhydrous $K_2CO_3$ (7.5 eq) and then 0.37 ml of 3-bromopropionitrile (3 eq) are successively added to this suspension. The reaction medium is stirred at room temperature for 24 hours. The solvents are evaporated off. The residue is taken up in ethyl acetate and washed twice with water. The organic phase obtained is dried over $MgSO_4$ and then evaporated under reduced pressure. The crude product is purified by chromatography on a column of silica treated with triethylamine (95/5 $CH_2Cl_2$/MeOH) to give 130 mg (54%) of derivative 74.

m.p.: 120–121° C. ($Et_2O$)

IR (KBr): v 2243, 1636, 1615, 1566, 1512 $cm^{-1}$ $^1$H NMR (250 MHz, $CDCl_3$): δ2.88 (t, 2H, J=6.5 hz, $CH_2$), 3.81 (s, 3H, $OCH_3$), 3.91 (s, 3H, $OCH_3$), 3.94 (s, 3H, $OCH_3$), 4.83 (t, 2H, J=6.5 Hz, $CH_2$), 6.16 (d, 1H, J=2.0 Hz, $H_{Ar}$), 6.37 (d, 1H, J=2.0 Hz, $H_{Ar}$), 6.89 (d, 2H, J=8.8 Hz, $H_{Ar}$), 7.45 (s, 1H, =CH), 7.53 (d, 2H, J=8.8 Hz, $H_{Ar}$)

$^{13}$C NMR (62.90 MHz, $CDCl_3$): δ17.5, 48.9, 55.4, 55.7, 56.4, 89.5, 94.2, 112.8, 113.6 (2), 116.5, 124.5, 127.5, 130.3 (2), 138.8, 142.5, 159.0, 163.2, 163.8, 176.0

MS (ion spray): m/z 365 $(M+H)^+$

Anal. calculated for $C_{21}H_{20}N_2O_4$: C, 69.22; H, 5.53; N, 7.69. Found: C, 65.97; H, 5.71; N, 7.53

EXAMPLE 49

[5,8-Dimethoxy-3-(4-methoxyphenyl)-4-oxo-1,4-dihydro-1-quinolinyl]acetonitrile (compound 75)-CRL 8413

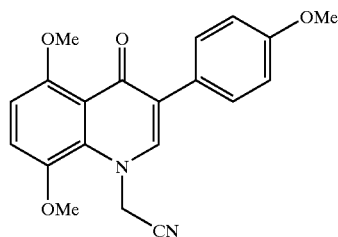

200 mg (0.64 mmol) of compound 29 are dissolved in 15 ml of anhydrous N,N-dimethylformamide under a nitrogen atmosphere. 665 mg of anhydrous potassium carbonate (7.5 eq) and then 0.09 mol of bromoacetonitrile (2 eq) are successively added to this solution. The reaction is stirred at room temperature for 18 hours. The potassium carbonate is removed by filtration and the solvents are evaporated off. The residue is taken up in ethyl acetate and washed twice with water. The organic phase obtained is dried over $MgSO_4$ and then evaporated under reduced pressure. The crude residue is purified by chromatography on a column of silica (eluent: 7.3 $CH_2Cl_2$/EtOAc) to give 115 mg (51%) of derivative 75.

m.p.: 207–208° C. (EtOAc)

IR (KBr): v 2216, 1628, 1594, 1571, 1511 $cm^{-1}$ $^1$H NMR (250 MHz, $CDCl_3$): δ3.81 (s, 3H, $OCH_3$), 3.90 (s, 3H, $OCH_3$), 3.97 (s, 3H, $OCH_3$), 5.15 (s, 2H, $CH_2$), 6.76 (d, 1H, J=9.1 Hz, $H_{Ar}$), 6.89 (d, 1H, J=8.8 Hz, $H_{Ar}$), 7.11 (d, 2H, J=9.1 Hz, $H_{Ar}$), 7.29 (s, 1H, =CH), 7.53 (d, 2H, J=8.8 Hz, $H_{Ar}$)

$^{13}$C NMR (62.90 MHz, $CDCl_3$): δ45.2, 55.4, 57.0, 57.3, 106.6, 113.7 (2), 115.3, 115.4, 119.8, 125.1, 126.8, 130.1 (2), 132.6, 141.1, 142.8, 155.2, 159.2, 176.4

MS (ion spray): m/z 351 $(M+H)^+$

Anal. calculated for $C_{20}H_{18}N_2O_4$: C, 68.56; H, 5.18; N. 8.00. Found: C. 68.75; H, 4.99; N, 8.04

EXAMPLE 50

5,7-Diacetoxy-3-[4-(acetoxy)phenyl]-1-methyl-1,4-dihydro-4-quinolmone (compound 76)-CRL 8513

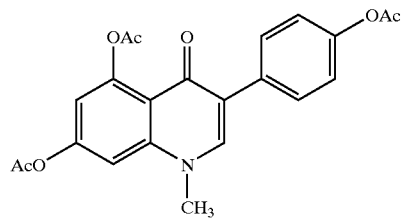

200 mg (0.61 mmol) of compound 40 are dissolved in 15 ml of dichloromethane under an inert atmosphere. 0.35 ml (3.7 mmol, 6 eq) of boron tribromide is added dropwise (exothermic reaction), at 0° C., to the reaction mixture. The final solution is stirred at room temperature for 96 hours. The reaction is hydrolyzed by addition (dropwise) of water, and then neutralized with 10% sodium hydroxide solution (pH =6–7). The final product is collected by filtration and then rinsed with ethanol (140 mg, 80%, m.p. 316° C. (EtOH). This compound is dissolved in 2 ml of pyridine and 2 ml of acetic anhydride at 0° C., under a nitrogen atmosphere. The reaction is stirred at room temperature for 48 hours. The solvents are evaporated off. The residue obtained is taken up in $CH_2Cl_2$ and washed twice with water. The organic phase obtained is dried over $MgSO_4$ and then evaporated under reduced pressure. The residue is purified by chromatography on a column of silica (eluent: 7/3 $CH_2Cl_2$/EtOAc) to give 235 mg (86%) of derivative 76.

m.p.: 219–220° C. (EtOAc/PE)

IR (KBr): v 1769, 1751, 1635, 1618, 1600, 1504 $cm^{-1}$ $^1$H NMR (250 MHz, DMSO-$d_6$): δ2.28 (s, 6H, $CH_3$), 2.33 (s, 3H, $CH_3$), 3.84 (s, 3H, $NCH_3$), 6.94 (d, 1H, J=2.2 Hz, $H_{Ar}$), 7.15 (d, 2H, J=8.8 Hz, $H_{Ar}$), 7.40 (d, 1H, J=2.2 Hz, $H_{Ar}$), 7.62 (d, 2H, J=8.8 Hz, $H_{Ar}$), 8.25 (s, 1H, =CH)

$^{13}$C NMR (62.90 MHz, DMSO-d$_6$): δ20.9, 21.2, 41.2, 107.4, 112.6, 117.0, 120.9, 121.3 (2), 121.5, 129.8 (2), 132.8, 142.4, 143.6, 149.3, 151.1, 152.6, 168.7, 168.9, 169.4, 173.1

MS (ion spray): m/z 410 (M+1)$^+$

Anal. calculated for C$_{22}$H$_{19}$NO$_7$: C, 64.54; H, 4.68; N, 3.42. Found: C, 64.77; H, 4.75; N, 3.25

EXAMPLE 51

5,8-Diacetoxy-3-[4-(acetoxy)phenyl]-1-methyl-1,4-dihydro-4-quinolmone acetate (compound 77)-CRL 8460

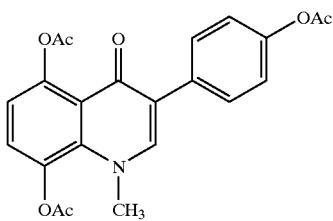

CRL8460

200 mg (0.61 mmol) of compound 56 are dissolved in 15 ml of dichloromethane under an inert atmosphere. 0.35 ml (3.7 mmol, 6 eq) of boron tribromide is added dropwise (exothermic reaction), at 0° C., to the reaction mixture. The final solution is stirred at room temperature for 96 hours. The reaction is hydrolyzed by addition (dropwise) of water, and then neutralized with 10% sodium hydroxide solution (pH =6–7). The product is collected by filtration and then rinsed with ethanol (131 mg, 75%). This compound is dissolved in 2 ml of pyridine and 2 ml of acetic anhydride at 0° C., under a nitrogen atmosphere. The reaction is stirred at room temperature for 48 hours. The solvents are evaporated off. The residue obtained is taken up in CH$_2$Cl$_2$ and washed twice with water. The organic phase obtained is dried over MgSO$_4$ and then evaporated under reduced pressure. The residue is purified by chromatography on a column of silica (eluent: 9/1 CH$_2$Cl$_2$/EtOAc) to give 149 mg (79%) of derivative 77.

m.p.: 183–184° C. (EtOAc/PE)

IR (KBr): ν 1775, 1756, 1628, 1598, 1562, 1513, 1499 cm$^{-1}$ $^1$H NMR (250 MHz, CDCl$_3$): δ2.29 (s, 3H, CH$_3$), 2.37 (s, 3H, CH$_3$), 2.42 (s, 3H, CH$_3$), 3.89 (s, 3H, NCH$_3$), 6.92 (d, 1H, J=8.5 Hz, H$_{Ar}$), 7.08 (d, 2H, J=8.8 Hz, H$_{Ar}$), 7.26 (d, 1H, J=8.5 Hz, H$_{Ar}$), 7.39 (s, 1H, =CH), 7.54 (d, 2H, J=8.8 Hz, H$_{Ar}$)

$^{13}$C NMR (62.90 MHz, CDCl$_3$): δ21.3, 21.4, 21.5, 45.4, 117.9, 121.5 (2), 121.9, 123.0, 127.3, 130.0 (2), 132.4, 135.8, 137.1, 144.5, 148.7, 150.1, 169.1, 169.7, 170.3, 174.5

MS (ion spray): m/z 410 (M+1)$^+$

Anal. calculated for C$_{22}$H$_{19}$NO$_7$: C, 64.54; H, 4.68; N, 3.42. Found: C, 64.66; H, 4.82; N, 3.53

EXAMPLE 52

4-[5,7-Dimethoxy-3-(4-methoxyphenyl)-4-oxo-1,4-dihydro-1-quinolinyl]butanenitrile (compound 78)-CRL 8420 and {[5,7-dimethoxy-3-(4-methoxyphenyl)-4-quinolyl]oxy}butanenitrile (compound 79)-CRL 8514

1) 4-[5,7-Dimethoxy-3-(4-methoxyphenyl)-4-oxo-1,4-dihydro-1-quinolinyl]butanenitrile (compound 78)-CRL 8420

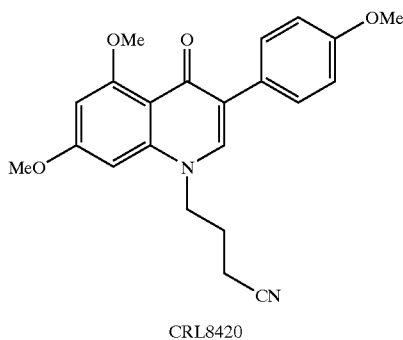

CRL8420

200 mg (6.43 mmol) of compound 33 are dissolved in 30 ml of anhydrous N,N-dimethylformamide (DMF) under a nitrogen atmosphere. 19 mg (1.2 eq) of sodium hydride, washed beforehand in petroleum ether, are added portionwise to the reaction medium (exothermic reaction). 4-Chlorobutyronitrile (0.12 ml, 2 eq) is added to the medium. The reaction is heated overnight at 90° C. After cooling and evaporating off the DMF, water is poured into the reaction mixture, which is then extracted with ethyl acetate (twice). The organic phase is dried over MgSO$_4$ and then evaporated under reduced pressure. The residue obtained is purified by chromatography on a column of silica treated with triethylamine (9/1 CH$_2$Cl$_2$/EtOAc) to give 110 mg (45%) of compound 78 and 40 mg (16%) of compound 79.

m.p.: 100–101° C. (ether)

IR (KBr): ν 2244, 1635, 1615, 1569, 1541, 1512 cm$^{-1}$ $^1$H NMR (250 MHz, CDCl$_3$): δ2.07–2.16 (m, 2H, CH$_2$), 2.38 (t, 2H, J=6.9 Hz, CH$_2$CN), 3.74 (s, 3H, OCH$_3$), 3.87 (s, 6H, OCH$_3$), 4.11 (t, 2H, J=6.9 Hz, NCH$_2$), 6.24 (d, 1H, J=1.9 Hz, H$_{Ar}$), 6.31 (d, 1H, J=1.9 Hz, H$_{Ar}$), 6.80 (d, 2H, J=8.8 Hz, H$_{Ar}$), 7.40 (s, 1H, =CH), 7.47 (d, 2H, J=8.8 Hz, H$_{Ar}$)

$^{13}$C NMR (62.90 MHz, CDCl$_3$): δ14.5, 24.2, 51.5, 55.2, 55.6, 56.2, 89.4, 94.6, 112.7, 113.4 (2), 118.7, 123.7, 127.7, 130.1 (2), 139.3, 142.9, 158.7, 162.9 (2), 175.8

MS (ion spray): m/z 379 (M+1)$^+$

Anal. calculated for C$_{22}$H$_{22}$N$_2$O$_4$: C, 69.83; H, 5.86; N, 7.40. Found: C, 69.56; H, 6.00; N, 7.25

2) {[5,7-Dimethoxy-3-(4-methoxyphenyl)-4-quinolyl]oxy}butanenitrile (compound 79)-CRL 8514

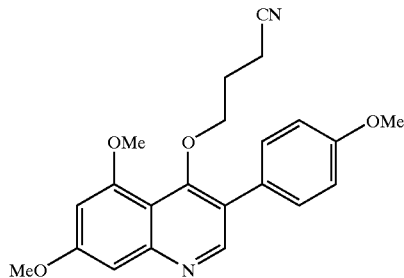

m.p.: 94–95° C. (ether)
IR (KBr): ν 2240, 1616, 1577, 1512 cm$^{-1}$
$^1$H NMR (250 MHz, CDCl$_3$): δ1.76–1.87 (m, 2H, CH$_2$), 2.32 (t, 2H, J=7.2 Hz, CH$_2$CN), 3.72 (t, 2H, J=7.2 Hz, OCH$_2$), 3.85 (s, 3H, OCH$_3$), 3.92 (s, 3H, OCH$_3$), 3.96 (s, 3H, OCH$_3$), 6.56 (d, 1H, J=2.2 Hz, H$_{Ar}$), 6.99 (d, 2H, J=8.8 Hz, H$_{Ar}$), 7.05 (d, 1H, J=2.2 Hz, H$_{Ar}$), 7.48 (d, 2H, J=8.8 Hz, H$_{Ar}$), 8.69 (s, 1, H$_{Ar}$)
$^{13}$C NMR (62.90 MHz, CDCl$_3$): δ14.0, 26.3, 55.4, 55.6, 56.3, 71.9, 99.6, 100.7, 111.5, 114.1 (2), 119.5, 125.5, 127.6, 130.9 (2), 152.9, 153.3, 156.7, 159.3, 159.6, 160.8
MS (ion spray): m/z 379 (M+1)$^+$
Anal. calculated for C$_{22}$H$_{22}$N$_2$O$_4$: C, 69.83; H, 5.86; N, 7.40. Found: C, 69.95; H, 5.97; N, 7.31

EXAMPLE 53

4-[5,8-Dimethoxy-3-(4-methoxyphenyl)-4-oxo-1,4-dihydro-1-quinolinyl]butanenitrile (compound 80)-CRL 8421 and {[5,8-dimethoxy-3-(4-methoxyphenyl)-4-quinolyl]oxy}butanenitrile (compound 81)-CRL 8501

1) 4-[5,8-Dimethoxy-3-(4-methoxyphenyl)-4-oxo-1,4-dihydro-1-quinolinyl]butanenitrile (compound 80)

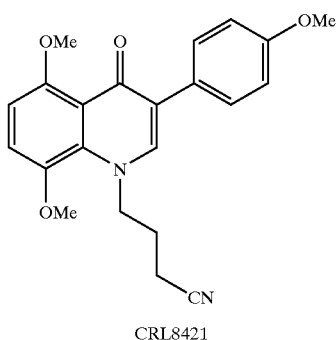

CRL8421

400 mg (1.28 mmol) of compound 29 are added to 10 ml of anhydrous N,N-dimethylformamide under a nitrogen atmosphere. 1.35 g of anhydrous potassium carbonate (7.5 eq) and then 0.35 ml of 4-chlorobutyronitrile (3 eq) are successively added to this suspension. The reaction is stirred at 90° C. for 18 hours. The solvents are evaporated off. The residue is taken up in CH$_2$Cl$_2$ and washed twice with water. The organic phase is dried over MgSO$_4$ and then evaporated under reduced pressure. The residue obtained is purified by chromatography on a column of silica treated with triethylamine (eluent: 7/3 CH$_2$Cl$_2$/EtOAc) to give 180 mg (37%) of compound 80 and 274 mg (56%) of derivative 81.
m.p.: 126–127° C. (ether)
IR (KBr): ν 2242, 1631, 1596, 1557, 1512 cm$^{-1}$
$^1$H NMR (250 MHz, CDCl$_3$): δ1.97–2.08 (m, 2H, CH$_2$), 2.27 (t, 2H, J=7.2 Hz, CH$_2$CN), 3.74 (s, 3H, OCH$_3$), 3.85 (s, 3H, OCH$_3$), 3.86 (s, 3H, OCH$_3$), 4.45 (t, 2H, J=7.2 Hz, NCH$_2$), 6.67 (d, 1H, J=9.1 Hz, H$_{Ar}$), 6.82 (d, 2H, J=9.1 Hz, H$_{Ar}$), 7.00 (d, 1H, J=9.1 Hz, H$_{Ar}$), 7.38 (s, 1H, =CH), 7.53 (d, 2H, J=9.1 Hz, H$_{Ar}$)
$^{13}$C NMR (62.90 MHz, CDCl$_3$): δ14.3, 26.4, 55.2, 56.5, 56.1, 56.8, 105.6, 113.4 (2), 114.2, 118.8, 120.1, 123.4, 127.5, 129.9 (2), 132.6, 142.2, 143.0, 155.0, 158.6, 176.1
MS (ion spray): m/z 379 (M+1)$^+$
Anal. calculated for C$_{22}$H$_{22}$N$_2$O$_4$: C, 69.83; H, 5.86; N, 7.40. Found: C, 69.65; H, 5.72; N, 7.49

2) {[5,8-Dimethoxy-3-(4-methoxyphenyl)-4-quinolyl]oxy}butanenitrile (compound 81)-CRL 8501

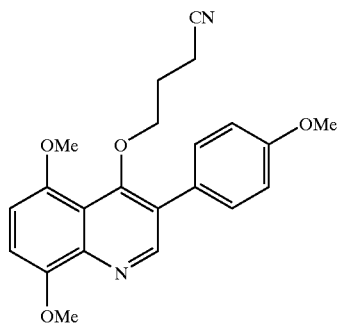

m.p.: 117–118° C. (ether)
IR (KBr): ν 2247, 1612, 1584, 1514, 1497 cm$^{-1}$
$^1$H NMR (250 MHz, CDCl$_3$): δ1.79–1.90 (m, 2H, CH$_2$), 2.34 (t, 2H, J=7.2 Hz, CH$_2$CN), 3.76 (t, 2H, J=7.2 Hz, OCH$_2$), 3.87 (s, 3H, OCH$_3$), 3.97 (s, 3H, OCH$_3$), 4.05 (s, 3H, OCH$_3$), 6.85 (d, 1H, J=8.8 hz, H$_{Ar}$), 6.96 (d, 1H, J=8.8 Hz, H$_{Ar}$), 7.02 (d, 2H, J=8.8 Hz, H$_{Ar}$), 7.53 (d, 2H, J=8.8 Hz, H$_{Ar}$), 8.85 (s, 1H, H$_{Ar}$)
$^{13}$C NMR (62.90 MHz, CDCl$_3$): δ14.2, 26.4, 55.5, 56.3, 56.6, 72.2, 106.2, 107.3, 114.2 (2), 117.1, 119.6, 127.3, 128.1, 131.1 (2), 143.0, 149.2, 150.0, 152.1, 159.4, 159.6
MS (ion spray): m/z 379 (M+1)$^+$
Anal. calculated for C$_{22}$H$_{22}$N$_2$O$_4$: C, 69.83; H, 5.86; N, 7.40. Found: C, 69.48; H, 5.70; N, 7.22

EXAMPLE 54

1-(2-Hydroxyethyl)-5,8-dimethoxy-3-(4-methoxyphenyl)-1,4-dihydro-4-quinolinone (compound 82)-CRL 8515 and 2-{[5,8-dimethoxy-3-(4-methoxyphenyl)-4-quinolyl]oxy}-1-ethanol (compound 83)-CRL 8516

1) 1(2-Hydroxyethyl)-5,8-dimethoxy-3-(4-methoxyphenyl)-1,4-dihydro-4-quinolinone (compound 82)-CRL 8515

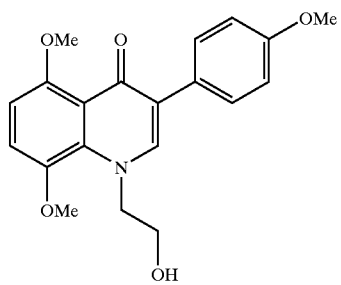

500 mg (1.61 mmol) of compound 29 are added to 20 ml of anhydrous N,N-dimethylformamide under a nitrogen atmosphere. 1.66 g of anhydrous potassium carbonate (7.5 eq) and then 0.34 ml of 2-bromoethanol (3 eq) are successively added to this suspension. The reaction is stirred at 90° C. for 24 hours. The solvents are evaporated off. The residue is taken up in ethyl acetate and washed twice with water. The organic phase is dried over MgSO$_4$ and then evaporated under reduced pressure. The residue obtained is purified by chromatography on a column of silica treated with triethylamine (eluent: 7/3 CH$_2$Cl$_2$/EtOAc) to give 330 mg (57%) of compound 82 and 147 mg (25%) of derivative 83.

m.p.: 126–127° C. (EtOAc)

IR (KBr): v 3296, 1628, 1591, 1568, 1512 cm$^{-1}$ $^1$H NMR (250 MHz, CDCl$_3$+D$_2$O): δ3.82 (s, 3H, OCH$_3$), 3.85 (s, 3H, OCH$_3$), 3.88 (s, 3H, OCH$_3$), 3.97 (t, 2H, J=5.0 Hz, CH$_2$), 4.58 (t, 2H, J=5.0 Hz, CH$_2$), 6.67 (d, 1H, J=8.8 Hz, H$_{Ar}$), 6.85 (d, 2H, J=8.8 Hz, H$_{Ar}$), 7.01 (d, 1H, J=8.8 Hz, H$_{Ar}$), 7.50 (d, 2H, J=8.8 Hz, H$_{Ar}$), 7.56 (s, 1H, =CH)

$^{13}$C NMR (62.90 MHz, CDCl$_3$): δ55.3, 56.4, 56.8, 61.3, 62.1, 105.0, 113.1 (2), 114.4, 120.0, 121.2, 127.9, 129.6 (2), 133.0, 143.4, 144.6, 154.9, 158.2, 176.0

MS (ion spray): m/z 356 (M+1)$^+$

Anal. calculated for C$_{20}$H$_{21}$NO$_5$: C, 67.59; H, 5.96; N, 3.94. Found: C, 67.29; H, 6.11; N, 4.07

2) 2-{[5,8-Dimethoxy-3-(4-methoxyphenyl)-4-quinolyl]oxy}-1-ethanol (compound 83)-CRL 8516

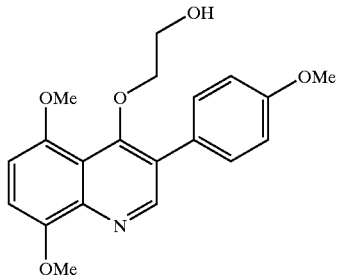

m.p.: 124–125° C. (EtOAc)

IR (KBr): v 3238, 1612, 1583, 1514, 1498 cm$^{-1}$ $^1$H NMR (250 MHz, CDCl$_3$+D$_2$O): δ3.58 (t, 2H, J=4.5 Hz, CH$_2$), 3.77 (t, 2H, J=4.5 Hz, CH$_2$), 3.84 (s, 3H, OCH$_3$), 3.95 (s, 3H, OCH$_3$), 4.02 (s, 3H, OCH$_3$), 6.88 (d, 1H, J=8.8 Hz, H$_{Ar}$), 6.94 (d, 2H, J=8.8 Hz, H$_{Ar}$), 7.00 (d, 1H, J=8.8 Hz, H$_{Ar}$), 7.55 (d, 2H, J=8.8 Hz, H$_{Ar}$), 8.81 (s, 1H, H$_{Ar}$)

$^{13}$C NMR (62.90 MHz, CDCl$_3$): δ55.4, 56.2, 57.3, 61.7, 76.3, 107.2, 107.7, 114.4 (2), 117.2, 127.0, 127.7, 130.8 (2), 142.4, 149.0, 150.4, 152.3, 159.6, 160.0

MS (ion spray): m/z 356 (M+1)$^+$

Anal. calculated for C$_{20}$H$_{21}$NO$_5$: C, 67.59; H, 5.96; N, 3.94. Found: C, 67.78; H, 5.79; N, 4.05

EXAMPLE 55

4-2-[5,8-Dimethoxy-3-(4-methoxyphenyl)-4-oxo-1,4-dihydro-1-quinolyl]ethyl p-Toluenesulfonate (compound 84)-CRL 8517

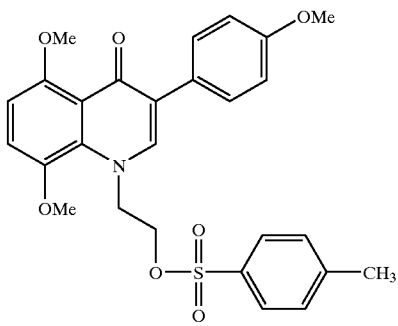

180 mg (0.5 mmol) of compound 82 are added to 10 ml of anhydrous CH$_2$Cl$_2$ under a nitrogen atmosphere. 0.21 ml of triethylamine (3 eq) is added to this solution, followed by addition, at 0° C., of 145 mg of p-toluenesulfonyl chloride (1.5 eq). The reaction mixture is then stirred at room temperature for 24 hours. The organic solution is washed twice with water. The organic phase obtained is dried over MgSO$_4$ and then evaporated under reduced pressure. The residue obtained is purified by chromatography on a column of silica (eluent: 7/3 CH$_2$Cl$_2$/EtOAc) to give 185 mg (72%) of compound 84.

m.p.: 85–86° C. (EtOAc/PE)

IR (KBr): v 1631, 1596, 1557, 1512 cm$^{-1}$ $^1$H NMR (250 MHz, CDCl$_3$): δ2.29 (s, 3H, CH$_3$), 3.79 (s, 3H, OCH$_3$), 3.82 (s, 3H, OCH$_3$), 3.88 (s, 3H, OCH$_3$), 4.39 (t, 2H, J=5.0 Hz, CH$_2$), 4.60 (t, 2H, J=5.0 Hz, CH$_2$), 6.65 (d, 1H, J=8.8 Hz, H$_{Ar}$), 6.90 (d, 2H, J=8.8 Hz, H$_{Ar}$), 6.95 (d, 2H, J=8.8 Hz, H$_{Ar}$), 7.08 (d, 1H, J=8.8 Hz, H$_{Ar}$), 7.29 (s, 1H, =CH), 7.51 (d, 2H, J=8.8 Hz, H$_{Ar}$), 7.54 (d, 2H, J=8.8 Hz, H$_{Ar}$)

$^{13}$C NMR (62.90 MHz, CDCl$_3$): δ21.5, 55.3, 56.4, 56.7, 56.8, 68.9, 105.3, 113.5 (2), 114.3, 120.0, 123.1, 127.5 (2), 129.8 (2), 130.0 (2), 131.8, 132.3, 142.5, 143.1, 145.3, 155.2, 158.8 176.0

MS (ion spray): m/z 510 (M+1)$^+$

Anal. calculated for C$_{27}$H$_{27}$NO$_7$S: C, 63.64; H, 5.34; N, 2.75. Found: C, 63.89; H, 5.40; N, 2.60

EXAMPLE 56
3-[5,8-Dimethoxy-3-(4-methoxyphenyl)-4-oxo-1,4-dihydro-1-quinolinyl]propanenitrile (compound 85)-CRL 8518

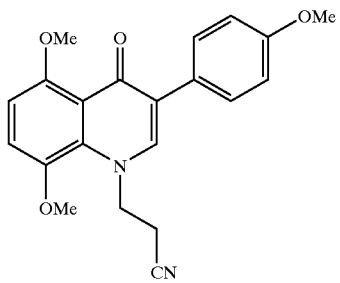

100 mg (0.20 mmol) of compound 84 are added to 3 ml of anhydrous dimethyl sulfoxide under a nitrogen atmosphere. 18 mg of sodium cyanide (2 eq) are added to this suspension. The final mixture is stirred at room temperature for 48 hours. The solution is diluted with ethyl acetate and washed twice with water. The organic phase is dried over $MgSO_4$ and then evaporated under reduced pressure. The residue obtained is purified by chromatography on a column of silica treated with triethylamine (eluent: 7/3 $CH_2Cl_2$/EtOAc) to give 30 mg (40%) of compound 85.

m.p.: 79–80° C. (EtOAc/PE)
IR (KBr): v 2252, 1631, 1596, 1562, 1512 $cm^{-1}$
$^1H$ NMR (250 MHz, $CDCl_3$): δ2.89 (t, 2H, J=5.0 Hz, $CH_2$), 3.81 (s, 3H, $OCH_3$), 3.90 (s, 3H, $OCH_3$), 3.93 (s, 3H, $OCH_3$), 4.64 (t, 2H, J=5.0 Hz, $CH_2$), 6.74 (d, 1H, J=8.8 Hz, $H_{Ar}$), 6.91 (d, 2H, J=8.8 Hz, $H_{Ar}$), 7.08 (d, 1H, J=8.8 Hz, $H_{Ar}$), 7.44 (s, 1H, =CH), 7.60 (d, 2H, J=8.8 Hz, $H_{Ar}$)
$^{13}C$ NMR (62.90 MHz, $CDCl_3$): δ19.8, 55.1, 55.4, 56.9, 57.1, 106.1, 113.7 (2), 114.5, 117.2, 120.2, 127.3, 130.2 (2), 132.6, 141.9, 142.6, 155.5, 159.0, 176.3
MS (ion spray): m/z 364 $(M+1)^+$
Anal. calculated for $C_{21}H_{20}N_2O_4$: C, 69.22; H, 5.53; N, 7.69. Found: C, 68.93; H, 5.35; N, 7.77

EXAMPLE 57
3-[5,8-Dimethoxy-3-(4-methoxyphenyl)-4-oxo-1,4-dihydro-1-quinolinyl]pentanenitrile (compound 86)-CRL 8463 and {[5,8-dimethoxy-3-(4-methoxyphenyl)-4-quinolyl]oxy}pentanenitrile (compound 87)-CRL 8519

1) 3-[5,8-Dimethoxy-3-(4-methoxyphenyl)-4-oxo-1,4-dihydro-1-quinolinyl]pentanenitrile (compound 86)-CRL 8463

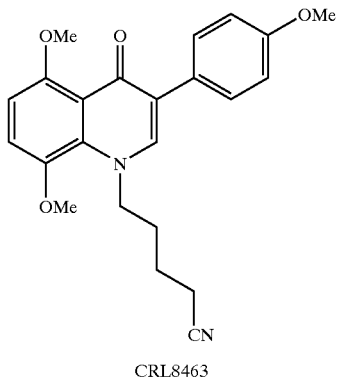

CRL8463

400 mg (1.28 mmol) of compound 29 are added to 15 ml of anhydrous N,N-dimethylformamide under a nitrogen atmosphere. 1.33 g of anhydrous potassium carbonate (7.5 eq) and then 0.44 ml of 5-chlorovaleronitrile (3 eq) are successively added to this suspension. The reaction is stirred at 80° C. for 5 hours. The solvents are evaporated off. The residue obtained is taken up in $CH_2Cl_2$ and washed twice with water. The organic phase obtained is dried over $MgSO_4$ and then evaporated under reduced pressure. The residue obtained is purified by chromatography on a column of silica treated with triethylamine (eluent: 9/1 $CH_2Cl_2$/EtOAc) to give 150 mg (30%) of compound 86 and 300 mg (59%) of derivative 87.

m.p.: 126–127° C. (EtOAc)
IR (KBr): v 2241, 1627, 1590, 1569, 1517 $cm^{-1}$
$^1H$ NMR (250 MHz, $CDCl_3$): δ1.54–1.66 (m, 2H, $CH_2$), 1.85–1.97 (m, 2H, $CH_2$), 2.33 (t, 2H, J=7.0 Hz, $CH_2CN$), 3.80 (s, 3H, $OCH_3$), 3.89 (s, 6H, $OCH_3$), 4.41 (t, 2H, J=7.0 Hz, $NCH_2$), 6.71 (d, 1H, J=8.9 Hz, $H_{Ar}$), 6.89 (d, 2H, J=8.8 Hz, $H_{Ar}$), 7.04 (d, 1H, J=8.9 Hz, $H_{Ar}$), 7.39 (s, 1H, =CH), 7.59 (d, 2H, J=8.8 Hz, $H_{Ar}$)
$^{13}C$ NMR (62.90 MHz, $CDCl_3$): δ17.0, 22.6, 30.0, 55.3, 56.8, 56.9, 57.2, 105.6, 113.5 (2), 114.4, 119.2, 120.3, 123.3, 127.7, 130.0 (2), 133.0, 142.5, 143.2, 155.2, 158.7, 176.1
MS (ion spray): m/z 393 $(M+1)^+$
Anal. calculated for $C_{23}H_{24}N_2O_4$: C, 70.39; H, 6.16; N, 7.14. Found: C, 70.65; H, 5.99; N, 7.26

2) {[5,8-Dimethoxy-3-(4-methoxyphenyl)-4-quinolyl]oxy}pentanenitrile (compound 87)-CRL 8519

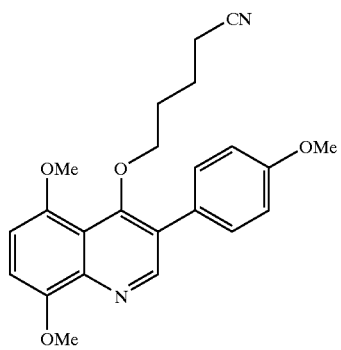

m.p.: 126–127° C. (EtOAc)
IR (KBr): v 2244, 1612, 1584, 1515 $cm^{-1}$
$^1H$ NMR (250 MHz, $CDCl_3$): δ1.65–1.70 (m, 4H, $CH_2$), 2.15 (t, 2H, J=7.0 Hz, $CH_2CN$), 3.67 (t, 2H, J=7.0 Hz, $OCH_2$), 3.87 (s, 3H, $OCH_3$), 3.95 (s, 3H, $OCH_3$), 4.04 (s, 3H, $OCH_3$), 6.83 (d, 1H, J=8.8 Hz, $H_{Ar}$), 6.95 (d, 2H, J=8.8 Hz, $H_{Ar}$), 7.01 (d, 1H, J=8.8 Hz, $H_{Ar}$), 7.53 (d, 2H, J=8.8 Hz, $H_{Ar}$), 8.85 (s, 1H, $H_{Ar}$)
$^{13}C$ NMR (62.90 MHz, $CDCl_3$): δ16.7, 22.3, 28.8, 55.5, 56.2, 56.6, 73.2, 106.1, 107.1, 114.0 (2), 117.2, 119.6, 127.5, 128.2, 131.2 (2), 142.6, 149.3, 150.0, 152.1, 159.5, 159.8
MS (ion spray): m/z 393 $(M+1)^+$
Anal. calculated for $C_{23}H_{24}N_2O_4$: C, 70.39; H, 6.16; N, 7.14. Found: C, 70.13; H, 6.30; N, 7.31

EXAMPLE 58
7-Methoxy-3-(4-methoxyphenyl)-1-methyl-5-piperidino-1,4-dihydro-4-quinolinone (compound 88)-CRL 8425

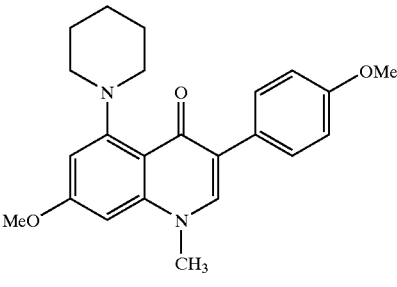

CRL8425

Compound 36 (90 mg, 2.03 mmol) and piperidine (0.1 ml, 1.0 mmol) are dissolved in dioxane (2 ml) in a sealed tube.

The final solution is heated at 100° C. for 6 hours. After cooling and evaporating off the solvent, the residue is purified by chromatography on a column of silica treated with triethylamine (eluent: 4/6 PE/EtOAc) to give 60 mg (75%) of compound 88.

m.p.: 197–198° C. (EtOAc/PE)

IR (KBr): v 1633, 1601, 1572, 1506, 1465 cm$^{-1}$ $^1$H NMR (250 MHz, CDCl$_3$): δ1.50–1.65 (m, 2H, CH$_2$), 1.70–1.90 (m, 4H, CH$_2$), 2.90–3.20 (m, 4H, CH$_2$), 3.67 (s, 3H, NCH$_3$), 3.81 (s, 3H, OCH$_3$), 3.89 (s, 3H, OCH$_3$), 6.23 (d, 1H, J=2.2 Hz, H$_{Ar}$), 6.45 (d, 1H, J=2.2 Hz, H$_{Ar}$), 6.91 (d, 2H, J=8.8 Hz, H$_{Ar}$), 7.38 (s, 1H, =CH), 7.54 (d, 2H, J=8.8 Hz, H$_{Ar}$)

$^{13}$C NMR (62.90 MHz, CDCl$_3$): δ24.6, 26.1 (2), 41.7, 54.6 (2), 55.3, 55.4, 90.6, 100.2, 113.7 (2), 114.6, 123.1, 128.9, 130.2 (2), 139.9, 145.1, 156.8, 158.6, 162.1, 175.5

MS (ion spray): m/z 379 (M+1)$^+$

Anal. calculated for C$_{23}$H$_{26}$N$_2$O$_3$: C, 72.99; H, 6.92; N, 7.40. Found: C, 73.27; H, 7.12; N, 7.26

EXAMPLE 59

7-Methoxy-3-(4-methoxyphenyl)-1-methyl-5-pyrrolidino-1,4-dihydro-4-quinolinone (compound 89)-CRL 8434

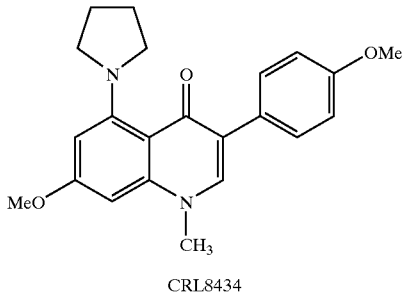

CRL8434

Compound 36 (100 mg, 2.2 mmol) and pyrrolidine (0.10 ml, 1.2 mmol) are dissolved in dioxane (4 ml) in a sealed tube. The final solution is heated at 100° C. for 6 hours. After cooling and evaporation of the solvent, the residue is purified by chromatography on a column of silica treated with triethylamine (eluent: 3/7 PE/EtOAc) to give 80 mg (97%) of compound 89.

m.p.: 201–202° C. (EtOAc/PE)

IR (KBr): v 1630, 1605, 1570, 1511, 1449 cm$^{-1}$ $^1$H NMR (250 MHz, CDCl$_3$): δ1.88–1.93 (m, 4H, CH$_2$), 3.35–3.40 (m, 4H, CH$_2$), 3.63 (s, 3H, NCH$_3$), 3.82 (s, 3H, OCH$_3$), 3.89 (s, 3H, OCH$_3$), 6.04 (d, 1H, J=2.2 Hz, H$_{Ar}$), 6.20 (d, 1H, J=2.2 Hz, H$_{Ar}$), 6.93 (d, 2H, J=8.8 Hz, CH$_2$), 7.34 (s, 1H, =CH), 7.56 (d, 2H, J=8.8 Hz, H$_{Ar}$)

$^{13}$C NMR (62.90 MHz, CDCl$_3$): δ25.9 (2), 41.3, 52.2 (2), 55.3, 55.4, 87.3, 94.1, 111.5, 113.8 (2), 122.2, 128.8, 129.8 (2), 139.4, 144.8, 152.1, 158.5, 162.1, 175.5

MS (ion spray): m/z 365 (M+1)$^+$

Anal. calculated for C$_{22}$H$_{24}$N$_2$O$_3$: C, 72.51; H, 6.64; N, 7.69. Found: C, 72.31; H, 6.53; N, 7.50

EXAMPLE 60

7-Methoxy-3-(4-methoxyphenyl)-1-methyl-5-morpholino-1,4-dihydro-4-quinolinone (compound 90)-CRL 8435

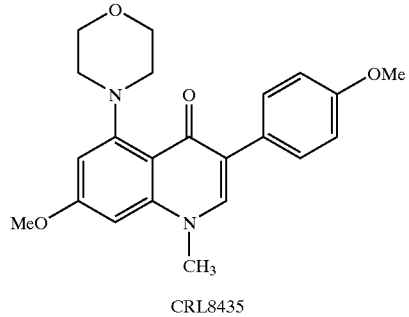

CRL8435

Compound 36 (150 mg, 0.33 mmol) and morpholine (0.15 ml, 1.69 mmol) are dissolved in dioxane (4 ml) in a sealed tube. The final solution is heated at 100° C. for 6 hours. After cooling and evaporating off the solvent, the residue is purified by chromatography on a column of silica treated with triethylamine (eluent: 1/9 PE/EtOAc) to give 120 mg (93%) of derivative 90.

m.p.: 194–195° C. (EtOAc)

IR (KBr): v 1636, 1606, 1583, 1557, 1503, 1446

$^1$H NMR (250 MHz, CDCl$_3$): δ3.05–3.17 (m, 4H, CH$_2$), 3.71 (s, 3H, NCH$_3$), 3.82 (s, 3H, OCH$_3$), 3.92 (s, 3H, OCH$_3$), 3.95–4.00 (m, 4H, CH$_2$), 6.32 (d, 1H, J=2.2 Hz, H$_{Ar}$), 6.44 (d, 1H, J=2.2 Hz, H$_{Ar}$), 6.93 (d, 2H, J=8.8 Hz, CH$_2$), 7.42 (s, 1H, =CH), 7.53 (d, 2H, J=8.8 Hz, H$_{Ar}$)

$^{13}$C NMR (62.90 MHz, CDCl$_3$): δ41.8 (2), 53.5 (2), 55.4, 55.5, 67.4, 91.4, 100.4, 113.8 (2), 114.8, 123.6, 128.7, 130.3 (2), 140.1, 145.3, 156.0, 158.8, 162.3, 175.4

MS (ion spray): m/z 381 (M+1)$^+$

Anal. calculated for C$_{22}$H$_{24}$N$_2$O$_4$: C, 69.46; H, 6.36; N, 7.36. Found: C, 69.72; H, 6.47; N, 7.30

EXAMPLE 61

7-Methoxy-3-(4-methoxyphenyl)-1-methyl-5-(1-methyl-piperazino)-1,4-dihydro-4-quinolinone (compound 91)-CRL 8436

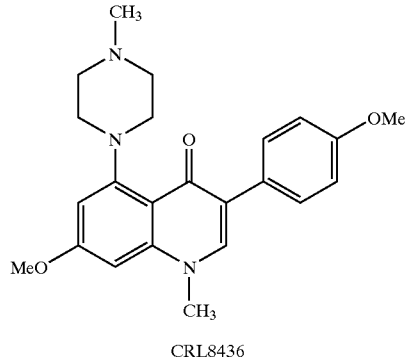

CRL8436

Compound 36 (100 mg, 0.22 mmol) and N-methylpiperazine (0.13 ml, 1.1 mmol) are dissolved in dioxane (2 ml) in a sealed tube. The final solution is heated at 100° C. for 5 hours. After cooling and evaporating off the solvent, the residue is purified by chromatography on a column of silica treated with triethylamine (eluent: 97/3 $CH_2Cl_2$/MeOH) to give 80 mg (90%) of derivative 91.

m.p.: 205–206° C. (EtOAc/PE)

IR (KBr): v 1632, 1610, 1558, 1531, 1513 $cm^{-1}$ $^1$H NMR (250 MHz, $CDCl_3$): δ2.40 (s, 3H, $NCH_3$), 2.76–2.80 (m, 4H, $CH_2$), 3.15–3.20 (m, 4H, $CH_2$), 3.70 (s, 3H, $NCH_3$), 3.81 (s, 3H, $OCH_3$), 3.90 (s, 3H, $OCH_3$), 6.31, (d, 1H, J=2.2 Hz, $H_{Ar}$), 6.45 (d, 1H, J=2.2 Hz, $H_{Ar}$), 6.92 (d, 2H, J=8.8 Hz, $H_{Ar}$) 7.42 (s, 1H, =CH), 7.52 (d, 2H, J=8.8 Hz, $H_{Ar}$)

$^{13}$C NMR (62.90 MHz, $CDCl_3$): δ41.9, 45.9, 52.7 (2), 55.3 (2), 55.4 (2), 91.4, 100.7, 113.8 (2), 114.6, 123.5, 128.7, 130.3 (2), 140.2, 145.1, 155.6, 158.7, 162.2, 175.4

MS (ion spray): m/z 394 $(M+1)^+$

Anal. calculated for $C_{23}H_{27}N_3O_3$: C, 70.21; H, 6.92; N, 10.68. Found: C, 69.89; H, 7.02; N, 10.81

EXAMPLE 62

5-Diethylamino-7-methoxy-3-(4-methoxyphenyl)-1-methyl-1,4-dihydro-4-quinolinone (compound 92)- CRL 8437

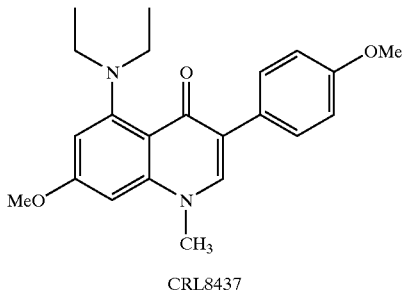

CRL8437

Compound 36 (100 mg, 2.2 mmol) and N,N-diethylamine (0.11 ml, 1.1 mmol) are dissolved in dioxane (4 ml) in a sealed tube. The final solution is heated at 100° C. for 24 hours. After cooling and evaporating off the solvent, the residue is purified by chromatography on a column of silica treated with triethylamine (eluent: 2/8 PE/EtOAc) to give 40 mg (50%) of compound 92.

oil

IR (film): v 1634, 1599, 1582, 1511 $cm^{-1}$ $^1$H NMR (250 MHz, $CDCl_3$): δ1.07 (t, 6H, J=7.2 Hz, $CH_3$), 3.34 (q, 4H, J=7.2 Hz, $CH_2$), 3.67 (s, 3H, $NCH_3$), 3.81 (s, 3H, $OCH_3$), 3.89 (s, 3H, $OCH_3$), 6.20 (d, 1H, J=2.2 Hz, $H_{Ar}$), 6.42 (d, 1H, J=2.2 Hz, $H_{Ar}$), 6.91 (d, 2H, J=8.8 Hz, $H_{Ar}$), 7.39 (s, 1H, =CH), 7.54 (d, 2H, J=8.8 Hz, $H_{Ar}$)

$^{13}$C NMR (62.90 MHz, $CDCl_3$): δ11.9 (2), 41.7, 46.6 (2), 55.3, 55.4, 90.1, 102.2, 113.7 (2), 115.0, 129.5, 128.8, 130.2 (2), 139.7, 145.2, 154.1, 158.6, 161.8, 175.3

MS (ion spray): m/z 367 $(M+1)^+$

Anal. calculated for $C_{22}H_{26}N_2O_3$: C, 72.11; H, 7.15; N, 7.64. Found: C, 71.84; H, 6.99; N, 7.76

EXAMPLE 63

5-Allylamino-7-methoxy-3-(4-methoxyphenyl)-1-methyl-1,4-dihydro-4-quinolinone (compound 93)- CRL 8520

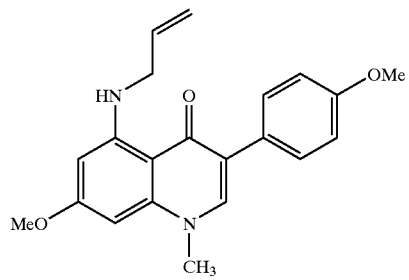

Compound 36 (100 mg, 2.2 mmol) and allylamine (84 μl, 1.1 mmol) are dissolved in dioxane (2 ml) in a sealed tube. The final solution is heated at 100° C. for 18 hours. After cooling and evaporating off the solvent, the residue is purified by chromatography on a column of silica treated with triethylamine (eluent: 3/7 PE/EtOAc) to give 71 mg (90%) of derivative 93.

m.p.: 154–155° C. (EtOAc/PE)

IR (KBr): v 1641, 1616, 1568, 1510 $cm^{-1}$ $^1$H NMR (250 MHz, $CDCl_3$): δ3.66 (s, 3H, $NCH_3$), 3.83 (s, 3H, $OCH_3$), 3.87 (broad s, 5H, $CH_2+OCH_3$), 5.17 (dd, 1H, J=1.3, 10.2 Hz, $CH_2$=), 5.32 (dd, 1H, J=1.3, 17.2 Hz, $CH_2$=), 5.85 (d, 1H, J=2.0 Hz, $H_{Ar}$), 5.91 (d, 1H, J=2.0 Hz, $H_{Ar}$), 5.85–6.02 (m, 1H, CH=), 6.94 (d, 2H, J=8.8 Hz, $H_{Ar}$), 7.39 (s, 1H, =CH), 7.47 (d, 2H, J=8.8 Hz, $H_{Ar}$), 10.71 (broad s, 1H, NH)

$^{13}$C NMR (62.90 MHz, $CDCl_3$): δ41.6, 45.6, 55.2, 55.5, 85.0, 89.3, 108.0, 113.8 (2), 116.3, 121.9, 128.1, 130.3 (2), 134.4, 140.5, 144.4, 153.9, 158.8, 163.7, 178.9

MS (ion spray): m/z 351 $(M+1)^+$

Anal. calculated for $C_{21}H_{22}N_2O_3$: C, 71.98; H, 6.33; N, 7.99. Found: C, 72.24; H, 6.25; N, 8.08

EXAMPLE 64

5-(4-Methoxybenzylamino)-7-methoxy-3-(4-methoxyphenyl)-1-methyl-1,4-dihydro-4-quinolinone (compound 94)-CRL 8521

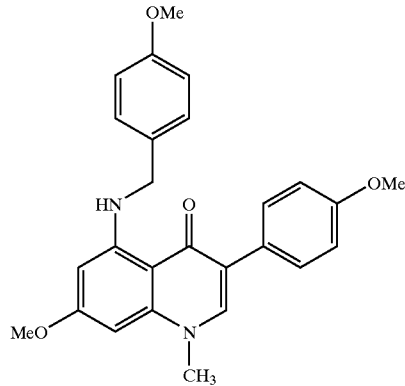

Compound 36 (200 mg, 0.45 mmol) and 4-methoxybenzylamine (0.30 ml, 2.2 mmol) are dissolved in dioxane (2 ml) in a sealed tube. The final solution is heated at 100° C. for 16 hours. After cooling and evaporating off the solvent, the residue is purified by chromatography on a column of silica treated with triethylamine (eluent: 1/1 PE/EtOAc) to give 168 mg (86%) of derivative 94.

m.p.: 144–145° C. (EtOAc/PE)

IR (KBr): ν 1638, 1613, 1572, 1521, 1509, 1465 cm$^{-1}$ $^1$H NMR (250 MHz, CDCl$_3$): δ3.65 (s, 3H, NCH$_3$), 3.78 (s, 3H, OCH$_3$), 3.80 (s, 3H, OCH$_3$), 3.82 (s, 3H, OCH$_3$), 4.36 (d, 2H, J=5.4 Hz, CH$_2$), 5.85 (d, 1H, J=2.2 Hz, H$_{Ar}$), 5.89 (d, 1H, J=2.2 Hz, H$_{Ar}$), 6.84 (d, 2H, J=8.5 Hz, H$_{Ar}$), 6.94 (d, 2H, J=8.8 Hz, H$_{Ar}$), 7.31 (d, 2H, J=8.5 Hz, H$_{Ar}$), 7.40 (s, 1H, =CH), 7.48 (d, 2H, J=8.8 Hz, H$_{Ar}$), 10.93 (t, 1H, J=5.4 Hz, NH)

$^{13}$C NMR (62.90 MHz, CDCl$_3$): δ41.4, 46.6, 55.1, 55.3, 55.4, 85.1, 89.6, 108.0, 113.7 (2), 114.0 (2), 121.8, 128.0, 128.6 (2), 130.1 (2), 130.8, 140.4, 144.3, 153.6, 158.7, 163.5, 178.8

MS (ion spray): m/z 431 (M+1)$^+$

Anal. calculated for C$_{26}$H$_{26}$N$_2$O$_4$: C, 72.54; H, 6.09; N, 6.51. Found: C, 72.80; H, 5.98; N, 6.71

EXAMPLE 65

5-Amino-7-methoxy-3-(4-methoxyphenyl)-1-methyl-1,4-dihydro-4-quinolinone (compound 95)-CRL 8461

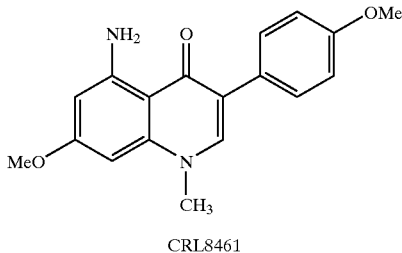

CRL8461

100 mg (0.23 mmol) of compound 94 are dissolved in 3 ml of trifluoroacetic acid under a nitrogen atmosphere. The reaction is stirred at 65° C. for 1 hour. The acid is evaporated off. The residue obtained is taken up in ethyl acetate and washed twice with 10% sodium hydroxide solution. The organic phase obtained is dried over MgSO$_4$ and then evaporated under reduced pressure. The residue is purified by chromatography on a column of silica treated with triethylamine (eluent: 3/7 PE/EtOAc) to give 50 mg (69%) of compound 95.

m.p.: 161–162° C. (EtOAc/PE)

IR (KBr): ν 3446, 3381, 1635, 1610, 1569, 1511 cm$^{-1}$

H NMR (250 MHz, CDCl$_3$): δ3.62 (s, 3H, NCH$_3$), 3.82 (s, 3H, OCH$_3$), 3.84 (s, 3H, OCH$_3$), 5.92 (d, 1H, J=2.2 Hz, H$_{Ar}$), 5.98 (d, 1H, J=2.2 Hz, H$_{Ar}$), 6.94 (d, 2H, J=8.8 Hz, H$_{Ar}$), 7.11 (broad s, 2H, NH$_2$), 7.40 (s, 1H, =CH), 7.49 (d, 2H, J=8.8 Hz, H$_{Ar}$)

$^{13}$C NMR (62.90 MHz, CDCl$_3$): δ41.5, 55.3, 55.5, 87.1, 93.8, 108.4, 113.8 (2), 121.8, 128.1, 130.2 (2), 140.9, 144.2, 153.7, 158.8, 163.2, 179.1

MS (ion spray): m/z 311 (M+1)$^+$

Anal. calculated for C$_{18}$H$_{18}$N$_2$O$_3$: C, 69.66; H, 5.85; N, 9.03. Found: C, 70.01; H, 5.69; N, 8.92

EXAMPLE 66

5-{[(Dimethylamino)ethyl]amino}-7-methoxy-3-(4-methoxyphenyl)-1-methyl-1,4-dihydro-4-quinolinone (compound 96)-CRL 8462

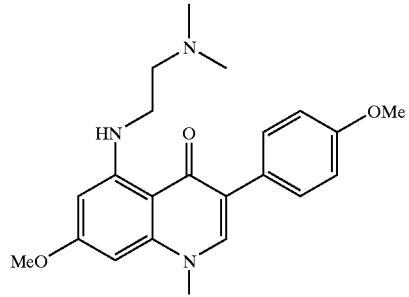

CRL8462

Compound 36 (200 mg, 0.45 mmol) and N,N-dimethylethylenediamine (0.25 ml, 2.2 mmol) are dissolved in dioxane (2 ml) in a sealed tube. The final solution is heated at 100° C. for 5 hours. After cooling and evaporating off the solvent, the residue is purified by chromatography on a column of silica treated with triethylamine (eluent: 97/3 CH$_2$Cl$_2$/MeOH) to give 155 mg (90%) of derivative 96.

m.p.: 130–131° C. (washing with ether)

IR (KBr): ν 1637, 1608, 1572, 1509, 1467 cm$^{-1}$ $^1$H NMR (250 MHz, CDCl$_3$): δ2.33 (s, 6H, CH$_3$), 2.68 (t, 2H, J=7.2 Hz, CH$_2$), 3.36–3.39 (m, 2H, CH$_2$), 3.63 (s, 3H, NCH$_3$), 3.81 (s, 3H, OCH$_3$), 3.88 (s, 3H, OCH$_3$), 5.85 (d, 1H, J=2.2 Hz, H$_{Ar}$), 5.93 (d, 1H, J=2.2 Hz, H$_{Ar}$), 6.93 (d, 2H, J=8.8 Hz, H$_{Ar}$), 7.38 (s, 1H, CH=), 7.46 (d, 2H, J=8.8 Hz, H$_{Ar}$), 10.51 (broad s, 1H, NH)

$^{13}$C NMR (62.90 MHz, CDCl$_3$): δ41.1, 41.6, 45.6 (2), 55.3, 55.5, 58.0, 85.1, 88.8, 108.0, 113.8 (2), 122.0, 128.1, 130.3 (2), 140.6, 144.5, 153.8, 158.8, 163.8, 178.9

MS (ion spray): m/z 382 (M+1)$^+$

Anal. calculated for C$_{22}$H$_{27}$N$_3$O$_3$: C, 69.27; H, 7.13; N, 11.02. Found: C, 68.93; H, 6.94; N, 10.98

EXAMPLE 67

7-Methoxy-3-(4-methoxyphenyl)-1-methyl-1,4-dihydro-4-quinolinone (compound 97)-CRL 8464

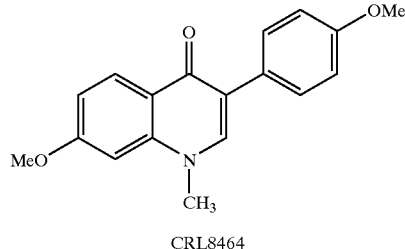

CRL8464

200 mg (0.71 mmol) of compound 26 are added to 10 ml of anhydrous N,N-dimethylformamide under a nitrogen atmosphere. 735 mg of anhydrous potassium carbonate (7.5 eq) and then 0.13 ml of methyl iodide (3 eq) are successively added to this suspension. The reaction is stirred at room temperature for 24 hours. The solvents are evaporated off.

The residue is taken up in $CH_2Cl_2$ and washed twice with water. The organic phase obtained is dried over $MgSO_4$ and then evaporated under reduced pressure. The residue is purified by chromatography on a column of silica treated with triethylamine (eluent: EtOAc) to give 171 mg (81%) of compound 97.

m.p.: 154–155° C. (EtOAc/PE)

IR (KBr): v 1622, 1570, 1549, 1511 $cm^{-1}$ $^1$H NMR (250 MHz, $CDCl_3$): δ3.69 (s, 3H, $NCH_3$), 3.79 (s, 3H, $OCH_3$), 3.88 (s, 3H, $OCH_3$), 6.61 (d, 1H, J=2.2 Hz, $H_{Ar}$), 6.88 (d, 2H, J=8.8 Hz, $H_{Ar}$), 6.94 (dd, 1H, J=2.2, 8.8 Hz, $H_{Ar}$), 7.51 (s, 1H, =CH), 7.53 (d, 2H, J=8.8 Hz, $H_{Ar}$), 8.42 (d, 1H, J=8.8 Hz, $H_{Ar}$)

$^{13}$C NMR (62.90 MHz, $CDCl_3$): δ40.7, 55.4, 55.6, 97.7, 112.4, 113.7 (2), 121.3, 121.4, 128.0, 129.3, 129.8 (2), 141.6, 141.9, 158.7, 162.6, 175.5

MS (ion spray): m/z 296 $(M+1)^+$

Anal. calculated for $C_{18}H_{17}NO_3$: C, 73.20; H, 5.80; N, 4.74. Found: C, 73.45; H, 5.63; N, 4.97

EXAMPLE 68

[7-Methoxy-3-(4-methoxyphenyl)-4-oxo-1,4-dihydro-1-quinolinyl]acetonitrile (compound 98)-CRL 8522

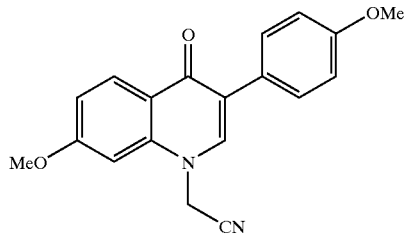

200 mg (0.71 mmol) of compound 26 are added to 10 ml of anhydrous N,N-dimethylformamide under a nitrogen atmosphere. 736 mg of anhydrous potassium carbonate (7.5 eq) and then 0.15 ml of bromoacetonitrile (3 eq) are successively added to this suspension. The reaction is stirred at room temperature for 18 hours. The solvents are evaporated off. The residue obtained is taken up in dichloromethane and washed twice with water. The organic phase obtained is dried over $MgSO_4$ and then evaporated under reduced pressure. The crude product is recrystallized from ethyl acetate to give 84 mg (37%) of compound 98.

m.p.: 206–207° C. (EtOAc)

IR (KBr): v 2240, 1622, 1576, 1513 $cm^{-1}$ $^1$H NMR (250 MHz, $CDCl_3$): δ3.82 (s, 3H, $OCH_3$), 3.97 (s, 3H, $OCH_3$), 4.91 (s, 2H, $CH_2$), 6.71 (d, 1H, J=2.2 Hz, $H_{Ar}$), 6.94 (d, 2H, J=8.8 Hz, $H_{Ar}$), 7.05 (dd, 1H, J=2.2, 8.8 Hz, $H_{Ar}$), 7.51 (s, 1H, =CH), 7.53 (d, 2H, J=8.8 Hz, $H_{Ar}$), 8.47 (d, 1H, J=8.8 Hz, $H_{Ar}$)

$^{13}$C NMR (62.90 MHz, $CDCl_3$): δ40.7, 55.4, 55.6, 97.7, 112.4, 113.7 (2), 121.3, 121.4, 128.0, 129.3, 129.8(2), 141.6, 141.9, 158.7, 162.6, 175.5

MS (ion spray): m/z 321 $(M+1)^+$

Anal. calculated for $C_{19}H_{16}N_2O_3$: C, 71.24; H, 5.03; N, 8.74. Found: C, 71.88; H, 4.89; N, 8.77

EXAMPLE 69

Ethyl 2-[7-methoxy-3-(4-methoxyphenyl)-4-oxo-1,4-dihydro-1-quinolinyl]acetate (compound 99)-CRL 8465

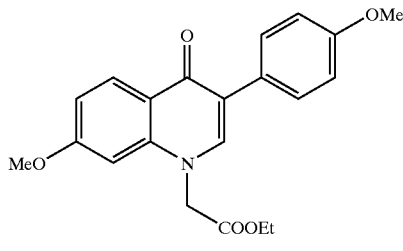

CRL8465

200 mg (0.71 mmol) of compound 26 are added to 10 ml of anhydrous N,N-dimethylformamide under a nitrogen atmosphere. 736 mg of anhydrous potassium carbonate (7.5 eq) and then 0.24 ml of ethyl bromoacetate (3 eq) are successively added to this suspension. The reaction is stirred at 90° C. for 3 hours. The solvents are evaporated off. The residue is taken up in dichloromethane and washed twice with water. The organic phase is dried over $MgSO_4$ and then evaporated under reduced pressure. The residue obtained is purified by chromatography on a column of silica treated with triethylamine (eluent: EtOAc) to give 220 mg (84%) of compound 99.

m.p.: 138–139° C. (EtOAc)

IR (KBr): v 1747, 1619, 1581, 1515, 1472 $cm^{-1}$ $^1$H NMR (250 MHz, $CDCl_3$): δ1.27 (t, 3H, J=7.2 Hz, $CH_3$), 3.83 (s, 3H, $OCH_3$), 3.90 (s, 3H, $OCH_3$), 4.26 (q, 2H, J=7.2 Hz, $CH_2$), 4.74 (s, 2H, $CH_2$), 6.55 (d, 1H, J=2.2 Hz, $H_{Ar}$), 6.94 (d, 2H, J=8.8 Hz, $H_{Ar}$), 6.98 (dd, 1H, J=2.2, 8.8 Hz, $H_{Ar}$), 7.53 (s, 1H, =CH), 7.59 (d, 2H, J=8.8 Hz, $H_{Ar}$), 8.47 (d, 1H, J=8.8 Hz, $H_{Ar}$)

$^{13}$C NMR (62.90 MHz, $CDCl_3$): δ14.2, 54.1, 55.3, 55.6, 62.3, 97.5, 112.9, 113.6 (2), 121.2, 122.0, 127.6, 129.6, 129.8 (2), 141.2, 141.8, 158.8, 162.8, 167.4, 175.8

MS (ion spray): m/z 368 $(M+1)^+$

Anal. calculated for $C_{21}H_{21}NO_5$: C, 68.65; H, 5.76; N, 3.81. Found: C, 68.93; H, 5.93; N, 3.98

EXAMPLE 70

N,N-Diethyl-2-[7-methoxy-3-(4-methoxyphenyl)-4-oxo-1,4-dihydro-1-quinolinyl]acetamide (compound 100)-CRL 8466

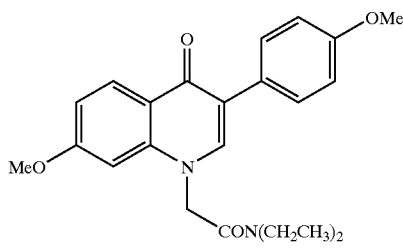

CRL8466

200 mg (0.71 mmol) of compound 26 are dissolved in 10 ml of anhydrous N,N-dimethylformamide under a nitrogen atmosphere. 26 mg (1.5 eq) of 60% sodium hydride, washed beforehand in petroleum ether, are added portionwise to the reaction medium (exothermic reaction). 2-Chloro-N,N-diethylacetamide (0.20 ml, 2 eq) is added to the medium. The reaction is heated at 90° C. for 18 hours. After cooling, water is poured into the reaction mixture, which is then extracted with ethyl acetate (twice). The organic phase is dried over MgSO$_4$ and then evaporated under reduced pressure. The residue obtained is purified by chromatography on a column of silica (EtOAc) to give 230 mg (82%) of compound 100.

m.p.: 166–167° C. (EtOAc)

IR (KBr): ν 1647, 1627, 1587, 1513, 1471 cm$^{-1}$ $^1$H NMR (250 MHz, CDCl$_3$): δ1.15 (t, 3H, J=7.2 Hz, CH$_3$), 1.30 (t, 3H, J=7.2 Hz, CH$_3$), 3.42 (q, 4H, J=7.2 Hz, CH$_2$), 3.81 (s, 3H, OCH$_3$), 3.84 (s, 3H, OCH$_3$), 4.74 (s, 2H, CH$_2$), 6.40 (d, 1H, J=2.2 Hz, H$_{Ar}$), 6.89 (d, 2H, J=8.8 Hz, H$_{Ar}$), 6.93 (dd, 1H, J=2.2, 8.8 Hz, H$_{Ar}$), 7.46 (s, 1H, =CH), 7.56 (d, 2H, J=8.8 Hz, H$_{Ar}$), 8.44 (d, 1H, J=8.8 Hz, H$_{Ar}$)

$^{13}$C NMR (62.90 MHz, CDCl$_3$): δ13.1, 14.7, 41.2, 41.7, 54.2, 55.4, 55.6, 98.0, 112.0, 113.7 (2), 121.5, 121.9, 128.0, 129.7, 130.0 (2), 141.6, 142.2, 158.8, 162.7, 164.7, 175.9

MS (ion spray): m/z 310 (M+1)$^+$

Anal. calculated for C$_{23}$H$_{26}$N$_2$O$_4$: C, 70.03; H, 6.64; N, 7.10. Found: C, 70.27; H, 6.76; N, 7.05

EXAMPLE 71

3-[7-Methoxy-3-(4-methoxyphenyl)-4-oxo-1,4-dihydro-1-quinolinyl]propanenitrile (compound 101)-CRL 8467

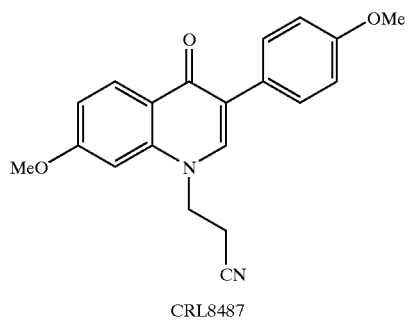

CRL8487

200 mg (0.71 mmol) of compound 26 are added to 10 ml of anhydrous N,N-dimethylformamide under a nitrogen atmosphere. 1.35 g of anhydrous potassium carbonate (7.5 eq) and then 0.35 ml of 1-bromopropionitrile (3 eq) are successively added to this suspension. The reaction is stirred at room temperature for 18 hours. The solvents are evaporated off. The residue is taken up in dichloromethane and washed twice with water. The organic phase obtained is dried over MgSO$_4$ and then evaporated under reduced pressure. The residue is purified by chromatography on a column of silica treated with triethylamine (eluent: EtOAc) to give 175 mg (74%) of compound 101.

m.p.: 179–180° C. (EtOAc/PE)

IR (KBr): ν 2248, 1624, 1582, 1550, 1512 cm$^{-1}$ $^1$H NMR (250 MHz, CDCl$_3$): δ2.91 (t, 2H, J=6.6 Hz, CH$_2$CN), 3.82 (s, 3H, OCH$_3$), 3.94 (s, 3H, OCH$_3$), 4.39 (t, 2H, J=6.6 Hz, NCH$_2$), 6.64 (d, 1H, J=2.2 Hz, H$_{Ar}$), 6.93 (d, 2, J=8.8 Hz, H$_{Ar}$), 7.01 (dd, 1H, J=2.2, 8.8 Hz, H$_{Ar}$), 7.57 (d, 2H, J=8.8 Hz, H$_{Ar}$), 7.63 (s, 1H, =CH), 8.49 (d, 1H, J=8,8 Hz, H$_{Ar}$)

$^{13}$C NMR (62.90 MHz, CDCl$_3$): δ17.8, 48.2, 55.5, 55.9, 97.7, 111.8, 113.9 (2), 116.5, 121.7, 122.6, 127.4, 130.0 (2); 130.5, 140.0, 140.6, 159.1, 163.1, 175.8

MS (ion spray): m/z 335 (M+1)$^+$

Anal. calculated for C$_{20}$H$_{18}$N$_2$O$_3$: C, 71.84; H, 5.43; N, 8.38. Found: C, 71.62; H, 5.55; N, 8.19

EXAMPLE 72

Ethyl 3-[7-methoxy-3-(4-methoxyphenyl)-4-oxo-1,4-dihydro-1-quinolinyl]propanoate (compound 102)-CRL 8468

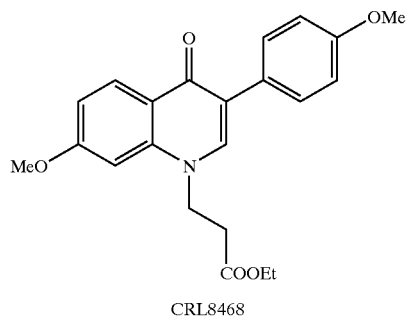

CRL8468

200 mg (0.71 mmol) of compound 26 are added to 10 ml of anhydrous N,N-dimethylformamide under a nitrogen atmosphere. 735 mg of anhydrous potassium carbonate (7.5 eq) and then 0.27 ml of ethyl 3-bromopropionate (3 eq) are successively added to this suspension. The reaction is stirred at room temperature for 18 hours. The solvents are evaporated off. The residue is taken up in CH$_2$Cl$_2$ and washed twice with water. The organic phase is dried over MgSO$_4$ and then evaporated under reduced pressure. The residue obtained is purified by chromatography on a column of silica treated with triethylamine (eluent: EtOAc) to give 166 mg (61%) of compound 102.

m.p.: 138–139° C. (EtOAc/PE)

IR (KBr): ν 1730, 1618, 1579, 1548, 1514 cm$^{-1}$ $^1$H NMR (250 MHz, CDCl$_3$): δ1.18 (t, 3H, J=7.0 Hz, CH$_3$), 2.84 (t, 2H, J=6.6 Hz, CH$_2$CO), 3.79 (s, 3H, OCH$_3$), 3.89 (s, 3H, OCH$_3$), 4.11 (q, 2H, J=7.0 Hz, OCH$_2$), 4.37 (t, 2H, J=6.6 Hz, NCH$_2$), 6.70 (d, 1H, J=2.2 Hz, H$_{Ar}$), 6.89 (d, 2H, J=8.8 Hz, H$_{Ar}$), 6.95 (dd, 1H, J=2.2, 8.8 Hz, H$_{Ar}$), 7.56 (d, 2H, J=8.8 Hz, H$_{Ar}$), 7.71 (s, 1H, =CH), 8.44 (d, 1H, J=8.8 Hz, H$_{Ar}$)

$^{13}$C NMR (62.90 MHz, CDCl$_3$): δ14.1, 33.3, 48.4, 55.3, 55.7, 61.4, 97.7, 112.0, 113.7 (2), 121.5, 121.6, 127.8, 129.8 (2), 129.8, 140.3, 141.8, 158.7, 162.7, 170.7, 175.5

MS (ion spray): m/z 382 (M+1)$^+$

Anal. calculated for C$_{22}$H$_{23}$NO$_5$: C, 69.28; H, 6.08; N, 3.67. Found: C, 68.98; H, 5.90; N, 3.55

EXAMPLE 73

N-[3-(Dimethylamino)ethyl]-7-methoxy-3-(4-methoxyphenyl)-1,4-dihydro-4-quinolinone (compound 103)-CRL 8469 and N-{2-[7-methoxy-3-(4-methoxyphenyl)-4-quinolyl]oxy}ethyl-N,N-dimethylamine (compound 104)-CRL 8523

1) N-[3-(Dimethylamino)ethyl]-7-methoxy-3-(4-methoxyphenyl)-1,4-dihydro-4-quinolinone (compound 103)-CRL 8469

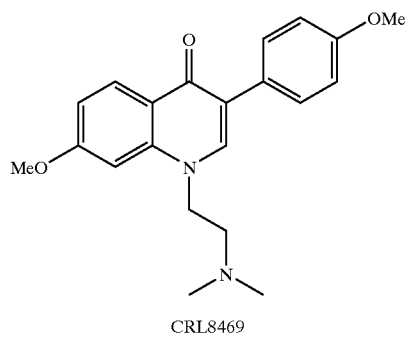

CRL8469

200 mg (0.71 mmol) of compound 26 are dissolved in 15 ml of anhydrous N,N-dimethylformamide (DMF) under a nitrogen atmosphere. 26 mg (1.5 eq) of NaH, washed beforehand in petroleum ether, are added portionwise to the reaction mixture (exothermic reaction), at 0° C. A solution of 3-dimethylaminoethyl chloride (205 mg, 2 eq) in 5 ml of DMF is added to the medium. The reaction is heated at 90° C. for 18 hours. After cooling, water is poured into the reaction mixture, which is then stirred for 15 minutes. The solution is extracted with ethyl acetate (twice). The organic phase is dried over MgSO$_4$ and then evaporated under reduced pressure. The residue obtained is purified by chromatography on a column of silica (eluent: EtOAc and then 97/3 Et$_2$OAc/MeOH) to give 180 mg (72%) of compound 103 and 30 mg (12%) of derivative 104.

m.p.: 142–143° C. (EtOAc)

IR (KBr): v 1616, 1572, 1546, 1512 cm$^{-1}$ $^1$H NMR (250 MHz, CDCl$_3$): δ2.29 (s, 6H, NCH$_3$), 2.68 (t, 2H, J=6.9 Hz, CH$_2$), 3.80 (s, 3H, OCH$_3$), 3.89 (s, 3H, OCH$_3$), 4.11 (t, 2H, J=6.9 Hz, CH$_2$), 6.74 (d, 1H, J=2.2 Hz, H$_{Ar}$), 6.89 (d, 2H, J=8.8 Hz, H$_{Ar}$), 6.95 (dd, 1H, J=2.2, 8.8 Hz, H$_{Ar}$), 7.57 (d, 2H, J=8.8 Hz, H$_{Ar}$), 7.59 (s, 1H, =CH), 8.44 (d, 1H, J=8.8 Hz, H$_{Ar}$)

$^{13}$C NMR (62.90 MHz, CDCl$_3$): δ45.8 (2), 51.3, 55.3, 55.6, 57.3, 97.7, 112.1, 113.6 (2), 121.2, 121.6, 128.0, 129.6, 129.7 (2), 140.7, 141.7, 158.6, 162.6, 175.4

MS (ion spray): m/z 353 (M+1)$^+$

Anal. calculated for C$_{21}$H$_{24}$N$_2$O$_3$: C, 71.57; H, 6.86; N, 7.95. Found: C, 71.43; H, 6.99; N, 8.09

2) N-{2-[7-Methoxy-3-(4-methoxyphenyl)-4-quinolyl]-oxy}ethyl-N,N-dimethylamine (compound 104)-CRL 8523

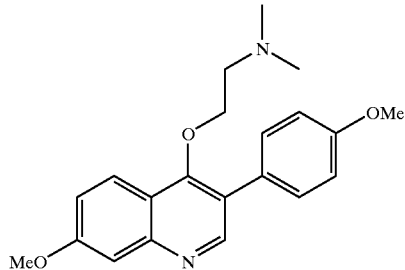

oil

IR (film): v 1620, 1566, 1515, 1492 cm$^{-1}$ $^1$H NMR (250 MHz, CDCl$_3$): δ2.20 (s, 6H, CH$_3$), 2.53 (t, 2H, J=6.0 Hz, CH$_2$), 3.77 (t, 2H, J=6.0 Hz, OCH$_2$), 3.87 (s, 3H, OCH$_3$), 3.95 (s, 3H, OCH$_3$), 7.01 (d, 2H, J=8.8 Hz, H$_{Ar}$), 7.21 (dd, 1H, J=2.2, 8.8 Hz, H$_{Ar}$), 7.40 (d, 1H, J=2.2 Hz, H$_{Ar}$), 7.56 (d, 2H, J=8.8 Hz, H$_{Ar}$), 8.17 (d, 1H, J=8.8 Hz, H$_{Ar}$), 8.75 (s, 1H, H$_{Ar}$)

$^{13}$C NMR (62.90 MHz, CDCl$_3$): δ45.8 (2), 55.5, 55.6, 59.1, 71.2, 107.3, 114.3 (2), 119.0, 119.5, 122.8, 123.9, 128.2, 130.6 (2), 151.0, 153.8, 159.4, 159.7, 161.0

MS (ion spray): m/z 353 (M+1)$^+$

Anal. calculated for C$_{21}$H$_{24}$N$_2$O$_3$: C, 71.57; H, 6.86; N, 7.95. Found: C, 71.67; H, 6.97; N, 7.89

EXAMPLE 74

4-[7-Methoxy-3-(4-methoxyphenyl)-4-oxo-1,4-dihydro-1-quinolinyl]butanenitrile (compound 105)-CRL 8470 and {[7-methoxy-3-(4-methoxyphenyl)-4-quinolyl]oxy}butanenitrile (compound 106)-CRL 8524

1) 4-[7-Methoxy-3-(4-methoxyphenyl)-4-oxo-1,4-dihydro-1-quinolinyl]butanenitrile (compound 105)-CRL 8470

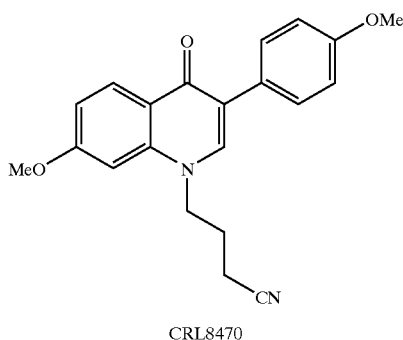

CRL8470

200 mg (0.71 mmol) of compound 26 are added to 10 ml of anhydrous N,N-dimethylformamide under a nitrogen atmosphere. 735 mg of anhydrous potassium carbonate (7.5 eq) and then 0.20 ml of 4-chlorobutyronitrile (3 eq) are successively added to this suspension. The reaction is stirred at 80° C. for 18 hours. The solvents are evaporated off. The residue is taken up in CH$_2$Cl$_2$ and washed twice with water. The organic phase is dried over MgSO$_4$ and then evaporated under reduced pressure. The residue obtained is purified by chromatography on a column of silica treated with triethylamine (eluent: EtOAc) to give 80 mg (32%) of compound 105 and 130 mg (53%) of derivative 106.

m.p.: 151–152° C. (EtOAc)

IR (KBr): v 2252, 1621, 1575, 1552, 1509 cm$^{-1}$ $^1$H NMR (250 MHz, CDCl$_3$): δ2.22–2.30 (m, 2H, CH$_2$), 2.46 (t, 2H, J=7.2 Hz, CH$_2$CN), 3.83 (s, 3H, OCH$_3$), 3.94 (s, 3H, OCH$_3$), 4.28 (t, 2H, J=7.2 Hz, NCH$_2$), 6.76 (d, 1H, J=2.2 Hz, H$_{Ar}$), 6.95 (d, 2H, J=8.8 Hz, H$_{Ar}$), 7.00 (dd, 1H, J=2.2, 8.8 Hz, H$_{Ar}$), 7.59 (d, 2H, J=8.8 Hz, H$_{Ar}$), 7.61 (s, 1H, =CH), 8.49 (d, 1H, J=8.8 Hz, H$_{Ar}$)

$^{13}$C NMR (62.90 MHz, CDCl$_3$): δ14.7, 24.6, 51.0, 55.4, 55.9, 97.6, 112.4, 113.9 (2), 118.5, 121.7, 122.2, 127.6, 129.9 (2), 130.1, 140.5, 140.8, 159.0, 163.1, 175.6

MS (ion spray): m/z 349 (M+1)$^+$

Anal. calculated for C$_{21}$H$_{20}$N$_2$O$_3$: C, 72.40; H, 5.79; N, 8.04. Found: C, 72.07; H, 5.65; N, 7.93

2) {[7-Methoxy-3-(4-methoxyphenyl)-4-quinolyl]oxy}-butanenitrile (compound 106)-CRL 8524

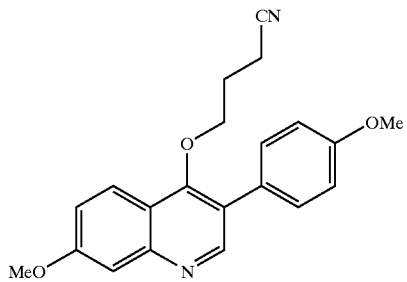

oil

IR (film): v 2248, 1620, 1565, 1514 cm$^{-1}$ $^1$H NMR (250 MHz, CDCl$_3$): δ1.87–1.97 (m, 2H, CH$_2$), 2.43 (t, 2H, J=7.2 Hz, CH$_2$), 3.80 (t, 2H, J=7.2 Hz, CH$_2$), 3.86 (s, 3H, OCH$_3$), 3.94 (s, 3H, OCH$_3$), 7.02 (d, 2H, J=8.8 Hz, H$_{Ar}$), 7.21 (dd, 1H, J=2.2, 8.8 Hz, H$_{Ar}$), 7.41 (d, 1H, J=2.2 Hz, H$_{Ar}$), 7.49 (d, 2H, J=8.8 Hz, H$_{Ar}$), 8.02 (d, 1H, J=8.8 Hz, H$_{Ar}$), 8.74 (s, 1H, H$_{Ar}$)

$^{13}$C NMR (62.90 MHz, CDCl$_3$): δ14.2, 26.3, 55.5, 55.6, 71.2, 107.5, 114.4 (2), 118.5, 119.1, 119.9, 123.1, 123.2, 127.7, 130.6 (2), 151.0, 153.7, 158.8, 159.5, 161.0

Anal. calculated for C$_{21}$H$_{20}$N$_2$O$_3$: C, 72.40; H, 5.79; N, 8.04. Found: C, 72.21; H, 5.93; N, 8.12

EXAMPLE 75

N,N-Diethyl-3-[7-methoxy-3-(4-methoxyphenyl)-4-oxo-1,4-dihydro-1-quinolinyl]propanamide (compound 107)-CRL 8525

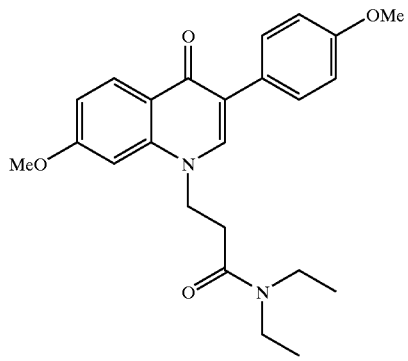

330 mg (1.1 mmol) of compound 26 are added to 10 ml of anhydrous N,N-dimethylformamide under a nitrogen atmosphere. 1.18 g of anhydrous potassium carbonate (7.5 eq) and then 546 mg of 3-bromopropionic acid (3 eq) are successively added to this suspension. The reaction is stirred at 80° C. for 45 hours. The solvents are evaporated off. The residue is taken up in CH$_2$Cl$_2$ and washed twice with water. The organic phase is dried over MgSO$_4$ and then evaporated under reduced pressure. The crude compound is dissolved in 10 ml of anhydrous CH$_2$Cl$_2$ under a nitrogen atmosphere. 263 mg (2.1 mmol) of dimethylaminopyridine and 275 mg (1.4 mmol) of EDCI are added to the reaction solution, at 0° C. The reaction is stirred for 10 minutes at 0° C., followed by addition of 0.15 ml (1.4 mmol) of diethylamine. The final solution is stirred at 0° C. for 2 hours and then at room temperature for 24 hours. The organic phase is washed several times with water. The organic phase is dried over MgSO$_4$ and then evaporated under reduced pressure. The residue obtained is purified by chromatography on a column of silica (EtOAc) to give 140 mg (26%) of compound 113.

m.p.: 158–159° C. (EtOAc)

IR (KBr): ν 1633, 1570, 1550, 1513 cm$^{-1}$ $^1$H NMR (250 MHz, CDCl$_3$): δ1.03 (t, 3H, J=7.2 Hz, CH$_3$), 1.07 (t, 3H, J=7.2 Hz, CH$_3$), 2.83 (t, 2H, J=7.0 Hz, COCH$_2$), 3.16 (q, 2H, J=7.0 Hz, NCH$_2$), 3.36 (q, 2H, J=7.0 Hz, NCH$_2$), 3.82 (s, 3H, OCH$_3$), 3.93 (s, 3H, OCH$_3$), 4.52 (t, 2H, J=7.0 Hz, NCH$_2$), 6.83 (d, 1H, J=2.2 Hz, H$_{Ar}$), 6.94 (d, 2H, J=8.8 Hz, H$_{Ar}$), 6.98 (dd, 1H, J=2.2, 8.8 Hz, H$_{Ar}$), 7.61 (d, 2H, J=8.8 Hz, H$_{Ar}$), 7.79 (s, 1H, =CH), 8.49 (d, 1H, J=8.8 Hz, H$_{Ar}$)

$^{13}$C NMR (62.90 MHz, CDCl$_3$): δ13.1, 14.4, 32.0, 40.7, 42.0, 49.1, 55.5, 55.9, 97.9, 111.9, 113.8 (2), 121.7, 121.9, 128.0, 129.9 (2), 130.1, 140.6, 141.8, 158.8, 162.8, 168.5, 175.7

MS (ion spray): m/z 409 (M+1)$^+$

Anal. calculated for C$_{24}$H$_{28}$N$_2$O$_4$: C, 70.57; H, 6.91; N, 6.86. Found: C, 70.21; H, 6.80; N, 6.77

EXAMPLE 76

7-Methoxy-3-(4-methoxyphenyl)-1-[2-(2H-1,2,3,4-tetrazol-5-yl)ethyl]-1,4-dihydro-4-quinolinone (compound 108)-CRL 8474

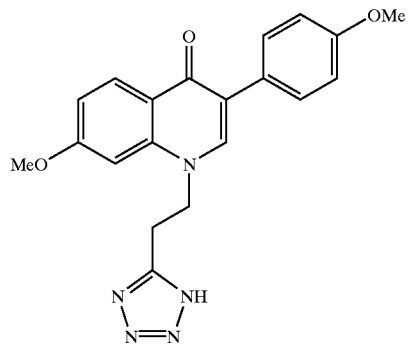

150 mg (0.45 mmol) of compound 101 and 0.19 ml (0.67 mmol) of tributyltin azide are dissolved in 20 ml of anhydrous toluene under an argon atmosphere. The reaction solution is stirred at 105° C. for 48 hours. After cooling, the solvent is evaporated off under reduced pressure. The residue obtained is purified by chromatography on a column of silica (97/3 CH$_2$Cl$_2$/MeOH) to give 152 mg (90%) of compound 108.

m.p.: 245–246° C. (washing with MeOH)

IR (KBr): ν 1617, 1556, 1524, 1511 cm$^{-1}$ $^1$H NMR (250 MHz, CDCl$_3$): δ3.46 (t, 2H, J=7.0 Hz, CH$_2$), 3.79 (s, 3H, OCH$_3$), 3.93 (s, 3H, OCH$_3$), 4.60 (t, 2H, J=7.0 Hz, CH$_2$), 6.86–6.93 (m, 3H, H$_{Ar}$), 6.97 (dd, 1H, J=2.2, 8.8 Hz, H$_{Ar}$), 7.43 (d, 2H, J=8.8 Hz, H$_{Ar}$), 7.64 (s, 1H, =CH), 8.38 (d, 1H, J=8.8 Hz, H$_{Ar}$)

$^{13}$C NMR (62.90 MHz, DMSO-d$_6$): δ25.1, 51.8, 55.4, 55.8, 97.6, 113.1, 113.9 (2), 121.5, 121.9, 127.7, 129.6, 130.0 (2), 140.7, 142.0, 158.9, 163.1, 175.7

MS (ion spray): m/z 378 (M+1)$^+$

Anal. calculated for C$_{20}$H$_{19}$N$_5$O$_3$: C, 61.91; H, 5.20; N, 17.19. Found: C, 62.00; H, 5.19; N, 17.30

The results of the pharmacological tests, presented below, demonstrate the properties of the compounds of formulae (I) and (Ia).

1—Cytotoxic Activity on Non-clonogenic Cell Lines in Culture: (MTT Test)

The influence of the compounds of formulae (I) and (Ia) on non-clonogenic cells was evaluated with the aid of the MTT colorimetric test (T. Mosman. J. Immunol Methods 1983; 65: 55–63, J. Carmichael et al., Cancer Res. 1987; 47: 936–942).

The principle of the MTT test is based on the mitochondrial reduction, by the metabolically active live cells, of the yellow-colored product MTT (3-(4,5-dimethylthiazol-2-yl)-2,5-diphenyltetrazolium bromide) to a blue-colored product, formazan. The amount of formazan thus obtained is directly proportional to the amount of live cells present in the culture well(s). This amount of formazan is measured by spectrophotometry.

The cell lines are maintained as a monolayer culture at 37° C. in stoppered culture dishes containing MEM 25 MM HEPES (Minimum Essential Medium) base medium. This medium is suited to the growth of a range of various mammalian diploid or primary cells. This medium is then supplemented with:

an amount of 5% of FCS (Fetal Calf Serum) decomplemented at 56° C. for 1 h, 0.6 mg/ml of L-glutamine, 200 UI/ml of penicillin, 200 µg/ml of streptomycin, 0.1 mg/ml of gentamicin.

The 12 human cancer cell lines which were used were obtained from the American Type Culture Collection (ATCC, Rockville, Md., USA). These 12 cell lines are:

U-373MG (code ATCC: HTB-17) and U-87MG (code ATCC: HTB-14) which are two glioblastomas, SW1088 (code ATCC: HTB-12) which is an astrocytoma, A549 (code ATCC: CCL-185) and A-427 (code ATCC: HTB-53) which are two non-small-cell lung cancers, HTC-15 (code ATCC: CCL-225) and LoVo (code ATCC: CCL-229) which are two colorectal cancers, T-47D (code ATCC: HTB-133) and MCF7 (code ATCC: HTB-22) which are two breast cancers, J82 (code ATCC: HTB-1) and T24 (code ATCC: HTB-4) which are two bladder cancers, PC-3 (code ATCC: CRL-1345) which is a prostate cancer.

Experimentally, 100 µl of a cell suspension containing 20 000 to 50 000 (depending on the cell type used) cells/ml of culture medium are inoculated -in 96-well flat-bottomed multi-well plates and are left to stand in an incubator at 37° C., 5% $CO_2$ and 70% humidity. After an incubation time of 24 hours, the culture medium is replaced with 100 µl of fresh medium containing either the various test compounds—at concentrations varying from $10^{-5}$ to $10^{-10}$ M—or the solvent having served for dissolving the products to be tested (control condition). After 72 hours of incubation under the conditions defined above, the culture medium is replaced with 100 µl of a yellowish solution of MTT dissolved at a rate of 1 mg/ml in RPMI 1640. The microplates are thus incubated for 3 hours at 37° C., then centrifuged for 10 minutes at 400 g. The yellowish solution of MTT is removed and the blue formazan crystals formed in the cell region are dissolved in 100 µl or DMSO. The microplates are then shaken for 5 minutes. The intensity of the blue coloration resulting from the conversion of the yellow product MTT into blue formazan by the cells that are still alive at the end of the experiment is quantified by spectrophotometry using a Dynatech Immunoassay System machine at wavelengths of 570 nm and 630 nm, corresponding respectively to the maximum absorbance wavelengths of formazan and to background noise. Software incorporated in the spectrophotometer calculates the average optical density values and the standard deviation (SD) and standard error of mean (SEM) values.

By way of example, the results of the mean optical density, expressed as percentages relative to the mean optical density measured under the control condition (also set at 100%), obtained at a concentration of $10^{-5}$ M on the 12 abovementioned tumor cell lines, will be given in Tables Ia, Ib, Ic and Id.

TABLE Ia

| 4-QUINOLONES | CELL LINES | | | | | |
|---|---|---|---|---|---|---|
| | U-87MG | U-373MG | SW1088 | T24 | J82 | HCT-16 |
| CRL8326 | 101.7 ± 2.6 NS | 96.9 ± 2.31 NS | 108 ± 2.3* | 92.6 ± 3 NS | 86.9 ± 1.4*** | 109.8 ± 2.5** |
| CRL8327 | 89 ± 3.1* | 58.7 ± 1.0*** | 99 ± 3.9 NS | 187.4 ± 4.2 NS | 85.1 ± 1.5*** | 87.5 ± 2.6* |
| CRL8328 | 85.7 ± 4.7 NS | 98.1 ± 2 NS | 91 ± 2.7* | 94.8 ± 4.4 NS | 95.9 ± 1.5 NS | 85.8 ± 2.3** |
| CRL8329 | 1.38 ± 3.1 NS | 94 ± 2.3 NS | 96.2 ± 3.9 NS | 95.4 ± 3 NS | 96.8 ± 0.7* | 98 ± 2 NS |
| CRL8337 | 84.4 ± 3.5** | 95.6 ± 4.4 NS | 84.9 ± 3.4** | 102.3 ± 1.6 NS | 90.9 ± 0.3*** | 98.5 ± 2.2 NS |
| CRL8340 | 87.6 ± 2.2* | 97.9 ± 2.5 NS | 84 ± 1.3** | 82.8 ± 1.8*** | 90.2 ± 1.1*** | 92.5 ± 2.2* |
| CRL8349 | 98.3 ± 0.8 NS | 66.7 ± 3.4** | 100.5 ± 2 NS | 95.1 ± 1.4* | 93.3 ± 0.6* | 91.2 ± 2.4* |
| CRL8350 | 85.6 ± 1.9 NS | 59.5 ± 1.8 NS | 100.7 ± 2 NS | 86.9 ± 2.3** | 91.5 ± 1.3** | 95.3 ± 2.8 NS |
| CRL8351 | 115.9 ± 2.7*** | 52.8 ± 1.4*** | 82.3 ± 1.4*** | 38.4 ± 1.3*** | 39.2 ± 8.5*** | 39.1 ± 0.3*** |
| CRL8352 | 158.1 ± 1.8 NS | 103.6 ± 2.7 NS | 96.8 ± 2.7 NS | 83.7 ± 2.4*** | 93 ± 1.7* | 105.7 ± 3.3 NS |
| CRL8353 | 107.4 ± 2.2 NS | 54.5 ± 1.6*** | 74 ± 2.6*** | 68.6 ± 1.9*** | 79.1 ± 1.1*** | 55.7 ± 0.9*** |
| CRL8354 | 102.4 ± 3.6 NS | 97.7 ± 2.2 NS | 93.2 ± 3.6 NS | 91.4 ± 0.8** | 98.2 ± 2.4 NS | 95.9 ± 2.1 NS |
| CRL8355 | 94.4 ± 1.8* | 97.7 ± 1.2 NS | 97.5 ± 3 NS | 89.4 ± 1.9** | 94.9 ± 2 NS | 99.5 ± 3.9 NS |
| CRL8357 | 84.4 ± 0.9*** | 96 ± 1.6 NS | 69.6 ± 1.8** | 99 ± 2 NS | 84.7 ± 1*** | 79.5 ± 1.8*** |

| 4-QUINOLONES | CELL LINES | | | | | |
|---|---|---|---|---|---|---|
| | LoVo | MCF7 | T-47D | A549 | A-427 | PC-3 |
| CRL8326 | 67.7 ± 1.8*** | 94.1 ± 2 NS | 50.2 ± 2.3*** | 104.2 ± 3.3 NS | 100.6 ± 1.1 NS | 95.4 ± 0.8* |
| CRL8327 | 47.3 ± 2.9*** | 90.7 ± 2.7* | 79 ± 1.4*** | 71.5 ± 2.8*** | 77.5 ± 3.7** | 87.4 ± 1.5*** |
| CRL8328 | 94.3 ± 4.5 NS | 93.7 ± 3.4 NS | 96 ± 3.6 NS | 92.5 ± 2.5 NS | 101 ± 4.1 NS | 91.9 ± 1.9* |

TABLE Ia-continued

| | | | | | | |
|---|---|---|---|---|---|---|
| CRL8329 | 94.6 ± 2.8 NS | 96.3 ± 1.5 NS | 78.5 ± 1.5*** | 96.5 ± 4.1 NS | 101.6 ± 2.4 NS | 93.1 ± 1.8* |
| CRL8337 | 93.3 ± 2.8 NS | 76.5 ± 0.6*** | 79.4 ± 4.2** | 96.9 ± 2.9 NS | 105.6 ± 3.4 NS | 92.8 ± 2.9 NS |
| CRL8340 | 93 ± 3.2 NS | 72.3 ± 1.3*** | 66.1 ± 2.7*** | 84 ± 4.4** | 84.2 ± 7.4*** | 84.8 ± 1.5*** |
| CRL8349 | 104.4 ± 3.4 NS | 97.4 ± 1.6 NS | 91 ± 2.4* | 96.2 ± 4.2 NS | 90.7 ± 2.9 NS | 98.6 ± 1.4 NS |
| CRL8350 | 92 ± 1.7* | 180.6 ± 1.5 NS | 87.1 ± 2.5* | 93 ± 4.7 NS | 99.5 ± 4.6 NS | 95.3 ± 2.8 NS |
| CRL8351 | 67 ± 1.8*** | 49 ± 0.7*** | 55 ± 2.4*** | 34.6 ± 1.6*** | 33.7 ± 0.4*** | 83.2 ± 1.7*** |
| CRL8352 | 102.6 ± 2.6 NS | 85.6 ± 1.5*** | 105 ± 4.1 NS | 94.2 ± 3.1 NS | 102.8 ± 2.4 NS | 97.3 ± 0.6 NS |
| CRL8353 | 85.5 ± 1.9** | 49.6 ± 1.5*** | 87.2 ± 2.3** | 42.3 ± 1.3*** | 52.5 ± 2.1*** | 81 ± 1*** |
| CRL8354 | 98.4 ± 1.8 NS | 101.7 ± 2.3 NS | 104.4 ± 3.8 NS | 98.5 ± 3.1 NS | 97.2 ± 4 NS | 93.7 ± 1.2* |
| CRL8355 | 98.7 ± 2.1 NS | 94.8 ± 2 NS | 98.5 ± 3.1* | 98.6 ± 4.7 NS | 102.8 ± 2.3 NS | 100.2 ± 1.2 NS |
| CRL8357 | 97.9 ± 2.7 NS | 95.8 ± 1.8 NS | 94.1 ± 1.9 | 73.3 ± 1.3* | 59.5 ± 2.8* | 85.6 ± 2.5 | x ± y = mean value ± standard error of mean
Control condition = 100%
(NS: $p > 0.05$; *: $p < 0.05$; : $p < 0.01$; *: $p < 0.001$)

TABLE Ib

| | CELL LINES | | | | | |
|---|---|---|---|---|---|---|
| 4-QUINOLONES | U-87MG | U-373MG | SW1088 | T24 | J82 | HCT-16 |
| CRL8358 | 80.1 ± 1.5*** | 41 ± 1*** | 98.3 ± 3.6* | 90.7 ± 1*** | 92.7 ± 1.3* | 89.1 ± 1.5*** |
| CRL8359 | 114.2 ± 1.4*** | 41.2 ± 0.5*** | 140.3 ± 2.2*** | 34.7 ± 0.5*** | 52.2 ± 0.8*** | 59.9 ± 0.9*** |
| CRL8360 | 97.6 ± 1.8*** | 88 ± 2** | 75.1 ± 3.2*** | 87.5 ± 3.2* | 81.2 ± 2.4*** | 91.8 ± 2.4* |
| CRL8370 | 104.3 ± 2.6 NS | 105.4 ± 4.4 NS | 99.4 ± 2.4 NS | 74.3 ± 1.3*** | 102.1 ± 0.8 NS | 103.3 ± 2.8 NS |
| CRL8371 | 58.7 ± 1.3*** | 42.8 ± 1.5*** | 40.8 ± 1*** | 52.2 ± 1.8*** | 76.3 ± 7.7*** | 25.2 ± 1.2*** |
| CRL8372 | 92.9 ± 2.7 NS | 94.8 ± 1.3* | 98.1 ± 0.5 NS | 81.2 ± 1.1** | 93 ± 1.1** | 84.3 ± 3.3** |
| CRL8377 | 49.5 ± 0.6*** | 56.7 ± 2.9*** | 99.8 ± 3.5 NS | 85 ± 1.3* | 98.7 ± 1.7 NS | 86.6 ± 3.3*** |
| CRL8378 | 73 ± 1.6*** | 98.1 ± 1.1 NS | 108.4 ± 4.4 NS | 89.2 ± 1.6 NS | 99.6 ± 0.9 NS | 104.6 ± 2.3 NS |
| CRL8379 | 95.3 ± 1.6 NS | 112.6 ± 0.8*** | 98.3 ± 3.7 NS | 101.7 ± 1.6 NS | 100.6 ± 2.7 NS | 105.7 ± 0.19 NS |
| CRL8380 | 87.5 ± 2.2** | 100.9 ± 0.7 NS | 100.3 ± 2.8 NS | 94.9 ± 1.2 NS | 98.9 ± 2 NS | 102.6 ± 2.3 NS |
| CRL8381 | 48.1 ± 1.4*** | 91.8 ± 2.2* | 55.9 ± 3*** | 83.2 ± 2.5*** | 90.9 ± 0.5*** | 90.5 ± 1.9** |
| CRL8382 | 59.2 ± 1.3** | 101.3 ± 1 NS | 117.8 ± 1.2*** | 99.7 ± 1.1 NS | 95.6 ± 1.4 NS | 93.1 ± 1.9** |
| CRL8383 | 69.5 ± 0.9*** | 83.5 ± 2* | 75.9 ± 1.3*** | 180.5 ± 1.3 NS | 94.6 ± 0.9** | 100.3 ± 0.9 NS |
| CRL8391 | 74 ± 2.1*** | 93.5 ± 0.9 NS | 92.5 ± 1.5* | 100.6 ± 0.8 NS | 99.6 ± 1.2 NS | 80.6 ± 2*** |

| | CELL LINES | | | | | |
|---|---|---|---|---|---|---|
| 4-QUINOLONES | LoVo | MCF7 | T-47D | A549 | A-427 | PC-3 |
| CRL8358 | 38 ± 1.7*** | 84.1 ± 2.5** | 92.1 ± 4.1** | 55 ± 2*** | 34.5 ± 0.8*** | 89.1 ± 2.3** |
| CRL8359 | 30.9 ± 1*** | 65.8 ± 1.8*** | 41.2 ± 2*** | 73.9 ± 0.8*** | 25.8 ± 0.9*** | 122.6 ± 4*** |
| CRL8360 | 98.6 ± 1.2 NS | 95.3 ± 3.5 NS | 82.1 ± 4.1** | 85.6 ± 2** | 71.3 ± 3*** | 81.5 ± 3.4** |
| CRL8370 | 95.1 ± 3.8 NS | 88.5 ± 2.5** | 88.5 ± 4.3* | 85.6 ± 1.3*** | 76 ± 3.2*** | 87.1 ± 2.3** |
| CRL8371 | 45.6 ± 2*** | 45.6 ± 2.6*** | 49.3 ± 4.1*** | 42.9 ± 0.8*** | 30.8 ± 0.7*** | 54.2 ± 0.6*** |
| CRL8372 | 83.9 ± 3** | 96.6 ± 1.4 NS | 65.7 ± 2.2** | 93.4 ± 6 NS | 93.9 ± 3.6 NS | 109.8 ± 2* |
| CRL8377 | 85 ± 3.4* | 104.2 ± 3.1 NS | 66.9 ± 3.1*** | 67 ± 1.9** | 26.5 ± 1.5*** | 87.4 ± 1.8*** |
| CRL8378 | 107.3 ± 4.1 NS | 93.5 ± 2.9 NS | 109.8 ± 3.1 NS | 91 ± 1** | 72.3 ± 2.8*** | 100.2 ± 1.6 NS |
| CRL8379 | 102.2 ± 1.3 NS | 91.6 ± 2.6 NS | 99.3 ± 3.5 NS | 94 ± 1.5 NS | 94.2 ± 1.9 NS | 99.2 ± 1.5 NS |
| CRL8380 | 107.8 ± 3 NS | 102.2 ± 2 NS | 88.1 ± 2.9** | 95 ± 3.5 NS | 89.3 ± 2.5** | 101.9 ± 1.1 NS |

TABLE Ib-continued

| | | | | | | |
|---|---|---|---|---|---|---|
| CRL8381 | 105 ± 3.4 NS | 67.2 ± 1.3*** | 92.6 ± 3.9 NS | 73.8 ± 1.2*** | 84.2 ± 1.7*** | 79.1 ± 1.3*** |
| CRL8382 | 96.7 ± 3 NS | 93 ± 1.9* | 94.7 ± 1.2 NS | 90.4 ± 1.7*** | 89.2 ± 1.7*** | 100.3 ± 0.9 NS |
| CRL8383 | 89.1 ± 2** | 85 ± 0.9*** | 75.3 ± 1.4*** | 84.1 ± 1.7*** | 92.1 ± 1.2 NS | 88.3 ± 0.9 NS |
| CRL8391 | 87.2 ± 3.2 | 97.3 ± 1 NS | 99.3 ± 3.6 NS | 88.3 ± 2.9 | 80.5 ± 1.4* | 80 ± 2.1* | x ± y = mean value ± standard error of mean
Control condition = 100%
(NS: p >0.05; *: p <0.05; : p <0.01; *: p <0.001)

TABLE Ic

| | CELL LINES | | | | | |
|---|---|---|---|---|---|---|
| 4-QUINOLONES | U-87MG | U-373MG | SW1088 | T24 | J82 | HCT-16 |
| CRL8392 | 82.7 ± 1** | 90.2 ± 2.7** | 89.8 ± 2.7*** | 63 ± 2.2*** | 70.6 ± 2.1*** | 77.4 ± 21.4*** |
| CRL8393 | 89.9 ± 1.6** | 74.7 ± 1.5*** | 82.8 ± 1.5** | 95.3 ± 1.3 NS | 97.9 ± 1.4 NS | 41.8 ± 0.9*** |
| CRL8394 | 42.2 ± 1.3*** | 73.5 ± 2*** | 68.5 ± 1.8*** | 92.9 ± 1** | 93.5 ± 1.3** | 37.7 ± 0.8*** |
| CRL8404 | 91.5 ± 2.5* | 104.5 ± 2.1 NS | 72.1 ± 4*** | 59.8 ± 1.1 NS | 83.8 ± 2.7 NS | 93.7 ± 2.3 NS |
| CRL8405 | 25.8 ± 0.7*** | 28.8 ± 0.7*** | 40.8 ± 1.6*** | 57.8 ± 3.5*** | 93.9 ± 0.9*** | 15.9 ± 0.7*** |
| CRL8412 | 83.4 ± 1.7** | 80.8 ± 0.4*** | 104.7 ± 3.3 NS | 100.3 ± 3.4 NS | 94.2 ± 2.7 NS | 83.6 ± 7.4*** |
| CRL8413 | 56 ± 0.6*** | 66.4 ± 0.7*** | 83.7 ± 2.2* | 71.8 ± 4.5*** | 88.4 ± 1.1*** | 65.9 ± 7.8*** |
| CRL8414 | 81.2 ± 3.8** | 81.7 ± 1.4*** | 94.4 ± 4.4 NS | 97.5 ± 3.4 NS | 109.8 ± 2.1 NS | 83.4 ± 1.3*** |
| CRL8420 | 92.9 ± 2.9 NS | 96.6 ± 3.5 NS | 117 ± 4.7* | 111.3 ± 4.7 NS | 92.3 ± 3.1 NS | 109.3 ± 1.9** |
| CRL8421 | 29.9 ± 3.8*** | 81.7 ± 2*** | 51 ± 2.5*** | 40.3 ± 2.3*** | 47.1 ± 1.2*** | 50 ± 2*** |
| CRL8424 | 87.9 ± 3.3*** | 82.5 ± 3*** | 82.7 ± 4.3*** | 101.5 ± 4.2 NS | 77.9 ± 2.9*** | 49.8 ± 2.9*** |
| CRL8425 | 92.6 ± 1.5* | 82.6 ± 2.5*** | 85.4 ± 3** | 98.2 ± 3.4 NS | 71.9 ± 4.4*** | 78.9 ± 2.2*** |
| CRL8434 | 89.7 ± 1*** | 92.2 ± 1*** | 99.9 ± 1.2 NS | 98.7 ± 1.6 NS | 99.3 ± 0.8 NS | 100.9 ± 1.1 NS |
| CRL8435 | 85 ± 0.8*** | 85 ± 1.9*** | 97.3 ± 0.7* | 89.4 ± 1.1 NS | 100.5 ± 1.2 NS | 101.4 ± 1.1 NS |

| | CELL LINES | | | | | |
|---|---|---|---|---|---|---|
| 4-QUINOLONES | LoVo | MCF7 | T-47D | A549 | A-427 | PC-3 |
| CRL8392 | 79.7 ± 1.7*** | 74 ± 1.3*** | 68.6 ± 0.8*** | 77.6 ± 1*** | 49.7 ± 2*** | 51.6 ± 1.7*** |
| CRL8393 | 84.6 ± 1.4*** | 89.7 ± 0.8*** | 68.8 ± 3.7*** | 93 ± 2.4 NS | 23.7 ± 0.5*** | 87.3 ± 2.9** |
| CRL8394 | 45.1 ± 0.7*** | 78 ± 1.1*** | 94.3 ± 3.7 NS | 52.9 ± 0.7*** | 38.9 ± 1.7*** | 83.2 ± 19*** |
| CRL8404 | 90.7 ± 7.3* | 93.4 ± 3.4 NS | 66.7 ± 3.4** | 93.5 ± 1.8* | 93.3 ± 1.7* | 99.7 ± 0.7 NS |
| CRL8405 | 32.3 ± 1.4*** | 68.2 ± 2.5*** | 77.1 ± 2.2*** | 32 ± 0.8*** | 19.4 ± 0.6*** | 85.5 ± 1.2*** |
| CRL8412 | 77 ± 1.9*** | 99.1 ± 3 NS | 109 ± 3.6 NS | 84.5 ± 1.8*** | 83.7 ± 2.3* | 103.9 ± 3.6 NS |
| CRL8413 | 85.6 ± 1.9** | 67.2 ± 0.5*** | 112.3 ± 4.9 NS | 48.7 ± 1.9*** | 73.3 ± 4.4*** | 63.4 ± 2*** |
| CRL8414 | 84.2 ± 1.7** | 104.5 ± 3.1 NS | 96.2 ± 2.9 NS | 71.8 ± 1.8*** | 82.2 ± 2.7* | 94.3 ± 1.5 NS |
| CRL8420 | 81.2 ± 3.8** | 102.9 ± 4.8 NS | 104.5 ± 2.2 NS | 94.5 ± 3.5 NS | 101.8 ± 4.2 NS | 86 ± 4.5 NS |
| CRL8421 | 60.8 ± 3.4*** | 49.5 ± 3.6*** | 83.5 ± 1.4*** | 97.5 ± 3.9 NS | 33 ± 0.9*** | 61.4 ± 4.2*** |
| CRL8424 | 69.8 ± 2.8*** | 95.4 ± 2.9* | 107.5 ± 3.3 NS | 111.2 ± 4.6 NS | 72.7 ± 3.1*** | 108.3 ± 1.7 NS |
| CRL8425 | 71 ± 3*** | 102 ± 3.8 NS | 97.3 ± 8.1 NS | 80.2 ± 1.4** | 81.9 ± 2.8*** | 88.2 ± 4.1 NS |
| CRL8434 | 106.2 ± 0.9 NS | 96.2 ± 0.7** | 85.8 ± 2.2*** | 99 ± 1.2 NS | 109.8 ± 2.1** | 113.1 ± 2.6* |
| CRL8435 | 105.6 ± 0.8* | 93.6 ± 1.3 | 95.7 ± 2 NS | 96.7 ± 0.7 NS | 115.2 ± 1.5*** | 104.7 ± 4.8 NS | x ± y = mean value ± standard error of mean
Control condition = 100%
(NS: p >0.05; *: p <0.05; : p <0.01; *: p <0.001)

TABLE Id

| 4-QUINOLONES | CELL LINES | | | | | |
|---|---|---|---|---|---|---|
| | U-87MG | U-373MG | SW1088 | T24 | J82 | HCT-16 |
| CRL8436 | 97.3 ± 0.9* | 97.2 ± 0.9* | 102.1 ± 1.7 NS | 99.2 ± 1.6 NS | 101 ± 0.9 NS | 101.4 ± 0.8 NS |
| CRL8437 | 99.4 ± 1.3 NS | 93.2 ± 1 NS | 99.7 ± 1.2 NS | 93.1 ± 1.3** | 98.7 ± 0.5*** | 109.5 ± 0.9 NS |
| CRL8460 | 71.5 ± 2.1*** | 52.2 ± 3.4*** | 65.7 ± 4.9*** | 14.2 ± 2.6*** | 45.7 ± 1.6*** | 53.7 ± 2.4*** |
| CRL8461 | 77.2 ± 1.6*** | 91.6 ± 0.9** | 91.9 ± 1.4** | 106.8 ± 2.9 NS | 94.9 ± 1.9 NS | 88.5 ± 4.8 NS |
| CRL8462 | 195.3 ± 1.1 NS | 110.7 ± 2.2** | 104.7 ± 3.5 | 110.9 ± 6 NS | 105 ± 2.3 NS | 77.4 ± 2.2*** |
| CRL8463 | 45.5 ± 1.1*** | 58.9 ± 3.1*** | 37.3 ± 1.1*** | 18.7 ± 1.1*** | 35.6 ± 1.7*** | 27.3 ± 1*** |
| CRL8464 | 104.7 ± 1.3 | 117.9 ± 4.6* | 95.6 ± 2.2 NS | 104.7 ± 1.9 NS | 95.4 ± 3.7 NS | 110.6 ± 3.2* |
| CRL8465 | 105 ± 2.5 NS | 100.5 ± 3.9 NS | 89.8 ± 2.1 NS | 91.2 ± 4 NS | 93.6 ± 2.1 NS | 165.2 ± 4.7 |
| CRL8466 | 97.2 ± 2.8 NS | 59.4 ± 1.9 NS | 102.4 ± 4.5 NS | 69.5 ± 4.8 NS | 93.1 ± 3 NS | 96.1 ± 2 NS |
| CRL8467 | 95.3 ± 2.1 NS | 107.7 ± 3.1 NS | 101.1 ± 1.2 NS | 94.6 ± 1.6* | 96.3 ± 0.8 NS | 108.5 ± 2 NS |
| CRL8468 | 92.7 ± 2.7 NS | 107.2 ± 4.1 NS | 103.9 ± 1.8 NS | 98.5 ± 2.1 NS | 91.9 ± 1.4** | 110.8 ± 2.9* |
| CRL8469 | 108.4 ± 1.4 NS | 102.2 ± 0.7 NS | 104.7 ± 0.7 NS | 98.1 ± 1.2 NS | 89.5 ± 1.2*** | 100.8 ± 3.4 NS |
| CRL8470 | 97.2 ± 4 NS | 103.9 ± 4.1 NS | 92.5 ± 1.2*** | 100.9 ± 3.7 NS | 85.6 ± 1.5* | 95.5 ± 4.3 NS |

| 4-QUINOLONES | CELL LINES | | | | | |
|---|---|---|---|---|---|---|
| | LoVo | MCF7 | T-47D | A549 | A-427 | PC-3 |
| CRL8436 | 107.5 ± 1.1** | 96.4 ± 0.6** | 89.4 ± 2.2** | 100.7 ± 0.7 NS | 108.7 ± 0.8*** | 99.9 ± 3.4 NS |
| CRL8437 | 104.9 ± 1.3** | 97.7 ± 1.4 NS | 92.1 ± 1.8** | 102 ± 0.7 NS | 108.2 ± 1.3* | 94.1 ± 1.4* |
| CRL8460 | 25.5 ± 1*** | 35 ± 2.3*** | 56.2 ± 3.4*** | 43.1 ± 4*** | 24.9 ± 2.9*** | 35.2 ± 3.2*** |
| CRL8461 | 92.7 ± 3.8 NS | 68.2 ± 2.1*** | 51.9 ± 3.9*** | 99.7 ± 2.2 NS | 90.5 ± 3.7* | 91.9 ± 4 NS |
| CRL8462 | 84.6 ± 3.2** | 89.4 ± 0.9** | 92.2 ± 3.4 NS | 86.8 ± 2.8* | 77.1 ± 1.6*** | 84 ± 3.7** |
| CRL8463 | 37.6 ± 1.3*** | 40.8 ± 2.1*** | 48.3 ± 4.3*** | 50.8 ± 1.9*** | 29.1 ± 1.1*** | 37.3 ± 1.1*** |
| CRL8464 | 100.6 ± 4.6 NS | 99.8 ± 3.5 NS | 109.7 ± 4.9 NS | 91.3 ± 1.7** | 101.5 ± 0.7 NS | 97.1 ± 1.6 NS |
| CRL8465 | 110.3 ± 4.4 NS | 94.3 ± 4.9 NS | 94.4 ± 4.9 NS | 80.1 ± 4** | 85.4 ± 3.2* | 96.9 ± 2.2 NS |
| CRL8466 | 98.9 ± 1.9 NS | 108.3 ± 4.6 NS | 95.2 ± 4.2 NS | 101.1 ± 1.9 NS | 97.5 ± 3.5 NS | 101.6 ± 2.2 NS |
| CRL8467 | 95.8 ± 3.1 NS | 98.3 ± 1.4 NS | 100.3 ± 3 NS | 90.8 ± 4* | 90 ± 1.1*** | 98.4 ± 2.3 NS |
| CRL8468 | 97.2 ± 4.7 NS | 79.1 ± 3** | 92.2 ± 1.7* | 93.6 ± 3.5 NS | 69.7 ± 1.8** | 95 ± 1.6* |
| CRL8469 | 95.9 ± 4.3 NS | 97.6 ± 1.4 NS | 102.8 ± 1.8 NS | 100.5 ± 2.2 NS | 101.7 ± 4.8 NS | 99.9 ± 0.7 NS |
| CRL8470 | 86.6 ± 2.3* | 92.8 ± 1.8* | 88.8 ± 4 NS | 80.2 ± 1.4** | 103.3 ± 2.4 NS | 94 ± 0.9* | x ± y = mean value ± standard error of mean
Control condition = 100%
(NS: p >0.05; *: p <0.05; : p <0.01; *: p <0.001)

These results show that these products of formulae (I) and (Ia) have weak antitumor power. These noncytotoxic products induce, when such is the case, an inhibition of the overall cell proliferation of these lines only at a concentration of $10^{-5}$ M and, with a few exceptions, this inhibition does not exceed 30%. At the other concentrations tested, only a few marginal effects may be revealed.

2—Determination of the Maximum Tolerated Dose (MTD)

The evaluation of the maximum tolerated dose was performed on 4- to 6-week-old B6D2F1/Jico mice. The compounds were administered intraperitoneally at increasing doses ranging from 2.5 to 160 mg/kg. The value of the MTD (expressed in mg/kg) is determined from the observation of the survival rate of the animals over a 14-day period after a single administration of the product under consideration. The change in weight of the animals is also monitored during this period. When the MTD value is greater than 160 mg/kg, the MTD value is considered as being 160 mg/kg by default.

The results of the estimation of the maximum tolerated dose (MTD) are collated in Table II below:

TABLE II

Maximum tolerated dose

| CRL compounds | MTD (mg/kg) |
|---|---|
| CRL8326 (Example 1) | >160 |
| CRL8327 (Example 11) | >160 |
| CRL8328 (Example 2) | 80 |
| CRL8329 (Example 12) | >160 |
| CRL8337 (Example 18) | >160 |
| CRL8340 (Example 25) | >160 |
| CRL8349 (Example 29) | >160 |
| CRL8350 (Example 33) | >160 |
| CRL8351 (Example 16) | 40 |
| CRL8352 (Example 9) | >160 |
| CRL8353 (Example 6) | >160 |
| CRL8354 (Example 17) | >160 |
| CRL8355 (Example 8) | >160 |
| CRL8357 (Example 32) | 80 |
| CRL8358 (Example 15) | >160 |
| CRL8359 (Example 5) | >160 |
| CRL8360 (Example 30) | >160 |
| CRL8371 (Example 34) | 40 |
| CRL8372 (Example 31) | >160 |
| CRL8377 (Example 20) | >160 |
| CRL8378 (Example 14) | >160 |
| CRL8379 (Example 4) | >160 |
| CRL8380 (Example 35) | >160 |
| CRL8381 (Example 36) | >160 |
| CRL8382 (Example 38) | >160 |
| CRL8383 (Example 7) | >160 |
| CRL8391 (Example 40) | >160 |
| CRL8392 (Example 41) | >160 |
| CRL8393 (Example 23) | >160 |
| CRL8394 (Example 24) | >160 |
| CRL8404 (Example 47) | >160 |
| CRL8405 (Example 45) | >160 |
| CRL8412 (Example 48) | >160 |
| CRL8413 (Example 49) | >160 |
| CRL8414 (Example 44) | >160 |
| CRL8420 (Example 52) | >160 |
| CRL8460 (Example 51) | >160 |
| CRL8424 (Example 46) | >160 |
| CRL8425 (Example 58) | >160 |
| CRL8434 (Example 59) | >160 |
| CRL8435 (Example 60) | >160 |
| CRL8436 (Example 61) | >160 |
| CRL8437 (Example 62) | >160 |
| CRL8461 (Example 65) | >160 |
| CRL8462 (Example 66) | >160 |
| CRL8464 (Example 67) | >160 |
| CRL8465 (Example 69) | >160 |
| CRL8466 (Example 70) | >160 |
| CRL8467 (Example 71) | >160 |
| CRL8468 (Example 72) | >160 |
| CRL8470 (Example 74) | >160 |

With a few very rare exceptions, the products of this family show no direct toxicity and may thus be used in vivo at high tissue concentrations, and thus at high doses.

3. Amplification Property of the Antitumor Response of the "4-quinolone-cytotoxic Drug" Combinations on Non-clonogenic Cell Lines in Culture The unexpected property of the 4-quinolones claimed relates to an amplifying activity of the antitumor response of established cytotoxic drugs when a 4-quinolone is added to the conventional treatment. This amplification property on the standard therapeutic response (with its claimed advantages: increase in efficacy and optimization of the benefit/risk ratio) is demonstrated by the results of the in vitro studies described below.

The in vitro antitumor activity of the combination of the "compounds of formulae (I) and (Ia) combined with various known cytotoxic agents used in chemotherapy" was evaluated on the two human tumor cell lines of colorectal origin, HCT-15 and LoVo, using the MTT calorimetric test as descibed in the preceding paragraph entitled "1—Cytotoxic activity on non-clonogenic cell lines in culture (MTT test)".

By way of nonlimiting example, the results obtained on the HCT-15 line are given below. In this example, the compounds of formulae (I) and (Ia), at a concentration of $10^{-5}$ M (not significantly cytotoxic), were combined with adriamycin (concentration $10^{-7}$ M) or with etoposide (concentration $10^{-6}$ M). The concentrations of $10^{-7}$ M for adriamycin and of $10^{-6}$ M for etoposide represent, respectively, the concentrations of the two cytotoxic agents that inhibit by 50% ($IC_{50}$) the in vitro cell growth of the HCT-15 line. The increase in antitumor activity obtained with the treatment "compounds of formula (I) or (Ia)" combined with "$10^{-6}$ M etoposide" relative to the antitumor activity of etoposide used alone (reference treatment) is calculated in the same manner.

The combination $10^{-5}$ M CRL8370 (compound 63)–$10^{-7}$ M adriamycin makes it possible to inhibit the growth of the HCT-15 cell line by 15.2% more (absolute value) than $10^{-7}$ M adriamycin used alone. $10^{-7}$ M adriamycin inhibits the proliferation of the HCT-15 line by 42.8% and the combined treatment $10^{-5}$ M CRL8370 +$10^{-7}$ M adriamycin by 58%, resulting in a 15.2% gain in activity (58%–42.8%) for the combined treatment compared with the activity of adriamycin used alone.

Under the same conditions as above, the combination of other claimed products with these same cytotoxic agents gave the following amplifications of antitumor response:

| with $10^{-7}$ M adriamycin | |
|---|---|
| CRL8327 (compound 19) | +16.0% |
| CRL8358 (compound 26) | +23.0% |
| CRL8424 (compound 72) | +15.0% |
| with $10^{-6}$ M etoposide | |
| CRL8327 (compound 19) | +20% |
| CRL8340 (compound 40) | +16% |
| CRL8350 (compound 54) | +15.5% |
| CRL8353 (compound 11) | +16.0% |
| CRL8354 (compound 31) | +15% |
| CRL8358 (compound 26) | +22% |
| CRL8370 (compound 63) | +23% |
| CRL8383 (compound 12) | +23% |
| CRL8382 (compound 62) | +27% |

The results obtained on the LoVo cell line are of the same amplitude as those obtained on the HCT-15 line.

These nonlimiting examples thus indicate that, although the compounds of formulae (I) and (Ia) show no cytotoxic activity when they are used alone [see the preceding paragraph entitled "1—Cytotoxic activity on non-clonogenic cell lines in cultures (MTT test)"], they significantly increase the antitumor activity of the cytotoxic agents used at the present time in chemotherapy when they are combined with these agents.

In point of fact, the amplification of the antitumor response is greater since, for example for compound CRL 8370, the increase in activity obtained with the combination (+15.20%) represents an amplification of about 35% (i.e. 15.2/42.8=35.5%) compared with the activity of adriamycin alone.

These results show that it is thus possible, by virtue of the combined treatments, between the noncytotoxic compounds of formula (I) or (Ia) with a common cytotoxic agent, to obtain higher antitumor activity, which could not be obtained with the cytotoxic agent under consideration used alone if said agent was used at a much higher concentration, which would—by way of consequence—also considerably increase the adverse side effects of the conventional therapeutic protocol. The compounds of formula (1) or (1a) thus improve the therapeutic benefit/risk ratio of each conventional chemotherapy.

Examples of the method for using the compounds of formulae (I) and (Ia) in mono- or polychemotherapy protocols with cytotoxic agents will be given below. In these protocols, the compounds of formulae (I) and (Ia) will be referred to for simplicity as "4-quinolone".

A. Solid Tumors

1/ Lung Cancers 1.1. Of non-small cells (advanced stage):
to the recommended protocol (T. Le Chevalier et al., J. Clin. Oncol. 1994; 12: 360–367) are added intravenous infusions of a 4-quinolone:

| | Dose | Route | Days |
|---|---|---|---|
| 4-quinolone | 40–2000 mg/m$^2$/day or 1–50 mg/kg/day infusion for 1 h to 3 h | i.v. | $D_1$, $D_8$, $D_{15}$, $D_{22}$, $D_{29}$ and $D_{36}$ |
| navelbine | 30 mg/m$^2$/day | i.v. | $D_1$, $D_8$, $D_{15}$, $D_{22}$, $D_{29}$ and $D_{36}$ |
| cisplatin | 120 mg/m$^2$ | i.v. | $D_1$ and $D_{29}$ |

This cure is to be repeated 8 times.

1.2. Of small cells (advanced stage):
to the recommended protocol CAV or VAC (B. J. Roth et al., J. Clin. Oncol.1992; 10: 282–291) are added infusions of 4-quinolone:

| | Dose | Route | Days |
|---|---|---|---|
| 4-quinolone | 40–2000 mg/m$^2$/day or 1–50 mg/kg/day infusion for 1 h to 3 h | i.v. | $D_1$ |
| cyclophosphamide | 1000 mg/m$^2$ bolus | i.v. | $D_1$ |
| doxorubicin | 40 to 50 mg/m$^2$ bolus | i.v. | $D_1$ |
| vincristine | 1 to 1.4 mg/m$^2$ bolus (max 2 mg) | i.v. | $D_1$ |

This cure is to be repeated 6 times every 21 days.

To the recommended Pt-E protocol (B. J. Roth et al., J. Clin. Oncol. 1992; 10: 282–291) are added infusions of 4-quinolone.

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| cisplatin | 20 mg mg/m$^2$/day infusion for 20 to 60 minutes | i.v. | $D_1$–$D_5$ |
| etoposide | 80 mg/m$^2$/day infusion for 60 minutes | i.v. | $D_1$–$D_5$ |

Each cycle is repeated every 21 days and the cure comprises 6 cycles.

1.3. Non-small-cell bronchial cancer, locally advanced or metastatic:
monochemotherapy:

| | Dose | Route | Days |
|---|---|---|---|
| 4-quinolone | 40–2000 mg/m$^2$/day or 1–50 mg/kg/day infusion for 1 h to 3 h | i.v. | $D_1$, $D_8$, $D_{15}$ and then 1 week/rest |
| gemcitabine | 1000 mg/m$^2$/day infusion for 0.5 hour | i.v. | $D_1$, $D_8$, $D_{15}$ and then 1 week/rest | the cure being able to comprise repetition of this 4-week cycle.

gemcitabine/cisplatin combination:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{15}$ |
| gemcitabine | 1000 mg/m$^2$/day infusion for 0.5 hour | i.v. | $D_1$, $D_8$, $D_{15}$ |
| cisplatin | 20 mg/m$^2$/day infusion for 20–60 minutes | i.v. | $D_1$ | the cure comprising the repetition of this cycle every 21 days.

2/ Breast Cancers

CMF protocol as auxiliary treatment for operable breast cancer (G. Bonnadonna et al., N. Engl. J. Med.; 1976; 294: 405–410):

| | Dose | Route | Days |
|---|---|---|---|
| 4-quinolone | 40–2000 mg/m$^2$/day or 1–50 mg/kg/day infusion for 1 h to 3 h | i.v. | $D_1$ to $D_{14}$ |
| cyclophosphamide | 100 mg/m$^2$/day | oral | $D_1$ to $D_{14}$ |
| methotrexate | 40 mg/m$^2$ bolus | i.v. | $D_1$ and $D_8$ |
| 5-FU | 600 mg/m$^2$ | i.v. | $D_1$ and $D_8$ | each cycle is repeated every 28 days and the cure comprises 6 cycles.

AC protocol (B. Fisher et al., J. Clin. Oncol. 1990; 8: 1483–1496) as an auxiliary treatment:

| | Dose | Route | Days |
|---|---|---|---|
| 4-quinolone | 40–2000 mg/m$^2$/day or 1–50 mg/kg/day infusion for 1 h to 3 h | i.v. | $D_1$ |
| doxorubicin | 60 mg/m$^2$ bolus | i.v. | $D_1$ |
| cyclophosphamide | 600 mg/m$^2$ bolus | i.v. | $D_1$ | each cycle is repeated every 21 days and the cure comprises 4 cycles.

Breast cancers with metastases:

in the FAC protocol (A. U. Buzdar et al., Cancer 1981; 47: 2537–2542) and its various adaptations, the infusions of 4-quinolone are added according to the following (non-limiting) scheme:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ and $D_8$–$D_{12}$ or $D_1$–$D_5$ |
| 5-FU | 500 mg/m$^2$/day bolus | i.v. | $D_1$ and $D_8$ or $D_1$–$D_2$ |
| doxorubicin | 50 mg/m$^2$ bolus | i.v. | $D_1$ or $D_1$ and $D_2$ |
| cyclophosphamide | 500 mg/m$^2$ | Bolus i.v. or oral | $D_1$ $D_1$ | each cycle is repeated every 3 weeks until a new progression of the disease is diagnosed.

in the CAF protocol (G. Falkson et al., Cancer 1985; 56: 219–224):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_{14}$ |
| cyclophosphamide | 100 mg/m$^2$/day | oral | $D_1$–$D_{14}$ |
| doxorubicin | 30 mg/m$^2$ bolus | i.v. | $D_1$ and $D_8$ |
| 5-FU | 500 mg/m$^2$ bolus | i.v. | $D_1$ and $D_8$ | each cycle is repeated every 28 days until a new progression of the disease is diagnosed.

in the CMF protocol:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ and $D_8$–$D_{12}$ |
| cyclophosphamide | 600 mg/m$^2$/day bolus | i.v. | $D_1$ and $D_8$ |
| methotrexate | 40 mg/m$^2$/day bolus | i.v. | $D_1$ and $D_8$ |
| 5-FU | 600 mg/m$^2$/day bolus | i.v. | $D_1$ and $D_8$ | this cycle is to be repeated every 3 to 5 weeks and the cure comprises 6 cycles.

In the CMF-VP protocol:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ $D_8$–$D_{12}$ $D_{15}$–$D_{19}$ $D_{22}$–$D_{26}$ |
| cyclophosphamide | 2 to 2.5 mg/kg/day | oral | daily |
| methotrexate | 25 to 50 mg/m$^2$/day | i.v. | $D_1$, $D_8$, $D_{15}$, $D_{22}$ |
| 5-FU | 300 to 500 mg/m$^2$/day | i.v. | $D_1$, $D_8$, $D_{15}$, $D_{22}$ |
| vincristine | 0.6 to 1.2 mg/m$^2$/day | i.v. | $D_1$, $D_8$, $D_{15}$, $D_{22}$ |
| prednisone | 30 mg/m$^2$/day | oral | from $D_1$ to $D_{10}$ | this cure is to be repeated every 4 weeks.

In the FEC protocol:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ and $D_8$–$D_{12}$ |
| 5-FU | 600 mg/m$^2$/day | i.v. | $D_1$ and $D_8$ |
| epirubicin | 50 mg/m$^2$ | i.v. | $D_1$ |
| cyclophosphamide | 600 mg/m$^2$ | i.v. | $D_1$ | this cure is to be repeated every 3 weeks.

in the MMC-VBC protocol (C. Brambilla et al., Tumori, 1989; 75: 141–144):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ and $D_{15}$–$D_{19}$ |
| mitomycin C | 10 mg/m$^2$ bolus | i.v. | $D_1$ |
| vinblastine | 50 mg/m$^2$/day bolus | i.v. | $D_1$ and $D_{15}$ | this cure is to be repeated every 28 days until a progression of the disease is diagnosed.

in the NFL protocol (S. E. Jones et al., J. Clin. Oncol. 1991; 9: 1736–1739):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| mitoxantrone | 10 mg/m$^2$ bolus | i.v. | $D_1$ |
| 5-FU | 1000 mg/m$^2$ infusion for 24 hours | i.v. | $D_1$–$D_5$ |
| leucovorin | 100 mg/m$^2$ bolus | i.v. | $D_1$ | the cure comprises two cycles with an interval of 21 days and then requires an evaluation.

The infusions of 4-quinolone can also be combined with the treatment of breast cancers with metastases when a taxoid is used, for example:

with paclitaxel (F. A. Holmes et al., J. Natl Cancer Inst. 1991; 83: 1797–1805) in the treatment of the forms with metastases which may be resistant to anthracyclins:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| paclitaxel | 175 mg/m² infusion for 3 to 24 hours | i.v. | $D_1$ |

This cycle is repeated every 21 days until a new progression of the disease is diagnosed.

with docetaxel (C. A. Hudis et al., J. Clin. Oncol. 1996; 14: 58–65), in locally advanced or metastatic breast cancer, resistant or in relapse after cytotoxic chemotherapy (having comprised an anthracyclin) or in relapse during an auxiliary treatment:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| docetaxel | 100 mg/m² or 60–100 mg/m² infusion for 1 h to 3 hour (or 24 hours) | i.v. | $D_1$ |

This cycle is repeated every 21 days for a cure of two cycles or until a progression of the disease appears.

in dose intensification protocols, combining a transplantation of autologous medullary cells and of peripheral blood stem cells, in consolidation of the primary treatment, for example:

CPB protocol (W. P. Peters et al., J. Clin. Oncol. 1993; 11: 132–1143), in which the i.v. infusion of stem cells takes place on days $D_{-1}$, $D_0$ and $D_1$:

| | Dose | Route | Days |
|---|---|---|---|
| 4-quinolone | 40–2000 mg/m²/day or 1–50 mg/kg/day infusion for 1 h to 3 h | i.v. | $D_{-6}$–$D_{-1}$ |
| cyclo-phosphamide | 1875 mg/m² infusion for 1 h | i.v. | $D_{-6}$ to $D_{-4}$ |
| cisplatin | 55 mg/m²/day continuous infusion for 24 hours | i.v. | $D_{-6}$ to $D_{-4}$ |
| carmustin (BCNU) | 600 mg/m²/day infusion for 2 hours | i.v. | $D_{-3}$ |

CTCb protocol (K. Antman et al., J. Clin. Oncol. 1992; 10: 102–110), in which the i.v. infusion of stem cells takes place on $D_0$:

| | Dose | Route | Days |
|---|---|---|---|
| 4-quinolone | 40–2000 mg/m²/day or 1–50 mg/kg/day infusion for 1 h to 3 h | i.v. | $D_{-7}$–$D_{-1}$ |
| cyclo-phosphamide | 1500 mg/m² continuous infusion for 24 hours (4 doses) | i.v. | $D_{-7}$ to $D_{-3}$ |
| thiotepa | 125 mg/m² continuous infusion for 24 hours (4 doses) | i.v. | $D_{-7}$ to $D_{-3}$ |
| carboplatin | 200 mg/m² continuous infusion for 24 hours (4 doses) | i.v. | $D_{-7}$ to $D_{-3}$ |

CTM protocol (L. E. Damon et al., J. Clin. Oncol. 1989; 7: 560–571 and I. C. Henderson et al., J. Cellular Biochem. 1994 (Suppl 18B): 95) in which the i.v. infusion of hematopoietic stem cells takes place on $D_0$

| | Dose | Route | Days |
|---|---|---|---|
| 4-quinolone | 40–2000 mg/m²/day or 1–50 mg/kg/day infusion for 1 h to 3 h | i.v. | $D_{-6}$–$D_{-3}$ |
| cyclo-phosphamide | 1500 mg/m²/day infusion for 1 h | i.v. | $D_{-6}$ to $D_{-3}$ |
| thiotepa | 150 mg/m²/day infusion for 2 hours | i.v. | $D_{-6}$ to $D_{-3}$ |
| mitoxantrone | 10–15 mg/m² infusion for 1 h | i.v. | $D_{-6}$ to $D_{-3}$ |

3/ Gynecological Cancers 3.1 Ovarian cancer:

for the treatment of ovarian carcinomas, in particular metastatic ones:

i) PAC protocol (G. A. Omura et al. J. Clin. Oncol. 1989; 7: 457–465): the infusions of 4-quinolones are administered according to the following scheme:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| cisplatin | 50 mg/m² (or 40–90 mg/m²) infusion for 1 to 2 hours | i.v. | $D_1$ |
| doxorubicin | 50 mg/m² bolus (or 30 to 50 mg/m²) | i.v. | |
| cyclo-phosphamide | 1000 mg/m² infusion for 1 to 2 hours (or 200 to 600 mg/m²) | i.v. | $D_1$ | this cycle is repeated every 21 to 28 days and the cure comprises 8 cycles.

ii) Altretamine protocol, according to A. Marietta et al. (Gynecol. Oncol. 1990; 36: 93–96):

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ $D_8$–$D_{12}$ |
| altretamine | 200 mg/m²/day divided into 4 doses | oral | $D_1$–$D_{15}$ | the cure comprising two cycles, with an interval of 28 days.

ii) Paclitaxel protocol: the 4-quinolones can be added to the paclitaxel protocol as described by W. P. McGuire et al. (Ann. Intern. Med. 1989; 111: 273–279):

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| paclitaxel | 135 mg/m² infusion for 3 hours or 24 hours | i.v. | $D_1$ | the cure comprising two of these cycles, with an interval of 28 days (with evaluation at the end).

for the treatment of metastatic and refractory ovarian carcinomas, the 4-quinolones may be added to the secondary protocol, based on topotecan:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| topotecan | 1.5 mg/m²/day infusion for 0.5 hours | i.v. | $D_1$–$D_5$ | the cure comprising two cycles, with an interval of 21 days (with evaluation at the end) according to A. P. Kudelka et al. (J. Clin. Oncol. 1996; 14: 1552–1557).
5 3.2 Trophoblastic tumors:

in patients at low risk, the 4-quinolones may be combined with the protocol described by H. Takamizawa et al. (Semin. Surg. Oncol. 1987; 3: 36–44):

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| methotrexate (MTX) | 20 mg/day | i.m. | $D_1$–$D_5$ |
| dactinomycin (DACT) | 0.5 mg/day as bolus | i.v. | $D_1$–$D_5$ |

(MTX-DATC protocol).
3.3 Uterine cancers:

the 4-quinolones may also be combined with the CAV (or VAC) protocol according to the scheme below:

| | Dose | Route | Days |
|---|---|---|---|
| 4-quinolone | 40–2000 mg/m²/day or 1–50 mg/kg/day infusion for 1 h to 3 h | i.v. | $D_1$–$D_3$ |
| cyclo-phosphamide | 750–1200 mg/m² infusion | i.v. | $D_1$ |
| doxorubicin | 45–50 mg/m² infusion | i.v. | $D_1$ |
| vincristine | 1.4 mg/m² | i.v. | $D_1$ | the cure comprising the repetition of this cycle every 21 days.

in the FAP protocol:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| fluorouracil (5-FU) | 600 mg/m²/day | i.v. | $D_1$, $D_8$ |
| doxorubicin | 30 mg/m² | i.v. | $D_1$ |
| cisplatin | 75 mg/m² | i.v. | $D_1$ | the cure comprising the repetition of this cycle every 21 or 28 days.
4/ Testicular Cancers The 4-quinolones may also be combined with testicular cancer protocols:
BEP protocol:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| bleomycin | 30 mg/m² infusion | i.v. | $D_1$ |
| etoposide | 100 mg/m²/day infusion | i.v. | $D_1$–$D_5$ |
| cisplatin | 20 mg/m²/day | i.v. | $D_1$–$D_5$ | the cure comprising 3 cycles, at a rate of 1 cycle every 21 days.
5/ Bladder Cancers The 4-quinolones may be combined with the CISCA2 (also known as PAC) protocol:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| cisplatin | 50 mg/m² | i.v. | $D_1$ |
| cyclophosphamide | 600 mg/m² infusion | i.v. | $D_1$ |
| doxorubicin | 75 mg/m² infusion | i.v. | $D_1$ | the cycle being repeated every 3 weeks.

In the MVAC protocol (according to C. N. Sternberg et al., J. Urol. 1988; 139: 461–469):

| | Dose | Route | Days |
|---|---|---|---|
| 4-quinolone | 40–2000 mg/m²/day or 1–50 mg/kg/day infusion for 1 h to 3 h | i.v. | $D_1$–$D_3$ $D_{15}$–$D_{18}$ $D_{22}$–$D_{25}$ |
| methotrexate | 30 mg/m² bolus | i.v. | $D_1$, $D_{15}$, $D_{22}$ |
| vinblastine | 3 mg/m² | i.v. | $D_2$ or $D_2$, $D_{15}$, $D_{22}$ |
| doxorubicin | 30 mg/m² bolus | i.v. | $D_2$ |
| cisplatin | 70–100 mg/m² infusion for 1 h | i.v. | $D_1$ or $D_2$ | this cycle being repeated every 4 to 5 weeks, for a minimum of 2 cycles.

6/ Nasopharyngeal Carcinomas/Head and Neck Cancers

The 4-quinolones may be viably combined with polychemotherapy protocols used in the treatment of these cancers:

6.1 Nasopharyngeal cancers:

ABVD protocol:

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$ $D_8$–$D_{10}$ or $D_{15}$–$D_{17}$ |
| doxorubicin | 30 mg/m$^2$/day | i.v. | $D_1$ and $D_8$ or $D_{15}$ |
| bleomycin | 10 mg/m$^2$/day | i.v. | $D_1$ and $D_8$ |
| vinblastine | 6 mg/m$^2$/day | i.v. | $D_1$ and $D_8$ or $D_{15}$ |
| dacarbazine | 200 mg/m$^2$/day | i.v. | $D_1$ and $D_8$ or $D_{15}$ | the cure comprising 1 to 6 cycles repeated at a rate of 1 cycle every 4 weeks.

6.2 Head and neck cancers with metastases:

in the Pt-FU protocol (e.g.: for pharyngeal cancers): according to the DVAL Study Group (New Engl. J. M. 1991; 324: 1685–1690):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| cisplatin | 100 mg/m$^2$ infusion for 1 h | i.v. | $D_1$ |
| fluorouracil (5-FU) | 1000 mg/m$^2$/day continuous infusion | i.v. | $D_1$–$D_5$ | the cure comprising two cycles, at a rate of 1 cycle every 3 weeks.

7/ Soft-tissue Sarcomas

The 4-quinolones may be introduced into a protocol such as the CYVADIC protocol:

according to H. M. Pinedo et al. (Cancer 1984; 53: 1825):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ $D_8$–$D_{10}$ $D_{15}$–$D_{17}$ |
| cyclophosphamide (Cy) | 500 mg/m$^2$ bolus | i.v. | $D_2$ |
| vincristine (V) | 1.5 mg/m$^2$/day bolus | i.v. | $D_1$, $D_8$, $D_{15}$ |
| doxorubicin (A) | 50 mg/m$^2$ bolus | i.v. | $D_2$ |
| dacarbazine (DIC) | 250 mg/m$^2$/day infusion for 15 minutes | i.v. | $D_1$–$D_5$ | the cure comprising the repetition of this cycle every 4 weeks, first for 2 cycles.

8/ Hormono-refractory Prostate Cancer, with Metastases

In the VBL-estramustine protocol, according to G. R. Hudis et al. (J. Clin. Oncol. 1992; 10: 1754–1761):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$, $D_8$–$D_{10}$ $D_{15}$–$D_{17}$, $D_{22}$–$D_{24}$ $D_{29}$–$D_{31}$, $D_{36}$–$D_{38}$ |
| vinblastine | 4 mg/m$^2$/day bolus | i.v. | $D_1$, $D_8$, $D_{15}$, $D_{22}$, $D_{29}$, $D_{36}$ |
| estramustine | 200 mg/m$^2$ tid (600 mg/m$^2$/day) | oral | every day for 6 weeks | a treatment cycle lasting 6 weeks and being followed by a 2-week free interval.

9/ Germinal Cell Cancers i) For tumors of favorable prognosis:

Pt-E protocol, according to G. J. Bosl et al. (J. Clin. Oncol. 1988; 6: 1231–1238)

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| cisplatin (Pt) | 20 mg/m$^2$/day infusion for 20 to 60 minutes | i.v. | $D_1$–$D_5$ |
| etoposide (E) | 100 mg/m$^2$/day infusion for 1 h | i.v. | $D_1$–$D_5$ | the cure comprising 4 cycles, at a rate of 1 cycle every 21 or 28 days.

ii) For tumors with metastases:

PEB protocol, according to S. D. Williams et al. (N. Eng. J. Med. 1987; 316: 1435–1440):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ $D_9$–$D_{11}$ $D_{16}$–$D_{18}$ |
| cisplatin (P) | 20 mg/m$^2$/day infusion for 20 to 60 minutes | i.v. | $D_1$–$D_8$ |
| etoposide (E) | 100 mg/m$^2$/day infusion for 1 hour | i.v. | $D_2$, $D_9$, $D_{16}$ |
| bleomycin (B) | 30U (or mg)/day bolus | i.v. | $D_1$–$D_5$ | the cure comprising 4 cycles, at a rate of 1 cycle every 21 days.

10/ Kidney Cancers

Metastatic renal carcinoma: the 4-quinolones may be introduced into the protocol described by M. J. Wilkinson et al. (Cancer 1993; 71: 3601–3604):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ $D_8$–$D_{15}$ |
| floxuridine | 0.075 mg/kg/day continuous infusion | i.v. | $D_1$–$D_{14}$ | the cure comprising two cycles with an interval of 28 days.

Nephroblastoma: the 4-quinolones may be introduced into the DAVE protocol:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$ $D_8$–$D_{10}$ |
| dactinomycin | 0.6 mg/m$^2$/day | i.v. | $D_1$, $D_8$ |
| doxorubicin | 30 mg/m$^2$/day | i.v. | $D_1$, $D_8$ |
| cyclophosphamide | 200 my/m$^2$/day infusion for 1 hour | i.v. | $D_1$, $D_8$ | at a rate of one cycle every 3 to 4 weeks.

11/ Cancers of the Digestive Tract 11.1 Esophageal cancers:

the 4-quinolones may be introduced into the FAP protocol according to:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$ $D_8$–$D_{10}$ |
| 5-fluorouracil (5-FU) | 600 mg/m$^2$ | i.v. | $D_1$, $D_8$ |
| doxorubicin | 30 mg/m$^2$ | i.v. | $D_1$ |
| cisplatin | 75 mg/m$^2$ | i.v. | $D_1$ | this cycle being repeated every 3 to 4 weeks.

11.2 Stomach cancers:

in gastric carcinomas that are advanced and/or with metastases:

EAP protocol (according to P. Preusser et al., J. Clin. Oncol. 1989; 7: 1310):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{10}$ |
| etoposide | 120 mg/m$^2$/day infusion for 1 hour | i.v. | $D_3$, $D_4$, $D_5$ or $D_4$–$D_6$ |
| doxorubicin | 20 mg/m$^2$/day bolus | i.v. | $D_1$, $D_7$ |
| cisplatin | 40 mg/m$^2$/day infusion for 1 hour | i.v. | $D_2$, $D_8$ | at a rate of 1 cycle every 28 days.

FAMtx protocol: according to J. A. Wils et al. (J. Clin. Oncol. 1991; 89: 827):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$ |
| fluorouracil (5-FU) (F) | 1500 mg/m$^2$ bolus 1 hour near methotrexate | i.v. | $D_1$ |
| doxorubicin (A) | 30 mg/m$^2$ bolus | i.v. | $D_{15}$ |
| methotrexate (Mtx) | 1500 mg/m$^2$ infusion for 30 minutes | i.v. | $D_1$ | the cure first comprising two cycles, with an interval of 28 days.

in certain patients, this protocol or its variant (epirubicin replacing doxorubicin) may be used according to the following scheme:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$ |
| fluorouracil (5-FU) | 1500 mg/m$^2$ | i.v. | $D_1$ |
| doxorubicin (A) or | 30 mg/m$^2$ bolus | i.v | $D_1$ = FAMTx |
| epirubicin | 60 mg/m$^2$ bolus | i.v. | $D_1$ = FEMTx |
| methotrexate (to be infused before 5-FU) | 1500 mg/m$^2$ | i.v. | $D_1$ |
| leucovorine | 15 mg/m$^2$/day | oral | $D_2$–$D_4$ |

12/ Colorectal Cancers the 4-quinolones may be introduced into the FU-Levamizole auxiliary treatment protocol for colorectal cancer (according to C. G. Moertel et al., N. Eng. J. Med. 1990; 322: 352):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ $D_{29}$–$D_{31}$ |
| 5-fluorouracil | 450 mg/m$^2$/day bolus | i.v. | $D_1$–$D_5$ |
| 5-fluorouracil | 450 mg/m$^2$ bolus | i.v. | $D_{29}$ |
| levamisole | 50 mg tid | oral | 3 days/week one week in two | the treatment in bolus with 5-FU being repeated every week after the induction phase $D_1$–$D_5$, for 52 weeks; the treatment with a 4-quinolone being repeated at the same rhythm, on the day of the bolus of 5-FU and then on the following 2 days.

for the treatment of colorectal cancer, which is resistant to treatment with 5-fluorouracil (5-FU) and with metastases:

according to M. L. Rothenberg et al. (J. Clin. Oncol. 1996; 14: 1128–1135):

| | Dose | Route | Days |
|---|---|---|---|
| 4-quinolone | 40–2000 mg/m²/day or 1–50 mg/kg/day infusion for 1 h to 3 h | i.v. | $D_1$–$D_3$, $D_8$–$D_{10}$, $D_{15}$–$D_{17}$, $D_{22}$–$D_{24}$ |
| irinotecan | 125 mg/m²/day | i.v. | $D_1$, $D_8$, $D_{15}$, $D_{22}$ | the cure comprising two cycles with an interval of 42 days.

13/ Kaposi's Sarcomas the 4-quinolones may be combined with the two protocols using antracyclines formulated as liposomes:

i) protocol described by P. S. Gill et al. (J. Clin. Oncol. 1995; 13: 996–1003) and C. A. Presant et al. (Lancet 1993; 341: 1242–1243):

| | Dose | Route | Days |
|---|---|---|---|
| 4-quinolone | 40–2000 mg/m²/day or 1–50 mg/kg/day infusion for 1 h to 3 h | i.v. | $D_1$–$D_3$ and $D_{15}$–$D_{17}$ |
| liposomal daunorubicin | 20 mg/m²/day infusion for 1 hour | i.v. | $D_1$, $D_{15}$ | the cure comprising two cycles repeated with an interval of 28 days before evaluating the effects.

ii) protocol of M. Harrison et al. (J. Clin. Oncol. 1995; 13: 914–920):

| | Dose | Route | Days |
|---|---|---|---|
| 4-quinolone | 40–2000 mg/m²/day or 1–50 mg/kg/day infusion for 1 h to 3 h | i.v. | $D_1$–$D_3$ |
| liposomal doxorubicin | 20 mg/m² infusion for 30 minutes | i.v. | $D_1$ | the cure comprising two cycles repeated with an interval of 28 days before evaluating the effects.

14/ Metastatic Melanomas the 4-quinolones may also be incorporated into combination protocols for treating metastatic malignant melanomas:

DTIC/TAM protocol: according to G. Cocconi et al. (N. Eng. J. Med. 1992; 327: 516), the cure comprising the repetition of 4 cycles, at a rate of 1 cycle every 21 days, according to the scheme below:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| dacarbazine (DTIC) | 250 mg/m²/day infusion [15 to 30 min if central catheter] or [30 min if peripheral infusion in 250 ml] | i.v. | $D_1$–$D_5$ |

-continued

| | Dose | Route | Days |
|---|---|---|---|
| tamoxifen (TAM) | 20 mg/m²/day | oral | $D_1$–$D_5$ | the cure comprising 4 cycles at a rate of 1 cycle every 21 days.

15/ Neuroendocrine Carcinoma the 4-quinolones may be combined with the protocol described by C. G Moertel et al. (Cancer 1991; 68: 227):

Pt-E protocol:

| | Dose | Route | Days |
|---|---|---|---|
| 4-quinolone | 40–2000 mg/m²/day or 1–50 mg/kg/day infusion for 1 h to 3 h | i.v. | $D_1D_3$ |
| etoposide | 130 mg/m²/day infusion for 1 hour | i.v. | $D_1D_3$ |
| cisplatin | 45 mg/m²/day infusion for 1 hour | i.v. | $D_2$, $D_3$ | the cure comprising two cycles repeated every 28 days.

16/ Pancreatic Cancer

Advanced pancreatic adenocarcinoma: the 4-quinolones may be combined with the treatment with gemcitabine, according to the protocol of M. Moore et al. (Proc. Am. Soc. Clin. Oncol. 1995; 14: 473):

| | Dose | Route | Days |
|---|---|---|---|
| 4-quinolone | 40–2000 mg/m²/day or 1–50 mg/kg/day infusion for 1 h to 3 h | i.v. | $D_1$–$D_3$, $D_8$–$D_{10}$, $D_{15}$, $D_{22}$, $D_{29}$, $D_{36}$, $D_{43}$, $D_{57}$ |
| gemcitabine | 1000 mg/m² infusion for 0.5 hour | i.v. | $D_1$, $D_8$, $D_{15}$, $D_{22}$, $D_{29}$, $D_{36}$, $D_{43}$, and then $D_{57}$ and then once/week for 3 weeks followed by 1 week of rest and evaluation |

B. Onco-hematology

1/ Acute Adult Leukemias 1.1. Acute lymphoblastic leukemia 1.1.1. Linker protocol The 4-quinolones may be added to the Linker protocols-induction chemotherapy and consolidation chemotherapy (see C. A. Linker et al. Blood 1987; 69: 1242–1248 and C. A. Linker et al. Blood 1991; 78: 2814–2822) according to the following schemes:

i) Induction chemotherapy:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$, $D_6$–$D_{12}$, $D_{15}$–$D_{19}$ |

-continued

| | Dose | Route | Days |
|---|---|---|---|
| daunorubicin | 50 mg/m2 bolus every 24 hours (30 mg/m$^2$ in the patients > 50 years old) | i.v. | $D_1, D_2, D_3$ |
| vincristine | 2 mg bolus | i.v. | $D_1, D_8, D_{15}, D_{22}$ |
| prednisone | 60 mg/m$^2$/day | Oral | $D_1$–$D_{28}$ |
| L-asparaginase | 6000 U/m$^2$ | i.m. | $D_{17}$–$D_{28}$ | ii) Consolidation chemotherapy (regimen A):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{12}$ |
| daunorubicin | 50 mg/m2 bolus every 24 hours | i.v. | $D_1, D_2$ |
| vincristine | 2 mg bolus | i.v. | $D_1, D_8$ |
| prednisone | 60 mg/m$^2$/day divided into 3 doses | Oral | $D_1$–$D_{14}$ |
| L-asparaginase | 12 000 U/m$^2$ | i.m. | $D_2, D_4, D_7, D_9$ and $D_{14}$ | the consolidation cure A comprises 4 consecutive cycles such as that described above=cycles 1, 3, 5 and 7.

iii) Consolidation chemotherapy (regimens B and C): The regimens described below correspond to the consolidation cycles 2, 4, 6 and 8 (regimen B) and 9 (regimen C), described by C. A. Linker et al.:

| Regimen B: | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{12}$ |
| Ara-C | 300 mg/m$^2$ infusion for 2 hours | i.v. | $D_1, D_4, D_8, D_{11}$ |
| teniposide | 165 mg/m$^2$ infusion for 2 hours (4 cycles) | i.v. | $D_1, D_4, D_8, D_{11}$ |

| Regimen C: | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| methotrexate | 690 mg/m$^2$ continuous infusion for 42 hours | i.v. | $D_1$–$D_2$ |
| leucovorin | 15 mg/m$^2$ every 6 hours | oral | $D_2$–$D_5$ |

1.1.2. Hoelzer protocol

The products claimed may be added to the cytotoxic agents of this polychemotherapy protocol (D. Hoelzer et al., Blood 1984; 64: 38–47, D. Hoelzer et al., Blood 1988; 71: 123–131) according to the following scheme:

i) Induction chemotherapy/Phase 1:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{12}$, $D_{15}$–$D_{19}$ |
| daunorubicin | 25 mg/m$^2$ | i.v. | $D_1, D_8, D_{15}, D_{22}$ |
| vincristine | 1.5 mg/m$^2$ (maximum 2 mg) | i.v. | $D_1, D_8, D_{15}, D_{22}$ |
| prednisone | 60 mg/m$^2$ | oral | $D_1$–$D_{28}$ |
| L-asparaginase | 5000 U/m$^2$ (maximum 2 mg) | i.m. | $D_1$–$D_{14}$ | ii) Induction chemotherapy/Phase 2:
Phase 2 of the induction may be carried out as follows:

| | Dose | Route | Days |
|---|---|---|---|
| 4-quinolone | 40–2000 mg/m$^2$/day or 1–50 mg/kg/day infusion for 1 h to 3 h | i.v. | $D_{29}$–$D_{33}$, $D_{36}$–$D_{40}$, $D_{43}$–$D_{47}$ |
| cyclosphosphamide | 650 mg/m$^2$ (maximum 1000 #9) | i v. | $D_{29}, D_{43}, D_{57}$ |
| cytarabine | 75 my/m$^2$/day infusion for 1 hour | i.v. | $D_{31}$–$D_{34}$, $D_{38}$–$D_{41}$, $D_{45}$–$D_{48}$, $D_{52}$–$D_{55}$ |
| mercaptopurine | 60 mg/m$^2$ | oral | $D_{29}$–$D_{57}$ |
| methotrexate | 10 mg/m$^2$/day (maximum 15 mg) | i.v. | $D_{31}, D_{38}, D_{45}, D_{52}$ | iii) Reinduction chemotherapy/Phase 1:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{12}$, $D_{15}$–$D_{19}$, $D_{22}$–$D_{26}$ |
| doxorubicin | 2.5 mg/m$^2$/day | i.v. | $D_1, D_8, D_{15}, D_{22}$ |
| dexamethasone | 10 mg/m$^2$/day | oral | $D_1$–$D_{28}$ |
| vincristine | 1.5 mg/m$^2$/day (maximum 2 mg) | oral | $D_1, D_8, D_{15}$ and $D_{22}$ | iv) Reinduction chemotherapy/Phase 2:

| | Dose | Route | Days |
|---|---|---|---|
| 4-quinolone | 40–2000 mg/m$^2$/day or 1–50 mg/kg/day infusion for 1 h to 3 h | i.v. | $D_{31}$–$D_{35}$, $D_{38}$–$D_{42}$ |
| cyclophosphamide | 650 mg/m$^2$ (maximum: 1000 mg) | i.v. | $D_{29}$ |
| cytarabine | 75 mg/m$^2$ | i.v. | $D_{31}$–$D_{34}$, $D_{38}$–$D_{41}$ |
| thioguanine | 60 mg/m$^2$ | oral | $D_{29}$–$D_{42}$ |

5 1.2. Acute myeloid leukemias:
1.2.1. Treatment of adults of any age

The 4-quinolones may be added, according to the scheme below, to the treatment incorporating the standard dose of cytarabine described previously by R. O. Dilleman et al. (Blood, 1991; 78: 2520–2526), Z. A. Arlin et al. (Leukemia 1990; 4: 177–183) and P. H. Wiernik et al. (Blood 1992; 79: 313–319):

| | Dose | Route | Days |
|---|---|---|---|
| 4-quinolone | 40–2000 mg/m²/day or 1–50 mg/kg/day infusion for 1 h to 3 h | i.v. | $D_1$–$D_{12}$ |
| cytarabine | 100–200 mg/m²/day in continuous infusion | i.v. | $D_1$–$D_7$ |
| daunorubicin or | 45 mg/m²/day in bolus (30 mg/m²/day if ≧ 60 years old) | i.v. | $D_1$–$D_3$ or $D_8$–$D_{10}$ |
| mitoxantrone or | 12 mg/m² as daily bolus | i.v. | $D_1$–$D_3$ |
| idarubicin | 13 mg/m² as daily bolus | i.v | $D_1$–$D_3$ |

1.2.2. Treatment of adults less than 60 years old i) Induction chemotherapy:

This induction cycle incorporates the administration of cytarabine at high dose according to the following scheme:

| | Dose | Route | Days |
|---|---|---|---|
| 4-quinolone | 40–2000 mg/m²/day or 1–50 mg/kg/day infusion for 1 h to 3h | i.v | $D_1$–$D_{10}$ |
| Ara-C (cytarabine) | 2000 mg/m²/day infusion for 2 hours, every 12 hours | i.v. | $D_1$–$D_6$ |
| Daunorubicin or | 60 mg/m²/day in continuous infusion for 24 hours | i.v. | $D_4$–$D_6$ |
| cytarabine | 3000 mg/m²/day infusion for 1 hour, every 12 hours | i.v. | $D_1$–$D_6$ |
| Daunorubicin | 45 mg/m² bolus every 24 hours | i.v. | $D_7$–$D_9$ |

(in order to reduce the risk of C.N.S. toxicity, in the event of renal insufficiency, adjust the dosage of cytarabine to the creatinine clearance) according to L. E. Damon et al. (Leukemia 1994; 8: 535–541), G. L. Phillips et al. (Blood 1991; 77: 1429–1435) and G. Smith et al. (J. Clin. Oncol. 1997; 15: 833–839).

ii) Consolidation chemotherapy:

The cycle described below will be repeated 8 times, at a rate of 1 cycle every 4 to 6 weeks (according to R. J. Mayer et al., N. Engl J. Med. 1994; 331: 896–903):

| | Dose | Route | Days |
|---|---|---|---|
| 4-quinolone | 40–2000 mg/m²/day or 1–50 mg/kg/day infusion for 1 h to 3h | i.v. | $D_1$–$D_5$ |
| cytarabine | 3000 mg/m² infusion for 3 hours, every 12 hours (4 cycles) | i.v. | $D_1$, $D_3$, $D_5$ |

| | Dose | Route | Days |
|---|---|---|---|
| and then cytarabine | 100 mg/m²/day every 12 hours | s.c. | $D_1$–$D_5$ |
| daunorubicin | 45 mg/m² bolus (4 cycles) | i.v. | $D_1$ | iii) Consolidation chemotherapy (with strong dose of cytarabine):

The cycle described below will have to be repeated twice and is suitable according to G. L. Phillips et al. (Blood 1991; 77: 1429–1435); S. N. Wolff et al. (J. Clin. Oncol. 1989; 7: 1260–1267); R. J. Mayer et al. (N. Engl J. Med. 1994; 331: 896–903):

| | Dose | Route | Days |
|---|---|---|---|
| 4-quinolone | 40–2000 mg/m²/day or 1–50 mg/kg/day infusion for 1 h to 3 h | i.v. | $D_1$–$D_{10}$ |
| cytarabine | 3000 mg/m² 1 hour every 12 hours | i.v. | $D_1$–$D_6$ |
| daunorubicin | 30–45 mg/m²/day bolus once/day | i.v. | $D_7$–$D_9$ |

1.2.3. Treatment of adults 60 years old or more

The substances claimed may be added to the consolidation chemotherapy protocols below:

i) according to R. O. Dilman et al. (Blood 1991; 78; 2520–2526), Z. A. Arlin et al. (Leukemia 1990; 4: 177–183), P. H. Wiernik et al. (1992; 79: 313–319):

| | Dose | Route | Days |
|---|---|---|---|
| 4-quinolone | 40–2000 mg/m²/day or 1–50 mg/kg/day infusion for 1 h to 3 h | i.v. | $D_1$–$D_6$ |
| cytarabine (Ara-C) | 100–200 mg/m² continuous infusion for 24 hours | i.v. | $D_1$–$D_5$ |
| daunorubicin or | 30–45 mg/m²/day bolus | i.v | $D_1$, $D_2$ |
| mitoxantrone or | 12 mg/m²/day bolus | i.v. | $D_1$, $D_2$ |
| idarubicin | 13 mg/m²/day bolus | i.v | $D_1$, $D_2$ | ii) According to R. J. Mayer et al. (N. Engl. J. Med. 194; 331: 896–903):

| | Dose | Route | Days |
|---|---|---|---|
| 4-quinolone | 40–2000 mg/m²/day or 1–50 mg/kg/day infusion for 1 h to 3h | i.v. | $D_1$–$D_6$ |

| | Dose | Route | Days |
|---|---|---|---|
| cytarabine | 100 mg/m² continuous infusion for 24 hours (4 cycles) | i.v. | $D_1-D_2$ |
| and then cytarabine | 100 mg/m² every 12 hours | s.c. | $D_1, D_5$ |
| daunorubicin | 45 mg/m²/day bolus (4 cycles) | i.v. | $J_1$ | iii) According to C. A. Linker et al. (Blood 1993; 81: 311–318), N. Chao et al. (Blood 1993; 81: 319–323) and A. M. Yeager et al. (N. Eng. J. Med. 1986; 315: 145–147):

This protocol comprises an autologous bone marrow transplantation (performed on day $D_0$):

| | Dose | Route | Days |
|---|---|---|---|
| 4-quinolone | 40–2000 mg/m²/day or 1–50 mg/kg/day infusion for 1 h to 3h | i.v. | $D_{-7}-D_{-2}$ |
| busulfan | 1 mg/kg qid (16 doses in total) | oral | $D_{-7}$ to $D_{-4}$ |
| etoposide | 60 mg/kg/day infusion for 10 hours | i.v. | $D_{-3}$ |
| or 4-quinolone | 40–2000 mg/m²/day or 1–50 mg/kg/day infusion for 1 h to 3h | i.v. | $D_{-9}-D_{-1}$ |
| busulfan | 1 mg/kg qid | oral | $D_{-9}$ to $D_{-6}$ |
| cyclophosphamide | 50 mg/kg/day infusion for 1 hour | i.v. | $D_{-5}$ to $D_{-2}$ | iv) In the case of HLA-compatible allogenic bone marrow transplantation, according to:

P. J. Tutscha et al. Blood 1987; 70: 1382–1388, F. R. Applebaum et al., Ann. Int. Med. 1984; 101: 581–588:

| | Dose | Route | Days |
|---|---|---|---|
| 4-quinolone | 40–2000 mg/m²/day or 1–50 mg/kg/day infusion for 1 h to 3h | i.v. | $D_{-7}-D_{-1}$ |
| busulfan | 1 mg/kg qid (16 doses in total) | oral | $D_{-7}$ to $D_{-4}$ |
| cyclophosphamide | 60 mg/kg/day infusion for 1 hour | i.v. | $D_{-3}$ to $D_{-2}$ |

2/ Chronic Adult Leukemias 2.1 Chronic myeloid leukemia

In the myeloblast phase, the 4-quinolones may be added to the HU-Mith treatment described by C. A. Koller et al. (N. Engl. J. Med. 1986; 315: 1433–1438):

| | Dose | Route | Days |
|---|---|---|---|
| 4-quinolone | 40–2000 mg/m²/day or 1–50 mg/kg/day infusion for 1 h to 3h | i.v. | $D_1-D_5$ $D_8-D_{12}$ $D_{15}-D_{19}$ $D_{22}-D_{26}$ |
| hydroxyurea | 500 mg/day | oral | every day |
| mithramycin | 25 µg/kg/day infusion for 2–4 hours | i.v. | daily for 3 weeks and then 3 times/week |

2.2. Chronic lymphocytic leukemia 2.2.1 FCG-CLL protocol

The 4-quinolones may be added to the "pulsed chlorambucil" combinations as described by E. Kimby et al. (Leuk. Lymphoma 1991; 5 (Suppl.) 93–96) and by FCGCLL (Blood 1990; 75: 1422–1425):

| | Dose | Route | Days |
|---|---|---|---|
| 4-quinolone | 40–2000 mg/m²/day or 1–50 mg/kg/day infusion for 1 h to 3 h | i.v. | $D_1-D_5, D_8-D_{12}, D_{15}-D_{22}$ |
| chlorambucil | 0.1 mg/kg/day | oral | once/day |
| or chlorambucil | 0.4 mg/kg/day every 14 days | oral | $D_1$ |
| and prednisone | 75 mg/day | oral | $D_1-D_3$ |

2.2.2 Fludarabine-CdA protocol

According to H. G. Chun et al. (J. Clin. Oncol. 1991; 9: 175–188), M. J. Keating et al. (Blood 1989; 74: 19–25/ J. Clin. Oncol. 1991; 9: 44–49) and A. Saven et al. (J. Clin. Oncol. 1995; 13: 570–574):

| | Dose | Route | Days |
|---|---|---|---|
| 4-quinolone | 40–2000 mg/m²/day or 1–50 mg/kg/day infusion for 1 h to 3h | i.v. | $D_1-D_8$ (once/month for 6 to 12 cycles) |
| fludarabine | 25–30 mg/m²/day infusion for 30 minutes [every 4 weeks for 6 to 12 cycles] | i.v. | $D_1-D_5$ |
| or cladibrine | 0.09 mg/kg/day in continuous infusion [1 cycle every 28 to 35 days for 1 to 9 cycles (median: 4 cycles)] | i.v. | $D_1-D_7$ |

3/ Lymphoproliferative Diseases 3.1 Hodgkin's disease

The 4-quinolones may be incorporated into the polychemotherapy protocols used conventionally for treating Hodgkin lymphoma:

3.1.1 AVDB protocol

According to G. Bonnadonna et al. (Cancer Clin. Trials 1979; 2: 217–226) and G. P. Canellos et al. (N. Engl. J. Med. 1993; 327: 1478–1484):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$, $D_{15}$–$D_{18}$ |
| doxorubicin (A) | 25 mg/m$^2$ bolus | i.v. | $D_1$, $D_{15}$ |
| bleomycin (B) | 10 U/m$^2$ bolus | i.v. | $D_1$, $D_{15}$ |
| vinblastine (V) | 6 mg/m$^2$ bolus | i.v. | $D_1$, $D_{15}$ |
| dacarbazine (D) | 375 mg/m$^2$ bolus | i.v. | $D_1$, $D_{15}$ | the cure comprising 6 to 8 cycles, at a rate of 1 cycle every 28 days.

3.1.2 MOPP/ABVD protocol

According to G. Bonnadonna et al. (Ann. Intern. Med. 1986; 104: 739–746) and G. P. Canellos et al. (N. Engl. J. Med. 1993; 327: 1478–1484):

the MOPP protocol should be alternated with the ABVD protocol (cf. §3.1.1) every 28 days, and the cure comprises 6 cycles:

| MOPP protocol: | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$, $D_8$–$D_{11}$ and $D_{14}$–$D_{17}$ |
| mechlorethamine (M) | 6 mg/m$^2$ bolus | i.v. | $D_1$, $D_8$ |
| vincristine (O) | 1.4 mg/m$^2$ bolus no maximum) | i.v | $D_1$, $D_8$ |
| procarbazine (P) | 100 mg/m$^2$/day | oral | $D_1$–$D_{14}$ |
| prednisone (P) | 40 mg/m$^2$/day | oral | $D_1$–$D_{14}$ |

3.1.3 Stanford ∀ protocol

According to N. L. Bartlett et al. (J. Clin. Oncol. 1995; 13: 1080–1088):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ $D_8$–$D_{12}$ $D_{15}$–$D_{19}$ $D_{22}$–$D_{26}$ |
| doxorubicin | 25 mg/m$^2$ | i.v | $D_1$, $D_{15}$ |
| vinblastine | 6 mg/m$^2$ bolus (4 mg/m$^2$ during cycle 3 if ≧ 50 years old) | i.v. | $D_1$, $D_{15}$ |
| mechlorethamine (M) | 6 mg/m$^2$ bolus | i.v. | $D_1$ |
| vincristine | 1.4 mg/m$^2$ bolus (max. dose: 2 mg) [1 mg/m$^2$ during cycle 3 if ≧ 50 years old) | i.v. | $D_1$, $D_{22}$ |
| bleomycin | 5 U/m$^2$ | i.v. | $D_8$, $D_{22}$ |
| etoposide | 60 mg/m$^2$ | oral | $D_{15}$, $D_{16}$ |
| prednisone | 40 mg/m$^2$/day | oral | once/week (weeks 1–9) | the cure comprising 3 cycles at a rate of 1 cycle every 28 days.

3.1.4 EVA protocol

According to G. P. Canellos et al. (Proc. Am. Soc. Clin. Oncol. 1991; 10: 273):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| etoposide (E) | 100 mg/m$^2$ infusion for 2 hours | oral | $D_1$, $D_2$, $D_3$ |
| vinblastine (V) | 6 mg/m$^2$ bolus | i.v. | $D_1$ |
| doxorubicin (A) | 50 mg/m$^2$ bolus | i.v. | $D_1$ | the cure comprising 6 cycles at a rate of 1 cycle every 28 days.

3.1.5 B-CAVe protocol

According to W. G. Harker et al. (Ann. Intern. Med. 1984; 101: 440–446):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_3$ |
| bleomycin (B) | 5 U/m$^2$ bolus | i.v. | $D_1$ |
| lomustine (CCNU) | 100 mg/m$^2$ | oral | $D_1$ |
| doxorubicin (A) | 60 mg/m$^2$ bolus | i.v. | $D_1$ |
| vinblastine (Ve) | 5 mg/m$^2$ bolus | i.v. | $D_1$ | the cure comprising 8 cycles, at a rate of 1 cycle every 28 days.

3.2. Non-Hodgkin lymphomas

3.2.1. With a low degree of malignance i)—CVP protocol

According to C. M. Bagley et al. (Ann. Intern. Med. 1972; 76: 227–234) and C. S. Portlock et al. (Blood 1976; 47: 747–756)

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| cyclophosphamide (c) | 300–400 mg/m$^2$/day | oral | $D_1$, $D_5$ |
| vincristine (V) | 1.4 mg/m$^2$ bolus (max. 2 mg) | i.v. | $D_1$ |
| prednisone (P) | 100 mg/m$^2$/day | oral | $D_1$, $D_5$ |

This cycle is repeated every 21 days up to the maximum response.

ii)—I-COPA protocol
According to R. V. Smalley et al. (N. Eng. J. Med. 1992; 327: 1336–1341)

| | Dose | Route | Days |
|---|---|---|---|
| 4-quinolone | 40–2000 mg/m²day or 1–50 mg/kg/day infusion for 1 h to 3 h | i.v. | $D_1$–$D_5$ |
| cyclophosphamide (C) | 600 mg/m² day | i.v. | $D_1$ |
| vincristine (O) | 1.2 mg/m² bolus (max: 2 mg) | i.v. | $D_1$ |
| prednisone (P) | 100 mg/m²/day | i.v. | $D_1$–$D_5$ |
| doxorubicin (A) | 50 mg/m² bolus | i.v. | $D_1$ |
| interferon-alpha (I) | 6 MU/m² | i.m. | $D_{22}$–$D_{26}$ |

The cure comprises 8 to 10 cycles, at a rate of one cycle every 28 days.

iii)—Fludarabine-CdA protocol
According to P. Solol-Celigny et al. (Blood 1994; 84 (Supp. 1): 383a), H. Hoeschster et al.; (Blood 1994; 84 (Suppl. 1): 564a and A. C. Kay (J. Clin. Oncol. 1992; 10: 371–377)

| | Dose | Route | Days |
|---|---|---|---|
| 4-quinolone | 40–2000 mg/m²/day or 1–50 mg/kg/day infusion for 1 h to 3 h | i.v. | $D_1$–$D_7$ |
| fludarabine | 25 mg/m² day infusion for 0.5 hour | i.v. | $D_1$–$D_5$ |
| or fludarabine and cyclophosphamide | 20 mg/m²/day 600–1000 mg/m²/day | i.v. i.v. | $D_1$–$D_5$ $D_1$ |
| or cladribine | 0.1 mg/m²/day infusion for 24 hours | i.v. | $D_1$–$D_7$ |

For fludaribine, each cycle is repeated every 28 days; for cladribine, each cycle is repeated every 35 days.

3.2.2. With an intermediate degree of malignancy
i)—CHOP or CNOP protocol
According to E M McKelvey et al. (Cancer 1976; 38: 1484–1493), J. O. Armitage et al. (J. Clin. Oncol. 1984; 2: 898–902), S. Paulovsky et al. (Ann. Oncol. 1992; 3: 205–209)

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| cyclophosphamide (C) | 750 mg/m² day | i.v. | $D_1$ |
| doxorubicin (H) | 50 mg/m² bolus | i.v. | $D_1$ |
| vincristine (O) | 1.4 mg/m² bolus (max: 2 mg) | i.v. | $D_1$ |
| prednisone (P) | 100 mg/m²/day (as 1 dose/day) | oral | $D_1$–$D_5$ | for the CHOP protocol

Mitoxantrone (N) may be used to replace (CNOP protocol) doxorubicin in patients over 60 years old (dose: 12 mg/m² as i.v. bolus on day $D_1$ of each cycle).

The cure with the CHOP or CNOP protocol comprises 6 to 8 cycles at a rate of 1 cycle every 21 days.

ii)—MACOP-B protocol

According to P. Klimo et al. (Ann. Intern. Med. 1985; 102: 596–602) and I. A. Cooper et al. (J. Clin. col. 1994; 12: 769–778)

| | Dose | Route | Days |
|---|---|---|---|
| 4-quinolone | 40–2000 mg/m²/day or 1–50 mg/kg/day infusion for 1 h to 3 h | i.v. | $D_1$–$D_5$, $D_6$–$D_{12}$ $D_{15}$–$D_{22}$, $D_{29}$–$D_{33}$ $D_{43}$–$D_{47}$, $D_{57}$–$D_{61}$, $D_{71}$–$D_{75}$ |
| methotrexate (M) | 100 mg/m² bolus then 300 mg/m² infusion for 4 hours | i.v. | $D_8$, $D_{36}$, $D_{64}$ |
| leucovorin | 15 mg qid | oral | $D_9$, $D_{37}$, $D_{65}$ |
| doxorubicin (A) | 50 mg/m² bolus | i.v. | $D_1$, $D_{15}$, $D_{29}$, $D_{43}$, $D_{57}$, $D_{71}$ |
| cyclophosphamide (c) | 350 mg/m² bolus | i.v. | $D_1$, $D_5$, $D_{29}$, $D_{43}$, $D_{57}$, $D_{71}$ |
| vincristine (O) | 1.4 mg/m² bolus (max. 2 mg) | i.v | $D_6$, $D_{22}$, $D_{36}$, $D_{50}$, $D_{64}$, $D_{78}$ |
| prednisone (P) | 75 mg/day | oral | Every day for 12 weeks |
| bleomycin (B) | 10 U/m² bolus | i.v. | $D_{22}$, $D_{50}$, $D_{78}$ |

This treatment protocol spreads over 12 weeks and corresponds to 1 cycle.

iii)—VACOP-B protocol

According to J. M. Connors et al. (Proc. Am. Soc. Clin. Oncol. 1990; 9: 254):

| | Dose | Route | Days |
|---|---|---|---|
| 4-quinolone | 40–2000 mg/m²/day or 1–50 mg/kg/day infusion for 1 h to 3 h | i.v. | $D_1$–$D_5$, $D_8$–$D_{12}$ $D_{15}$–$D_{22}$, $D_{29}$–$D_{34}$, $D_{43}$–$D_{47}$, $D_{57}$–$D_{61}$, $D_{71}$–$D_{75}$ |
| etoposide (V) | 50 mg/m² | i.v. | $D_{15}$, $D_{43}$, $D_{71}$ |
| etoposide | 100 mg/m² | oral | $D_{16}$, $D_{17}$, $D_{44}$, $D_{45}$, $D_{72}$, $D_{73}$ |
| doxorubicin (A) | 50 mg/m² bolus | i.v. | $D_1$, $D_{15}$, $D_{29}$, $D_{43}$, $D_{57}$, $D_{71}$ |
| cyclophosphamide (c) | 350 mg/m²/day bolus | i.v. | $D_8$, $D_{22}$, $D_{36}$, $D_{50}$, $D_{64}$, $D_{78}$ |
| vincristine (O) | 1.2 mg/m² bolus | i.v. | $D_8$, $D_{22}$, $D_{36}$, $D_{50}$, $D_{64}$, $D_{78}$ |
| prednisone (P) | 45 mg/m²/day | oral | 1/day for 1 week, then 4/day for the next 11 weeks |

Each cycle lasting 12 weeks.

iv)—m-BACOD/M-BACOD protocol

According to M. A. Shipp et al. (Ann. Int. Med. 1986; 140; 757–765) and A. T. Skarin et al. (J. Clin. Oncol. 1983; 1: 91–98)

|  | Dose | Route | Days |
|---|---|---|---|
| 4-quinolone | 40–2000 mg/m$^2$/day or 1–50 mg/kg/day infusion for 1 h to 3 | i.v. | $D_1$–$D_5$, $D_8$–$D_{12}$ $D_{15}$–$D_{19}$ |
| methotrexate (m) or | 200 mg/m$^2$ infusion for 4 hours | i.v. | $D_8$, $D_{15}$ or |
| (M) | 3000 mg/m$^2$ infusion for 4 hours | i.v. | $D_{15}$ |
| leucovorin | 10 mg/m$^2$ qid (6 doses in total) | oral | $D_9$, $D_{16}$ or $D_{16}$ |
| bleomycin (B) | 4 U/m$^2$ bolus | i.v. | $D_1$ |
| doxorubicin (A) | 45 mg/m$^2$ bolus | i.v. | $D_1$ |
| cyclophosphamide (C) | 600 mg/m$^2$ bolus | i.v. | $D_1$ |
| vincristine (O) | 1 mg/m$^2$ bolus | i.v. | $D_1$ |
| dexamethasone (D) | 6 mg/m$^2$/day | oral | $D_3$–$D_5$ |

The cure comprising 10 cycles, at a rate of 1 cycle every 21 days.

v)—ProMACE/CytaBOM protocol

According to D. L. Longo et al. (J. Clin. Oncol. 1991; 9: 25–38):

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{12}$ |
| cyclophosphamide (C) | 650 mg/m$^2$ infusion for 0.5 hour | i.v. | $D_1$ |
| doxorubicin (A) | 25 mg/m$^2$ bolus | i.v | $D_1$ |
| etoposide | 120 mg/m$^2$ infusion for 1 hour | i.v. | $D_1$ |
| prednisone (P) | 60 mg/day | oral | $D_1$–$D_{14}$ |
| cytarabine | 300 mg/m$^2$ bolus | i.v. | $D_8$ |
| bleomycin (B) | 5 U/m$^2$ bolus | i.v. | $D_8$ |
| vincristine (O) | 1.4 mg/m$^2$ bolus | i.v. | $D_8$ |
| methotrexate | 120 mg/m$^2$ bolus | i.v. | $D_8$ |
| leucovorin | 25 mg/m$^2$ qid (4 doses in total) | oral | $D_9$ |

The cure comprising 6 to 8 cycles, at a rate of 1 cycle every 14 days.

3.2.3. With a low or intermediate degree of malignance i)—ESHAP rescue protocol

In the event of a relapse or of a failure of the first line treatment, according to W. S. Velasquez et al. (J. Clin. Oncol. 1994; 12: 1169–1176)

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| etoposide (E) | 40 mg/m$^2$ infusion for 2 hours | i.v. | $D_1$–$D_4$ |
| methyl-prednisolone (S) | 500 mg/day infusion for 15 minutes | i.v. | $D_1$, $D_4$ |
| cytarabine (HA) | 2000 mg/m$^2$ infusion for 3 hours | i.v. | $D_5$ |
| cisplatin (P) | 25 mg/m$^2$/days bolus continuous infusion for 24 hours | i.v. | $D_1$–$D_4$ |

The cure comprising 6 cycles, at a rate of 1 cycle every 28 days.

ii)—MINE rescue protocol

In the event of a relapse or of a failure of the first line treatment, according to F. Cabanillas et al. (Semin. Oncol. 1990; 17 (suppl. 10): 28–33)

|  | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$ |
| ifosfamide (I) | 1330 mg/m$^2$ infusion for 1 hour | i.v. | $D_1$–$D_3$ |
| mesna (M) | 1330 mg/m$^2$ in the infusion of ifosfamide and then 266 mg/m$^2$ bolus 4 and 8 hours after each dose of ifosfamide | i.v. | $D_1$–$D_3$ |
| mitoxantrone (M) | 8 mg/m$^2$ infusion for 15 minutes | i.v. | $D_1$ |
| etoposide (E) | 65 mg/m$^2$/day infusion for 1 hour | i.v. | $D_1$–$D_3$ |

This cycle being repeated every 21 days.

3.3. Non-Hodgkin lymphomas: Burkitt's lymphoma, small-cell lymphoma, lymphoblast lymphoma

3.3.1. Magrath protocol

The products claimed may be combined with the Magrath protocols according to the following schemes:

i)—cycle 1
according to I. T. Magrath et al. (Blood 1984; 63: 1102–1111)

|  | Dose | Route | Days |
|---|---|---|---|
| 4-quinolone | 40–2000 mg/m²/day<br>or<br>1–50 mg/kg/day<br>infusion for 1 h<br>to 3 h | i.v. | $D_1-D_5$,<br>$D_8-D_{12}$ |
| cytarabine | 30 mg/m² | intra-thecal | $D_1, D_2, D_3, D_7$ |
| cyclophosphamide | 1200 mg/m² bolus | i.v. | $D_1$ |
| methotrexate | 12.5 mg/m²<br>(max: 12.5 mg) | intra-thecal | $D_{10}$ |
| methotrexate | 300 mg/m²/day<br>infusion for 1<br>hour and then<br>60 mg/m²/h<br>infusion for 41<br>hours | i.v. | $D_{10}-D_{11}$ |
| leucovorin | 15 mg/m² bolus<br>qid (8<br>successive<br>doses) | i.v. | to be started 42 hours after the start of the administration of methotrexate | ii)—Cycles 2 to 15
According to I. T. Magrath et al. (1984) also.

|  | Dose | Route | Days |
|---|---|---|---|
| 4-quinolone | 40–2000 mg/m²/day<br>or<br>1–50 mg/kg/day<br>infusion for 1 h<br>to 3 h | i.v. | $D_1-D_3$<br>$D_{10}-D_{11}$ |
| cytarabine | 45 mg/m² | intra-thecal | $D_1, D_2$<br>(cycles 2 and 3)<br>$D_1$<br>(cycles 4 and 6) |
| cyclophosphamide | 1200 mg/m² bolus | i.v | $D_1$ |
| doxorubicin | 40 mg/m² bolus | i.v | $D_1$ |
| vincristine | 1.4 mg/m² bolus<br>(max: 2 mg) | i.v. | $D_1$ |
| methotrexate | 12.5 mg/m²<br>(max: 12.5 mg) | intra-thecal | $D_3, D_{10}$<br>(cycles 2 and 3)<br>$D_{10}$<br>(cycles 4, 5, 6) |
| methotrexate | 300 mg/m²<br>infusion for 1<br>hour and then<br>60 mg/m²<br>continuous<br>infusion for 41<br>hours | i.v. | $D_{10}, D_{11}$<br>(cycles 2 and 6)<br>$D_{14}, D_{15}$<br>(cycles 7-15) |
| leucovorin | 15 mg/m² bolus<br>qid (8 consecutive doses) | i.v. | start at the 42nd hour of the treatment with methotrexate | the cure comprising 14 cycles, at a rate of one cycle every 28 days.

3.4 Waldenström's macroglobulinemia

3.4.1 CVP protocol according to the CVP protocol described by M. A. Dimopoulous et al. (Blood 1994; 83: 1452–1459) and C. S. Portlock et al. (Blood 1976; 47: 747–756):

|  | Dose | Route | Days |
|---|---|---|---|
| 4-quinolone | 40–2000 mg/m²/day<br>or<br>1–50 mg/kg/day<br>infusion for 1 h<br>to 3 h | i.v. | $D^1-D_5$ |
| cyclophosphamide (C) | 300–400 mg/m²/day | oral | $D_1-D_5$ |
| vincristine (V) | 1.4 mg/m²/day bolus<br>(max: 2 mg) | i.v. | $D_1$ |
| prednisone (P) | 100 mg/m²/day | oral | $D_1-D_5$ | the cure being continued indefinitely (1 cycle every 21 days).

3.4.2 Fludarabine-CdA protocol according to H. M. Kantarjian et al. (Blood 1990; 75: 1928–1931) and M. A. Dinopoulous et al. (Ann. Intern. Med. 1993; 118: 195–198):

|  | Dose | Route | Days |
|---|---|---|---|
| 4-quinolone | 40–2000 mg/m²/day or<br>1–50 mg/kg/day<br>infusion for 1 h to 3h | i.v. | $D_1-D_5$ |
| fludarabine | 25–30 mg/m²<br>infusion for<br>0.5 hour | i.v. | $D_1-D_5$ |
| or |  |  |  |
| 4-quinolone | 40–2000 mg/m²/day or<br>1–50 mg/kg/day<br>infusion for 1 h to 3h | i.v. | $D_1-D_7$ |
| cladribine (CdA) | 0.09 mg/m²/day<br>continuous infusion | i.v. | $D_1-D_7$ | the cure comprising 6 to 12 cycles with an interval of 28 days in the case of fludarabine and 2 cycles with an interval of 28 days also in the case of cladribine.

3.5 Multiple myeloma

3.5.1 MP protocol according to R. Alexanian et al. (JAMA 1969; 208: 1680–1685), A. Belch et al. (Br. J. Cancer 1988; 57: 94–99) and F. Mandelli et al. (N. Engl. J. med. 1990; 322: 1430–1434):

|  | Dose | Route | Days |
|---|---|---|---|
| 4-quinolone | 40–2000 mg/m²/day or<br>1–50 mg/kg/day<br>infusion for<br>1 h to 3 h | i.v. | $D_1-D_5$ |
| melphalan (M) | 0.25 mg/kg/day | oral | $D_1-D_4$ |
| prednisone (P) | 100 mg/day | oral | $D_1-D_4$ | or

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| melphalan (M) | 9 mg/m²/day | oral | $D_1$–$D_4$ |
| prednisone (P) | 100 mg/day | oral | $D_1$–$D_4$ | the cure comprising at least 12 cycles, at a rate of 1 cycle every 4 to 6 weeks.

5 3.5.2 VAD protocol

According to B. Barlogie et al. (N. Engl. J. Med. 1984; 310: 1353–1356):

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| vincristine (V) | 0.4 mg/day continuous 24-hour infusion | i.v. | $D_1$–$D_4$ |
| doxorubicin (A) | 9 mg/m²/day continuous 24-hour infusion | i.v. | $D_1$–$D_4$ |
| dexamethasone (D) | 40 mg/day | i.v. | $D_1$–$D_4$, $D_9$–$D_{12}$, $D_{17}$–$D_{20}$ |

3.5.3 MP-interferon ∀ protocol according to O. Osterborg et al. (Blood 1993; 81: 1428–1434):

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| melphalan (M) | 0.25 mg/kg/day | oral | $D_1$–$D_4$ |
| prednisone (P) | 2 mg/kg/day | oral | $D_1$–$D_4$ |
| interferon-alpha | 7 MU/m²/day | s.c. | $D_1$–$D_5$ and $D_{22}$–$D_{26}$ | the cure comprising the indefinite repetition of this cycle, at a rate of 1 cycle every 42 days.

3.5.4 VCAP or VBAP protocol according to S. E. Salmon et al. (J. Clin. Oncol. 1983; 1: 453–461):

VCAP protocol:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ |
| vincristine (V) | 1 mg/m² bolus (max: 1.5 mg) | i.v. | $D_1$ |

-continued

| | Dose | Route | Days |
|---|---|---|---|
| doxorubicin (A) | 30 mg/m² bolus | i.v. | $D_1$ |
| prednisone (P) | 60 mg/m²/day | oral | $D_1$–$D_4$ |
| cyclophospha-mide (C) | 125 mg/m² infusion for 1 hour | oral | $D_1$–$D_4$ |

VBAP protocol: the cyclophosphamide is replaced with carmustine (BCNU), the remainder being identical:

| | Dose | Route | Days |
|---|---|---|---|
| carmustine | 30 mg/m² infusion for 1 hour | i.v. | $D_1$ |

C. Tumors in Children—Pediatric Oncology

The 4-quinolones can also be incorporated into polychemotherapy protocols for treating pediatric tumors in order to improve the antitumor efficacy while at the same time reducing the severity of the side effects by virtue of the action on the recruitment and mobilization of the clonogenic cells and by virtue of the possibility of reducing the active doses.

1/ Ewing's Sarcoma/Primitive Neuroectodermal Tumor

The 4-quinolones may be introduced into the VCR-Doxo-CY-Ifos-Mesna-E protocol (E. D. Berger et al., J. Clin. Oncol. 1990; 8: 1514–1524; W. H. Meyer et al., J. Clin. Oncol. 1992; 10: 1737–1742):

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ and $D_{22}$–$D_{27}$ and $D_{43}$–$D_{48}$ and $D_{63}$–$D_{68}$ |
| vincristine | 2 mg/m² bolus (maximum dose = 2 mg) | i.v. | $D_1$, $D_8$, $D_{15}$, $D_{43}$ |
| doxorubicin | 30 mg/m²/day in infusion for 24 hours | i.v. | $D_1$–$D_3$, $D_{43}$–$D_{45}$ |
| cyclophos-phamide | 2.2 g/m² in infusion for 0.5 hour | i.v. | $D_1$, $D_{43}$ |
| ifosfamide | 1800 mg/m²/day in infusion for 1 hour | i.v. | $D_{22}$–$D_{26}$ $D_{63}$–$D_{67}$ |
| mesna | 360 mg/m² in infusion for 15 minutes at a rate of 5 doses every 3 hours | i.v. | administered with cyclo-phosphamide and ifosfamide |
| etoposide | 100 mg/m² in infusion for 1 hour | i.v. | $D_{22}$–$D_{26}$ $D_{63}$–$D_{67}$ | the cure comprises 6 to 10 of these cycles depending on the initial severity of the sarcoma and the amplitude of the response.

2/ Acute Pediatric Lymphoblast Leukemia 2.1. Induction chemotherapy (days $D_1$–$D_{30}$)

The 4-quinolones may be added to the recommended protocols (P. S. Gaynon et al., J. Clin. Oncol., 1993, 11, 2234–2242; J. Pullen et al., J. Clin. Oncol. 1993; 11: 2234–2242; J. Pullen et al., J. Clin. Oncol. 1993; 11: 839–849; V. J. Land et al., J. Clin. Oncol. 1994; 12: 1939–1945)

|  | Dose | Route | Days |
|---|---|---|---|
| 4-quinolone | 40–2000 mg/m²/day or 1–50 mg/kg/day infusion for 1 h to 3 h | i.v. | $D_1$–$D_5$, $D_8$–$D_{11}$, $D_{15}$–$D_{18}$, $D_{22}$–$D_{27}$ |
| vincristine | 1.5 mg/m² bolus (maximum dose = 2 mg) | i.v. | $D_1$, $D_8$, $D_{15}$, $D_{22}$ |
| L-asparaginase | 6000 IU/m² | i.m. | 3 times/week for 3 weeks |
| prednisone | 60 mg/m² in 3 doses/day | oral | $D_1$ to $D_{28}$ |
| daunorubicin | 25 mg/m²/day in infusion for 15 minutes | i.v. | $D_1$, $D_8$, $D_{15}$ and $D_{22}$ |
| methotrexate | Depending on the age | intra-thecal | $D_{15}$, $D_{28}$ |
| cytarabine | Depending on the age | intra-thecal | $D_1$ | depending on the result of the bone marrow examination, passage to the consolidation phase takes place on day $D_{28}$ of the treatment protocol.

2.2. Consolidation/maintenance chemotherapy

The 4-quinolones may be introduced into the maintenance protocol (P. S. Gaynon et al., J. Clin. Oncol., 1993, 11: 2234–2242; J. Pullen et al., J. Clin. Oncol. 1993; 11: 839–849; V. J. Land et al., J. Clin. Oncol. 1994; 12: 1939–1945) according to the following scheme:

|  | Dose | Route | Days |
|---|---|---|---|
| 4-quinolone | 40–2000 mg/m²/day or 1–50 mg/kg/day infusion for 1 h to 3 h | i.v. | $D_1$–$D_5$, $D_{15}$–$D_{20}$ and $D_{94}$–$D_{99}$, $D_{101}$–$D_{106}$ $D_{108}$–$D_{113}$, $D_{122}$–$D_{127}$ |
| cyclophos-phamide | 1000 mg/m² in infusion for 0.5 hour | i.v. | $D_1$, $D_{15}$, $D_{122}$ |
| L-asparaginase | 6000 U/m² | i.m. | 3 times/week between $D_{97}$ and $D_{122}$ |
| cytarabine | 75 mg/m²/day in infusion for 15 minutes | i.v./ s.c. | a sequence of 4 days starting $D_2$, $D_9$, $D_{16}$, $D_{23}$, $D_{123}$, $D_{130}$ |
| doxorubicin | 25 mg/m²/day in infusion for 15 minutes | i.v. | $D_{94}$, $D_{101}$, $D_{108}$ |
| mercaptopurine | 60 mg/m²/day | oral | $D_1$–$D_{93}$, $D_{143}$ to the end of the treatment |
| methotrexate | 20 mg/m²/day | oral | once/week between $D_{36}$ and $D_{72}$ and between $D_{143}$ and the end of the treatment |
| prednisone | 40 mg/m²/day (divided into 3 doses/day) | oral | 5 consecutive days per month between $D_{143}$ and the end of the treatment |

-continued

|  | Dose | Route | Days |
|---|---|---|---|
| thioguanine | 60 mg/m²/day | oral | $D_{122}$–$D_{135}$ |
| vincristine | 1.5 mg/m² bolus (maximum dose = 2 mg) | i.v. | $D_{94}$, $D_{101}$, $D_{108}$, then once/month between $D_{143}$ and the end of the treatment |
| methotrexate | Depending on the age | intra-thecal | $D_1$, $D_8$, $D_{15}$, $D_{22}$, $D_{123}$, $D_{130}$ then once/3 months between $D_{143}$ and the end of the treatment |

3/ Acute Pediatric Myeloid Leukemia

The 4-quinolones are added to the induction and consolidation/maintenance protocols according to the following schemes:

3.1. Induction chemotherapy

According to Y. Ravindranath et al., J. Clin. Oncol. 1991; 9: 572–580; M. E. Nesbit et al., J. Clin. Oncol. 1994; 12: 127–135; R. J. Wells et al., J. Clin. Oncol. 1994; 12: 2367–2377):

|  | Dose | Route | Days |
|---|---|---|---|
| 4-quinolone | 40–2000 mg/m²/day or 1–50 mg/kg/day infusion for 1 h to 3 h | i.v. | $D_1$–$D_5$, $D_{10}$–$D_{13}$ |
| cytarabine | depending on the age | intra-thecal | $D_1$ |
| daunorubicin | 20 mg/m²/day in infusion for 24 hours | i.v. | $D_1$–$D_4$, $D_{10}$–$D_{13}$ |
| cytarabine | 200 mg/m²/day in infusion for 24 hours | i.v. | $D_1$–$D_4$, $D_{10}$–$D_{13}$ |
| thioguanine | 100 mg/m²/day divided into 2 doses/day | oral | $D_1$–$D_4$, $D_{10}$–$D_{13}$ |
| etoposide | 100 mg/m²/day in infusion for 24 hours | i.v | $D_1$–$D_4$, $D_{10}$–$D_{13}$ |
| dexamethasone | 6 mg/m² divided into 3 doses/day | i.v./ oral | $D_1$–$D_4$, $D_{10}$–$D_{13}$ | this cycle being repeated from $D_{28}$.

3.2. Consolidation/maintenance chemotherapy

According to Y. Ravindranath et al., J. Clin. Oncol. 1991; 9: 572–580; M. E. Nesbit et al., J. Clin. Oncol. 1994; 12: 127–135; R. J. Wells et al., J. Clin. Oncol. 1994; 12: 2367–2377):

|  | Dose | Route | Days |
|---|---|---|---|
| cytarabine | depending on the age | intra-thecal | $D_1$, $D_{28}$, $D_{56}$ |
| 4-quinolone | 40–2000 mg/m²/day or 1–50 mg/kg/day infusion for 1 h to 3 h | i.v. | $D_1$–$D_5$, $D_8$–$D_{13}$, $D_{28}$–$D_{33}$, $D_{56}$–$D_{61}$ $D_{89}$–$D_{94}$ |
| cytarabine | 3000 mg/m² in infusion for 3 hours every 12 hours | i.v. | $D_1$–$D_2$, and $D_8$–$D_9$ |

-continued

| | Dose | Route | Days |
|---|---|---|---|
| L-asparaginase | 6000 IU/m² 3 hours after cytarabine | i.m. | $D_2$, $D_9$ |
| vincristine | 1.5 mg/m² bolus (maximum dose = 2 mg) | i.v. | $D_{28}$, $D_{56}$ |
| thioguanine | 75 mg/m²/day | oral | $D_{28}$–$D_{84}$ |
| cytarabine | 75 mg/m²/day bolus | i.v. | $D_{28}$–$D_{31}$, $D_{56}$–$D_{59}$ |
| cyclophosphamide | 75 mg/m²/day in infusion for 0.5 hour | i.v. | $D_{28}$–$D_{31}$, $D_{56}$–$D_{59}$ |
| cytarabine | 25 mg/m²/day bolus | sc/i.v. | $D_{89}$–$D_{93}$ |
| thioguanine | 50 mg/m²/day | oral | $D_{89}$–$D_{93}$ |
| etoposide | 100 mg/m²/day in infusion for 1 hour | i.v. | $D_{89}$, $D_{92}$ |
| dexamethasone | 2 mg/m²/day | oral | $D_{89}$–$D_{92}$ |
| daunorubicin | 30 mg/m² in infusion for 15 minutes | i.v. | $D_{89}$ |

4/ Pediatric Hodgkin's Disease

The 4-quinolones may be added to the MOPP-ABVD protocol 5 according to E. A. Gehan et al. (Cancer 1990; 65: 1429–1437), S. P. Hunger et al. (J. Clin. Oncol. 1994; 12: 2160–2166) and M. M. Hudson et al. (J. Clin. Oncol. 1993; 11: 100–108):

| | Dose | Route | Days |
|---|---|---|---|
| 4-quinolone | 40–2000 mg/m²/day or 1–50 mg/kg/day infusion for 1 h to 3 h | i.v. | $D_1$–$D_5$ and $D_8$–$D_{12}$ |
| mechlorethamine (M) | 6 mg/m² bolus | i.v. | $D_1$, $D_8$ |
| vincristine (O) | 1.5 mg/m² bolus (maximum 2 mg) | i.v. | $D_1$, $D_8$ |
| procarbazine (P) | 100 mg/m²/day | oral | $D_1$–$D_{14}$ |
| prednisone (P) | 40 mg/m²/day (divided into 3 doses/d) | oral | $D_1$–$D_{14}$ |
| doxorubicin (A) | 25 mg/m²/day in infusion for 15 minutes | i.v. | $D_{29}$, $D_{43}$ |
| bleomycin (B) | 10 U/m² in infusion for 15 minutes | i.v. | $D_{29}$, $D_{43}$ |
| vinblastine (V) | 6 mg/m² bolus (maximum 2 mg) | i.v. | $D_{29}$, $D_{43}$ |
| dacarbazine (D) | 375 mg/m² in infusion for 15 minutes | i.v. | $D_{29}$, $D_{43}$ |

This cycle should be repeated 6 times at a rate of 1 cycle every 8 weeks, the cure comprising 6 cycles.

If an autologous bone marrow transplant (auto-graft) is prescribed, the CVB protocol described by R. Chopra et al. (Blood 1993; 81: 1137–1145), C. Wheeler et al. (J. Clin. Oncol. 1990; 8: 648–656) and R. J. Jones et al. (J. Clin. Oncol. 1990, 8, 527–537) may be used according to the following scheme (the allograft taking place on day $D_0$):

| | Dose | Route | Days |
|---|---|---|---|
| 4-quinolone | 40–2000 mg/m²/day or 1–50 mg/kg/day infusion for 1 h to 3 h | i.v. | $D_{-7}$, $D_{-1}$ |
| cyclophosphamide | 1800 mg/m²/day in 2 infusions for 1 hour | i.v. | $D_{-7}$, $D_{-6}$ $D_{-5}$, $D_{-4}$ |
| carmustine (BCNU) | 112 mg/m²/day in infusion for 0.5 hour | i.v. | $D_{-7}$, $D_{-6}$ $D_{-5}$, $D_{-4}$ |
| etoposide | 500 mg/m²/day in 2 infusions for 1 hour | i.v. | $D_{-7}$, $D_{-6}$ $D_{-5}$, $D_{-4}$ |

5/ Pediatric Lymphoblast Lymphoma

The compounds claimed may also be combined with the induction chemotherapy protocols (A. T. Meadows et al., J. Clin. Oncol. 1989; 7: 92–99-C. Patte et al., Med. Ped. Oncol. 1992; 20: 105–113 and A. Reiter et al., J. Clin. Oncol. 1995; 13: 359–372) and the maintenance chemotherapy protocols:

5.1 Induction chemotherapy

| | Dose | Route | Days |
|---|---|---|---|
| 4-quinolone | 40–2000 mg/m²/day or 1–50 mg/kg/day infusion for 1 h to 3 h | i.v. | $D_1$–$D_5$, $D_{17}$–$D_{22}$, $D_{24}$–$D_{29}$ |
| cyclophosphamide | 1200 mg/m² in infusion for 0.5 hour | i.v. | $D_1$ |
| cytarabine | depending on the age | intra-thecal | $D_1$ |
| vincristine | 1.5 mg/m² bolus (maximum 2 mg) | i.v. | $D_3$, $D_{10}$, $D_{17}$, $D_{24}$ |
| prednisone | 60 mg/m²/day divided into 3 doses/day | oral | $D_3$–$D_{28}$ |
| daunorubicin | 60 mg/m² in infusion for 15 minutes | i.v. | $D_{17}$ |
| L-asparaginase | 6000 U/m²/day in infusion for 15 minutes | im | $D_{17}$–$D_{35}$ 3 times/ week |
| methotrexate | depending on the age | intra-thecal | $D_{17}$, $D_{31}$ |

5.2 Maintenance chemotherapy:
according to the following scheme:

| | Dose | Route | Days |
|---|---|---|---|
| 4-quinolone | 40–2000 mg/m²/day or 1–50 mg/kg/day infusion for 1 h to 3 h | i.v. | $D_1$–$D_5$, $D_{15}$–$D_{20}$, $D_{29}$–$D_{34}$ |
| cyclophosphamide | 1000 mg/m² in infusion for 0.5 hour | i.v. | $D_1$ |
| vincristine | 1.5 mg/m² bolus (maximum 2 mg) | oral | $D_1$, $D_5$ (from cycles 2 to 10) |
| methotrexate | 300 mg/m²/day (60% in infusion for 15 minutes and 40% in infusion for 4 hours) | i.v. | $D_{15}$ |

-continued

| | Dose | Route | Days |
|---|---|---|---|
| leucovorin | 10 mg/m$^2$/ every 4 h | oral | $D_{16}$ |
| daunorubicin | 30 mg/m$^2$ in infusion for 0.5 hour | i.v. | $D_{29}$ |
| methotrexate | depending on the age | intra-thecal | $D_1$, $D_8$, $D_{15}$ (cycle 1) and then once/ month (cycles 2 to 10) | the cure comprising 10 cycles.

6/ Pediatric Neuroblastoma

The recommended polychemotherapy protocol Doxo-E-Cy-Pt is adapted from R. P. Castleberry et al. (J. Clin. Oncol. 1992; 10: 1299–1304), A. Garaventa et al. (J. Clin. Oncol. 1993; 11: 1770–1779) and D. C. West et al. (J. Clin. Oncol. 1992; 11: 84–90):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_{28}$–$D_{35}$, $D_{58}$–$D_{65}$ |
| doxorubicin | 25 mg/m$^2$/day in infusion for 15 minutes | i.v. | $D_2$, $D_{30}$, $D_{58}$ |
| etoposide | 100 mg/m$^2$ in infusion for 1 hour | oral/ naso-gastric | $D_2$, $D_5$, $D_{30}$, $D_{33}$, $D_{58}$, $D_{61}$ |
| cyclophos-phamide | 1000 mg/m$^2$ in infusion for 0.5 hour | i.v. | $D_3$, $D_4$, $D_{31}$, $D_{32}$, $D_{59}$, $D_{60}$ |
| cisplatin | 60 mg/m$^2$ in infusion for 6 hours | i.v. | $D_1$, $D_{28}$, $D_{56}$ |

The evaluation of the therapeutic response is carried out after 9 weeks in order to determine the approach: surgical resection, radiotherapy or new chemotherapy.

7/ Pediatric Osteosarcoma

The 4-quinolones may be added to the Doxo-Pt-Mtx-Lcv protocol as described by M. Hudson et al. (J. Clin. Oncol. 1990; 8: 1988–1997), P. A. Meyers (J. Clin. Oncol. 1992; 10: 5–15) and V. H. C. Bramwell et al. (J. Clin. Oncol. 1992; 10: 1579–1591):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_{21}$–$D_{26}$, $D_{28}$–$D_{33}$ |
| doxorubicin | 25 mg/m$^2$/day in infusion for 24 hours | i.v. | $D_1$–$D_3$ |
| cisplatin | 120 mg/m$^2$ in infusion for 6 hours | i.v. | $D_1$ |
| methotrexate | 12 mg/m$^2$/day in infusion for 1 hour | i.v. | $D_{21}$, $D_{28}$ |
| leucovorin | 100 mg/m$^2$ every 6 hours | oral | $D_{22}$, $D_{29}$ |

8/ Pediatric Rhabdomyosarcoma

The Vcr-Dact-CY-Mesna protocol (H. Maurer et al., Cancer 1993; 71: 1904–1922 and L. R. Mandell et al., Oncology 1993; 7: 71–83) may include the i.v. infusion of the compounds claimed according to the following scheme:

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{12}$, $D_{22}$–$D_{27}$, $D_{43}$–$D_{47}$ |
| vincristine | 1.5 mg/m$^2$ bolus (max. 2 mg) | i.v. | $D_1$, $D_8$, $D_{15}$, $D_{22}$, $D_{29}$, $D_{36}$, $D_{43}$, $D_{50}$ and $D_{57}$ |
| dactinomycin | 0.015 mg/kg bolus (max. daily dose: 0.5 mg) | i.v. | $D_1$–$D_5$, $D_{22}$–$D_{27}$, $D_{43}$–$D_{47}$ |
| cyclophos-phamide | 2.2 g/m$^2$ in infusion for 1 hour | i.v. | $D_1$, $D_{22}$, $D_{43}$ |
| mesna | 360 mg/m$^2$ in infusion for 1 hour every 3 hours for 5 doses | i.v. | $D_1$, $D_{22}$, $D_{43}$ |

At the end of the 9th week of treatment, the efficacy should be evaluated to decide the follow-up treatment (surgery, radiotherapy, continuation of the chemo-therapy).

9/ Wilms' Tumor in Children

In the Vcr-Dact protocol as described by G. J. D'Angio et al. (Cancer, 1989; 64: 349–360) and D. M. Green et al. (J. Clin. Oncol. 1993; 11: 91–95):

| | Dose | Route | Days |
|---|---|---|---|
| 4-quinolone | 40–2000 mg/m$^2$/day or 1–50 mg/kg/day infusion for 1 h to 3 h | i.v. | $D_1$–$D_5$, $D_8$–$D_{12}$ and then every week |
| vincristine | 2 mg/m$^2$ bolus (max. dose: 2 mg) | i.v. | $D_7$ and then every week |
| dactinomycin | 0.045 mg/kg bolus (P ≤ 30 kg) 1.35 mg/m$^2$ (P > 30 kg) (max. dose: 3 mg) | i.v. | $D_1$ and then every 3 weeks |

This protocol being started after the surgical resection.

In the event of autologous bone marrow transplant (autograft) according to A. Garaventar et al. (Med. Pediatr. Oncol. 1994; 22: 11–14), the E-Thio-Cy protocol may be modified as follows:

| | Dose | Route | Days |
|---|---|---|---|
| 4-quinolone | 40–2000 mg/m$^2$/day or 1–50 mg/kg/day infusion for 1 h to 3 h | i.v. | $D_{-8}$–$D_{-1}$ |
| etoposide | 1800 mg/m$^2$ (infusion for 24 hours) | i.v. | $D_{-8}$ |
| thiotepa | 300 mg/m$^2$/day in infusion for 2 hours | i.v. | $D_{-7}$, $D_{-6}$, $D_{-5}$ |

| | Dose | Route | Days |
|---|---|---|---|
| cyclophosphamide | 50 mg/kg/day in infusion for 1 hour | i.v. | $D_{-4}, D_{-3}, D_{-2}, D_{-1}$ | the bone marrow transplant taking place on day $D_0$.

What is claimed is:

1. A pharmaceutical composition with activity on the proliferation of clonogenic cells in tumors and which comprises an effective amount of a compound chosen from the compounds of formulae:

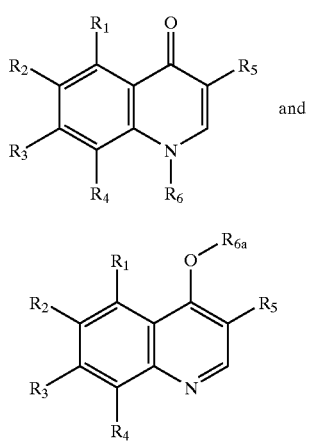

in which:
  $R_1$ is chosen from H, OH, $C_1$–$C_4$ alkyl groups, $C_2$–$C_4$ alkenyl groups, $C_1$–$C_4$ alkoxy groups, phenyl groups or a phenyl group substituted 1 to 3 times with groups chosen from H, OH, a group —$OCOR_7$, wherein $R_7$ is a $C_1$–$C_4$ alkyl group, a group —O—$SO_2$—$R'_7$, $R'_7$ is a $C_1$–$C_4$ alkyl group or a $CF_3$ group, and a group —$NR_{16}R_{17}$, wherein $R_{16}$ and $R_{17}$ are chosen, independently of each other, from hydrogen, $C_1$–$C_4$ alkyl groups, $C_2$–$C_4$ alkenyl groups, phenyl($C_1$–$C_4$)alkyl groups or a phenyl($C_1$–$C_4$)alkyl group substituted 1 to 3 times on the alkyl group with groups chosen from H, OH and $C_1$–$C_4$ alkoxy, or a dimethylamino ($C_1$–$C_4$) alkyl group, or together forming, with the nitrogen atom, a 5- or 6-membered heterocycle optionally comprising one or more hetero atoms chosen from oxygen, nitrogen and sulfur, or a methylpiperazinyl group;
  $R_2$, $R_3$ and $R_4$ are chosen, independently of each other, from H, OH, a $C_1$–$C_4$ alkyl group, a $C_1$–$C_4$ alkoxy group, a group —OCO—$R_7$, and a group derived from a saccharide, optionally $R_2$ and $R_3$ together forming a methylenedioxy group, $R_5$ is a phenyl group or a phenyl group substituted 1 to 3 times with groups chosen from H, a $C_1$–$C_4$ alkoxy group, a group —$OCOR_7$, a phenyl ($C_1$–$C_4$) alkoxy group, a group —O—$SO_2$—$R'_7$, wherein $R'_7$ is a $C_1$–$C_4$ alkyl group or a $CF_3$ group, a benzylamino group and a group derived from a saccharide;
  $R_6$ is chosen from H, a $C_1$–$C_4$ alkyl group, a $C_2$–$C_4$ alkenyl group, a group —CO—$R_8$ and a group —A—$R_9$;
  $R_{6a}$ is chosen from a $C_1$–$C_4$ alkyl group, a $C_2$–$C_4$ alkenyl group, a group —CO—$R_8$ and a group —A—$R_9$;
  $R_8$ is a $C_1C_4$ alkyl group;
  A is a $C_1$–$C_4$ alkylene group;
  $R_9$ is chosen from 5- or 6-membered heterocyclic groups containing 1 to 4 hetero atoms chosen from oxygen, sulfur and nitrogen, CN, hydroxyl, —$COOR_{10}$ and $CONR_{11}R_{12}$ groups, a group —$NR_{13}R_{14}$, a group —$COR_{15}$ and a group $OSO_2R_{16}$;
  $R_{10}$, $R_{11}$, $R_{12}$, $R_{13}$, $R_{14}$ and $R_{15}$ are independently chosen from a hydrogen atom, a $C_1$–$C_4$ alkyl group and a phenyl ($C_1$–$C_4$) alkyl group,
  $R_{16}$ is chosen from a phenyl group and a ($C_1$–$C_4$) alkylphenyl group, and
  optionally $R_4$ and $R_6$ are together and form a —CO—$CH_2$—$CH_2$-group.

2. The pharmaceutical composition as claimed in claim 1, which comprises an effective amount of a compound of formula I or Ia in which:
  $R_1$ is chosen from H, OH, $C_1$–$C_4$ alkyl groups, $C_2$–$C_4$ alkenyl groups, $C_1$–$C_4$ alkoxy groups, phenyl groups or a phenyl group substituted 1 to 3 times with groups chosen from H, OH, a group —$OCOR_7$, wherein $R_7$ is a $C_1$–$C_4$ alkyl group, a group —O—$SO_2$—$R'_7$, wherein $R'_7$ is a $C_1$–$C_4$ alkyl group or a $CF_3$ group, and a benzylamino group;
  $R_2$, $R_3$ and $R_4$ are chosen, independently of each other, from H, OH, a $C_1$–$C_4$ alkyl group, a $C_1$–$C_4$ alkoxy group, a group —OCO—$R_7$, and a group derived from a saccharide, and optionally $R_2$ and $R_3$ together forming a methylenedioxy group;
  $R_5$ is a phenyl group or a phenyl group substituted 1 to 3 times with groups chosen from H, a $C_1$–$C_4$ alkoxy group, a group —$OCOR_7$, a phenyl ($C_1$–$C_4$) alkoxy group, a group —O—$SO_2$—$R'_7$, wherein $R'_7$ is a $C_1$–$C_4$ alkyl group or a $CF_3$ group, a benzylamino group and a group derived from a saccharide;
  $R_6$ is chosen from H, a $C_1$–$C_4$ alkyl group, a group —CO—$R_8$ and a group —A—$R_9$;
  $R_{6a}$ is chosen from a $C_1$–$C_4$ alkyl group, a group —CO—$R_8$ and a group —A—$R_9$;
  $R_8$ is a $C_1$–$C_4$ alkyl group;
  A is a $C_1$–$C_4$ alkylene group;
  $R_9$ is chosen from 5- or 6-membered heterocyclic groups containing 1 to 4 hetero atoms chosen from oxygen, sulfur and nitrogen, a CN group, —$COOR_{10}$ and —$CONR_{11}R_{12}$ groups, a group —$NR_{13}R_{14}$ and a group —$COR_{15}$;
  $R_{10}$, $R_{11}$, $R_{12}$, $R_{13}$, $R_{14}$ and $R_{15}$ are independently chosen from a hydrogen atom, a $C_1$–$C_4$ alkyl group and a phenyl ($C_1$–$C_4$) alkyl group, and
  optionally $R_4$ and $R_6$ are together forming a —CO—$CH_2$—$CH_2$— group.

3. The pharmaceutical composition as claimed in claim 1, which comprises an effective amount of a compound chosen from the compounds of formulae I and Ia in which:
  $R_5$ is a phenyl, 4-methoxyphenyl, 2,4-dimethoxyphenyl or 2,5-dimethoxyphenyl group.

4. The pharmaceutical composition as claimed in claim 3, which comprises an effective amount of a compound chosen from the compounds of formulae I and Ia in which:
  $R_1$ is chosen from $C_1$–$C_4$ alkyl groups, $C_2$–$C_4$ alkenyl groups, phenyl groups or a phenyl group substituted 1 to 3 times with groups chosen from H, OH, a group —$OCOR_7$, wherein $R_7$ is a $C_1$–$C_4$ alkyl group, a group —O—$SO_2$-$R'_7$, $R'_7$ being a $C_1$–$C_4$ alkyl group or a $CF_3$ group, and a group —NR$_{16}$R$_{17}$, wherein R$_{16}$ and R$_{17}$ are chosen, independently of each other, from hydrogen, C$_1$–C$_4$ alkyl groups, C$_2$–C$_4$ alkenyl groups, phenyl (C$_1$–C$_4$) alkyl groups or a phenyl (C$_1$–C$_4$) alkyl group substituted 1 to 3 times on the alkyl group with groups chosen from H, OH and C$_1$–C$_4$ alkoxy, or a dimethylamino (C$_1$–C$_4$) alkyl group, or together forming, with the nitrogen atom, a 5- or 6-membered heterocycle optionally comprising one or more hetero atoms chosen from oxygen, nitrogen and sulfur, or a methylpiperazinyl group;

and R$_2$, R$_3$ and R$_4$ are chosen from a hydrogen atom and a C$_1$–C$_4$ alkoxy group.

5. The pharmaceutical composition as claimed in claim 3, which comprises an effective amount of a compound chosen from compounds of formulae I and Ia in which:

R$_1$, R$_2$, R$_3$ and R$_4$ are chosen from a hydrogen atom and a C$_1$–C$_4$ alkoxy group.

6. The pharmaceutical composition as claimed in claim 1, which comprises an effective amount of a compound selected from the group consisting of:
3-(4-methoxyphenyl)-1,4-dihydro-4-quinolinone,
7-methoxy-3-(4-methoxyphenyl)-1,4-dihydro-4-quinolinone,
N-{2-[5,8-dimethoxy-3-(4-methoxyphenyl)-4-quinolyl]-oxy}ethyl-N,N-dimethylamine,
5-benzylamino-7-methoxy-3-(4-methoxyphenyl)-1-methyl-1,4-dihydro-4-quinolinone,
ethyl 2-[5,8-dimethoxy-3-(4-methoxyphenyl)-4-oxo-1,4-dihydro-1-quinolinyl]acetate,
N-[3-(dimethylamino)ethyl]-5,8-dimethoxy-3-(4-methoxyphenyl)-1,4-dihydro-4-quinolinone, and
5,7-dimethoxy-3-(4-methoxyphenyl)-1-methyl-1,4-dihydro-4-quinolinone.

7. A method for modulating the proliferation of clonogenic cells in a tumor of a patient, comprising administering to said patient an effective amount of a compound chosen from the compounds of formulae:

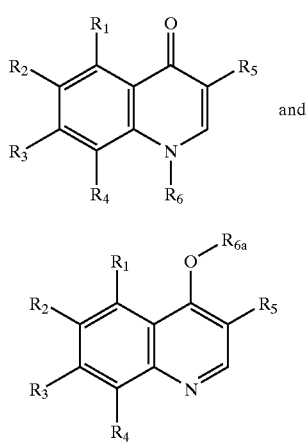

in which:
R$_1$ is chosen from H, OH, C$_1$–C$_4$ alkyl groups, C$_2$–C$_4$ alkenyl groups, C$_1$–C$_4$ alkoxy groups, phenyl groups or a phenyl group substituted 1 to 3 times with groups chosen from H, OH, a group —OCOR$_7$, wherein R$_7$ is a C$_1$–C$_4$ alkyl group, a group —O—SO$_2$-R'$_7$, wherein R'$_7$ is a C$_1$–C$_4$ alkyl group or a CF$_3$ group, and a group —NR$_{16}$R$_{17}$, wherein R$_{16}$ and R$_{17}$ are chosen, independently of each other, from hydrogen, C$_1$–C$_4$ alkyl groups, C$_2$–C$_4$ alkenyl groups, phenyl(C$_1$–C$_4$) alkyl groups or a phenyl(C$_1$–C$_4$) alkyl group substituted 1 to 3 times on the alkyl group with groups chosen from H, OH and C$_1$–C$_4$ alkoxy, or a dimethylamino (C$_1$–C$_4$) alkyl group, or together forming, with the nitrogen atom, a 5- or 6-membered heterocycle optionally comprising one or more hetero atoms chosen from oxygen, nitrogen and sulfur, or a methylpiperazinyl group;

R$_2$, R$_3$ and R$_4$ are chosen, independently of each other, from H, OH, a C$_1$–C$_4$ alkyl group, a C$_1$–C$_4$ alkoxy group, a group —OCO—R$_7$, and a group derived from a saccharide, at least one of the substituents R$_2$, R$_3$ or R$_4$ being other than H, and optionally R$_2$ and R$_3$ together forming a methylenedioxy group;

R$_5$ is a phenyl group or a phenyl group substituted 1 to 3 times with groups chosen from H, a C$_1$–C$_4$ alkoxy group, a group —OCOR$_7$, a phenyl (C$_1$–C$_4$) alkoxy group, a group —O—SO$_2$—R'$_7$, wherein R'$_7$ is a C$_1$–C$_4$ alkyl group or a CF$_3$ group, a berzylamino group and a group derived from a saccharide;

R$_6$ is chosen from H, a C$_1$–C$_4$ alkyl group, a C$_2$–C$_4$ alkenyl group, a group —CO—R$_8$ and a group —A—R$_9$, R$_{6a}$ is chosen from a C$_1$–C$_4$ alkyl group, a C$_2$–C$_4$ alkenyl group, a group —CO—R$_8$ and a group —A—R$_9$, R$_8$ is a C$_1$–C$_4$ alkyl group, A is a C$_1$–C$_4$ alkylene group, R$_9$ is chosen from 5- or 6-membered heterocyclic groups containing 1 to 4 hetero atoms chosen from oxygen, sulfur and nitrogen, CN, hydroxyl, —COOR$_{10}$ and —CONR$_{11}$R$_{12}$ groups, a group —NR$_{13}$R$_{14}$, a group —COR$_{15}$ and a group OSO$_2$R$_{16}$, R$_{10}$, R$_{11}$, R$_{12}$, R$_{13}$, R$_{14}$ and R$_{15}$ are independently chosen from a hydrogen atom, C$_1$–C$_4$ alkyl group and a phenyl(C$_1$–C$_4$) alkyl group, R$_{16}$ is chosen from a phenyl group and a (C$_1$–C$_4$) alkylphenyl group; and optionally R$_4$ and R$_6$ together forming a —CO—CH$_2$—CH$_2$-group.

8. The method according to claim 7, wherein said compound is chosen from the compounds of formulae I and Ia in which:

R$_1$ is chosen from H, OH, C$_1$–C$_4$ alkyl groups, C$_2$–C$_4$ alkenyl groups, C$_1$–C$_4$ alkoxy groups, phenyl groups or a phenyl group substituted 1 to 3 times with groups chosen from H, OH, a group —OCOR$_7$, wherein R$_7$ is a C$_1$–C$_4$ alkyl group, a group —O—SO$_2$—R'$_7$, wherein R'$_7$ is a C$_1$–C$_4$ alkyl group or a CF$_3$ group, and a benzylamino group;

R$_2$, R$_3$ and R$_4$ are chosen, independently of each other, from H, OH, a C$_1$–C$_4$ alkyl group, a C$_1$–C$_4$ alkoxy group, a group —OCO—R$_7$, and a group derived from a saccharide, and optionally R$_2$ and R$_3$ are together forming a methylenedioxy group;

R$_5$ is a phenyl group or a phenyl group substituted 1 to 3 times with groups chosen from H, a C$_1$–C$_4$ alkoxy group, a group —OCOR$_7$, a phenyl (C$_1$–C$_4$) alkoxy group, a group —O—SO$_2$—R'$_7$, wherein R'$_7$ is a C$_1$–C$_4$ alkyl group or a CF$_3$ group, a benzylamino group and a group derived from a saccharide;

R$_6$ is chosen from H, a C$_1$–C$_4$ alkyl group, a group —CO—R$_8$ and a group —A—R$_9$;

R$_{6a}$ is chosen from a C$_1$–C$_4$ alkyl group, a group —CO—R$_8$ and a group —A—R$_9$;

$R_8$ is a $C_1$–$C_4$ alkyl group;

A is a $C_1$–$C_4$ alkylene group;

$R_9$ is chosen from 5- or 6-membered heterocyclic groups containing 1 to 4 hetero atoms chosen from oxygen, sulfur and nitrogen, a CN group, —COOR$_{10}$ and —CONR$_{11}$R$_{12}$ groups, a group —NR$_{13}$R$_{14}$ and a group —COR$_{15}$;

$R_{10}$, $R_{11}$, $R_{12}$, $R_{13}$, $R_{14}$ and $R_{15}$ are independently chosen from a hydrogen atom, a $C_1$–$C_4$ alkyl group and a phenyl($C_1$–$C_4$) alkyl group; and optionally $R_4$ and $R_6$ together forming a —CO—CH$_2$—CH$_2$-group.

9. The method according to claim 7, wherein said compound is chosen from the compounds of formulae I and Ia, in which:

$R_5$ is a phenyl, 4-methoxyphenyl, 2,4-dimethoxyphenyl or 2,5-dimethoxyphenyl group.

10. The method according to claim 9, wherein said compound is chosen from the compound of formula (I) in which:

$R_1$ is chosen from $C_1$–$C_4$ alkyl groups, $C_2$–$C_4$ alkenyl groups, phenyl groups or a phenyl group substituted 1 to 3 times with groups chosen from H, OH, a group —OCOR$_7$, wherein R$_7$ is a $C_1$–$C_4$ alkyl group, a group —O—SO$_2$—R'$_7$, wherein R'$_7$ is a $C_1$–$C_4$ alkyl group or a CF$_3$ group, and a group —NR$_{16}$R$_{17}$, wherein R$_{16}$ and R$_{17}$ are chosen, independently of each other, from hydrogen, $C_1$–$C_4$ alkyl groups, $C_2$–$C_4$ alkenyl groups, phenyl ($C_1$–$C_4$) alkyl groups, a phenyl ($C_1$–$C_4$) alkyl group substituted 1 to 3 times on the alkyl group with groups chosen from H, OH and $C_1$–$C_4$ alkoxy, or a dimethylamino ($C_1$–$C_4$) alkyl group, or together forming, with the nitrogen atom, a 5- or 6-membered heterocycle optionally comprising one or more hetero atoms chosen from oxygen, nitrogen and sulfur, or a methylpiperazinyl group;

and $R_2$, $R_3$ and $R_4$ are chosen from a hydrogen atom and a $C_1$–$C_4$ alkoxy group.

11. The method according to claim 9, wherein said compound is chosen from the compounds of formulae I and Ia in which:

$R_1$, $R_2$, $R_3$ and $R_4$ are chosen from a hydrogen atom and a $C_1$–$C_4$ alkoxy group.

12. The method according to claim 7, wherein said compound is selected from the group consisting of:

3-(4-methoxyphenyl)-1,4-dihydro-4-quinolinone, 7-methoxy-3-(4-methoxyphenyl)-1,4-dihydro-4-quinolinone, N-{2-[5,8-dimethoxy-3-(4-methoxyphenyl)-4-quinolyl]-oxy}ethyl-N,N-dimethylamine, 5-benzylamino-7-methoxy-3-(4-methoxyphenyl)-1-methyl-1,4-dihydro-4-quinolinone, ethyl 2-[5,8-dimethoxy-3-(4-methoxyphenyl)-4-oxo-1,4-dihydro-1-quinolinyl]acetate, N-[3-(dimethylamino)ethyl]-5,8-dimethoxy-3-(4-methoxyphenyl)-1,4-dihydro-4-quinolinone, and 5,7-dimethoxy-3-(4-methoxyphenyl)-1-methyl-1,4-dihydro-4-quinolinone.

13. A compound of formula:

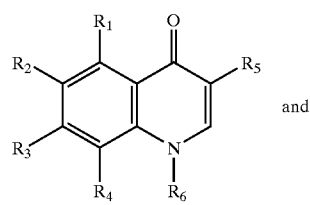

and

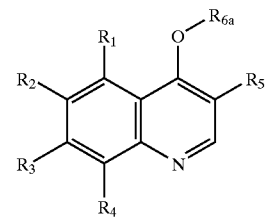

in which:

$R_1$ is chosen from H, OH, $C_1$–$C_4$ alkyl groups, $C_2$–$C_4$ alkenyl groups, $C_1$–$C_4$ alkoxy groups, phenyl groups or a phenyl group substituted 1 to 3 times with groups chosen from H, OH, a group —OCOR$_7$, wherein R$_7$ is a $C_1$–$C_4$ alkyl group, a group —O—SO$_2$—R'$_7$, R'$_7$ being a $C_1$–$C_4$ alkyl group or a CF$_3$ group, and a group —NR$_{16}$R$_{17}$, wherein R$_{16}$ and R$_{17}$ are chosen, independently of each other, from hydrogen, $C_1$–$C_4$ alkyl groups, $C_2$–$C_4$ alkenyl groups, phenyl($C_1$–$C_4$)alkyl groups, a phenyl($C_1$–$C_4$)alkyl group substituted 1 to 3 times on the alkyl group with groups chosen from H, OH and $C_1$–$C_4$ alkoxy, or a dimethylamino ($C_1$–$C_4$) alkyl group, or together forming, with the nitrogen atom, a 5- or 6-membered heterocycle optionally comprising one or more hetero atoms chosen from oxygen, nitrogen and sulfur, or a methylpiperazinyl group;

$R_2$, $R_3$ and $R_4$ are chosen, independently of each other, from H, OH, a $C_1$–$C_4$ alkyl group, a $C_1$–$C_4$ alkoxy group, a group —OCO—R$_7$, and a group derived from a saccharide, optionally $R_2$ and $R_3$ together forming a methylenedioxy group;

$R_5$ is a phenyl group or a phenyl group substituted 1 to 3 times with groups chosen from H, a $C_1$–$C_4$ alkoxy group, a group —OCOR$_7$, a phenyl($C_1$–$C_4$)alkoxy group, a group —O—SO$_2$—R'$_7$, wherein R'$_7$ is a $C_1$–$C_4$ alkyl group or a CF$_3$ group, a benzylamino group and a group derived from a saccharide;

$R_6$ is chosen from H, a $C_1$–$C_4$ alkyl group, a $C_2$–$C_4$ alkenyl group, a group —CO—R$_8$ and a group —A—R$_9$;

$R_{6a}$ is chosen from a $C_1$–$C_4$ alkyl group, a $C_2$–$C_4$ alkenyl group, a group —CO—R$_8$ and a group —A—R$_9$;

$R_8$ is a $C_1$–$C_4$ alkyl group;

A is a $C_1$–$C_4$ alkylene group;

$R_9$ is chosen from 5- or 6-membered heterocyclic groups containing 1 to 4 hetero atoms chosen from oxygen, sulfur and nitrogen, CN, hydroxyl, —COOR$_{10}$ and —CONR$_{11}$R$_{12}$ groups, a group —NR$_{13}$R$_{14}$, a group —COR$_{15}$ and a group OSO$_2$R$_{16}$;

$R_{10}$, $R_{11}$, $R_{12}$, $R_{13}$, $R_{14}$ and $R_{15}$ is independently chosen from a hydrogen atom, a $C_1$–$C_4$ alkyl group and a phenyl($C_1$–$C_4$)alkyl group;

$R_{16}$ is chosen from a phenyl group and a ($C_1$–$C_4$) alkylphenyl group; and optionally $R_4$ and $R_6$ together forming a —CO—$CH_2$—$CH_2$— group, with the exclusion of the compounds in which:

$R_1$, $R_2$, $R_4$, $R_6$=H, $R_3$=OH and $R_5$ is a phenyl, 4-methoxyphenyl, 2,4-dimethoxyphenyl or 2,5-dimethoxyphenyl group;

$R_1$=OH or $OCH_3$, $R_2$=H, $R_3$=$OCH_3$, $R_4$=H, $R_5$=4-methoxyphenyl and $R_6$=H;

$R_1$=$OCH_3$, $R_2$=H, $R_3$=$OCH_3$, $R_4$=H, $R_5$=4-methoxyphenyl and $R_6$=$CH_3$;

$R_1$=OH, $R_2$=H, $R_3$=OH, $R_4$=H, $R_5$=4-hydroxyphenyl and $R_6$=$CH_3$;

$R_1$=H, $R_2$=H, $R_3$=$OCH_3$, $R_4$=H, $R_5$=phehyl and $R_6$=H;

$R_1$=H, $R_2$=H, $R_3$=$OCH_3$, $R_4$=H, $R_5$=phenyl and $R_6$=$CH_3$;

$R_1$=H, $R_2$=H, $R_3$=OH, $R_4$=$OCH_3$, $R_5$=phenyl and $R_6$=H;

$R_1$, $R_2$, $R_3$, $R_4$, $R_6$=H and $R_5$=phenyl or 4-methoxyphenyl;

$R_1$, $R_2$, $R_3$, $R_4$, =H, $R_5$=phenyl or 4-methoxyphenyl and $R_6$=$COCH_3$;

$R_1$, $R_2$, $R_3$, $R_4$, =H, $R_5$=phenyl and $R_6$=$CH_3$;

$R_1$, $R_2$, $R_3$, $R_4$, $R_6$=H and $R_5$=4-methoxyphenyl, 2-methoxyphenyl or 4-methylphenyl; or $R_1$=OH, $R_2$, $R_3$, $R_4$=H and $R_5$=phenyl, 4-methoxyphenyl, 2,4-ethoxyphenyl or 2,5-dimethylphenyl.

14. The compound as claimed in claim 13, chosen from the compounds of formulae I and Ia in which:

$R_1$ is chosen from H, OH, $C_1$–$C_4$ alkyl groups, $C_2$–$C_4$ alkenyl groups, $C_1$–$C_4$ alkoxy groups, phenyl groups or a phenyl group substituted 1 to 3 times with groups chosen from H, OH, a group —$OCOR_7$, wherein $R_7$ is a $C_1$–$C_4$ alkyl group, a group —O—$SO_2$—$R'_7$, wherein $R'_7$ is a $C_1$–$C_4$ alkyl group or a $CF_3$ group, and a benzylamino group;

$R_2$, $R_3$ and $R_4$ are chosen, independently of each other, from H, OH, a $C_1$–$C_4$ alkyl group, a $C_1$–$C_4$ alkoxy group, a group —OCO—$R_7$, and a group derived from a saccharide, and optionally $R_2$ and $R_3$ together forming a methylenedioxy group;

$R_5$ is a phenyl group or a phenyl group substituted 1 to 3 times with groups chosen from H, a $C_1$–$C_4$ alkoxy group, a group —$OCOR_7$, a phenyl($C_1$–$C_4$)alkoxy group, a group —O—$SO_2$—$R'_7$, wherein $R'_7$ is a $C_1$–$C_4$ alkyl group or a $CF_3$ group, a benzylamino group and a group derived from a saccharide;

$R_6$ is chosen from H, a $C_1$–$C_4$ alkyl group, a group —CO—$R_8$ and a up —A—$R_9$;

$R_{6a}$ is chosen from a $C_1$–$C_4$ alkyl group, a group —CO—$R_8$ and a group —A—$R_9$;

$R_8$ is a $C_1$–$C_4$ alkyl group;

A is a $C_1$–$C_4$ alkylene group;

$R_9$ is chosen from 5- or 6-membered heterocyclic groups containing 1 to 4 hetero atoms chosen from oxygen, sulfur and nitrogen, a CN group, —$COOR_{10}$ and —$CONR_{11}R_{12}$ groups, a group —$NR_{13}R_{14}$ and a group —$COR_{15}$;

$R_{10}$, $R_{11}$, $R_{12}$, $R_{13}$, $R_{14}$ and $R_{15}$ are independently chosen from a hydrogen atom, a $C_1$–$C_4$ alkyl group and a phenyl($C_1$–$C_4$)alkyl group; and optionally $R_4$ and $R_6$ together forming a —CO—$CH_2$—$CH_2$— group.

15. The compound as claimed in claim 13, chosen from the compounds of formula I and Ia in which:

$R_5$ is a phenyl, 4-methoxyphenyl, 2,4-dimethoxyphenyl or 2,5-dimethoxyphenyl group.

16. The compound as claimed in claim 13, chosen from the compounds of formulae I and Ia in which:

$R_1$ is chosen from $C_1$–$C_4$ alkyl groups, $C_2$–$C_4$ alkenyl groups, phenyl groups or a phenyl group substituted 1 to 3 times with groups chosen from H, OH, a group —$OCOR_7$, wherein $R_7$ is a $C_1$–$C_4$ alkyl group, a group —O—$SO_2$—$R'_7$, wherein $R'_7$ is a $C_1$–$C_4$ alkyl group or a $CF_3$ group, and a group —$NR_{16}R_{17}$, wherein $R_{16}$ and $R_{17}$ are chosen, independently of each other, from hydrogen, $C_1$–$C_4$ alkyl groups, $C_2$–$C_4$ alkenyl groups, phenyl($C_1$–$C_4$)alkyl groups or a phenyl($C_1$–$C_4$)alkyl group substituted 1 to 3 times on the alkyl group with groups chosen from H, OH and $C_1$–$C_4$ alkoxy, or a dimethylamino ($C_1$–$C_4$)alkyl group, or together forming, with the nitrogen atom, a 5- or 6-membered heterocycle optionally comprising one or more hetero atoms chosen from oxygen, nitrogen and sulfur, or a methylpiperazinyl group; and $R_2$, $R_3$ and $R_4$ are chosen from a hydrogen atom and a $C_1$–$C_4$ alkoxy group.

17. The compound as claimed in claim 13, wherein said compound is selected from the group consisting of 7-methoxy-3-(4-methoxyphenyl)-1,4-dihydro-4-quinolinone, N-{2-[5,8-dimethoxy-3-(4-methoxyphenyl)-4-quinolyl]oxy}ethyl-N,N-dimethylamine, 5-benzylamino-7-methoxy-3-(4-methoxyphenyl)-1-methyl-1,4-dihydro-4-quinolinone, ethyl 2-[5,8-dimethoxy-3-(4-methoxyphenyl)-4-oxo-1,4-dihydro-1-quinolinyl]acetate, and N-[3-(dimethylamino)ethyl]-5,8-dimethoxy-3-(4-methoxyphenyl)-1,4-dihydro-4-quinolinone.

* * * * *